(12) United States Patent
Walz et al.

(10) Patent No.: US 10,450,346 B2
(45) Date of Patent: Oct. 22, 2019

(54) IMMUNOTHERAPY AGAINST SEVERAL TUMORS OF THE BLOOD, IN PARTICULAR CHRONIC LYMPHOID LEUKEMIA (CLL)

(71) Applicant: Immatics biotechnologies GmbH, Tuebingen (DE)

(72) Inventors: Juliane Walz, Tuebingen (DE); Daniel Johannes Kowalewski, Tuebingen (DE); Hans-Georg Rammensee, Unterjesingen (DE); Stefan Stevanovic, Tuebingen (DE)

(73) Assignee: IMMATICS BIOTECHNOLOGIES GMBH, Tuebingen (DE)

(*) Notice: Subject to any disclaimer, the term of this patent is extended or adjusted under 35 U.S.C. 154(b) by 0 days.

(21) Appl. No.: 16/421,552

(22) Filed: May 24, 2019

(65) Prior Publication Data

US 2019/0284234 A1 Sep. 19, 2019

Related U.S. Application Data

(63) Continuation of application No. 16/179,677, filed on Nov. 2, 2018, now Pat. No. 10,364,271, which is a continuation of application No. 16/126,751, filed on Sep. 10, 2018, now Pat. No. 10,167,317, which is a continuation of application No. 15/965,212, filed on Apr. 27, 2018, now Pat. No. 10,144,763, which is a continuation of application No. 14/743,335, filed on Jun. 18, 2015, now Pat. No. 10,000,533.

(60) Provisional application No. 62/014,849, filed on Jun. 20, 2014.

(30) Foreign Application Priority Data

Jun. 20, 2014 (GB) .................................. 1411037.3
Jun. 17, 2015 (WO) ................. PCT/EP2015/063566

(51) Int. Cl.
| | | |
|---|---|---|
| A61K 39/00 | (2006.01) |
| C07K 7/06 | (2006.01) |
| G16B 35/00 | (2019.01) |
| C07K 14/47 | (2006.01) |
| C07K 14/74 | (2006.01) |
| C12N 5/0783 | (2010.01) |
| C12Q 1/6886 | (2018.01) |
| G01N 33/574 | (2006.01) |
| G16C 20/60 | (2019.01) |

(52) U.S. Cl.
CPC ............ C07K 7/06 (2013.01); A61K 39/0011 (2013.01); C07K 14/4748 (2013.01); C07K 14/70539 (2013.01); C12N 5/0638 (2013.01); C12Q 1/6886 (2013.01); G01N 33/574 (2013.01); G16B 35/00 (2019.02); G16C 20/60 (2019.02); A61K 39/00 (2013.01); A61K 2039/5158 (2013.01); A61K 2039/585 (2013.01); C12N 2501/998 (2013.01); C12Q 2600/136 (2013.01); C12Q 2600/158 (2013.01); G01N 2333/70539 (2013.01)

(58) Field of Classification Search
CPC ........................................................ C07K 7/06
See application file for complete search history.

(56) References Cited

FOREIGN PATENT DOCUMENTS

| WO | 2005114221 A2 | 12/2005 |
| WO | 2007150077 A2 | 12/2007 |
| WO | 2008070047 A2 | 6/2008 |

OTHER PUBLICATIONS

Combined Search and Examination Report from corresponding GB 1411037.3, dated Mar. 27, 2015.
C. Berlin et al.; "Mapping the HLA ligandome landscape of acute myeloid leukemia: a targeted approach toward peptide-based immunotherapy"; Leukemia; vol. 29; No. 3; Aug. 5, 2014; pp. 647-659; XP055207425.
Etienne Caron et al.; "An open-source computational and data resource to analyze digital maps of immunopeptidomes"; ELIFE; vol. 4; Jul. 8, 2015; XP055207421.
Kowalewski et al.; "HLA ligandome analysis identifies the underlying specificities of spontaneous antileukemia immune responses in chronic lymphocytic leukemia (CLL)"; Proceedings of the National Academy of Sciences; vol. 112; No. 2; Jan. 13, 2015; pp. E166-E175; XP055207429.
Kowalewski et al.; "Identification of Novel Tumor-Associated Antigens for Chronic Lymphocytic Leukemia (CLL) Based on HLA Ligandome Analysis—New Tragets for Peptide Based Immunotherapy"; Blood; vol. 120; No. 21; Dec. 1, 2012; pp. 4119; XP055207460.
Engelhard, Current Opinion in Immunology vol. 6 p. 13 (1994).
Guo, et al Nature vol. 360 p. 384 (1992).
Rammensee et al, Immunogenetics vol. 41 p. 178 (1995).
Shastri et al J. Immunol. vol. 1995 vol. 155 p. 4339.
Ezzell (J. NIH Res. 1995 7:46).

(Continued)

*Primary Examiner* — Sheela J. Huff
(74) *Attorney, Agent, or Firm* — McBee Moore Woodward & Vanik IP, LLC

(57) ABSTRACT

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to several novel peptide sequences and their variants derived from HLA class I and HLA class II molecules of human tumor cells that can be used in vaccine compositions for eliciting anti-tumor immune responses.

20 Claims, 11 Drawing Sheets
(4 of 11 Drawing Sheet(s) Filed in Color)
Specification includes a Sequence Listing.

(56) References Cited

OTHER PUBLICATIONS

Spitler (Cancer Biotherapy, 1995, 1 O: 1-3).
Boon (Adv. Can. Res. 1992 58:177-210).
Freshney (Culture of Animal Cells, A Manual of Basic Technique, Alan R. Liss, Inc., 1983, New York, p. 4).
Dermer (Bio/Technology, 1994, 12:320).
Gura (Science, 1997, 278:1041-1042).
Jain (Sci. Am., 1994, 271 :58-65).
Haigh et al Oncology vol. 13 p. 1561 (1999).
Johnson et al Cancer Treatment Reviews vol. 2 p. 1 (1975).
Accession No. M1 EL34 MUSPF, May 2013, 1 page.
International Search Report dated Dec. 16, 2015.

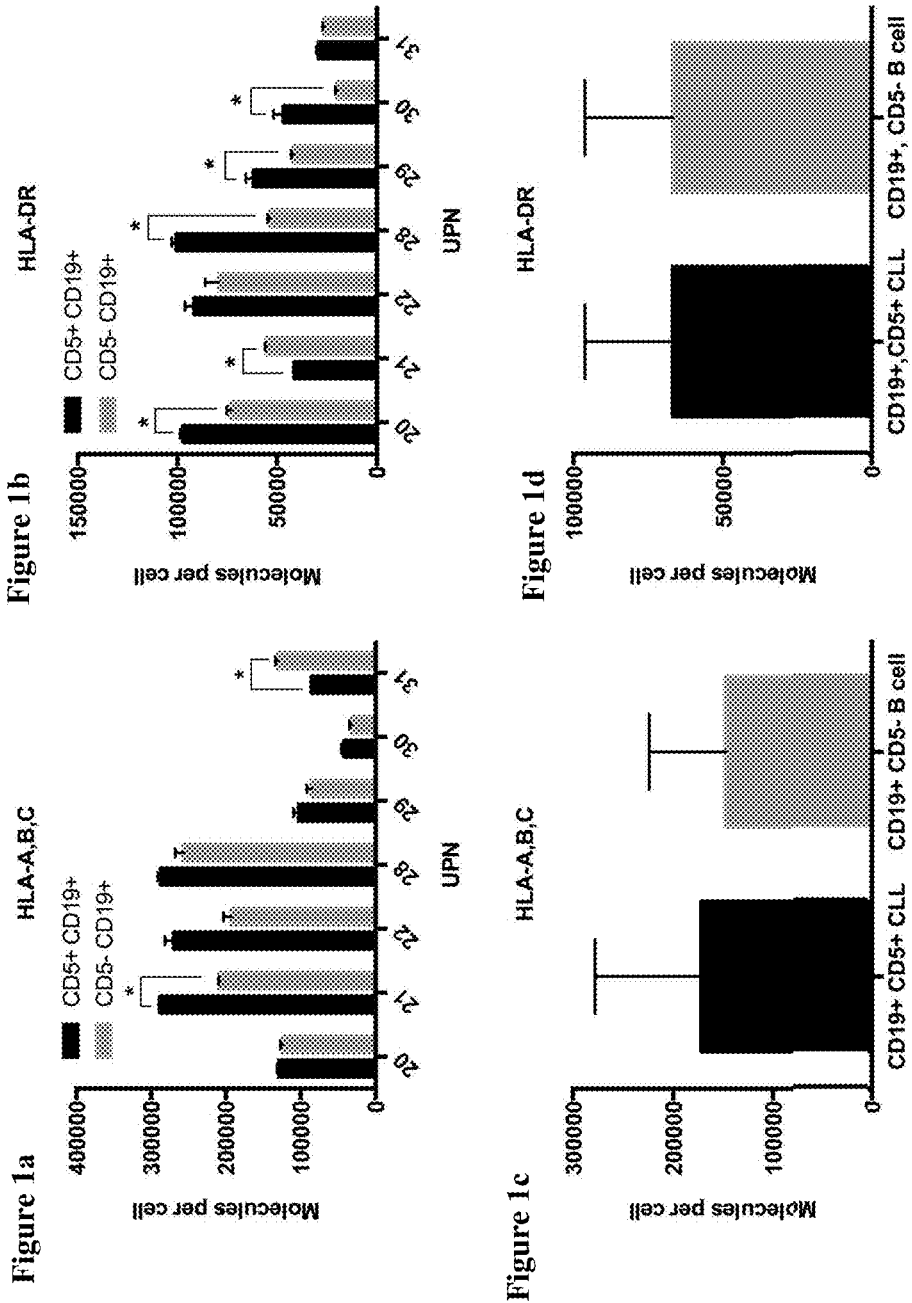

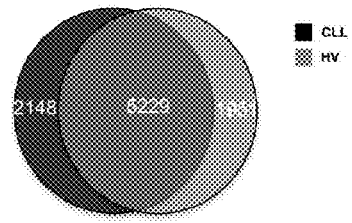
Figure 2a
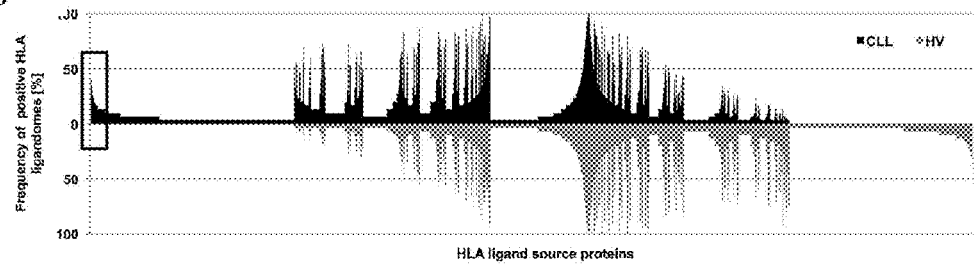
Figure 2b
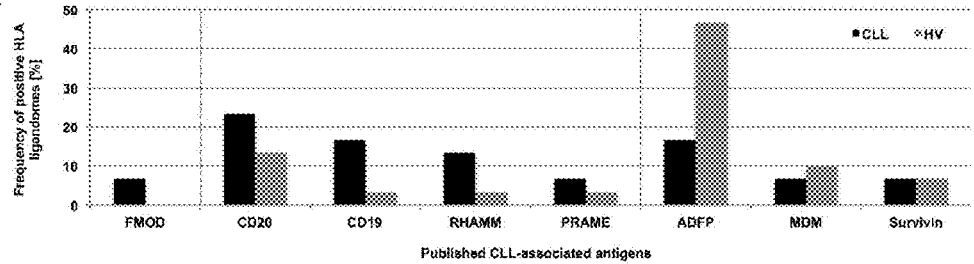
Figure 2c
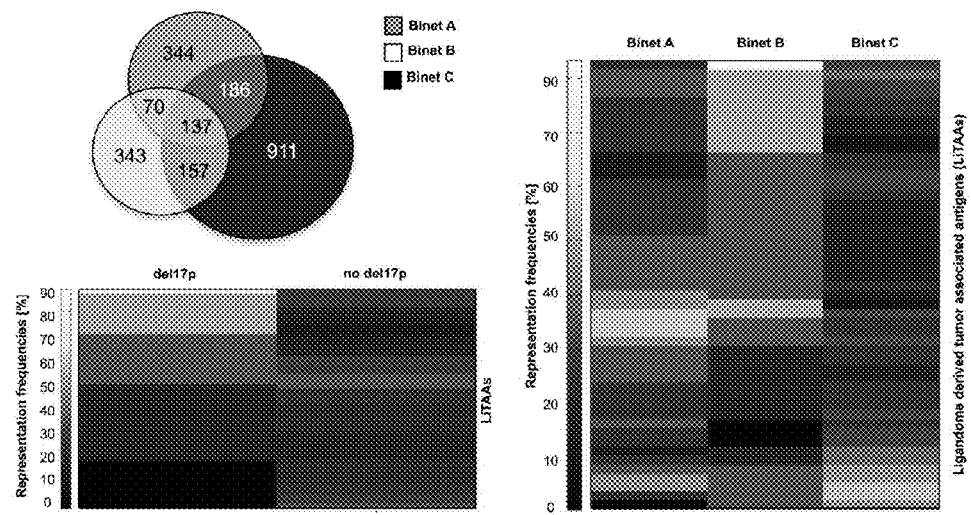
Figure 2d
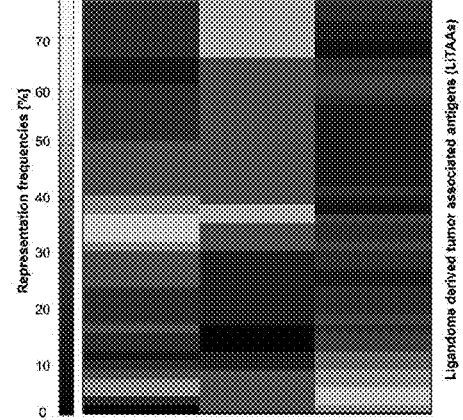
Figure 2f
Figure 2e Figure 3a
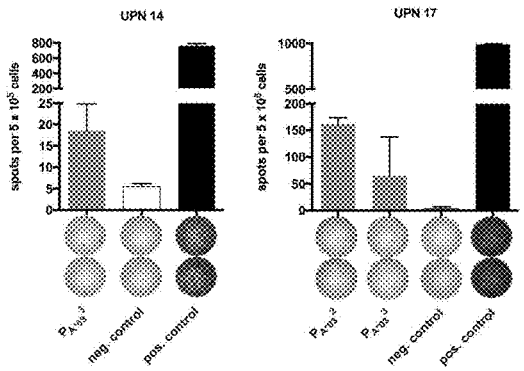
Figure 3b
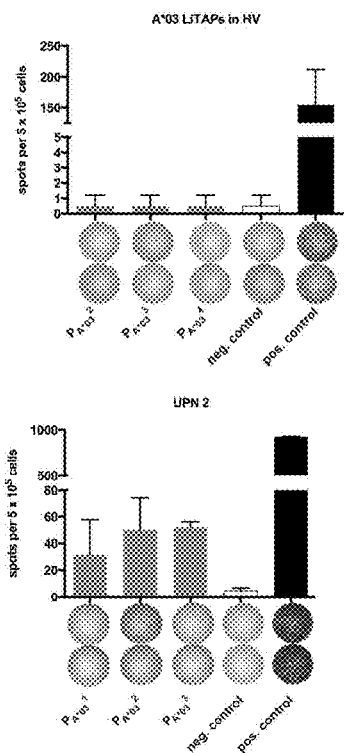
Figure 3c
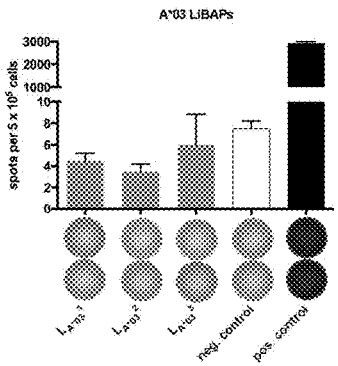
Figure 3d
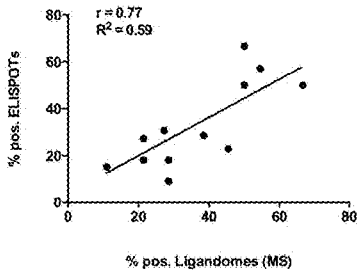
Figure 3e

Figure 4a
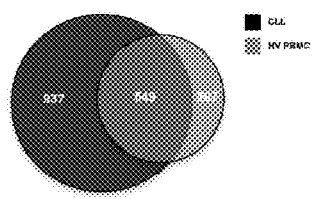
Figure 4b
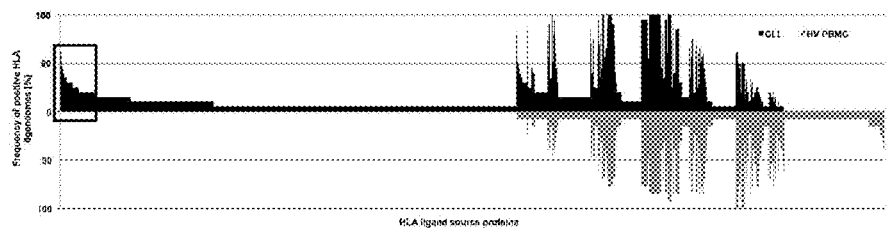
Figure 4c
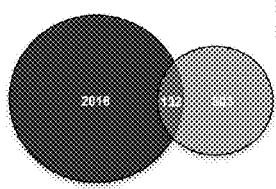
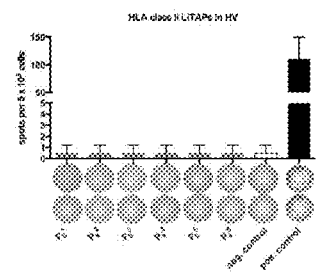
Figure 4d
Figure 4e
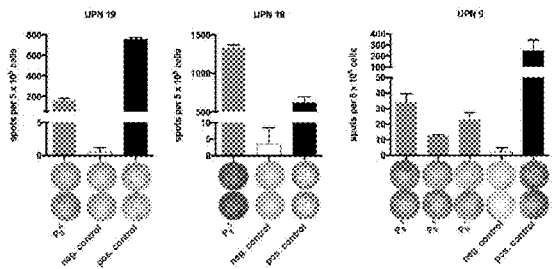
Figure 4f
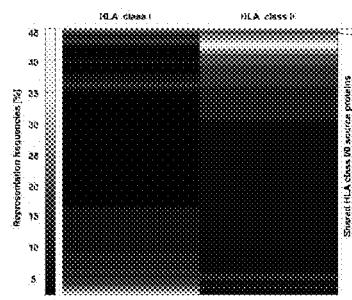
Figure 4g

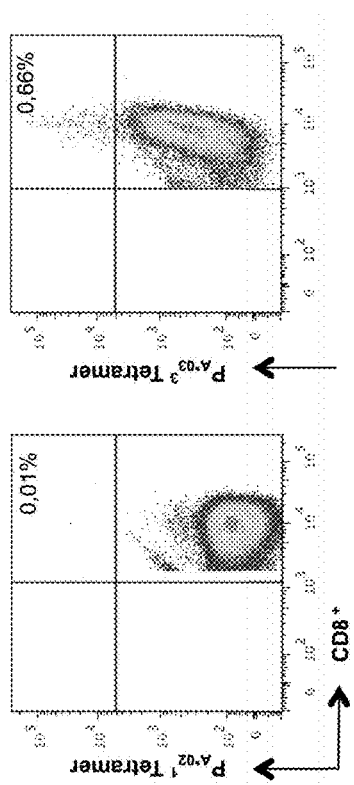
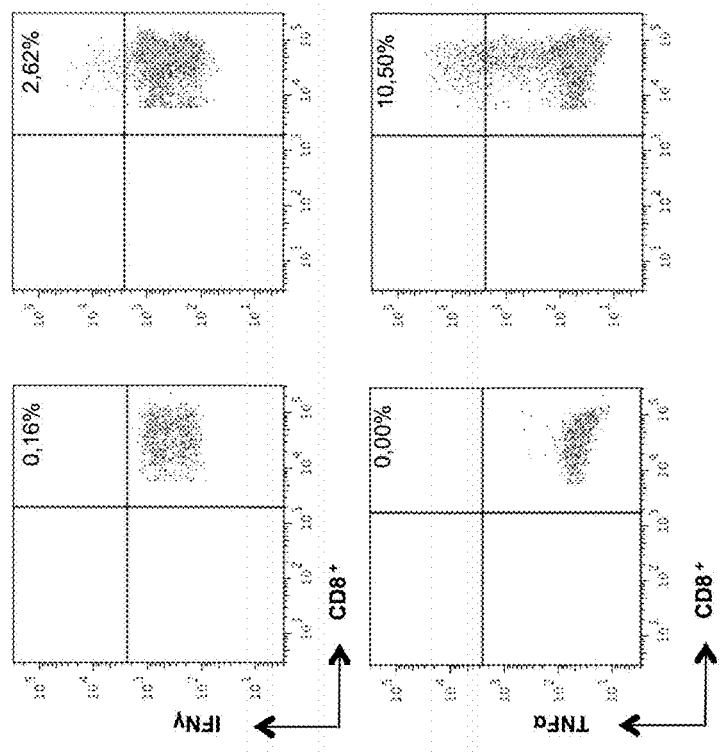
Figure 9a
Figure 9b

SEQUENCE LISTING

<160> NUMBER OF SEQ ID NOS: 1018

<210> SEQ ID NO 1
<211> LENGTH: 10
<212> TYPE: PRT
<213> ORGANISM: Homo sapiens

<400> SEQUENCE: 1

Ala Glu His Pro Asn Val Thr Leu Thr Ile
1               5                   10

<210> SEQ ID NO 2
<211> LENGTH: 10
<212> TYPE: PRT
<213> ORGANISM: Homo sapiens

<400> SEQUENCE: 2

Phe Leu Ala Glu His Pro Asn Val Thr Leu

<210> SEQ ID NO 3
<211> LENGTH: 9
<212> TYPE: PRT
<213> ORGANISM: Homo sapiens

<400> SEQUENCE: 3

Ile Leu Tyr Gly Arg Ser Tyr Thr Trp
1               5

<210> SEQ ID NO 4
<211> LENGTH: 9
<212> TYPE: PRT
<213> ORGANISM: Homo sapiens

<400> SEQUENCE: 4

Glu Val Ala Glu Phe Leu Ala Arg His
1               5

<210> SEQ ID NO 5
<211> LENGTH: 9
<212> TYPE: PRT
<213> ORGANISM: Homo sapiens

<400> SEQUENCE: 5

Arg His Ser Asn Val Asn Leu Thr Ile
1               5

<210> SEQ ID NO 6
<211> LENGTH: 9
<212> TYPE: PRT
<213> ORGANISM: Homo sapiens

<400> SEQUENCE: 6

His Pro Asp Asn Val Lys Leu Phe Leu
1               5

<210> SEQ ID NO 7
<211> LENGTH: 9
<212> TYPE: PRT
<213> ORGANISM: Homo sapiens

<400> SEQUENCE: 7

Ile Ser Asp Thr Gly Glu Leu Lys Leu
1               5

<210> SEQ ID NO 8
<211> LENGTH: 10
<212> TYPE: PRT
<213> ORGANISM: Homo sapiens

<400> SEQUENCE: 8

Lys Val Asn Gly Lys Leu Val Ala Leu Lys
1               5                   10

<210> SEQ ID NO 9
<211> LENGTH: 9
<212> TYPE: PRT
<213> ORGANISM: Homo sapiens

<400> SEQUENCE: 9

Asn Arg Leu Ser Ala Gln Ala Ala Leu
1               5

```
<210> SEQ ID NO 10
<211> LENGTH: 9
<212> TYPE: PRT
<213> ORGANISM: Homo sapiens

<400> SEQUENCE: 10

Thr Pro Phe Thr Ala Ile Arg Glu Ala
1               5

<210> SEQ ID NO 11
<211> LENGTH: 9
<212> TYPE: PRT
<213> ORGANISM: Homo sapiens

<400> SEQUENCE: 11

Phe Gly Leu Ala Arg Ala Lys Ser Val
1               5

<210> SEQ ID NO 12
<211> LENGTH: 9
<212> TYPE: PRT
<213> ORGANISM: Homo sapiens

<400> SEQUENCE: 12

Lys Ile Ala Asp Phe Gly Leu Ala Arg
1               5

<210> SEQ ID NO 13
<211> LENGTH: 9
<212> TYPE: PRT
<213> ORGANISM: Homo sapiens

<400> SEQUENCE: 13

Ala Ala Ala Asn Ile Ile Arg Thr Leu
1               5

<210> SEQ ID NO 14
<211> LENGTH: 10
<212> TYPE: PRT
<213> ORGANISM: Homo sapiens

<400> SEQUENCE: 14

Gly Arg Phe Lys Asn Leu Arg Glu Ala Leu
1               5                   10

<210> SEQ ID NO 15
<211> LENGTH: 9
<212> TYPE: PRT
<213> ORGANISM: Homo sapiens

<400> SEQUENCE: 15

Met Ser Pro Phe Ser Lys Ala Thr Leu
1               5

<210> SEQ ID NO 16
<211> LENGTH: 11
<212> TYPE: PRT
<213> ORGANISM: Homo sapiens

<400> SEQUENCE: 16

Gln Glu Asp Pro Gly Asp Asn Gln Ile Thr Leu
1               5                   10

<210> SEQ ID NO 17
```

-continued

```
<211> LENGTH: 8
<212> TYPE: PRT
<213> ORGANISM: Homo sapiens

<400> SEQUENCE: 17

Ser Pro Phe Ser Lys Ala Thr Leu
1               5

<210> SEQ ID NO 18
<211> LENGTH: 8
<212> TYPE: PRT
<213> ORGANISM: Homo sapiens

<400> SEQUENCE: 18

Asp Ala Leu Leu Lys Arg Thr Met
1               5

<210> SEQ ID NO 19
<211> LENGTH: 9
<212> TYPE: PRT
<213> ORGANISM: Homo sapiens

<400> SEQUENCE: 19

Gly Glu Asp Val Arg Ser Ala Leu Leu
1               5

<210> SEQ ID NO 20
<211> LENGTH: 9
<212> TYPE: PRT
<213> ORGANISM: Homo sapiens

<400> SEQUENCE: 20

Lys Phe Ala Glu Glu Phe Tyr Ser Phe
1               5

<210> SEQ ID NO 21
<211> LENGTH: 9
<212> TYPE: PRT
<213> ORGANISM: Homo sapiens

<400> SEQUENCE: 21

Tyr Gly Tyr Asp Asn Val Lys Glu Tyr
1               5

<210> SEQ ID NO 22
<211> LENGTH: 10
<212> TYPE: PRT
<213> ORGANISM: Homo sapiens

<400> SEQUENCE: 22

Leu Glu Val Glu Glu Arg Thr Lys Pro Val
1               5                   10

<210> SEQ ID NO 23
<211> LENGTH: 11
<212> TYPE: PRT
<213> ORGANISM: Homo sapiens

<400> SEQUENCE: 23

Arg Asp Ser Pro Ile Asn Ala Asn Leu Arg Tyr
1               5                   10

<210> SEQ ID NO 24
<211> LENGTH: 8
<212> TYPE: PRT
```

```
<213> ORGANISM: Homo sapiens

<400> SEQUENCE: 24

Arg Pro Phe Val Ile Val Thr Ala
1               5

<210> SEQ ID NO 25
<211> LENGTH: 9
<212> TYPE: PRT
<213> ORGANISM: Homo sapiens

<400> SEQUENCE: 25

Arg Pro Ile Ile Asn Thr Pro Met Val
1               5

<210> SEQ ID NO 26
<211> LENGTH: 10
<212> TYPE: PRT
<213> ORGANISM: Homo sapiens

<400> SEQUENCE: 26

Ser Pro Thr Ser Ser Arg Thr Ser Ser Leu
1               5                   10

<210> SEQ ID NO 27
<211> LENGTH: 9
<212> TYPE: PRT
<213> ORGANISM: Homo sapiens

<400> SEQUENCE: 27

Ala Thr Ser Ala Pro Leu Val Ser Arg
1               5

<210> SEQ ID NO 28
<211> LENGTH: 10
<212> TYPE: PRT
<213> ORGANISM: Homo sapiens

<400> SEQUENCE: 28

Ala Glu Leu Arg Ser Thr Ala Ser Leu Leu
1               5                   10

<210> SEQ ID NO 29
<211> LENGTH: 11
<212> TYPE: PRT
<213> ORGANISM: Homo sapiens

<400> SEQUENCE: 29

Ala Pro Ala Ser Ser His Glu Arg Ala Ser Met
1               5                   10

<210> SEQ ID NO 30
<211> LENGTH: 9
<212> TYPE: PRT
<213> ORGANISM: Homo sapiens

<400> SEQUENCE: 30

Ala Ser Arg Gln Ala Pro Pro His Ile
1               5

<210> SEQ ID NO 31
<211> LENGTH: 10
<212> TYPE: PRT
<213> ORGANISM: Homo sapiens
```

```
<400> SEQUENCE: 31

Ala Val Lys Lys Asn Pro Gly Ile Ala Ala
1               5                   10

<210> SEQ ID NO 32
<211> LENGTH: 10
<212> TYPE: PRT
<213> ORGANISM: Homo sapiens

<400> SEQUENCE: 32

Glu Glu His Leu Glu Ser His Lys Lys Tyr
1               5                   10

<210> SEQ ID NO 33
<211> LENGTH: 9
<212> TYPE: PRT
<213> ORGANISM: Homo sapiens

<400> SEQUENCE: 33

Gly Glu Phe Thr Ser Ala Arg Ala Val
1               5

<210> SEQ ID NO 34
<211> LENGTH: 10
<212> TYPE: PRT
<213> ORGANISM: Homo sapiens

<400> SEQUENCE: 34

Gly Gln Ser Thr Pro Arg Leu Phe Ser Ile
1               5                   10

<210> SEQ ID NO 35
<211> LENGTH: 8
<212> TYPE: PRT
<213> ORGANISM: Homo sapiens

<400> SEQUENCE: 35

Leu Val Asp Asp Pro Leu Glu Tyr
1               5

<210> SEQ ID NO 36
<211> LENGTH: 9
<212> TYPE: PRT
<213> ORGANISM: Homo sapiens

<400> SEQUENCE: 36

Arg Pro Lys Asn Leu Met Gln Thr Leu
1               5

<210> SEQ ID NO 37
<211> LENGTH: 9
<212> TYPE: PRT
<213> ORGANISM: Homo sapiens

<400> SEQUENCE: 37

Arg Gln Ala Pro Pro His Ile Glu Leu
1               5

<210> SEQ ID NO 38
<211> LENGTH: 10
<212> TYPE: PRT
<213> ORGANISM: Homo sapiens

<400> SEQUENCE: 38
```

Ser Glu Ala Ala Glu Leu Arg Ser Thr Ala
1               5                   10

<210> SEQ ID NO 39
<211> LENGTH: 9
<212> TYPE: PRT
<213> ORGANISM: Homo sapiens

<400> SEQUENCE: 39

Ala Ala Val Arg Ile Gly Ser Val Leu
1               5

<210> SEQ ID NO 40
<211> LENGTH: 9
<212> TYPE: PRT
<213> ORGANISM: Homo sapiens

<400> SEQUENCE: 40

Glu Arg Ala Gly Val Val Arg Glu Leu
1               5

<210> SEQ ID NO 41
<211> LENGTH: 10
<212> TYPE: PRT
<213> ORGANISM: Homo sapiens

<400> SEQUENCE: 41

Gly Ala Ala Val Arg Ile Gly Ser Val Leu
1               5                   10

<210> SEQ ID NO 42
<211> LENGTH: 10
<212> TYPE: PRT
<213> ORGANISM: Homo sapiens

<400> SEQUENCE: 42

Lys Leu Tyr Glu Leu His Val Phe Thr Phe
1               5                   10

<210> SEQ ID NO 43
<211> LENGTH: 9
<212> TYPE: PRT
<213> ORGANISM: Homo sapiens

<400> SEQUENCE: 43

Leu Tyr Glu Leu His Val Phe Thr Phe
1               5

<210> SEQ ID NO 44
<211> LENGTH: 9
<212> TYPE: PRT
<213> ORGANISM: Homo sapiens

<400> SEQUENCE: 44

Tyr Leu Asn Lys Glu Ile Glu Glu Ala
1               5

<210> SEQ ID NO 45
<211> LENGTH: 9
<212> TYPE: PRT
<213> ORGANISM: Homo sapiens

<400> SEQUENCE: 45

Asp Glu Leu Pro Lys Phe His Gln Tyr
1               5

```
<210> SEQ ID NO 46
<211> LENGTH: 10
<212> TYPE: PRT
<213> ORGANISM: Homo sapiens

<400> SEQUENCE: 46

Asp Val Thr Gly Gln Phe Pro Ser Ser Phe
1               5                   10

<210> SEQ ID NO 47
<211> LENGTH: 9
<212> TYPE: PRT
<213> ORGANISM: Homo sapiens

<400> SEQUENCE: 47

Glu His Ser Arg Val Leu Gln Gln Leu
1               5

<210> SEQ ID NO 48
<211> LENGTH: 8
<212> TYPE: PRT
<213> ORGANISM: Homo sapiens

<400> SEQUENCE: 48

Ile Lys Val Ser Lys Gln Leu Leu
1               5

<210> SEQ ID NO 49
<211> LENGTH: 9
<212> TYPE: PRT
<213> ORGANISM: Homo sapiens

<400> SEQUENCE: 49

Lys Pro Arg Gln Ser Ser Pro Gln Leu
1               5

<210> SEQ ID NO 50
<211> LENGTH: 9
<212> TYPE: PRT
<213> ORGANISM: Homo sapiens

<400> SEQUENCE: 50

Lys Gln Leu Leu Ala Ala Leu Glu Ile
1               5

<210> SEQ ID NO 51
<211> LENGTH: 9
<212> TYPE: PRT
<213> ORGANISM: Homo sapiens

<400> SEQUENCE: 51

Arg Arg Lys Asp Leu Val Leu Lys Tyr
1               5

<210> SEQ ID NO 52
<211> LENGTH: 11
<212> TYPE: PRT
<213> ORGANISM: Homo sapiens

<400> SEQUENCE: 52

Arg Thr Arg Asp Tyr Ala Ser Leu Pro Pro Lys
1               5                   10
```

<210> SEQ ID NO 53
<211> LENGTH: 10
<212> TYPE: PRT
<213> ORGANISM: Homo sapiens

<400> SEQUENCE: 53

Ala Pro Gly Ser Val Leu Pro Arg Ala Leu
1               5                   10

<210> SEQ ID NO 54
<211> LENGTH: 8
<212> TYPE: PRT
<213> ORGANISM: Homo sapiens

<400> SEQUENCE: 54

Asp Ile Lys Glu His Pro Leu Leu
1               5

<210> SEQ ID NO 55
<211> LENGTH: 9
<212> TYPE: PRT
<213> ORGANISM: Homo sapiens

<400> SEQUENCE: 55

Asp Ser Ala Gly Pro Gln Asp Ala Arg
1               5

<210> SEQ ID NO 56
<211> LENGTH: 9
<212> TYPE: PRT
<213> ORGANISM: Homo sapiens

<400> SEQUENCE: 56

Phe Gln Tyr Ala Lys Glu Ser Tyr Ile
1               5

<210> SEQ ID NO 57
<211> LENGTH: 9
<212> TYPE: PRT
<213> ORGANISM: Homo sapiens

<400> SEQUENCE: 57

Lys Val Leu Ser Trp Pro Phe Leu Met
1               5

<210> SEQ ID NO 58
<211> LENGTH: 9
<212> TYPE: PRT
<213> ORGANISM: Homo sapiens

<400> SEQUENCE: 58

Leu Glu Asn Asp Gln Ser Leu Ser Phe
1               5

<210> SEQ ID NO 59
<211> LENGTH: 8
<212> TYPE: PRT
<213> ORGANISM: Homo sapiens

<400> SEQUENCE: 59

Ser Pro Ser Arg Gln Pro Gln Val
1               5

<210> SEQ ID NO 60
<211> LENGTH: 9

```
<212> TYPE: PRT
<213> ORGANISM: Homo sapiens

<400> SEQUENCE: 60

Ser Arg His Gln Ser Phe Thr Thr Lys
1               5

<210> SEQ ID NO 61
<211> LENGTH: 9
<212> TYPE: PRT
<213> ORGANISM: Homo sapiens

<400> SEQUENCE: 61

Ser Ser His Asn Ala Ser Lys Thr Leu
1               5

<210> SEQ ID NO 62
<211> LENGTH: 9
<212> TYPE: PRT
<213> ORGANISM: Homo sapiens

<400> SEQUENCE: 62

Glu Glu Ile Asp Thr Thr Met Arg Trp
1               5

<210> SEQ ID NO 63
<211> LENGTH: 9
<212> TYPE: PRT
<213> ORGANISM: Homo sapiens

<400> SEQUENCE: 63

Ile Leu Asp Glu Lys Pro Val Ile Ile
1               5

<210> SEQ ID NO 64
<211> LENGTH: 9
<212> TYPE: PRT
<213> ORGANISM: Homo sapiens

<400> SEQUENCE: 64

Leu Pro Gln Glu Pro Arg Thr Ser Leu
1               5

<210> SEQ ID NO 65
<211> LENGTH: 8
<212> TYPE: PRT
<213> ORGANISM: Homo sapiens

<400> SEQUENCE: 65

Leu Thr Tyr Lys Leu Pro Val Ala
1               5

<210> SEQ ID NO 66
<211> LENGTH: 10
<212> TYPE: PRT
<213> ORGANISM: Homo sapiens

<400> SEQUENCE: 66

Asn Glu Met Glu Leu Ala His Ser Ser Phe
1               5                   10

<210> SEQ ID NO 67
<211> LENGTH: 10
<212> TYPE: PRT
<213> ORGANISM: Homo sapiens
```

<400> SEQUENCE: 67

Arg Glu Phe Pro Glu Ala Asn Phe Glu Leu
1               5                   10

<210> SEQ ID NO 68
<211> LENGTH: 9
<212> TYPE: PRT
<213> ORGANISM: Homo sapiens

<400> SEQUENCE: 68

Thr His His Ile Pro Asp Ala Lys Leu
1               5

<210> SEQ ID NO 69
<211> LENGTH: 9
<212> TYPE: PRT
<213> ORGANISM: Homo sapiens

<400> SEQUENCE: 69

Thr Val Lys Glu Asn Leu Ser Leu Phe
1               5

<210> SEQ ID NO 70
<211> LENGTH: 8
<212> TYPE: PRT
<213> ORGANISM: Homo sapiens

<400> SEQUENCE: 70

Val Leu Leu Lys Lys Ala Val Leu
1               5

<210> SEQ ID NO 71
<211> LENGTH: 9
<212> TYPE: PRT
<213> ORGANISM: Homo sapiens

<400> SEQUENCE: 71

His Leu Lys Ser Ile Pro Val Ser Leu
1               5

<210> SEQ ID NO 72
<211> LENGTH: 9
<212> TYPE: PRT
<213> ORGANISM: Homo sapiens

<400> SEQUENCE: 72

Lys Val Trp Tyr Asn Val Glu Asn Trp
1               5

<210> SEQ ID NO 73
<211> LENGTH: 9
<212> TYPE: PRT
<213> ORGANISM: Homo sapiens

<400> SEQUENCE: 73

Leu Pro Ala Tyr Arg Ala Gln Leu Leu
1               5

<210> SEQ ID NO 74
<211> LENGTH: 9
<212> TYPE: PRT
<213> ORGANISM: Homo sapiens

<400> SEQUENCE: 74

Leu Ser Glu Gln Thr Ser Val Pro Leu
1               5

<210> SEQ ID NO 75
<211> LENGTH: 9
<212> TYPE: PRT
<213> ORGANISM: Homo sapiens

<400> SEQUENCE: 75

Ser Leu Asn Gln Trp Leu Val Ser Phe
1               5

<210> SEQ ID NO 76
<211> LENGTH: 9
<212> TYPE: PRT
<213> ORGANISM: Homo sapiens

<400> SEQUENCE: 76

Ser Met Thr Ser Leu Ala Gln Lys Ile
1               5

<210> SEQ ID NO 77
<211> LENGTH: 9
<212> TYPE: PRT
<213> ORGANISM: Homo sapiens

<400> SEQUENCE: 77

Ser Ser Ser Gly Leu His Pro Pro Lys
1               5

<210> SEQ ID NO 78
<211> LENGTH: 9
<212> TYPE: PRT
<213> ORGANISM: Homo sapiens

<400> SEQUENCE: 78

Asp Leu Asp Val Lys Lys Met Pro Leu
1               5

<210> SEQ ID NO 79
<211> LENGTH: 9
<212> TYPE: PRT
<213> ORGANISM: Homo sapiens

<400> SEQUENCE: 79

Phe Tyr Thr Val Ile Pro His Asn Phe
1               5

<210> SEQ ID NO 80
<211> LENGTH: 10
<212> TYPE: PRT
<213> ORGANISM: Homo sapiens

<400> SEQUENCE: 80

His His Ile Asn Thr Asp Asn Pro Ser Leu
1               5                   10

<210> SEQ ID NO 81
<211> LENGTH: 9
<212> TYPE: PRT
<213> ORGANISM: Homo sapiens

<400> SEQUENCE: 81

Arg Val Gly Glu Val Gly Gln Ser Lys

```
<210> SEQ ID NO 82
<211> LENGTH: 11
<212> TYPE: PRT
<213> ORGANISM: Homo sapiens

<400> SEQUENCE: 82

Ala Val Phe Asp Gly Ala Gln Val Thr Ser Lys
1               5                   10

<210> SEQ ID NO 83
<211> LENGTH: 9
<212> TYPE: PRT
<213> ORGANISM: Homo sapiens

<400> SEQUENCE: 83

Ser Gln Thr Asp Leu Val Ser Arg Leu
1               5

<210> SEQ ID NO 84
<211> LENGTH: 9
<212> TYPE: PRT
<213> ORGANISM: Homo sapiens

<400> SEQUENCE: 84

Val Pro Val Pro His Thr Thr Ala Leu
1               5

<210> SEQ ID NO 85
<211> LENGTH: 9
<212> TYPE: PRT
<213> ORGANISM: Homo sapiens

<400> SEQUENCE: 85

Tyr Gln Val Leu Asp Val Gln Arg Tyr
1               5

<210> SEQ ID NO 86
<211> LENGTH: 10
<212> TYPE: PRT
<213> ORGANISM: Homo sapiens

<400> SEQUENCE: 86

Ala Pro Phe Gln Gly Asp Gln Arg Ser Leu
1               5                   10

<210> SEQ ID NO 87
<211> LENGTH: 9
<212> TYPE: PRT
<213> ORGANISM: Homo sapiens

<400> SEQUENCE: 87

Asp Val Ala Glu Pro Tyr Lys Val Tyr
1               5

<210> SEQ ID NO 88
<211> LENGTH: 10
<212> TYPE: PRT
<213> ORGANISM: Homo sapiens

<400> SEQUENCE: 88

Ile Val Ser Gly Gln Pro Gly Thr Gln Lys
1               5                   10
```

<210> SEQ ID NO 89
<211> LENGTH: 9
<212> TYPE: PRT
<213> ORGANISM: Homo sapiens

<400> SEQUENCE: 89

Thr Pro Glu Gln Gln Ala Ala Ile Leu
1               5

<210> SEQ ID NO 90
<211> LENGTH: 9
<212> TYPE: PRT
<213> ORGANISM: Homo sapiens

<400> SEQUENCE: 90

Val Glu Leu Phe Arg Thr Ala Tyr Phe
1               5

<210> SEQ ID NO 91
<211> LENGTH: 9
<212> TYPE: PRT
<213> ORGANISM: Homo sapiens

<400> SEQUENCE: 91

Glu His Ala Asp Asp Pro Ser Leu
1               5

<210> SEQ ID NO 92
<211> LENGTH: 10
<212> TYPE: PRT
<213> ORGANISM: Homo sapiens

<400> SEQUENCE: 92

Ser Glu Glu Ser Val Lys Ser Thr Thr Leu
1               5                   10

<210> SEQ ID NO 93
<211> LENGTH: 10
<212> TYPE: PRT
<213> ORGANISM: Homo sapiens

<400> SEQUENCE: 93

Ser Pro Arg Pro Pro Leu Gly Ser Ser Leu
1               5                   10

<210> SEQ ID NO 94
<211> LENGTH: 8
<212> TYPE: PRT
<213> ORGANISM: Homo sapiens

<400> SEQUENCE: 94

Ser Pro Trp Trp Arg Ser Ser Leu
1               5

<210> SEQ ID NO 95
<211> LENGTH: 10
<212> TYPE: PRT
<213> ORGANISM: Homo sapiens

<400> SEQUENCE: 95

Val Tyr Thr Pro Val Asp Ser Leu Val Phe
1               5                   10

<210> SEQ ID NO 96

```
<211> LENGTH: 9
<212> TYPE: PRT
<213> ORGANISM: Homo sapiens

<400> SEQUENCE: 96

Ala Pro Leu Gln Arg Ser Gln Ser Leu
1               5

<210> SEQ ID NO 97
<211> LENGTH: 8
<212> TYPE: PRT
<213> ORGANISM: Homo sapiens

<400> SEQUENCE: 97

Asp Glu Val His Gln Asp Thr Tyr
1               5

<210> SEQ ID NO 98
<211> LENGTH: 9
<212> TYPE: PRT
<213> ORGANISM: Homo sapiens

<400> SEQUENCE: 98

Leu Pro His Ser Ala Thr Val Thr Leu
1               5

<210> SEQ ID NO 99
<211> LENGTH: 9
<212> TYPE: PRT
<213> ORGANISM: Homo sapiens

<400> SEQUENCE: 99

Ser Glu Ala Pro Glu Ala Pro Leu Leu
1               5

<210> SEQ ID NO 100
<211> LENGTH: 9
<212> TYPE: PRT
<213> ORGANISM: Homo sapiens

<400> SEQUENCE: 100

Ser Pro Arg Ala Ser Gly Ser Gly Leu
1               5

<210> SEQ ID NO 101
<211> LENGTH: 9
<212> TYPE: PRT
<213> ORGANISM: Homo sapiens

<400> SEQUENCE: 101

Val Val Gly Pro Ala Ala Glu Ala Lys
1               5

<210> SEQ ID NO 102
<211> LENGTH: 9
<212> TYPE: PRT
<213> ORGANISM: Homo sapiens

<400> SEQUENCE: 102

Phe Ser Ile Thr Lys Ser Val Glu Leu
1               5

<210> SEQ ID NO 103
<211> LENGTH: 9
<212> TYPE: PRT
```

<213> ORGANISM: Homo sapiens

<400> SEQUENCE: 103

Gly Gln Thr Lys Asn Asp Leu Val Val
1               5

<210> SEQ ID NO 104
<211> LENGTH: 8
<212> TYPE: PRT
<213> ORGANISM: Homo sapiens

<400> SEQUENCE: 104

Leu Ser Gln Glu Val Cys Arg Asp
1               5

<210> SEQ ID NO 105
<211> LENGTH: 9
<212> TYPE: PRT
<213> ORGANISM: Homo sapiens

<400> SEQUENCE: 105

Arg Asp Ile Gln Ser Pro Glu Gln Ile
1               5

<210> SEQ ID NO 106
<211> LENGTH: 9
<212> TYPE: PRT
<213> ORGANISM: Homo sapiens

<400> SEQUENCE: 106

Arg Glu Asp Asn Ser Ser Asn Ser Leu
1               5

<210> SEQ ID NO 107
<211> LENGTH: 8
<212> TYPE: PRT
<213> ORGANISM: Homo sapiens

<400> SEQUENCE: 107

Thr Glu His Gln Glu Pro Gly Leu
1               5

<210> SEQ ID NO 108
<211> LENGTH: 9
<212> TYPE: PRT
<213> ORGANISM: Homo sapiens

<400> SEQUENCE: 108

Thr Lys Asn Asp Leu Val Val Ser Leu
1               5

<210> SEQ ID NO 109
<211> LENGTH: 9
<212> TYPE: PRT
<213> ORGANISM: Homo sapiens

<400> SEQUENCE: 109

Ala Glu Glu Ala Gly Gly Thr Arg Leu
1               5

<210> SEQ ID NO 110
<211> LENGTH: 8
<212> TYPE: PRT
<213> ORGANISM: Homo sapiens

```
<400> SEQUENCE: 110

Glu Asn Val Asn Lys Lys Asp Tyr
1               5

<210> SEQ ID NO 111
<211> LENGTH: 10
<212> TYPE: PRT
<213> ORGANISM: Homo sapiens

<400> SEQUENCE: 111

Gly Leu Asp Pro Asn Lys Pro Pro Glu Leu
1               5                   10

<210> SEQ ID NO 112
<211> LENGTH: 12
<212> TYPE: PRT
<213> ORGANISM: Homo sapiens

<400> SEQUENCE: 112

Arg Pro Ala Gly Glu Pro Tyr Asn Arg Lys Thr Leu
1               5                   10

<210> SEQ ID NO 113
<211> LENGTH: 11
<212> TYPE: PRT
<213> ORGANISM: Homo sapiens

<400> SEQUENCE: 113

Ser Ala Ser Val Gln Arg Ala Asp Thr Ser Leu
1               5                   10

<210> SEQ ID NO 114
<211> LENGTH: 9
<212> TYPE: PRT
<213> ORGANISM: Homo sapiens

<400> SEQUENCE: 114

Tyr Gly Asn Pro Arg Thr Asn Gly Met
1               5

<210> SEQ ID NO 115
<211> LENGTH: 9
<212> TYPE: PRT
<213> ORGANISM: Homo sapiens

<400> SEQUENCE: 115

Leu Ile Arg Pro Val Ser Ala Ser Phe
1               5

<210> SEQ ID NO 116
<211> LENGTH: 11
<212> TYPE: PRT
<213> ORGANISM: Homo sapiens

<400> SEQUENCE: 116

Ser Pro Val Asn Ser Ser Lys Gln Pro Ser Tyr
1               5                   10

<210> SEQ ID NO 117
<211> LENGTH: 10
<212> TYPE: PRT
<213> ORGANISM: Homo sapiens

<400> SEQUENCE: 117
```

Gln Leu Phe Ser Tyr Ala Ile Leu Gly Phe
1               5                   10

<210> SEQ ID NO 118
<211> LENGTH: 9
<212> TYPE: PRT
<213> ORGANISM: Homo sapiens

<400> SEQUENCE: 118

Asp Glu His Leu Leu Ile Gln His Tyr
1               5

<210> SEQ ID NO 119
<211> LENGTH: 9
<212> TYPE: PRT
<213> ORGANISM: Homo sapiens

<400> SEQUENCE: 119

Lys Gln Val Ala Ser Ser Thr Gly Phe
1               5

<210> SEQ ID NO 120
<211> LENGTH: 11
<212> TYPE: PRT
<213> ORGANISM: Homo sapiens

<400> SEQUENCE: 120

Arg Asp Phe Gly Pro Ala Ser Gln His Phe Leu
1               5                   10

<210> SEQ ID NO 121
<211> LENGTH: 9
<212> TYPE: PRT
<213> ORGANISM: Homo sapiens

<400> SEQUENCE: 121

Arg Gln Leu Gly Glu Val Ala Ser Phe
1               5

<210> SEQ ID NO 122
<211> LENGTH: 10
<212> TYPE: PRT
<213> ORGANISM: Homo sapiens

<400> SEQUENCE: 122

Thr Glu Ala Glu Thr Thr Ala Asn Val Leu
1               5                   10

<210> SEQ ID NO 123
<211> LENGTH: 9
<212> TYPE: PRT
<213> ORGANISM: Homo sapiens

<400> SEQUENCE: 123

Gly Tyr Leu Pro Val Gln Thr Val Leu
1               5

<210> SEQ ID NO 124
<211> LENGTH: 9
<212> TYPE: PRT
<213> ORGANISM: Homo sapiens

<400> SEQUENCE: 124

Gly Gln Lys Glu Ala Leu Leu Lys Tyr
1               5

```
<210> SEQ ID NO 125
<211> LENGTH: 9
<212> TYPE: PRT
<213> ORGANISM: Homo sapiens

<400> SEQUENCE: 125

Lys Pro Ser Glu Glu Arg Lys Thr Ile
1               5

<210> SEQ ID NO 126
<211> LENGTH: 9
<212> TYPE: PRT
<213> ORGANISM: Homo sapiens

<400> SEQUENCE: 126

Lys Gln Thr Pro Lys Val Leu Val Val
1               5

<210> SEQ ID NO 127
<211> LENGTH: 9
<212> TYPE: PRT
<213> ORGANISM: Homo sapiens

<400> SEQUENCE: 127

Ser Val Ile Gln His Val Gln Ser Phe
1               5

<210> SEQ ID NO 128
<211> LENGTH: 9
<212> TYPE: PRT
<213> ORGANISM: Homo sapiens

<400> SEQUENCE: 128

Thr Pro Ile Glu Arg Ile Pro Tyr Leu
1               5

<210> SEQ ID NO 129
<211> LENGTH: 9
<212> TYPE: PRT
<213> ORGANISM: Homo sapiens

<400> SEQUENCE: 129

Ala Glu Val Glu Lys Asn Glu Thr Val
1               5

<210> SEQ ID NO 130
<211> LENGTH: 9
<212> TYPE: PRT
<213> ORGANISM: Homo sapiens

<400> SEQUENCE: 130

Glu Val Lys Glu Glu Ile Pro Leu Val
1               5

<210> SEQ ID NO 131
<211> LENGTH: 9
<212> TYPE: PRT
<213> ORGANISM: Homo sapiens

<400> SEQUENCE: 131

Lys Pro Thr Ser Ala Arg Ser Gly Leu
1               5
```

```
<210> SEQ ID NO 132
<211> LENGTH: 10
<212> TYPE: PRT
<213> ORGANISM: Homo sapiens

<400> SEQUENCE: 132

Lys Tyr Ile Glu Thr Thr Pro Leu Thr Ile
1               5                   10

<210> SEQ ID NO 133
<211> LENGTH: 9
<212> TYPE: PRT
<213> ORGANISM: Homo sapiens

<400> SEQUENCE: 133

Ser Glu Ile Lys Thr Ser Ile Glu Val
1               5

<210> SEQ ID NO 134
<211> LENGTH: 9
<212> TYPE: PRT
<213> ORGANISM: Homo sapiens

<400> SEQUENCE: 134

Ser Val Lys Pro Thr Ser Ala Thr Lys
1               5

<210> SEQ ID NO 135
<211> LENGTH: 9
<212> TYPE: PRT
<213> ORGANISM: Homo sapiens

<400> SEQUENCE: 135

Tyr Pro Asn Lys Gly Val Gly Gln Ala
1               5

<210> SEQ ID NO 136
<211> LENGTH: 9
<212> TYPE: PRT
<213> ORGANISM: Homo sapiens

<400> SEQUENCE: 136

Ile Ser Met Lys Ile Leu Asn Ser Leu
1               5

<210> SEQ ID NO 137
<211> LENGTH: 10
<212> TYPE: PRT
<213> ORGANISM: Homo sapiens

<400> SEQUENCE: 137

Lys Thr Ile Ala Phe Leu Leu Pro Met Phe
1               5                   10

<210> SEQ ID NO 138
<211> LENGTH: 8
<212> TYPE: PRT
<213> ORGANISM: Homo sapiens

<400> SEQUENCE: 138

Arg Asp Ser Ile Ile Asn Asp Phe
1               5

<210> SEQ ID NO 139
<211> LENGTH: 10
```

<212> TYPE: PRT
<213> ORGANISM: Homo sapiens

<400> SEQUENCE: 139

Ser Val Lys Gly Gly Gly Asn Glu Lys
1               5                  10

<210> SEQ ID NO 140
<211> LENGTH: 9
<212> TYPE: PRT
<213> ORGANISM: Homo sapiens

<400> SEQUENCE: 140

Gly Ile Ala Lys Thr Gly Ser Gly Lys
1               5

<210> SEQ ID NO 141
<211> LENGTH: 10
<212> TYPE: PRT
<213> ORGANISM: Homo sapiens

<400> SEQUENCE: 141

Ala Glu Thr Thr Asp Asn Val Phe Thr Leu
1               5                   10

<210> SEQ ID NO 142
<211> LENGTH: 9
<212> TYPE: PRT
<213> ORGANISM: Homo sapiens

<400> SEQUENCE: 142

Ser Glu Tyr Gln Arg Phe Ala Val Met
1               5

<210> SEQ ID NO 143
<211> LENGTH: 9
<212> TYPE: PRT
<213> ORGANISM: Homo sapiens

<400> SEQUENCE: 143

Thr Phe Gly Glu Arg Val Val Ala Phe
1               5

<210> SEQ ID NO 144
<211> LENGTH: 8
<212> TYPE: PRT
<213> ORGANISM: Homo sapiens

<400> SEQUENCE: 144

Asn Glu Asn Leu Val Glu Arg Phe
1               5

<210> SEQ ID NO 145
<211> LENGTH: 9
<212> TYPE: PRT
<213> ORGANISM: Homo sapiens

<400> SEQUENCE: 145

Lys Ile Thr Val Pro Ala Ser Gln Lys
1               5

<210> SEQ ID NO 146
<211> LENGTH: 10
<212> TYPE: PRT
<213> ORGANISM: Homo sapiens

<400> SEQUENCE: 146

Lys Ile Thr Val Pro Ala Ser Gln Lys Leu
1               5                   10

<210> SEQ ID NO 147
<211> LENGTH: 10
<212> TYPE: PRT
<213> ORGANISM: Homo sapiens

<400> SEQUENCE: 147

Val Pro Ala Ser Gln Lys Leu Arg Gln Leu
1               5                   10

<210> SEQ ID NO 148
<211> LENGTH: 9
<212> TYPE: PRT
<213> ORGANISM: Homo sapiens

<400> SEQUENCE: 148

His Val Gly Tyr Thr Leu Ser Tyr Lys
1               5

<210> SEQ ID NO 149
<211> LENGTH: 10
<212> TYPE: PRT
<213> ORGANISM: Homo sapiens

<400> SEQUENCE: 149

Lys Leu Pro Leu Pro Leu Pro Pro Arg Leu
1               5                   10

<210> SEQ ID NO 150
<211> LENGTH: 9
<212> TYPE: PRT
<213> ORGANISM: Homo sapiens

<400> SEQUENCE: 150

Lys Pro Ile Glu Pro Arg Arg Glu Leu
1               5

<210> SEQ ID NO 151
<211> LENGTH: 9
<212> TYPE: PRT
<213> ORGANISM: Homo sapiens

<400> SEQUENCE: 151

Ser His Ser His Val Gly Tyr Thr Leu
1               5

<210> SEQ ID NO 152
<211> LENGTH: 9
<212> TYPE: PRT
<213> ORGANISM: Homo sapiens

<400> SEQUENCE: 152

Ala Pro Ser Glu Tyr Arg Tyr Thr Leu
1               5

<210> SEQ ID NO 153
<211> LENGTH: 10
<212> TYPE: PRT
<213> ORGANISM: Homo sapiens

<400> SEQUENCE: 153

Ala Pro Ser Glu Tyr Arg Tyr Thr Leu Leu
1               5                   10

<210> SEQ ID NO 154
<211> LENGTH: 9
<212> TYPE: PRT
<213> ORGANISM: Homo sapiens

<400> SEQUENCE: 154

Glu Ile Phe Gln Asn Glu Val Ala Arg
1               5

<210> SEQ ID NO 155
<211> LENGTH: 9
<212> TYPE: PRT
<213> ORGANISM: Homo sapiens

<400> SEQUENCE: 155

Lys Asp Val Leu Ile Pro Gly Lys Leu
1               5

<210> SEQ ID NO 156
<211> LENGTH: 9
<212> TYPE: PRT
<213> ORGANISM: Homo sapiens

<400> SEQUENCE: 156

Val Pro Leu Val Arg Glu Ile Thr Phe
1               5

<210> SEQ ID NO 157
<211> LENGTH: 9
<212> TYPE: PRT
<213> ORGANISM: Homo sapiens

<400> SEQUENCE: 157

Asp Pro Asn Pro Asn Phe Glu Lys Phe
1               5

<210> SEQ ID NO 158
<211> LENGTH: 9
<212> TYPE: PRT
<213> ORGANISM: Homo sapiens

<400> SEQUENCE: 158

Ile Gln Ala Pro Leu Ser Trp Glu Leu
1               5

<210> SEQ ID NO 159
<211> LENGTH: 10
<212> TYPE: PRT
<213> ORGANISM: Homo sapiens

<400> SEQUENCE: 159

Val Ile Tyr Asn Glu Gln Met Ala Ser Lys
1               5                   10

<210> SEQ ID NO 160
<211> LENGTH: 9
<212> TYPE: PRT
<213> ORGANISM: Homo sapiens

<400> SEQUENCE: 160

Val Leu Arg Pro Gly Gly Ala Phe Tyr

```
1               5

<210> SEQ ID NO 161
<211> LENGTH: 9
<212> TYPE: PRT
<213> ORGANISM: Homo sapiens

<400> SEQUENCE: 161

Glu Asp Pro Asp Gln Asp Ile Leu Ile
1               5

<210> SEQ ID NO 162
<211> LENGTH: 9
<212> TYPE: PRT
<213> ORGANISM: Homo sapiens

<400> SEQUENCE: 162

His Gly Asn Leu Arg Glu Leu Ala Leu
1               5

<210> SEQ ID NO 163
<211> LENGTH: 9
<212> TYPE: PRT
<213> ORGANISM: Homo sapiens

<400> SEQUENCE: 163

Lys Leu Tyr Pro Thr Leu Val Ile Arg
1               5

<210> SEQ ID NO 164
<211> LENGTH: 9
<212> TYPE: PRT
<213> ORGANISM: Homo sapiens

<400> SEQUENCE: 164

Ser Glu Glu Thr Phe Arg Phe Glu Leu
1               5

<210> SEQ ID NO 165
<211> LENGTH: 9
<212> TYPE: PRT
<213> ORGANISM: Homo sapiens

<400> SEQUENCE: 165

Glu Leu Asn Lys Leu Leu Glu Glu Ile
1               5

<210> SEQ ID NO 166
<211> LENGTH: 9
<212> TYPE: PRT
<213> ORGANISM: Homo sapiens

<400> SEQUENCE: 166

Ile Pro Phe Ser Asn Pro Arg Val Leu
1               5

<210> SEQ ID NO 167
<211> LENGTH: 10
<212> TYPE: PRT
<213> ORGANISM: Homo sapiens

<400> SEQUENCE: 167

Leu Leu Asp Glu Gly Ala Lys Leu Leu Tyr
1               5                   10
```

```
<210> SEQ ID NO 168
<211> LENGTH: 9
<212> TYPE: PRT
<213> ORGANISM: Homo sapiens

<400> SEQUENCE: 168

Ser Pro Ala Asp Ala His Arg Asn Leu
1               5

<210> SEQ ID NO 169
<211> LENGTH: 9
<212> TYPE: PRT
<213> ORGANISM: Homo sapiens

<400> SEQUENCE: 169

Ala Glu Leu Glu Arg Gln Ala Val Leu
1               5

<210> SEQ ID NO 170
<211> LENGTH: 9
<212> TYPE: PRT
<213> ORGANISM: Homo sapiens

<400> SEQUENCE: 170

Gly Arg Val Pro Gly Pro Leu Ser Leu
1               5

<210> SEQ ID NO 171
<211> LENGTH: 9
<212> TYPE: PRT
<213> ORGANISM: Homo sapiens

<400> SEQUENCE: 171

Ser Asp Leu Ala Arg Leu Ile Leu Leu
1               5

<210> SEQ ID NO 172
<211> LENGTH: 9
<212> TYPE: PRT
<213> ORGANISM: Homo sapiens

<400> SEQUENCE: 172

Thr Pro Ile Arg Glu Gln His Val Leu
1               5

<210> SEQ ID NO 173
<211> LENGTH: 8
<212> TYPE: PRT
<213> ORGANISM: Homo sapiens

<400> SEQUENCE: 173

Ala Pro Arg Lys Gly Asn Thr Leu
1               5

<210> SEQ ID NO 174
<211> LENGTH: 10
<212> TYPE: PRT
<213> ORGANISM: Homo sapiens

<400> SEQUENCE: 174

Glu Glu Glu Glu Ala Leu Gln Lys Lys Phe
1               5                   10

<210> SEQ ID NO 175
```

```
<211> LENGTH: 8
<212> TYPE: PRT
<213> ORGANISM: Homo sapiens

<400> SEQUENCE: 175

Lys Glu Asn Leu Val Asp Gly Phe
1               5

<210> SEQ ID NO 176
<211> LENGTH: 10
<212> TYPE: PRT
<213> ORGANISM: Homo sapiens

<400> SEQUENCE: 176

Val Tyr Lys Glu Asn Leu Val Asp Gly Phe
1               5                   10

<210> SEQ ID NO 177
<211> LENGTH: 9
<212> TYPE: PRT
<213> ORGANISM: Homo sapiens

<400> SEQUENCE: 177

Thr Leu Leu Val Val Val Pro Lys Leu
1               5

<210> SEQ ID NO 178
<211> LENGTH: 9
<212> TYPE: PRT
<213> ORGANISM: Homo sapiens

<400> SEQUENCE: 178

His Glu Ile Asp Arg Tyr Thr Ala Ile
1               5

<210> SEQ ID NO 179
<211> LENGTH: 9
<212> TYPE: PRT
<213> ORGANISM: Homo sapiens

<400> SEQUENCE: 179

Val Phe Thr Leu Lys Pro Leu Glu Phe
1               5

<210> SEQ ID NO 180
<211> LENGTH: 8
<212> TYPE: PRT
<213> ORGANISM: Homo sapiens

<400> SEQUENCE: 180

Tyr Trp Val Pro Arg Asn Ala Leu
1               5

<210> SEQ ID NO 181
<211> LENGTH: 9
<212> TYPE: PRT
<213> ORGANISM: Homo sapiens

<400> SEQUENCE: 181

Ile Gly Val Glu His Val Val Val Tyr
1               5

<210> SEQ ID NO 182
<211> LENGTH: 8
<212> TYPE: PRT
```

<213> ORGANISM: Homo sapiens

<400> SEQUENCE: 182

Arg Asp Lys Pro His Val Asn Val
1               5

<210> SEQ ID NO 183
<211> LENGTH: 9
<212> TYPE: PRT
<213> ORGANISM: Homo sapiens

<400> SEQUENCE: 183

Ala Asp Val Leu Lys Val Glu Val Phe
1               5

<210> SEQ ID NO 184
<211> LENGTH: 8
<212> TYPE: PRT
<213> ORGANISM: Homo sapiens

<400> SEQUENCE: 184

Ile Pro Val Val His Ala Ser Ile
1               5

<210> SEQ ID NO 185
<211> LENGTH: 9
<212> TYPE: PRT
<213> ORGANISM: Homo sapiens

<400> SEQUENCE: 185

Arg Asp Ser Leu Ile Asp Ser Leu Thr
1               5

<210> SEQ ID NO 186
<211> LENGTH: 11
<212> TYPE: PRT
<213> ORGANISM: Homo sapiens

<400> SEQUENCE: 186

Thr Val Ala Asp Gln Val Leu Val Gly Ser Tyr
1               5                   10

<210> SEQ ID NO 187
<211> LENGTH: 9
<212> TYPE: PRT
<213> ORGANISM: Homo sapiens

<400> SEQUENCE: 187

Ala Ala Asp Thr Glu Arg Leu Ala Leu
1               5

<210> SEQ ID NO 188
<211> LENGTH: 9
<212> TYPE: PRT
<213> ORGANISM: Homo sapiens

<400> SEQUENCE: 188

Asp Met Lys Ala Lys Val Ala Ser Leu
1               5

<210> SEQ ID NO 189
<211> LENGTH: 9
<212> TYPE: PRT
<213> ORGANISM: Homo sapiens

<400> SEQUENCE: 189

His Val Leu Glu Glu Val Gln Gln Val
1               5

<210> SEQ ID NO 190
<211> LENGTH: 9
<212> TYPE: PRT
<213> ORGANISM: Homo sapiens

<400> SEQUENCE: 190

Lys Glu Ala Ala Asp Thr Glu Arg Leu
1               5

<210> SEQ ID NO 191
<211> LENGTH: 9
<212> TYPE: PRT
<213> ORGANISM: Homo sapiens

<400> SEQUENCE: 191

Arg Ile Ser Glu Val Leu Gln Lys Leu
1               5

<210> SEQ ID NO 192
<211> LENGTH: 9
<212> TYPE: PRT
<213> ORGANISM: Homo sapiens

<400> SEQUENCE: 192

Thr Glu Val Arg Glu Leu Val Ser Leu
1               5

<210> SEQ ID NO 193
<211> LENGTH: 10
<212> TYPE: PRT
<213> ORGANISM: Homo sapiens

<400> SEQUENCE: 193

Ala Ile Arg Ser Gly Glu Ala Ala Ala Lys
1               5                   10

<210> SEQ ID NO 194
<211> LENGTH: 9
<212> TYPE: PRT
<213> ORGANISM: Homo sapiens

<400> SEQUENCE: 194

Ala Pro Asn Pro Ala Pro Lys Glu Leu
1               5

<210> SEQ ID NO 195
<211> LENGTH: 8
<212> TYPE: PRT
<213> ORGANISM: Homo sapiens

<400> SEQUENCE: 195

Arg Gln Ser Leu Leu Thr Ala Ile
1               5

<210> SEQ ID NO 196
<211> LENGTH: 9
<212> TYPE: PRT
<213> ORGANISM: Homo sapiens

<400> SEQUENCE: 196

```
Ser Pro Glu Gln Thr Leu Ser Pro Leu
1               5

<210> SEQ ID NO 197
<211> LENGTH: 9
<212> TYPE: PRT
<213> ORGANISM: Homo sapiens

<400> SEQUENCE: 197

Thr Glu His Gln Val Pro Ser Ser Val
1               5

<210> SEQ ID NO 198
<211> LENGTH: 9
<212> TYPE: PRT
<213> ORGANISM: Homo sapiens

<400> SEQUENCE: 198

Thr Thr Tyr Lys Ile Val Pro Pro Lys
1               5

<210> SEQ ID NO 199
<211> LENGTH: 9
<212> TYPE: PRT
<213> ORGANISM: Homo sapiens

<400> SEQUENCE: 199

Gln Leu Leu Asp Gln Val Glu Gln Ile
1               5

<210> SEQ ID NO 200
<211> LENGTH: 9
<212> TYPE: PRT
<213> ORGANISM: Homo sapiens

<400> SEQUENCE: 200

Asp Glu Thr Met Val Ile Gly Asn Tyr
1               5

<210> SEQ ID NO 201
<211> LENGTH: 11
<212> TYPE: PRT
<213> ORGANISM: Homo sapiens

<400> SEQUENCE: 201

Arg Gln Tyr Gly Ser Glu Gly Arg Phe Thr Phe
1               5                   10

<210> SEQ ID NO 202
<211> LENGTH: 8
<212> TYPE: PRT
<213> ORGANISM: Homo sapiens

<400> SEQUENCE: 202

Ser Pro Ala Pro Arg Thr Ala Leu
1               5

<210> SEQ ID NO 203
<211> LENGTH: 10
<212> TYPE: PRT
<213> ORGANISM: Homo sapiens

<400> SEQUENCE: 203

Gly Pro Arg Pro Ile Thr Gln Ser Glu Leu
1               5                   10
```

<210> SEQ ID NO 204
<211> LENGTH: 9
<212> TYPE: PRT
<213> ORGANISM: Homo sapiens

<400> SEQUENCE: 204

Lys Pro Glu Pro Val Asp Lys Val Ala
1               5

<210> SEQ ID NO 205
<211> LENGTH: 9
<212> TYPE: PRT
<213> ORGANISM: Homo sapiens

<400> SEQUENCE: 205

Thr Pro Ser Ser Arg Pro Ala Ser Leu
1               5

<210> SEQ ID NO 206
<211> LENGTH: 9
<212> TYPE: PRT
<213> ORGANISM: Homo sapiens

<400> SEQUENCE: 206

Asp Glu Thr Gln Val Arg Ser Leu Tyr
1               5

<210> SEQ ID NO 207
<211> LENGTH: 11
<212> TYPE: PRT
<213> ORGANISM: Homo sapiens

<400> SEQUENCE: 207

Lys Glu Glu Glu Thr Asn Ser Val Ala Thr Leu
1               5                   10

<210> SEQ ID NO 208
<211> LENGTH: 9
<212> TYPE: PRT
<213> ORGANISM: Homo sapiens

<400> SEQUENCE: 208

Leu Glu Gln Lys Val Val Glu Leu Tyr
1               5

<210> SEQ ID NO 209
<211> LENGTH: 11
<212> TYPE: PRT
<213> ORGANISM: Homo sapiens

<400> SEQUENCE: 209

Asn Pro Ile Ser Asn Ala Val Leu Asn Glu Tyr
1               5                   10

<210> SEQ ID NO 210
<211> LENGTH: 8
<212> TYPE: PRT
<213> ORGANISM: Homo sapiens

<400> SEQUENCE: 210

Ser Ile Lys Glu Lys Ser Ser Leu
1               5

```
<210> SEQ ID NO 211
<211> LENGTH: 11
<212> TYPE: PRT
<213> ORGANISM: Homo sapiens

<400> SEQUENCE: 211

Thr Glu Ile Thr Glu Ile Ser Thr Pro Ser Leu
1               5                   10

<210> SEQ ID NO 212
<211> LENGTH: 9
<212> TYPE: PRT
<213> ORGANISM: Homo sapiens

<400> SEQUENCE: 212

Gly Arg Leu Asn Ser Val Asn Asn Arg
1               5

<210> SEQ ID NO 213
<211> LENGTH: 9
<212> TYPE: PRT
<213> ORGANISM: Homo sapiens

<400> SEQUENCE: 213

Ser Ile Leu Glu Asp Pro Pro Ser Ile
1               5

<210> SEQ ID NO 214
<211> LENGTH: 9
<212> TYPE: PRT
<213> ORGANISM: Homo sapiens

<400> SEQUENCE: 214

Thr Pro Arg Thr Asn Asn Ile Glu Leu
1               5

<210> SEQ ID NO 215
<211> LENGTH: 9
<212> TYPE: PRT
<213> ORGANISM: Homo sapiens

<400> SEQUENCE: 215

Asp Ala Met Lys Arg Val Glu Glu Ile
1               5

<210> SEQ ID NO 216
<211> LENGTH: 9
<212> TYPE: PRT
<213> ORGANISM: Homo sapiens

<400> SEQUENCE: 216

Asp Ile Lys Glu Val Lys Gln Asn Ile
1               5

<210> SEQ ID NO 217
<211> LENGTH: 9
<212> TYPE: PRT
<213> ORGANISM: Homo sapiens

<400> SEQUENCE: 217

Gly Pro Ile Tyr Pro Gly His Gly Met
1               5

<210> SEQ ID NO 218
<211> LENGTH: 9
```

```
<212> TYPE: PRT
<213> ORGANISM: Homo sapiens

<400> SEQUENCE: 218

Gly Asp Tyr Gly Arg Ala Phe Asn Leu
1               5

<210> SEQ ID NO 219
<211> LENGTH: 9
<212> TYPE: PRT
<213> ORGANISM: Homo sapiens

<400> SEQUENCE: 219

Thr Arg His Lys Ile Val His Thr Lys
1               5

<210> SEQ ID NO 220
<211> LENGTH: 10
<212> TYPE: PRT
<213> ORGANISM: Homo sapiens

<400> SEQUENCE: 220

Arg Ile His Thr Gly Glu Lys Pro Tyr Lys
1               5                   10

<210> SEQ ID NO 221
<211> LENGTH: 9
<212> TYPE: PRT
<213> ORGANISM: Homo sapiens

<400> SEQUENCE: 221

Lys Ala Phe Asn Trp Phe Ser Thr Leu
1               5

<210> SEQ ID NO 222
<211> LENGTH: 9
<212> TYPE: PRT
<213> ORGANISM: Homo sapiens

<400> SEQUENCE: 222

Gln Ser Thr Gln Arg Ser Leu Ala Leu
1               5

<210> SEQ ID NO 223
<211> LENGTH: 11
<212> TYPE: PRT
<213> ORGANISM: Homo sapiens

<400> SEQUENCE: 223

Arg Asp Leu Gln Met Asn Gln Ala Leu Arg Phe
1               5                   10

<210> SEQ ID NO 224
<211> LENGTH: 10
<212> TYPE: PRT
<213> ORGANISM: Homo sapiens

<400> SEQUENCE: 224

Arg Glu Leu Glu Ser Gln Leu His Val Leu
1               5                   10

<210> SEQ ID NO 225
<211> LENGTH: 9
<212> TYPE: PRT
<213> ORGANISM: Homo sapiens
```

<400> SEQUENCE: 225

Ser Glu Ala Glu Lys Leu Thr Leu Val
1               5

<210> SEQ ID NO 226
<211> LENGTH: 9
<212> TYPE: PRT
<213> ORGANISM: Homo sapiens

<400> SEQUENCE: 226

Ala Ala Ala Lys Pro Val Ala Thr Lys
1               5

<210> SEQ ID NO 227
<211> LENGTH: 10
<212> TYPE: PRT
<213> ORGANISM: Homo sapiens

<400> SEQUENCE: 227

Ala Thr Tyr His Gly Ser Phe Ser Thr Lys
1               5                   10

<210> SEQ ID NO 228
<211> LENGTH: 9
<212> TYPE: PRT
<213> ORGANISM: Homo sapiens

<400> SEQUENCE: 228

Phe Met Tyr Asp Arg Pro Leu Arg Leu
1               5

<210> SEQ ID NO 229
<211> LENGTH: 9
<212> TYPE: PRT
<213> ORGANISM: Homo sapiens

<400> SEQUENCE: 229

Phe Arg Val Gly Asn Val Gln Glu Leu
1               5

<210> SEQ ID NO 230
<211> LENGTH: 9
<212> TYPE: PRT
<213> ORGANISM: Homo sapiens

<400> SEQUENCE: 230

Gly Val Ala Pro Phe Thr Ile Ala Arg
1               5

<210> SEQ ID NO 231
<211> LENGTH: 11
<212> TYPE: PRT
<213> ORGANISM: Homo sapiens

<400> SEQUENCE: 231

Lys Met Lys Pro Leu Asp Gly Ser Ala Leu Tyr
1               5                   10

<210> SEQ ID NO 232
<211> LENGTH: 9
<212> TYPE: PRT
<213> ORGANISM: Homo sapiens

<400> SEQUENCE: 232

Lys Pro Ala Pro Ala Lys Pro Val Ala
1               5

<210> SEQ ID NO 233
<211> LENGTH: 9
<212> TYPE: PRT
<213> ORGANISM: Homo sapiens

<400> SEQUENCE: 233

Lys Pro Val Ala Ala Lys Pro Ala Ala
1               5

<210> SEQ ID NO 234
<211> LENGTH: 10
<212> TYPE: PRT
<213> ORGANISM: Homo sapiens

<400> SEQUENCE: 234

Lys Gln Phe Gly Val Ala Pro Phe Thr Ile
1               5                   10

<210> SEQ ID NO 235
<211> LENGTH: 9
<212> TYPE: PRT
<213> ORGANISM: Homo sapiens

<400> SEQUENCE: 235

Gln Glu Glu Leu Val Lys Ile Ser Leu
1               5

<210> SEQ ID NO 236
<211> LENGTH: 10
<212> TYPE: PRT
<213> ORGANISM: Homo sapiens

<400> SEQUENCE: 236

Arg Gln Leu Gly Thr Val Gln Gln Val Ile
1               5                   10

<210> SEQ ID NO 237
<211> LENGTH: 9
<212> TYPE: PRT
<213> ORGANISM: Homo sapiens

<400> SEQUENCE: 237

Arg Gln Leu Ile Asn Ala Leu Gln Ile
1               5

<210> SEQ ID NO 238
<211> LENGTH: 12
<212> TYPE: PRT
<213> ORGANISM: Homo sapiens

<400> SEQUENCE: 238

Arg Val Ile Gly Gly Leu Leu Ala Gly Gln Thr Tyr
1               5                   10

<210> SEQ ID NO 239
<211> LENGTH: 9
<212> TYPE: PRT
<213> ORGANISM: Homo sapiens

<400> SEQUENCE: 239

Ser Glu Asn Ala Phe Tyr Leu Ser Pro

```
1               5

<210> SEQ ID NO 240
<211> LENGTH: 9
<212> TYPE: PRT
<213> ORGANISM: Homo sapiens

<400> SEQUENCE: 240

Ser Gln Ala Pro Val Leu Asp Ala Ile
1               5

<210> SEQ ID NO 241
<211> LENGTH: 9
<212> TYPE: PRT
<213> ORGANISM: Homo sapiens

<400> SEQUENCE: 241

Ser Thr Arg Tyr Pro Pro Pro Ala Val
1               5

<210> SEQ ID NO 242
<211> LENGTH: 9
<212> TYPE: PRT
<213> ORGANISM: Homo sapiens

<400> SEQUENCE: 242

Thr Glu Asp Thr Leu Lys Val Tyr Leu
1               5

<210> SEQ ID NO 243
<211> LENGTH: 9
<212> TYPE: PRT
<213> ORGANISM: Homo sapiens

<400> SEQUENCE: 243

Val Ala Ala Lys Pro Val Ala Thr Lys
1               5

<210> SEQ ID NO 244
<211> LENGTH: 8
<212> TYPE: PRT
<213> ORGANISM: Homo sapiens

<400> SEQUENCE: 244

Val Gln Arg Val Val Glu Ser Leu
1               5

<210> SEQ ID NO 245
<211> LENGTH: 9
<212> TYPE: PRT
<213> ORGANISM: Homo sapiens

<400> SEQUENCE: 245

Val Arg Asn Pro Ser Val Val Val Lys
1               5

<210> SEQ ID NO 246
<211> LENGTH: 9
<212> TYPE: PRT
<213> ORGANISM: Homo sapiens

<400> SEQUENCE: 246

Gly Glu Ser Glu Val Ala Ile Lys Ile
1               5
```

<210> SEQ ID NO 247
<211> LENGTH: 10
<212> TYPE: PRT
<213> ORGANISM: Homo sapiens

<400> SEQUENCE: 247

Leu Ile Tyr Ser Val Gly Leu Leu Leu Ala
1               5                   10

<210> SEQ ID NO 248
<211> LENGTH: 9
<212> TYPE: PRT
<213> ORGANISM: Homo sapiens

<400> SEQUENCE: 248

Ser Ala Tyr Pro His Gln Leu Ser Phe
1               5

<210> SEQ ID NO 249
<211> LENGTH: 9
<212> TYPE: PRT
<213> ORGANISM: Homo sapiens

<400> SEQUENCE: 249

Ser Val Ile Gly Val Phe Ile Thr Lys
1               5

<210> SEQ ID NO 250
<211> LENGTH: 10
<212> TYPE: PRT
<213> ORGANISM: Homo sapiens

<400> SEQUENCE: 250

Ala Glu Leu Gly Asn Ser Val Gln Leu Ile
1               5                   10

<210> SEQ ID NO 251
<211> LENGTH: 8
<212> TYPE: PRT
<213> ORGANISM: Homo sapiens

<400> SEQUENCE: 251

Ala Asn Met Thr Val Thr Arg Ile
1               5

<210> SEQ ID NO 252
<211> LENGTH: 9
<212> TYPE: PRT
<213> ORGANISM: Homo sapiens

<400> SEQUENCE: 252

Ala Arg Ile Ser Asn Val Glu Phe Tyr
1               5

<210> SEQ ID NO 253
<211> LENGTH: 9
<212> TYPE: PRT
<213> ORGANISM: Homo sapiens

<400> SEQUENCE: 253

Ala Val Phe Ile Gly Asn Gln Gln Phe
1               5

<210> SEQ ID NO 254

```
<211> LENGTH: 9
<212> TYPE: PRT
<213> ORGANISM: Homo sapiens

<400> SEQUENCE: 254

Asp Ile Glu Leu Gln Ala Glu Asn Ile
1               5

<210> SEQ ID NO 255
<211> LENGTH: 9
<212> TYPE: PRT
<213> ORGANISM: Homo sapiens

<400> SEQUENCE: 255

Asp Ser Tyr Thr Val Arg Val Ser Val
1               5

<210> SEQ ID NO 256
<211> LENGTH: 9
<212> TYPE: PRT
<213> ORGANISM: Homo sapiens

<400> SEQUENCE: 256

Asp Val Lys Ile Phe Val Asn Thr Ile
1               5

<210> SEQ ID NO 257
<211> LENGTH: 9
<212> TYPE: PRT
<213> ORGANISM: Homo sapiens

<400> SEQUENCE: 257

Glu Ile Ile Pro Lys Tyr Gly Ser Ile
1               5

<210> SEQ ID NO 258
<211> LENGTH: 9
<212> TYPE: PRT
<213> ORGANISM: Homo sapiens

<400> SEQUENCE: 258

Glu Gln Ser Lys Ile Phe Ile His Arg
1               5

<210> SEQ ID NO 259
<211> LENGTH: 9
<212> TYPE: PRT
<213> ORGANISM: Homo sapiens

<400> SEQUENCE: 259

Phe Val Asp Val Gly Leu Tyr Gln Tyr
1               5

<210> SEQ ID NO 260
<211> LENGTH: 9
<212> TYPE: PRT
<213> ORGANISM: Homo sapiens

<400> SEQUENCE: 260

Gly His Thr Ser Thr Ile Ser Thr Leu
1               5

<210> SEQ ID NO 261
<211> LENGTH: 9
<212> TYPE: PRT
```

<213> ORGANISM: Homo sapiens

<400> SEQUENCE: 261

Gly Arg Ile Glu Tyr Val Glu Val Phe
1               5

<210> SEQ ID NO 262
<211> LENGTH: 9
<212> TYPE: PRT
<213> ORGANISM: Homo sapiens

<400> SEQUENCE: 262

Gly Thr Ser Ile Ile Pro Phe Gln Lys
1               5

<210> SEQ ID NO 263
<211> LENGTH: 9
<212> TYPE: PRT
<213> ORGANISM: Homo sapiens

<400> SEQUENCE: 263

His Pro Phe Leu Arg Gly Ile Gly Tyr
1               5

<210> SEQ ID NO 264
<211> LENGTH: 8
<212> TYPE: PRT
<213> ORGANISM: Homo sapiens

<400> SEQUENCE: 264

Ile Pro Val Glu Ile His Thr Ala
1               5

<210> SEQ ID NO 265
<211> LENGTH: 9
<212> TYPE: PRT
<213> ORGANISM: Homo sapiens

<400> SEQUENCE: 265

Lys Ile Phe Val Asn Thr Ile Ala Tyr
1               5

<210> SEQ ID NO 266
<211> LENGTH: 10
<212> TYPE: PRT
<213> ORGANISM: Homo sapiens

<400> SEQUENCE: 266

Leu Pro Glu Asp Lys Val Arg Ile Ala Tyr
1               5                   10

<210> SEQ ID NO 267
<211> LENGTH: 9
<212> TYPE: PRT
<213> ORGANISM: Homo sapiens

<400> SEQUENCE: 267

Leu Pro Phe Ser Glu Gly Leu Thr Val
1               5

<210> SEQ ID NO 268
<211> LENGTH: 9
<212> TYPE: PRT
<213> ORGANISM: Homo sapiens

<400> SEQUENCE: 268

Leu Pro Trp Ala Asn Lys Val Thr Ile
1               5

<210> SEQ ID NO 269
<211> LENGTH: 8
<212> TYPE: PRT
<213> ORGANISM: Homo sapiens

<400> SEQUENCE: 269

Pro Trp Ala Asn Lys Val Thr Ile
1               5

<210> SEQ ID NO 270
<211> LENGTH: 9
<212> TYPE: PRT
<213> ORGANISM: Homo sapiens

<400> SEQUENCE: 270

Gln Ala Tyr Asn Arg Ala Val Thr Ile
1               5

<210> SEQ ID NO 271
<211> LENGTH: 9
<212> TYPE: PRT
<213> ORGANISM: Homo sapiens

<400> SEQUENCE: 271

Arg Ser Phe Pro Gln Lys Met Ala Tyr
1               5

<210> SEQ ID NO 272
<211> LENGTH: 9
<212> TYPE: PRT
<213> ORGANISM: Homo sapiens

<400> SEQUENCE: 272

Arg Tyr Pro Ile His Trp His Leu Leu
1               5

<210> SEQ ID NO 273
<211> LENGTH: 9
<212> TYPE: PRT
<213> ORGANISM: Homo sapiens

<400> SEQUENCE: 273

Ser Pro Gln Asn Leu Arg Leu Met Leu
1               5

<210> SEQ ID NO 274
<211> LENGTH: 9
<212> TYPE: PRT
<213> ORGANISM: Homo sapiens

<400> SEQUENCE: 274

Ser Tyr Phe Ser Ser Pro Thr Gln Arg
1               5

<210> SEQ ID NO 275
<211> LENGTH: 8
<212> TYPE: PRT
<213> ORGANISM: Homo sapiens

<400> SEQUENCE: 275

Val Gln Ile Lys Ser Ser Leu Ile
1               5

<210> SEQ ID NO 276
<211> LENGTH: 9
<212> TYPE: PRT
<213> ORGANISM: Homo sapiens

<400> SEQUENCE: 276

Val Tyr Ile Gly His Thr Ser Thr Ile
1               5

<210> SEQ ID NO 277
<211> LENGTH: 10
<212> TYPE: PRT
<213> ORGANISM: Homo sapiens

<400> SEQUENCE: 277

Tyr His Val Pro Gly Thr Gly Glu Ser Tyr
1               5                   10

<210> SEQ ID NO 278
<211> LENGTH: 9
<212> TYPE: PRT
<213> ORGANISM: Homo sapiens

<400> SEQUENCE: 278

Ala Thr Asn Gly Asp Leu Ala Ser Arg
1               5

<210> SEQ ID NO 279
<211> LENGTH: 11
<212> TYPE: PRT
<213> ORGANISM: Homo sapiens

<400> SEQUENCE: 279

Gly Leu His Ala Glu Val Thr Gly Val Gly Tyr
1               5                   10

<210> SEQ ID NO 280
<211> LENGTH: 9
<212> TYPE: PRT
<213> ORGANISM: Homo sapiens

<400> SEQUENCE: 280

His Val Ser Ser Thr Ser Ser Ser Phe
1               5

<210> SEQ ID NO 281
<211> LENGTH: 9
<212> TYPE: PRT
<213> ORGANISM: Homo sapiens

<400> SEQUENCE: 281

Leu Gln Ala Asp Leu Gln Asn Gly Leu
1               5

<210> SEQ ID NO 282
<211> LENGTH: 9
<212> TYPE: PRT
<213> ORGANISM: Homo sapiens

<400> SEQUENCE: 282

Ser Glu Leu Pro Val Ser Glu Val Ala
1               5

<210> SEQ ID NO 283
<211> LENGTH: 9
<212> TYPE: PRT
<213> ORGANISM: Homo sapiens

<400> SEQUENCE: 283

Ser Gln Thr Lys Ser Val Phe Glu Ile
1               5

<210> SEQ ID NO 284
<211> LENGTH: 9
<212> TYPE: PRT
<213> ORGANISM: Homo sapiens

<400> SEQUENCE: 284

Thr His Ile Phe Thr Ser Asp Gly Leu
1               5

<210> SEQ ID NO 285
<211> LENGTH: 9
<212> TYPE: PRT
<213> ORGANISM: Homo sapiens

<400> SEQUENCE: 285

Val Ile Tyr Phe Pro Pro Leu Gln Lys
1               5

<210> SEQ ID NO 286
<211> LENGTH: 9
<212> TYPE: PRT
<213> ORGANISM: Homo sapiens

<400> SEQUENCE: 286

Tyr Pro Phe Ser Ser Glu Gln Lys Trp
1               5

<210> SEQ ID NO 287
<211> LENGTH: 9
<212> TYPE: PRT
<213> ORGANISM: Homo sapiens

<400> SEQUENCE: 287

Gly Gln Tyr Phe Gly Glu Leu Ala Leu
1               5

<210> SEQ ID NO 288
<211> LENGTH: 9
<212> TYPE: PRT
<213> ORGANISM: Homo sapiens

<400> SEQUENCE: 288

Arg Ile Ile Val Lys Asn Asn Ala Lys
1               5

<210> SEQ ID NO 289
<211> LENGTH: 10
<212> TYPE: PRT
<213> ORGANISM: Homo sapiens

<400> SEQUENCE: 289

Arg Arg Ile Ile Val Lys Asn Asn Ala Lys
1               5                   10

```
<210> SEQ ID NO 290
<211> LENGTH: 9
<212> TYPE: PRT
<213> ORGANISM: Homo sapiens

<400> SEQUENCE: 290

Ser Phe Gly Glu Leu Ala Leu Met Tyr
1               5

<210> SEQ ID NO 291
<211> LENGTH: 9
<212> TYPE: PRT
<213> ORGANISM: Homo sapiens

<400> SEQUENCE: 291

Ala Phe Asn Ala Pro Val Ile Asn Arg
1               5

<210> SEQ ID NO 292
<211> LENGTH: 9
<212> TYPE: PRT
<213> ORGANISM: Homo sapiens

<400> SEQUENCE: 292

Ile Met Lys Arg Asn Ile Ala Thr Tyr
1               5

<210> SEQ ID NO 293
<211> LENGTH: 9
<212> TYPE: PRT
<213> ORGANISM: Homo sapiens

<400> SEQUENCE: 293

Lys Val Val Asp Val Ile Gly Thr Lys
1               5

<210> SEQ ID NO 294
<211> LENGTH: 9
<212> TYPE: PRT
<213> ORGANISM: Homo sapiens

<400> SEQUENCE: 294

Leu Pro Phe Leu Lys Ser Leu Glu Phe
1               5

<210> SEQ ID NO 295
<211> LENGTH: 11
<212> TYPE: PRT
<213> ORGANISM: Homo sapiens

<400> SEQUENCE: 295

Arg Leu Lys Val Val Asp Val Ile Gly Thr Lys
1               5                   10

<210> SEQ ID NO 296
<211> LENGTH: 9
<212> TYPE: PRT
<213> ORGANISM: Homo sapiens

<400> SEQUENCE: 296

Thr Pro Arg Ala Ala Thr Ile Thr Ala
1               5

<210> SEQ ID NO 297
<211> LENGTH: 9
```

```
<212> TYPE: PRT
<213> ORGANISM: Homo sapiens

<400> SEQUENCE: 297

Lys Pro Ser Glu Lys Ile Gln Val Leu
1               5

<210> SEQ ID NO 298
<211> LENGTH: 9
<212> TYPE: PRT
<213> ORGANISM: Homo sapiens

<400> SEQUENCE: 298

Val Pro Tyr Pro Val Thr Thr Thr Val
1               5

<210> SEQ ID NO 299
<211> LENGTH: 9
<212> TYPE: PRT
<213> ORGANISM: Homo sapiens

<400> SEQUENCE: 299

Ala Ser Phe Pro Pro Phe Val Glu Lys
1               5

<210> SEQ ID NO 300
<211> LENGTH: 9
<212> TYPE: PRT
<213> ORGANISM: Homo sapiens

<400> SEQUENCE: 300

Ala Phe Ile His Ile Ser Thr Ala Tyr
1               5

<210> SEQ ID NO 301
<211> LENGTH: 10
<212> TYPE: PRT
<213> ORGANISM: Homo sapiens

<400> SEQUENCE: 301

Ala Thr Phe Glu Lys Ile Pro Phe Glu Arg
1               5                   10

<210> SEQ ID NO 302
<211> LENGTH: 9
<212> TYPE: PRT
<213> ORGANISM: Homo sapiens

<400> SEQUENCE: 302

Lys Leu Phe Glu Lys Val Lys Glu Val
1               5

<210> SEQ ID NO 303
<211> LENGTH: 9
<212> TYPE: PRT
<213> ORGANISM: Homo sapiens

<400> SEQUENCE: 303

Ser Gln Met Pro Lys Leu Glu Ala Phe
1               5

<210> SEQ ID NO 304
<211> LENGTH: 9
<212> TYPE: PRT
<213> ORGANISM: Homo sapiens
```

<400> SEQUENCE: 304

Ala Val Leu Gly Gln His His Asn Tyr
1               5

<210> SEQ ID NO 305
<211> LENGTH: 8
<212> TYPE: PRT
<213> ORGANISM: Homo sapiens

<400> SEQUENCE: 305

Gly Pro Pro Ala His Lys Pro Arg
1               5

<210> SEQ ID NO 306
<211> LENGTH: 9
<212> TYPE: PRT
<213> ORGANISM: Homo sapiens

<400> SEQUENCE: 306

Arg Val Tyr Asp Val Leu Val Leu Lys
1               5

<210> SEQ ID NO 307
<211> LENGTH: 9
<212> TYPE: PRT
<213> ORGANISM: Homo sapiens

<400> SEQUENCE: 307

Leu Pro Arg Pro Gln Gly Ile Thr Val
1               5

<210> SEQ ID NO 308
<211> LENGTH: 9
<212> TYPE: PRT
<213> ORGANISM: Homo sapiens

<400> SEQUENCE: 308

Val Leu Tyr Val Gly Ser Lys Thr Lys
1               5

<210> SEQ ID NO 309
<211> LENGTH: 9
<212> TYPE: PRT
<213> ORGANISM: Homo sapiens

<400> SEQUENCE: 309

Lys Thr Lys Glu Gln Val Thr Asn Val
1               5

<210> SEQ ID NO 310
<211> LENGTH: 10
<212> TYPE: PRT
<213> ORGANISM: Homo sapiens

<400> SEQUENCE: 310

Met Pro Val Asp Pro Asp Asn Glu Ala Tyr
1               5                   10

<210> SEQ ID NO 311
<211> LENGTH: 9
<212> TYPE: PRT
<213> ORGANISM: Homo sapiens

<400> SEQUENCE: 311

Ala Glu Lys Thr Lys Gln Gly Val Ala
1               5

<210> SEQ ID NO 312
<211> LENGTH: 9
<212> TYPE: PRT
<213> ORGANISM: Homo sapiens

<400> SEQUENCE: 312

Asp Ile Ala Asp Phe Phe Thr Thr Arg
1               5

<210> SEQ ID NO 313
<211> LENGTH: 9
<212> TYPE: PRT
<213> ORGANISM: Homo sapiens

<400> SEQUENCE: 313

His Ser Tyr Leu Gln Arg Gln Ser Val
1               5

<210> SEQ ID NO 314
<211> LENGTH: 9
<212> TYPE: PRT
<213> ORGANISM: Homo sapiens

<400> SEQUENCE: 314

Lys Glu Val Thr Leu Ile Glu Glu Leu
1               5

<210> SEQ ID NO 315
<211> LENGTH: 9
<212> TYPE: PRT
<213> ORGANISM: Homo sapiens

<400> SEQUENCE: 315

Arg Glu Asp Gly Pro Gly Val Ala Leu
1               5

<210> SEQ ID NO 316
<211> LENGTH: 9
<212> TYPE: PRT
<213> ORGANISM: Homo sapiens

<400> SEQUENCE: 316

Arg Glu Asp Pro Leu Pro Pro Gly Leu
1               5

<210> SEQ ID NO 317
<211> LENGTH: 11
<212> TYPE: PRT
<213> ORGANISM: Homo sapiens

<400> SEQUENCE: 317

Ser Leu Phe Gly Gly Ser Gln Gly Leu Arg Lys
1               5                   10

<210> SEQ ID NO 318
<211> LENGTH: 9
<212> TYPE: PRT
<213> ORGANISM: Homo sapiens

<400> SEQUENCE: 318

Ala Glu Phe Gln Arg Leu Lys Gln Ala

```
1               5
```

<210> SEQ ID NO 319
<211> LENGTH: 10
<212> TYPE: PRT
<213> ORGANISM: Homo sapiens

<400> SEQUENCE: 319

```
Glu Val Ile Asp Gly Val Pro Gly Lys Trp
1               5                   10
```

<210> SEQ ID NO 320
<211> LENGTH: 9
<212> TYPE: PRT
<213> ORGANISM: Homo sapiens

<400> SEQUENCE: 320

```
Ile Pro Lys Ala Pro Gly Lys Ile Ile
1               5
```

<210> SEQ ID NO 321
<211> LENGTH: 9
<212> TYPE: PRT
<213> ORGANISM: Homo sapiens

<400> SEQUENCE: 321

```
Ser His Asn Gly Ser Ala Ile Arg Tyr
1               5
```

<210> SEQ ID NO 322
<211> LENGTH: 10
<212> TYPE: PRT
<213> ORGANISM: Homo sapiens

<400> SEQUENCE: 322

```
Thr Glu Val Thr Val Val Gly Asp Lys Leu
1               5                   10
```

<210> SEQ ID NO 323
<211> LENGTH: 9
<212> TYPE: PRT
<213> ORGANISM: Homo sapiens

<400> SEQUENCE: 323

```
Tyr Ala Ser Val Val Val Lys Arg Tyr
1               5
```

<210> SEQ ID NO 324
<211> LENGTH: 9
<212> TYPE: PRT
<213> ORGANISM: Homo sapiens

<400> SEQUENCE: 324

```
Ala Thr Asp Leu Ala Leu Tyr Ile Lys
1               5
```

<210> SEQ ID NO 325
<211> LENGTH: 9
<212> TYPE: PRT
<213> ORGANISM: Homo sapiens

<400> SEQUENCE: 325

```
Ala Tyr His Asn Trp Arg His Ala Phe
1               5
```

```
<210> SEQ ID NO 326
<211> LENGTH: 9
<212> TYPE: PRT
<213> ORGANISM: Homo sapiens

<400> SEQUENCE: 326

Glu Pro Leu Asn Ile Lys Asp Ala Tyr
1               5

<210> SEQ ID NO 327
<211> LENGTH: 9
<212> TYPE: PRT
<213> ORGANISM: Homo sapiens

<400> SEQUENCE: 327

Lys Ile Ala Ala Thr Ile Ile Ser Phe
1               5

<210> SEQ ID NO 328
<211> LENGTH: 9
<212> TYPE: PRT
<213> ORGANISM: Homo sapiens

<400> SEQUENCE: 328

Lys Ile Phe Leu His Ile His Gly Leu
1               5

<210> SEQ ID NO 329
<211> LENGTH: 8
<212> TYPE: PRT
<213> ORGANISM: Homo sapiens

<400> SEQUENCE: 329

Leu Glu Val Ile Leu Lys Lys Ile
1               5

<210> SEQ ID NO 330
<211> LENGTH: 9
<212> TYPE: PRT
<213> ORGANISM: Homo sapiens

<400> SEQUENCE: 330

Ser Glu His Pro Leu Ala Gln Leu Tyr
1               5

<210> SEQ ID NO 331
<211> LENGTH: 9
<212> TYPE: PRT
<213> ORGANISM: Homo sapiens

<400> SEQUENCE: 331

Val Pro Ser Ala Gln Thr Leu Lys Ile
1               5

<210> SEQ ID NO 332
<211> LENGTH: 8
<212> TYPE: PRT
<213> ORGANISM: Homo sapiens

<400> SEQUENCE: 332

Ala Glu Tyr Arg Ser Tyr Val Ala
1               5

<210> SEQ ID NO 333
```

```
<210> SEQ ID NO 333
<211> LENGTH: 10
<212> TYPE: PRT
<213> ORGANISM: Homo sapiens

<400> SEQUENCE: 333

Ala Leu Ala Pro Gly Arg Gly Thr Leu Tyr
1               5                   10

<210> SEQ ID NO 334
<211> LENGTH: 9
<212> TYPE: PRT
<213> ORGANISM: Homo sapiens

<400> SEQUENCE: 334

Gly Pro Arg Gly Thr Gln Ala Ala Leu
1               5

<210> SEQ ID NO 335
<211> LENGTH: 9
<212> TYPE: PRT
<213> ORGANISM: Homo sapiens

<400> SEQUENCE: 335

Ile Glu Asp Pro Gly Thr Leu His Ile
1               5

<210> SEQ ID NO 336
<211> LENGTH: 10
<212> TYPE: PRT
<213> ORGANISM: Homo sapiens

<400> SEQUENCE: 336

Ile Glu Asp Pro Gly Thr Leu His Ile Trp
1               5                   10

<210> SEQ ID NO 337
<211> LENGTH: 9
<212> TYPE: PRT
<213> ORGANISM: Homo sapiens

<400> SEQUENCE: 337

Arg Pro Ile Pro Ile Ala Val Lys Tyr
1               5

<210> SEQ ID NO 338
<211> LENGTH: 8
<212> TYPE: PRT
<213> ORGANISM: Homo sapiens

<400> SEQUENCE: 338

Val Glu Lys Leu Leu Thr Asn Trp
1               5

<210> SEQ ID NO 339
<211> LENGTH: 11
<212> TYPE: PRT
<213> ORGANISM: Homo sapiens

<400> SEQUENCE: 339

Phe Leu Asp Pro Asp Ile Gly Gly Val Ala Val
1               5                   10

<210> SEQ ID NO 340
<211> LENGTH: 10
<212> TYPE: PRT
```

-continued

```
<213> ORGANISM: Homo sapiens

<400> SEQUENCE: 340

His Thr Ala Pro Pro Glu Asn Lys Thr Trp
1               5                   10

<210> SEQ ID NO 341
<211> LENGTH: 10
<212> TYPE: PRT
<213> ORGANISM: Homo sapiens

<400> SEQUENCE: 341

Leu Leu Asp Thr Pro Val Lys Thr Gln Tyr
1               5                   10

<210> SEQ ID NO 342
<211> LENGTH: 9
<212> TYPE: PRT
<213> ORGANISM: Homo sapiens

<400> SEQUENCE: 342

Asn Ala Val Lys Asp Phe Thr Ser Phe
1               5

<210> SEQ ID NO 343
<211> LENGTH: 9
<212> TYPE: PRT
<213> ORGANISM: Homo sapiens

<400> SEQUENCE: 343

Ser Gly Leu Leu Gln Ile Lys Lys Leu
1               5

<210> SEQ ID NO 344
<211> LENGTH: 9
<212> TYPE: PRT
<213> ORGANISM: Homo sapiens

<400> SEQUENCE: 344

Tyr His Asp Lys Asn Ile Val Leu Leu
1               5

<210> SEQ ID NO 345
<211> LENGTH: 9
<212> TYPE: PRT
<213> ORGANISM: Homo sapiens

<400> SEQUENCE: 345

Ser Val Asp Pro Lys Asn Tyr Pro Lys
1               5

<210> SEQ ID NO 346
<211> LENGTH: 9
<212> TYPE: PRT
<213> ORGANISM: Homo sapiens

<400> SEQUENCE: 346

Ala Val Gly Leu Val Leu Pro Ala Lys
1               5

<210> SEQ ID NO 347
<211> LENGTH: 10
<212> TYPE: PRT
<213> ORGANISM: Homo sapiens
```

```
<400> SEQUENCE: 347

Ala Val Gly Leu Val Leu Pro Ala Lys Leu
1               5                   10

<210> SEQ ID NO 348
<211> LENGTH: 9
<212> TYPE: PRT
<213> ORGANISM: Homo sapiens

<400> SEQUENCE: 348

Ala Leu Leu Glu Val Leu Ser Gln Lys
1               5

<210> SEQ ID NO 349
<211> LENGTH: 9
<212> TYPE: PRT
<213> ORGANISM: Homo sapiens

<400> SEQUENCE: 349

His Glu Lys Gln Asp Thr Leu Val Ala
1               5

<210> SEQ ID NO 350
<211> LENGTH: 9
<212> TYPE: PRT
<213> ORGANISM: Homo sapiens

<400> SEQUENCE: 350

Lys Glu Leu Glu Leu Gln Ile Gly Met
1               5

<210> SEQ ID NO 351
<211> LENGTH: 9
<212> TYPE: PRT
<213> ORGANISM: Homo sapiens

<400> SEQUENCE: 351

Met Tyr Ser Asp Val Trp Lys Gln Leu
1               5

<210> SEQ ID NO 352
<211> LENGTH: 10
<212> TYPE: PRT
<213> ORGANISM: Homo sapiens

<400> SEQUENCE: 352

Arg Glu Leu Gln Asp Glu Lys Ala Glu Leu
1               5                   10

<210> SEQ ID NO 353
<211> LENGTH: 9
<212> TYPE: PRT
<213> ORGANISM: Homo sapiens

<400> SEQUENCE: 353

Arg Ile Thr Asp Val Leu Asp Gln Lys
1               5

<210> SEQ ID NO 354
<211> LENGTH: 9
<212> TYPE: PRT
<213> ORGANISM: Homo sapiens

<400> SEQUENCE: 354
```

Glu Val Ile Lys Ile Thr Gly Leu Lys
1               5

<210> SEQ ID NO 355
<211> LENGTH: 9
<212> TYPE: PRT
<213> ORGANISM: Homo sapiens

<400> SEQUENCE: 355

His His Val Asp Ile Thr Lys Lys Leu
1               5

<210> SEQ ID NO 356
<211> LENGTH: 9
<212> TYPE: PRT
<213> ORGANISM: Homo sapiens

<400> SEQUENCE: 356

Leu Pro Phe Asn Val Lys Val Ser Val
1               5

<210> SEQ ID NO 357
<211> LENGTH: 8
<212> TYPE: PRT
<213> ORGANISM: Homo sapiens

<400> SEQUENCE: 357

Thr Leu Pro Arg Val Leu Glu Ile
1               5

<210> SEQ ID NO 358
<211> LENGTH: 9
<212> TYPE: PRT
<213> ORGANISM: Homo sapiens

<400> SEQUENCE: 358

Thr Val Asp Leu Pro Lys Ser Pro Lys
1               5

<210> SEQ ID NO 359
<211> LENGTH: 9
<212> TYPE: PRT
<213> ORGANISM: Homo sapiens

<400> SEQUENCE: 359

Ala Glu His Gly Leu Leu Leu Thr Ala
1               5

<210> SEQ ID NO 360
<211> LENGTH: 9
<212> TYPE: PRT
<213> ORGANISM: Homo sapiens

<400> SEQUENCE: 360

Ala Gln Ala Gly Ala Leu Leu Gln Val
1               5

<210> SEQ ID NO 361
<211> LENGTH: 8
<212> TYPE: PRT
<213> ORGANISM: Homo sapiens

<400> SEQUENCE: 361

Asp Gly Gly Phe Val Leu Lys Val
1               5

<210> SEQ ID NO 362
<211> LENGTH: 9
<212> TYPE: PRT
<213> ORGANISM: Homo sapiens

<400> SEQUENCE: 362

Ile Val Tyr Pro Ser Gly Lys Val Tyr
1               5

<210> SEQ ID NO 363
<211> LENGTH: 9
<212> TYPE: PRT
<213> ORGANISM: Homo sapiens

<400> SEQUENCE: 363

Lys Leu Asp Asn Gln Val Ser Lys Val
1               5

<210> SEQ ID NO 364
<211> LENGTH: 9
<212> TYPE: PRT
<213> ORGANISM: Homo sapiens

<400> SEQUENCE: 364

Ser Glu Asn Val Lys Leu Phe Ser Ala
1               5

<210> SEQ ID NO 365
<211> LENGTH: 8
<212> TYPE: PRT
<213> ORGANISM: Homo sapiens

<400> SEQUENCE: 365

Val Gln Lys Leu Gln Asn Ile Ile
1               5

<210> SEQ ID NO 366
<211> LENGTH: 9
<212> TYPE: PRT
<213> ORGANISM: Homo sapiens

<400> SEQUENCE: 366

Phe Ser Thr Pro His Gly Leu Glu Val
1               5

<210> SEQ ID NO 367
<211> LENGTH: 9
<212> TYPE: PRT
<213> ORGANISM: Homo sapiens

<400> SEQUENCE: 367

Lys Arg Phe His Gln Lys Ser Asp Met
1               5

<210> SEQ ID NO 368
<211> LENGTH: 9
<212> TYPE: PRT
<213> ORGANISM: Homo sapiens

<400> SEQUENCE: 368

Lys Thr Phe Gly His Ala Val Ser Leu
1               5

```
<210> SEQ ID NO 369
<211> LENGTH: 9
<212> TYPE: PRT
<213> ORGANISM: Homo sapiens

<400> SEQUENCE: 369

Ser Ser Asn Leu Ile Thr His Ser Arg
1               5

<210> SEQ ID NO 370
<211> LENGTH: 10
<212> TYPE: PRT
<213> ORGANISM: Homo sapiens

<400> SEQUENCE: 370

Gly Val Ile Asp Gly His Ile Tyr Ala Val
1               5                   10

<210> SEQ ID NO 371
<211> LENGTH: 11
<212> TYPE: PRT
<213> ORGANISM: Homo sapiens

<400> SEQUENCE: 371

Ile Glu Pro Ala Lys Glu Thr Thr Thr Asn Val
1               5                   10

<210> SEQ ID NO 372
<211> LENGTH: 9
<212> TYPE: PRT
<213> ORGANISM: Homo sapiens

<400> SEQUENCE: 372

Asn Ala Pro Pro Ser Glu Val Leu Leu
1               5

<210> SEQ ID NO 373
<211> LENGTH: 12
<212> TYPE: PRT
<213> ORGANISM: Homo sapiens

<400> SEQUENCE: 373

Ser Ile Glu Pro Ala Lys Glu Thr Thr Thr Asn Val
1               5                   10

<210> SEQ ID NO 374
<211> LENGTH: 9
<212> TYPE: PRT
<213> ORGANISM: Homo sapiens

<400> SEQUENCE: 374

Ala Gln Ser Gln His Asn Gln Ser Leu
1               5

<210> SEQ ID NO 375
<211> LENGTH: 9
<212> TYPE: PRT
<213> ORGANISM: Homo sapiens

<400> SEQUENCE: 375

Ala Gln Ser Arg Thr Asn Pro Gln Val
1               5

<210> SEQ ID NO 376
<211> LENGTH: 9
```

```
<212> TYPE: PRT
<213> ORGANISM: Homo sapiens

<400> SEQUENCE: 376

Lys Met His Asp Lys Val Phe Ala Tyr
1               5

<210> SEQ ID NO 377
<211> LENGTH: 9
<212> TYPE: PRT
<213> ORGANISM: Homo sapiens

<400> SEQUENCE: 377

Thr Ala Lys Ala Pro Leu Ser Thr Val
1               5

<210> SEQ ID NO 378
<211> LENGTH: 8
<212> TYPE: PRT
<213> ORGANISM: Homo sapiens

<400> SEQUENCE: 378

Ile Pro Thr Arg Thr Val Ala Ile
1               5

<210> SEQ ID NO 379
<211> LENGTH: 8
<212> TYPE: PRT
<213> ORGANISM: Homo sapiens

<400> SEQUENCE: 379

Asn His Asp Arg Lys His Ala Val
1               5

<210> SEQ ID NO 380
<211> LENGTH: 9
<212> TYPE: PRT
<213> ORGANISM: Homo sapiens

<400> SEQUENCE: 380

Asn Asn His Asp Arg Lys His Ala Val
1               5

<210> SEQ ID NO 381
<211> LENGTH: 9
<212> TYPE: PRT
<213> ORGANISM: Homo sapiens

<400> SEQUENCE: 381

Thr Pro Gly Gly Thr Arg Ile Ile Tyr
1               5

<210> SEQ ID NO 382
<211> LENGTH: 9
<212> TYPE: PRT
<213> ORGANISM: Homo sapiens

<400> SEQUENCE: 382

Glu His Trp Pro Ser Pro Glu Thr Phe
1               5

<210> SEQ ID NO 383
<211> LENGTH: 9
<212> TYPE: PRT
<213> ORGANISM: Homo sapiens
```

```
<400> SEQUENCE: 383

Glu Ile Ile Thr Asn Thr Leu Ser Phe
1               5

<210> SEQ ID NO 384
<211> LENGTH: 10
<212> TYPE: PRT
<213> ORGANISM: Homo sapiens

<400> SEQUENCE: 384

Glu Val Arg Gly Ala Leu Met Ser Ala Phe
1               5                   10

<210> SEQ ID NO 385
<211> LENGTH: 9
<212> TYPE: PRT
<213> ORGANISM: Homo sapiens

<400> SEQUENCE: 385

Ile Pro Arg Pro Ile Leu Val Leu Leu
1               5

<210> SEQ ID NO 386
<211> LENGTH: 9
<212> TYPE: PRT
<213> ORGANISM: Homo sapiens

<400> SEQUENCE: 386

Leu Pro Asn Lys Asn Arg Asp Glu Leu
1               5

<210> SEQ ID NO 387
<211> LENGTH: 9
<212> TYPE: PRT
<213> ORGANISM: Homo sapiens

<400> SEQUENCE: 387

Gln Arg Ile Pro Ala Gly Ala Val Leu
1               5

<210> SEQ ID NO 388
<211> LENGTH: 11
<212> TYPE: PRT
<213> ORGANISM: Homo sapiens

<400> SEQUENCE: 388

Ala Glu Gly Pro Ala Gly Gly Phe Met Val Val
1               5                   10

<210> SEQ ID NO 389
<211> LENGTH: 9
<212> TYPE: PRT
<213> ORGANISM: Homo sapiens

<400> SEQUENCE: 389

Ala Tyr Tyr Arg Asp Ala Glu Ala Tyr
1               5

<210> SEQ ID NO 390
<211> LENGTH: 9
<212> TYPE: PRT
<213> ORGANISM: Homo sapiens

<400> SEQUENCE: 390
```

-continued

Gln Val Asn Arg Pro Leu Thr Met Arg
1               5

<210> SEQ ID NO 391
<211> LENGTH: 9
<212> TYPE: PRT
<213> ORGANISM: Homo sapiens

<400> SEQUENCE: 391

Arg His Ser Pro Val Phe Gln Val Tyr
1               5

<210> SEQ ID NO 392
<211> LENGTH: 9
<212> TYPE: PRT
<213> ORGANISM: Homo sapiens

<400> SEQUENCE: 392

Ser Leu Pro Val Pro Asn Ser Ala Tyr
1               5

<210> SEQ ID NO 393
<211> LENGTH: 11
<212> TYPE: PRT
<213> ORGANISM: Homo sapiens

<400> SEQUENCE: 393

Thr Leu Gly Pro Pro Gly Thr Ala His Leu Tyr
1               5                   10

<210> SEQ ID NO 394
<211> LENGTH: 11
<212> TYPE: PRT
<213> ORGANISM: Homo sapiens

<400> SEQUENCE: 394

Ile Glu Pro Ala Lys Glu Thr Thr Thr Asn Val
1               5                   10

<210> SEQ ID NO 395
<211> LENGTH: 9
<212> TYPE: PRT
<213> ORGANISM: Homo sapiens

<400> SEQUENCE: 395

Asn Ala Pro Pro Ser Glu Val Leu Leu
1               5

<210> SEQ ID NO 396
<211> LENGTH: 12
<212> TYPE: PRT
<213> ORGANISM: Homo sapiens

<400> SEQUENCE: 396

Ser Ile Glu Pro Ala Lys Glu Thr Thr Thr Asn Val
1               5                   10

<210> SEQ ID NO 397
<211> LENGTH: 9
<212> TYPE: PRT
<213> ORGANISM: Homo sapiens

<400> SEQUENCE: 397

Asp Leu Tyr Ser Gly Leu Asn Gln Arg

```
1               5

<210> SEQ ID NO 398
<211> LENGTH: 9
<212> TYPE: PRT
<213> ORGANISM: Homo sapiens

<400> SEQUENCE: 398

Lys Ala Lys Ala Lys Pro Val Thr Arg
1               5

<210> SEQ ID NO 399
<211> LENGTH: 10
<212> TYPE: PRT
<213> ORGANISM: Homo sapiens

<400> SEQUENCE: 399

Ala Val Leu Asp Lys Ala Met Lys Ala Lys
1               5                   10

<210> SEQ ID NO 400
<211> LENGTH: 9
<212> TYPE: PRT
<213> ORGANISM: Homo sapiens

<400> SEQUENCE: 400

Leu Glu Leu Ser Thr Pro Leu Lys Ile
1               5

<210> SEQ ID NO 401
<211> LENGTH: 9
<212> TYPE: PRT
<213> ORGANISM: Homo sapiens

<400> SEQUENCE: 401

Leu Pro Leu Asn Leu Asp Thr Lys Tyr
1               5

<210> SEQ ID NO 402
<211> LENGTH: 9
<212> TYPE: PRT
<213> ORGANISM: Homo sapiens

<400> SEQUENCE: 402

Thr Val Ile Tyr Arg Ile Gln Ala Leu
1               5

<210> SEQ ID NO 403
<211> LENGTH: 9
<212> TYPE: PRT
<213> ORGANISM: Homo sapiens

<400> SEQUENCE: 403

Asp Ala His Ile Tyr Leu Asn His Ile
1               5

<210> SEQ ID NO 404
<211> LENGTH: 10
<212> TYPE: PRT
<213> ORGANISM: Homo sapiens

<400> SEQUENCE: 404

Asn His Ile Glu Pro Leu Lys Ile Gln Leu
1               5                   10
```

<210> SEQ ID NO 405
<211> LENGTH: 9
<212> TYPE: PRT
<213> ORGANISM: Homo sapiens

<400> SEQUENCE: 405

Ala Tyr Arg Pro Ala Val His Pro Arg
1               5

<210> SEQ ID NO 406
<211> LENGTH: 9
<212> TYPE: PRT
<213> ORGANISM: Homo sapiens

<400> SEQUENCE: 406

Leu Arg Ala Pro Leu Glu His Glu Leu
1               5

<210> SEQ ID NO 407
<211> LENGTH: 9
<212> TYPE: PRT
<213> ORGANISM: Homo sapiens

<400> SEQUENCE: 407

Arg Leu Phe Met Val Leu Leu Leu Lys
1               5

<210> SEQ ID NO 408
<211> LENGTH: 9
<212> TYPE: PRT
<213> ORGANISM: Homo sapiens

<400> SEQUENCE: 408

Arg Ser Pro Asp Val Leu Lys Asp Phe
1               5

<210> SEQ ID NO 409
<211> LENGTH: 9
<212> TYPE: PRT
<213> ORGANISM: Homo sapiens

<400> SEQUENCE: 409

Glu Thr Ala Pro Gly Val His Lys Arg
1               5

<210> SEQ ID NO 410
<211> LENGTH: 9
<212> TYPE: PRT
<213> ORGANISM: Homo sapiens

<400> SEQUENCE: 410

Leu Tyr His Gly Tyr Ile Tyr Thr Tyr
1               5

<210> SEQ ID NO 411
<211> LENGTH: 9
<212> TYPE: PRT
<213> ORGANISM: Homo sapiens

<400> SEQUENCE: 411

Gly Gln His Val Ala Thr Gln His Phe
1               5

<210> SEQ ID NO 412

```
<210> SEQ ID NO 412
<211> LENGTH: 8
<212> TYPE: PRT
<213> ORGANISM: Homo sapiens

<400> SEQUENCE: 412

Leu Asn Gly Gln Leu Pro Asn Leu
1               5

<210> SEQ ID NO 413
<211> LENGTH: 11
<212> TYPE: PRT
<213> ORGANISM: Homo sapiens

<400> SEQUENCE: 413

Leu Pro Phe Pro Asp Glu Thr His Glu Arg Tyr
1               5                   10

<210> SEQ ID NO 414
<211> LENGTH: 9
<212> TYPE: PRT
<213> ORGANISM: Homo sapiens

<400> SEQUENCE: 414

Leu Pro His Asn Thr His Arg Val Val
1               5

<210> SEQ ID NO 415
<211> LENGTH: 9
<212> TYPE: PRT
<213> ORGANISM: Homo sapiens

<400> SEQUENCE: 415

Val Val Phe Asp Ser Pro Arg Asn Arg
1               5

<210> SEQ ID NO 416
<211> LENGTH: 8
<212> TYPE: PRT
<213> ORGANISM: Homo sapiens

<400> SEQUENCE: 416

Tyr Pro Leu Gly Arg Ile Leu Ile
1               5

<210> SEQ ID NO 417
<211> LENGTH: 9
<212> TYPE: PRT
<213> ORGANISM: Homo sapiens

<400> SEQUENCE: 417

Lys Glu Phe Ala Glu Phe Val Thr Ser
1               5

<210> SEQ ID NO 418
<211> LENGTH: 9
<212> TYPE: PRT
<213> ORGANISM: Homo sapiens

<400> SEQUENCE: 418

Val Met Leu Asp Val Pro Ile Arg Leu
1               5

<210> SEQ ID NO 419
<211> LENGTH: 9
<212> TYPE: PRT
```

<213> ORGANISM: Homo sapiens

<400> SEQUENCE: 419

Val Pro Met Thr Pro Leu Arg Thr Val
1               5

<210> SEQ ID NO 420
<211> LENGTH: 9
<212> TYPE: PRT
<213> ORGANISM: Homo sapiens

<400> SEQUENCE: 420

Gln Ile Asp Tyr Lys Thr Leu Val Leu
1               5

<210> SEQ ID NO 421
<211> LENGTH: 9
<212> TYPE: PRT
<213> ORGANISM: Homo sapiens

<400> SEQUENCE: 421

Val Glu Asp Pro Thr Ile Val Arg Ile
1               5

<210> SEQ ID NO 422
<211> LENGTH: 9
<212> TYPE: PRT
<213> ORGANISM: Homo sapiens

<400> SEQUENCE: 422

Ile Pro Tyr Gln Asp Leu Pro His Leu
1               5

<210> SEQ ID NO 423
<211> LENGTH: 10
<212> TYPE: PRT
<213> ORGANISM: Homo sapiens

<400> SEQUENCE: 423

Asp Thr Pro Phe Leu Thr Gly His Gly Arg
1               5                   10

<210> SEQ ID NO 424
<211> LENGTH: 8
<212> TYPE: PRT
<213> ORGANISM: Homo sapiens

<400> SEQUENCE: 424

Glu Phe Tyr Arg Ala Leu Tyr Ile
1               5

<210> SEQ ID NO 425
<211> LENGTH: 10
<212> TYPE: PRT
<213> ORGANISM: Homo sapiens

<400> SEQUENCE: 425

Arg Tyr Tyr Pro Gln Ile Leu Thr Asn Lys
1               5                   10

<210> SEQ ID NO 426
<211> LENGTH: 8
<212> TYPE: PRT
<213> ORGANISM: Homo sapiens

```
<400> SEQUENCE: 426

Lys Ala Tyr Glu Arg His Val Leu
1               5

<210> SEQ ID NO 427
<211> LENGTH: 9
<212> TYPE: PRT
<213> ORGANISM: Homo sapiens

<400> SEQUENCE: 427

Leu Pro Ser Pro Glu Phe His Asp Tyr
1               5

<210> SEQ ID NO 428
<211> LENGTH: 9
<212> TYPE: PRT
<213> ORGANISM: Homo sapiens

<400> SEQUENCE: 428

Ser Leu Tyr Ala His Pro Ile Glu His
1               5

<210> SEQ ID NO 429
<211> LENGTH: 9
<212> TYPE: PRT
<213> ORGANISM: Homo sapiens

<400> SEQUENCE: 429

Leu Val Arg Glu Pro Gly Ser Gln Ala
1               5

<210> SEQ ID NO 430
<211> LENGTH: 10
<212> TYPE: PRT
<213> ORGANISM: Homo sapiens

<400> SEQUENCE: 430

Arg Leu Ala Gly Pro Gly Ser Glu Lys Tyr
1               5                   10

<210> SEQ ID NO 431
<211> LENGTH: 10
<212> TYPE: PRT
<213> ORGANISM: Homo sapiens

<400> SEQUENCE: 431

Ser Pro Gly Ala Gly Arg Asn Ser Val Leu
1               5                   10

<210> SEQ ID NO 432
<211> LENGTH: 11
<212> TYPE: PRT
<213> ORGANISM: Homo sapiens

<400> SEQUENCE: 432

Ser Val Gln Ser Asp Gln Gly Tyr Ile Ser Arg
1               5                   10

<210> SEQ ID NO 433
<211> LENGTH: 9
<212> TYPE: PRT
<213> ORGANISM: Homo sapiens

<400> SEQUENCE: 433
```

```
Gly Val Arg Pro Pro Ala Pro Ser Leu
1               5

<210> SEQ ID NO 434
<211> LENGTH: 9
<212> TYPE: PRT
<213> ORGANISM: Homo sapiens

<400> SEQUENCE: 434

Ile Phe Ser Glu Lys Pro Val Phe Val
1               5

<210> SEQ ID NO 435
<211> LENGTH: 9
<212> TYPE: PRT
<213> ORGANISM: Homo sapiens

<400> SEQUENCE: 435

Lys Ala Ser Asn Leu Leu Leu Gly Phe
1               5

<210> SEQ ID NO 436
<211> LENGTH: 9
<212> TYPE: PRT
<213> ORGANISM: Homo sapiens

<400> SEQUENCE: 436

Lys Arg Tyr Ile Phe Ala Asp Ala Tyr
1               5

<210> SEQ ID NO 437
<211> LENGTH: 9
<212> TYPE: PRT
<213> ORGANISM: Homo sapiens

<400> SEQUENCE: 437

Arg Asn Leu Gln Leu Ser Leu Pro Arg
1               5

<210> SEQ ID NO 438
<211> LENGTH: 9
<212> TYPE: PRT
<213> ORGANISM: Homo sapiens

<400> SEQUENCE: 438

Glu Ala Ser Glu Pro Val Ala Leu Arg
1               5

<210> SEQ ID NO 439
<211> LENGTH: 9
<212> TYPE: PRT
<213> ORGANISM: Homo sapiens

<400> SEQUENCE: 439

Arg Pro Lys Val Pro Asp Gln Ser Val
1               5

<210> SEQ ID NO 440
<211> LENGTH: 9
<212> TYPE: PRT
<213> ORGANISM: Homo sapiens

<400> SEQUENCE: 440

Val Leu Tyr Glu Asn Ala Leu Lys Leu
1               5
```

```
<210> SEQ ID NO 441
<211> LENGTH: 10
<212> TYPE: PRT
<213> ORGANISM: Homo sapiens

<400> SEQUENCE: 441

Glu Val Leu Asp Lys Ser Gln Thr Asn Tyr
1               5                   10

<210> SEQ ID NO 442
<211> LENGTH: 9
<212> TYPE: PRT
<213> ORGANISM: Homo sapiens

<400> SEQUENCE: 442

Met Pro Ser Pro Ile Pro Ala Lys Tyr
1               5

<210> SEQ ID NO 443
<211> LENGTH: 9
<212> TYPE: PRT
<213> ORGANISM: Homo sapiens

<400> SEQUENCE: 443

Tyr Gly Ile Glu Asn Phe Thr Ser Val
1               5

<210> SEQ ID NO 444
<211> LENGTH: 9
<212> TYPE: PRT
<213> ORGANISM: Homo sapiens

<400> SEQUENCE: 444

Ala Arg Ala Ala Gln Val Phe Phe Leu
1               5

<210> SEQ ID NO 445
<211> LENGTH: 9
<212> TYPE: PRT
<213> ORGANISM: Homo sapiens

<400> SEQUENCE: 445

Glu His Ile Val Pro Asn Ala Glu Leu
1               5

<210> SEQ ID NO 446
<211> LENGTH: 9
<212> TYPE: PRT
<213> ORGANISM: Homo sapiens

<400> SEQUENCE: 446

Glu Ala Phe Glu Phe Val Lys Gln Arg
1               5

<210> SEQ ID NO 447
<211> LENGTH: 9
<212> TYPE: PRT
<213> ORGANISM: Homo sapiens

<400> SEQUENCE: 447

Asn His Phe Glu Gly His Tyr Gln Tyr
1               5
```

<210> SEQ ID NO 448
<211> LENGTH: 9
<212> TYPE: PRT
<213> ORGANISM: Homo sapiens

<400> SEQUENCE: 448

Asp Ala Tyr Pro Lys Asn Pro His Leu
1               5

<210> SEQ ID NO 449
<211> LENGTH: 9
<212> TYPE: PRT
<213> ORGANISM: Homo sapiens

<400> SEQUENCE: 449

Asp Val Asn Ile Lys Ser Thr Glu Arg
1               5

<210> SEQ ID NO 450
<211> LENGTH: 9
<212> TYPE: PRT
<213> ORGANISM: Homo sapiens

<400> SEQUENCE: 450

His Ile Asn Ser Ile Lys Ser Val Phe
1               5

<210> SEQ ID NO 451
<211> LENGTH: 9
<212> TYPE: PRT
<213> ORGANISM: Homo sapiens

<400> SEQUENCE: 451

Tyr Glu Ser Glu Lys Val Gly Val Ala
1               5

<210> SEQ ID NO 452
<211> LENGTH: 9
<212> TYPE: PRT
<213> ORGANISM: Homo sapiens

<400> SEQUENCE: 452

Glu Asn Ala Pro Thr Thr Val Ser Arg
1               5

<210> SEQ ID NO 453
<211> LENGTH: 10
<212> TYPE: PRT
<213> ORGANISM: Homo sapiens

<400> SEQUENCE: 453

Arg Phe Pro His Leu Leu Ala His Thr Tyr
1               5                   10

<210> SEQ ID NO 454
<211> LENGTH: 9
<212> TYPE: PRT
<213> ORGANISM: Homo sapiens

<400> SEQUENCE: 454

Thr Leu Asp Gly Ser Leu His Ala Val
1               5

<210> SEQ ID NO 455
<211> LENGTH: 11

```
<212> TYPE: PRT
<213> ORGANISM: Homo sapiens

<400> SEQUENCE: 455

Arg Thr Val Leu Lys Asn Leu Ser Leu Leu Lys
1               5                   10

<210> SEQ ID NO 456
<211> LENGTH: 8
<212> TYPE: PRT
<213> ORGANISM: Homo sapiens

<400> SEQUENCE: 456

Phe Glu Ala Lys Val Gln Ala Ile
1               5

<210> SEQ ID NO 457
<211> LENGTH: 9
<212> TYPE: PRT
<213> ORGANISM: Homo sapiens

<400> SEQUENCE: 457

Phe Phe Glu Ala Lys Val Gln Ala Ile
1               5

<210> SEQ ID NO 458
<211> LENGTH: 8
<212> TYPE: PRT
<213> ORGANISM: Homo sapiens

<400> SEQUENCE: 458

Lys Glu Leu Gln Ser Thr Phe Lys
1               5

<210> SEQ ID NO 459
<211> LENGTH: 10
<212> TYPE: PRT
<213> ORGANISM: Homo sapiens

<400> SEQUENCE: 459

Asn Val Ser Ser Arg Phe Glu Glu Glu Ile
1               5                   10

<210> SEQ ID NO 460
<211> LENGTH: 10
<212> TYPE: PRT
<213> ORGANISM: Homo sapiens

<400> SEQUENCE: 460

Glu Val Trp Asn Asn Leu Gly Thr Thr Lys
1               5                   10

<210> SEQ ID NO 461
<211> LENGTH: 9
<212> TYPE: PRT
<213> ORGANISM: Homo sapiens

<400> SEQUENCE: 461

Met Ile Phe Arg Ser Gly Ser Leu Ile
1               5

<210> SEQ ID NO 462
<211> LENGTH: 9
<212> TYPE: PRT
<213> ORGANISM: Homo sapiens
```

<400> SEQUENCE: 462

Asn His Ala Leu Pro Leu Pro Gly Phe
1               5

<210> SEQ ID NO 463
<211> LENGTH: 10
<212> TYPE: PRT
<213> ORGANISM: Homo sapiens

<400> SEQUENCE: 463

Ala Ser Val Phe Gly Thr Met Pro Leu Lys
1               5                   10

<210> SEQ ID NO 464
<211> LENGTH: 10
<212> TYPE: PRT
<213> ORGANISM: Homo sapiens

<400> SEQUENCE: 464

Arg Glu Phe Pro Asp Arg Leu Val Gly Tyr
1               5                   10

<210> SEQ ID NO 465
<211> LENGTH: 9
<212> TYPE: PRT
<213> ORGANISM: Homo sapiens

<400> SEQUENCE: 465

Ser Val Phe Gly Thr Met Pro Leu Lys
1               5

<210> SEQ ID NO 466
<211> LENGTH: 9
<212> TYPE: PRT
<213> ORGANISM: Homo sapiens

<400> SEQUENCE: 466

Asp Glu Met Arg Phe Val Thr Gln Ile
1               5

<210> SEQ ID NO 467
<211> LENGTH: 10
<212> TYPE: PRT
<213> ORGANISM: Homo sapiens

<400> SEQUENCE: 467

Glu Thr Val His Phe Ala Thr Thr Gln Trp
1               5                   10

<210> SEQ ID NO 468
<211> LENGTH: 8
<212> TYPE: PRT
<213> ORGANISM: Homo sapiens

<400> SEQUENCE: 468

Leu Pro Pro Pro Ala Thr Gln Ile
1               5

<210> SEQ ID NO 469
<211> LENGTH: 8
<212> TYPE: PRT
<213> ORGANISM: Homo sapiens

<400> SEQUENCE: 469

Leu Ala Arg Asp Leu Tyr Ala Phe
1               5

<210> SEQ ID NO 470
<211> LENGTH: 10
<212> TYPE: PRT
<213> ORGANISM: Homo sapiens

<400> SEQUENCE: 470

Leu Pro Gly Ile Gly Leu Ser Thr Ser Leu
1               5                   10

<210> SEQ ID NO 471
<211> LENGTH: 8
<212> TYPE: PRT
<213> ORGANISM: Homo sapiens

<400> SEQUENCE: 471

Met Glu Val Ile Leu Pro Met Leu
1               5

<210> SEQ ID NO 472
<211> LENGTH: 9
<212> TYPE: PRT
<213> ORGANISM: Homo sapiens

<400> SEQUENCE: 472

Ala Ile Leu Asp Tyr Ile Leu Ala Lys
1               5

<210> SEQ ID NO 473
<211> LENGTH: 9
<212> TYPE: PRT
<213> ORGANISM: Homo sapiens

<400> SEQUENCE: 473

Lys Ile Ala Ser Gln Leu Ser Lys Leu
1               5

<210> SEQ ID NO 474
<211> LENGTH: 9
<212> TYPE: PRT
<213> ORGANISM: Homo sapiens

<400> SEQUENCE: 474

Lys Val Thr Ser Thr Thr Thr Val Lys
1               5

<210> SEQ ID NO 475
<211> LENGTH: 9
<212> TYPE: PRT
<213> ORGANISM: Homo sapiens

<400> SEQUENCE: 475

Tyr Asn Thr Leu Leu Pro Tyr Thr Phe
1               5

<210> SEQ ID NO 476
<211> LENGTH: 9
<212> TYPE: PRT
<213> ORGANISM: Homo sapiens

<400> SEQUENCE: 476

Phe Leu Asp Pro Arg Pro Leu Thr Val

```
1               5

<210> SEQ ID NO 477
<211> LENGTH: 9
<212> TYPE: PRT
<213> ORGANISM: Homo sapiens

<400> SEQUENCE: 477

Ser Ala Phe Ala Asp Arg Pro Ala Phe
1               5

<210> SEQ ID NO 478
<211> LENGTH: 9
<212> TYPE: PRT
<213> ORGANISM: Homo sapiens

<400> SEQUENCE: 478

Ala Ala Val Pro Val Ile Ile Ser Arg
1               5

<210> SEQ ID NO 479
<211> LENGTH: 9
<212> TYPE: PRT
<213> ORGANISM: Homo sapiens

<400> SEQUENCE: 479

Glu Glu Ile Gly Lys Val Ala Ala Ala
1               5

<210> SEQ ID NO 480
<211> LENGTH: 9
<212> TYPE: PRT
<213> ORGANISM: Homo sapiens

<400> SEQUENCE: 480

Phe Leu Lys Asp Leu Val Ala Ser Val
1               5

<210> SEQ ID NO 481
<211> LENGTH: 9
<212> TYPE: PRT
<213> ORGANISM: Homo sapiens

<400> SEQUENCE: 481

Val Ile Ile Ser Arg Ala Leu Glu Leu
1               5

<210> SEQ ID NO 482
<211> LENGTH: 12
<212> TYPE: PRT
<213> ORGANISM: Homo sapiens

<400> SEQUENCE: 482

Ala Pro Arg Thr Thr Gly Thr Pro Arg Thr Ser Leu
1               5                   10

<210> SEQ ID NO 483
<211> LENGTH: 10
<212> TYPE: PRT
<213> ORGANISM: Homo sapiens

<400> SEQUENCE: 483

Glu Ser Val Gly Gly Ser Pro Gln Thr Lys
1               5                   10
```

<210> SEQ ID NO 484
<211> LENGTH: 8
<212> TYPE: PRT
<213> ORGANISM: Homo sapiens

<400> SEQUENCE: 484

Ile Pro Lys Asp Lys Ala Ile Leu
1               5

<210> SEQ ID NO 485
<211> LENGTH: 9
<212> TYPE: PRT
<213> ORGANISM: Homo sapiens

<400> SEQUENCE: 485

Leu Pro Ala Tyr Gly Arg Thr Thr Leu
1               5

<210> SEQ ID NO 486
<211> LENGTH: 9
<212> TYPE: PRT
<213> ORGANISM: Homo sapiens

<400> SEQUENCE: 486

His Gln Ala Ala Ile Val Ser Lys Ile
1               5

<210> SEQ ID NO 487
<211> LENGTH: 8
<212> TYPE: PRT
<213> ORGANISM: Homo sapiens

<400> SEQUENCE: 487

Gln Ala Ala Ile Val Ser Lys Ile
1               5

<210> SEQ ID NO 488
<211> LENGTH: 9
<212> TYPE: PRT
<213> ORGANISM: Homo sapiens

<400> SEQUENCE: 488

Arg Gln Lys Met Pro Glu Asp Gly Leu
1               5

<210> SEQ ID NO 489
<211> LENGTH: 9
<212> TYPE: PRT
<213> ORGANISM: Homo sapiens

<400> SEQUENCE: 489

Ser Val Gln Lys Ser Ser Gly Val Lys
1               5

<210> SEQ ID NO 490
<211> LENGTH: 11
<212> TYPE: PRT
<213> ORGANISM: Homo sapiens

<400> SEQUENCE: 490

Asp Ser Ile Gly Ser Thr Val Ser Ser Glu Arg
1               5                   10

<210> SEQ ID NO 491

```
<211> LENGTH: 11
<212> TYPE: PRT
<213> ORGANISM: Homo sapiens

<400> SEQUENCE: 491

Leu Pro Tyr Asn Asn Lys Asp Arg Asp Ala Leu
1               5                   10

<210> SEQ ID NO 492
<211> LENGTH: 9
<212> TYPE: PRT
<213> ORGANISM: Homo sapiens

<400> SEQUENCE: 492

Ile Tyr Asp Glu Ile Gln Gln Glu Met
1               5

<210> SEQ ID NO 493
<211> LENGTH: 9
<212> TYPE: PRT
<213> ORGANISM: Homo sapiens

<400> SEQUENCE: 493

Ala Gln Ala Lys Gly Leu Ile Gln Val
1               5

<210> SEQ ID NO 494
<211> LENGTH: 9
<212> TYPE: PRT
<213> ORGANISM: Homo sapiens

<400> SEQUENCE: 494

Glu Val Ser Ser Glu Ile Tyr Gln Trp
1               5

<210> SEQ ID NO 495
<211> LENGTH: 9
<212> TYPE: PRT
<213> ORGANISM: Homo sapiens

<400> SEQUENCE: 495

Lys Trp Asn Pro Val Pro Leu Ser Tyr
1               5

<210> SEQ ID NO 496
<211> LENGTH: 9
<212> TYPE: PRT
<213> ORGANISM: Homo sapiens

<400> SEQUENCE: 496

Asn Arg Leu Leu Ala Gln Gln Ser Leu
1               5

<210> SEQ ID NO 497
<211> LENGTH: 9
<212> TYPE: PRT
<213> ORGANISM: Homo sapiens

<400> SEQUENCE: 497

Ala Pro Arg Pro Val Ala Val Ala Val
1               5

<210> SEQ ID NO 498
<211> LENGTH: 10
<212> TYPE: PRT
```

<213> ORGANISM: Homo sapiens

<400> SEQUENCE: 498

Phe Tyr Arg Glu Thr Val Gln Val Gly Arg
1               5                   10

<210> SEQ ID NO 499
<211> LENGTH: 9
<212> TYPE: PRT
<213> ORGANISM: Homo sapiens

<400> SEQUENCE: 499

Leu Leu Ala Pro Arg Pro Val Ala Val
1               5

<210> SEQ ID NO 500
<211> LENGTH: 9
<212> TYPE: PRT
<213> ORGANISM: Homo sapiens

<400> SEQUENCE: 500

Gly Leu Ala Ala Leu Val Ile Leu Lys
1               5

<210> SEQ ID NO 501
<211> LENGTH: 9
<212> TYPE: PRT
<213> ORGANISM: Homo sapiens

<400> SEQUENCE: 501

Lys Ile Gln Glu Val Phe Ser Ser Tyr
1               5

<210> SEQ ID NO 502
<211> LENGTH: 9
<212> TYPE: PRT
<213> ORGANISM: Homo sapiens

<400> SEQUENCE: 502

Ala Ser Leu Asp Lys Phe Leu Ser His
1               5

<210> SEQ ID NO 503
<211> LENGTH: 9
<212> TYPE: PRT
<213> ORGANISM: Homo sapiens

<400> SEQUENCE: 503

Ala Leu Tyr Ala Thr Lys Thr Leu Arg
1               5

<210> SEQ ID NO 504
<211> LENGTH: 8
<212> TYPE: PRT
<213> ORGANISM: Homo sapiens

<400> SEQUENCE: 504

Met Glu Tyr Val Ile Ser Arg Ile
1               5

<210> SEQ ID NO 505
<211> LENGTH: 9
<212> TYPE: PRT
<213> ORGANISM: Homo sapiens

```
<400> SEQUENCE: 505

Val Pro Val Gly Arg Gln Pro Ile Ile
1               5

<210> SEQ ID NO 506
<211> LENGTH: 10
<212> TYPE: PRT
<213> ORGANISM: Homo sapiens

<400> SEQUENCE: 506

Lys Leu Leu Ile Gly Val Ile Ala Ala Val
1               5                   10

<210> SEQ ID NO 507
<211> LENGTH: 8
<212> TYPE: PRT
<213> ORGANISM: Homo sapiens

<400> SEQUENCE: 507

Leu Pro Ser Leu Ile Lys Leu Asp
1               5

<210> SEQ ID NO 508
<211> LENGTH: 8
<212> TYPE: PRT
<213> ORGANISM: Homo sapiens

<400> SEQUENCE: 508

Pro Ser Leu Ile Lys Leu Asp Leu
1               5

<210> SEQ ID NO 509
<211> LENGTH: 9
<212> TYPE: PRT
<213> ORGANISM: Homo sapiens

<400> SEQUENCE: 509

Ala Arg Asn Lys Glu Leu Ile Gly Lys
1               5

<210> SEQ ID NO 510
<211> LENGTH: 9
<212> TYPE: PRT
<213> ORGANISM: Homo sapiens

<400> SEQUENCE: 510

Ala Val Lys Ser Asn Ala Ala Ala Tyr
1               5

<210> SEQ ID NO 511
<211> LENGTH: 9
<212> TYPE: PRT
<213> ORGANISM: Homo sapiens

<400> SEQUENCE: 511

Glu Val Ile Ile Pro His Ser Gly Trp
1               5

<210> SEQ ID NO 512
<211> LENGTH: 9
<212> TYPE: PRT
<213> ORGANISM: Homo sapiens

<400> SEQUENCE: 512
```

Ser Val Lys Glu Gln Glu Ala Gln Phe
1               5

<210> SEQ ID NO 513
<211> LENGTH: 10
<212> TYPE: PRT
<213> ORGANISM: Homo sapiens

<400> SEQUENCE: 513

Ala Pro Arg Gly Leu Glu Pro Ile Ala Ile
1               5                   10

<210> SEQ ID NO 514
<211> LENGTH: 9
<212> TYPE: PRT
<213> ORGANISM: Homo sapiens

<400> SEQUENCE: 514

Gly Arg Phe Gly Gly Val Ile Thr Ile
1               5

<210> SEQ ID NO 515
<211> LENGTH: 9
<212> TYPE: PRT
<213> ORGANISM: Homo sapiens

<400> SEQUENCE: 515

Pro Val Ala Gly Phe Phe Ile Asn Arg
1               5

<210> SEQ ID NO 516
<211> LENGTH: 9
<212> TYPE: PRT
<213> ORGANISM: Homo sapiens

<400> SEQUENCE: 516

Thr Pro Lys Thr Pro Ser Arg Asp Ala
1               5

<210> SEQ ID NO 517
<211> LENGTH: 10
<212> TYPE: PRT
<213> ORGANISM: Homo sapiens

<400> SEQUENCE: 517

Val Leu Phe Gly Gly Lys Val Ser Gly Ala
1               5                   10

<210> SEQ ID NO 518
<211> LENGTH: 9
<212> TYPE: PRT
<213> ORGANISM: Homo sapiens

<400> SEQUENCE: 518

Ala Glu His Ile Glu Ser Arg Thr Leu
1               5

<210> SEQ ID NO 519
<211> LENGTH: 9
<212> TYPE: PRT
<213> ORGANISM: Homo sapiens

<400> SEQUENCE: 519

Asp Gln Tyr Pro Tyr Leu Lys Ser Val
1               5

<210> SEQ ID NO 520
<211> LENGTH: 9
<212> TYPE: PRT
<213> ORGANISM: Homo sapiens

<400> SEQUENCE: 520

Ile Ala Arg Asn Leu Thr Gln Gln Leu
1               5

<210> SEQ ID NO 521
<211> LENGTH: 9
<212> TYPE: PRT
<213> ORGANISM: Homo sapiens

<400> SEQUENCE: 521

Ile Glu Ser Arg Thr Leu Ala Ile Ala
1               5

<210> SEQ ID NO 522
<211> LENGTH: 10
<212> TYPE: PRT
<213> ORGANISM: Homo sapiens

<400> SEQUENCE: 522

Met Thr Ser Ala Leu Pro Ile Ile Gln Lys
1               5                   10

<210> SEQ ID NO 523
<211> LENGTH: 12
<212> TYPE: PRT
<213> ORGANISM: Homo sapiens

<400> SEQUENCE: 523

Ser Leu Leu Thr Ser Ser Lys Gly Gln Leu Gln Lys
1               5                   10

<210> SEQ ID NO 524
<211> LENGTH: 9
<212> TYPE: PRT
<213> ORGANISM: Homo sapiens

<400> SEQUENCE: 524

Thr Ser Ala Leu Pro Ile Ile Gln Lys
1               5

<210> SEQ ID NO 525
<211> LENGTH: 9
<212> TYPE: PRT
<213> ORGANISM: Homo sapiens

<400> SEQUENCE: 525

Val Arg Leu Gly Ser Leu Ser Thr Lys
1               5

<210> SEQ ID NO 526
<211> LENGTH: 10
<212> TYPE: PRT
<213> ORGANISM: Homo sapiens

<400> SEQUENCE: 526

Arg Ile Asn Glu Phe Ser Ile Ser Ser Phe
1               5                   10

```
<210> SEQ ID NO 527
<211> LENGTH: 9
<212> TYPE: PRT
<213> ORGANISM: Homo sapiens

<400> SEQUENCE: 527

Asp Glu Lys Gln Gln His Ile Val Tyr
1               5

<210> SEQ ID NO 528
<211> LENGTH: 9
<212> TYPE: PRT
<213> ORGANISM: Homo sapiens

<400> SEQUENCE: 528

Asp Glu Val Tyr Gln Val Thr Val Tyr
1               5

<210> SEQ ID NO 529
<211> LENGTH: 9
<212> TYPE: PRT
<213> ORGANISM: Homo sapiens

<400> SEQUENCE: 529

Gly Glu Ile Ser Glu Lys Ala Lys Leu
1               5

<210> SEQ ID NO 530
<211> LENGTH: 9
<212> TYPE: PRT
<213> ORGANISM: Homo sapiens

<400> SEQUENCE: 530

Tyr Thr Met Lys Glu Val Leu Phe Tyr
1               5

<210> SEQ ID NO 531
<211> LENGTH: 9
<212> TYPE: PRT
<213> ORGANISM: Homo sapiens

<400> SEQUENCE: 531

Ser Gln Leu Thr Thr Leu Ser Phe Tyr
1               5

<210> SEQ ID NO 532
<211> LENGTH: 8
<212> TYPE: PRT
<213> ORGANISM: Homo sapiens

<400> SEQUENCE: 532

Leu Glu Lys Gln Leu Ile Glu Leu
1               5

<210> SEQ ID NO 533
<211> LENGTH: 9
<212> TYPE: PRT
<213> ORGANISM: Homo sapiens

<400> SEQUENCE: 533

Glu Leu Thr Leu Gly Glu Phe Leu Lys
1               5

<210> SEQ ID NO 534
<211> LENGTH: 8
```

<212> TYPE: PRT
<213> ORGANISM: Homo sapiens

<400> SEQUENCE: 534

Leu Thr Leu Gly Glu Phe Leu Lys
1               5

<210> SEQ ID NO 535
<211> LENGTH: 9
<212> TYPE: PRT
<213> ORGANISM: Homo sapiens

<400> SEQUENCE: 535

Leu Thr Leu Gly Glu Phe Leu Lys Leu
1               5

<210> SEQ ID NO 536
<211> LENGTH: 8
<212> TYPE: PRT
<213> ORGANISM: Homo sapiens

<400> SEQUENCE: 536

Thr Leu Gly Glu Phe Leu Lys Leu
1               5

<210> SEQ ID NO 537
<211> LENGTH: 8
<212> TYPE: PRT
<213> ORGANISM: Homo sapiens

<400> SEQUENCE: 537

Ile Thr Ala Arg Pro Val Leu Trp
1               5

<210> SEQ ID NO 538
<211> LENGTH: 10
<212> TYPE: PRT
<213> ORGANISM: Homo sapiens

<400> SEQUENCE: 538

Lys Leu Met Ser Pro Lys Leu Tyr Val Trp
1               5                   10

<210> SEQ ID NO 539
<211> LENGTH: 9
<212> TYPE: PRT
<213> ORGANISM: Homo sapiens

<400> SEQUENCE: 539

Lys Val Ser Ala Val Thr Leu Ala Tyr
1               5

<210> SEQ ID NO 540
<211> LENGTH: 10
<212> TYPE: PRT
<213> ORGANISM: Homo sapiens

<400> SEQUENCE: 540

Val Glu Gly Ser Gly Glu Leu Phe Arg Trp
1               5                   10

<210> SEQ ID NO 541
<211> LENGTH: 8
<212> TYPE: PRT
<213> ORGANISM: Homo sapiens

<400> SEQUENCE: 541

Arg Pro Lys Ser Asn Ile Val Leu
1               5

<210> SEQ ID NO 542
<211> LENGTH: 9
<212> TYPE: PRT
<213> ORGANISM: Homo sapiens

<400> SEQUENCE: 542

Arg Pro Lys Ser Asn Ile Val Leu Leu
1               5

<210> SEQ ID NO 543
<211> LENGTH: 14
<212> TYPE: PRT
<213> ORGANISM: Homo sapiens

<400> SEQUENCE: 543

Gly Glu Pro Leu Ser Tyr Thr Arg Phe Ser Leu Ala Arg Gln
1               5                   10

<210> SEQ ID NO 544
<211> LENGTH: 16
<212> TYPE: PRT
<213> ORGANISM: Homo sapiens

<400> SEQUENCE: 544

Gly Glu Pro Leu Ser Tyr Thr Arg Phe Ser Leu Ala Arg Gln Val Asp
1               5                   10                  15

<210> SEQ ID NO 545
<211> LENGTH: 17
<212> TYPE: PRT
<213> ORGANISM: Homo sapiens

<400> SEQUENCE: 545

Gly Glu Pro Leu Ser Tyr Thr Arg Phe Ser Leu Ala Arg Gln Val Asp
1               5                   10                  15

Gly

<210> SEQ ID NO 546
<211> LENGTH: 17
<212> TYPE: PRT
<213> ORGANISM: Homo sapiens

<400> SEQUENCE: 546

Gly Gly Glu Pro Leu Ser Tyr Thr Arg Phe Ser Leu Ala Arg Gln Val
1               5                   10                  15

Asp

<210> SEQ ID NO 547
<211> LENGTH: 18
<212> TYPE: PRT
<213> ORGANISM: Homo sapiens

<400> SEQUENCE: 547

Gly Gly Glu Pro Leu Ser Tyr Thr Arg Phe Ser Leu Ala Arg Gln Val
1               5                   10                  15

Asp Gly

```
<210> SEQ ID NO 548
<211> LENGTH: 16
<212> TYPE: PRT
<213> ORGANISM: Homo sapiens

<400> SEQUENCE: 548

Asn Pro Gly Gly Tyr Val Ala Tyr Ser Lys Ala Ala Thr Val Thr Gly
1               5                   10                  15

<210> SEQ ID NO 549
<211> LENGTH: 17
<212> TYPE: PRT
<213> ORGANISM: Homo sapiens

<400> SEQUENCE: 549

Asn Pro Gly Gly Tyr Val Ala Tyr Ser Lys Ala Ala Thr Val Thr Gly
1               5                   10                  15

Lys

<210> SEQ ID NO 550
<211> LENGTH: 18
<212> TYPE: PRT
<213> ORGANISM: Homo sapiens

<400> SEQUENCE: 550

Asn Pro Gly Gly Tyr Val Ala Tyr Ser Lys Ala Ala Thr Val Thr Gly
1               5                   10                  15

Lys Leu

<210> SEQ ID NO 551
<211> LENGTH: 12
<212> TYPE: PRT
<213> ORGANISM: Homo sapiens

<400> SEQUENCE: 551

Asn Ser Val Ile Ile Val Asp Lys Asn Gly Arg Leu
1               5                   10

<210> SEQ ID NO 552
<211> LENGTH: 13
<212> TYPE: PRT
<213> ORGANISM: Homo sapiens

<400> SEQUENCE: 552

Asn Ser Val Ile Ile Val Asp Lys Asn Gly Arg Leu Val
1               5                   10

<210> SEQ ID NO 553
<211> LENGTH: 14
<212> TYPE: PRT
<213> ORGANISM: Homo sapiens

<400> SEQUENCE: 553

Asn Ser Val Ile Ile Val Asp Lys Asn Gly Arg Leu Val Tyr
1               5                   10

<210> SEQ ID NO 554
<211> LENGTH: 14
<212> TYPE: PRT
<213> ORGANISM: Homo sapiens

<400> SEQUENCE: 554

Arg Val Glu Tyr His Phe Leu Ser Pro Tyr Val Ser Pro Lys
1               5                   10
```

<210> SEQ ID NO 555
<211> LENGTH: 15
<212> TYPE: PRT
<213> ORGANISM: Homo sapiens

<400> SEQUENCE: 555

Arg Val Glu Tyr His Phe Leu Ser Pro Tyr Val Ser Pro Lys Glu
1               5                   10                  15

<210> SEQ ID NO 556
<211> LENGTH: 18
<212> TYPE: PRT
<213> ORGANISM: Homo sapiens

<400> SEQUENCE: 556

Arg Val Glu Tyr His Phe Leu Ser Pro Tyr Val Ser Pro Lys Glu Ser
1               5                   10                  15

Pro Phe

<210> SEQ ID NO 557
<211> LENGTH: 15
<212> TYPE: PRT
<213> ORGANISM: Homo sapiens

<400> SEQUENCE: 557

Ser Pro Phe Arg His Val Phe Trp Gly Ser Gly Ser His Thr Leu
1               5                   10                  15

<210> SEQ ID NO 558
<211> LENGTH: 12
<212> TYPE: PRT
<213> ORGANISM: Homo sapiens

<400> SEQUENCE: 558

Ser Val Ile Ile Val Asp Lys Asn Gly Arg Leu Val
1               5                   10

<210> SEQ ID NO 559
<211> LENGTH: 13
<212> TYPE: PRT
<213> ORGANISM: Homo sapiens

<400> SEQUENCE: 559

Val Glu Tyr His Phe Leu Ser Pro Tyr Val Ser Pro Lys
1               5                   10

<210> SEQ ID NO 560
<211> LENGTH: 14
<212> TYPE: PRT
<213> ORGANISM: Homo sapiens

<400> SEQUENCE: 560

Val Glu Tyr His Phe Leu Ser Pro Tyr Val Ser Pro Lys Glu
1               5                   10

<210> SEQ ID NO 561
<211> LENGTH: 14
<212> TYPE: PRT
<213> ORGANISM: Homo sapiens

<400> SEQUENCE: 561

Leu Pro Ser Gln Ala Phe Glu Tyr Ile Leu Tyr Asn Lys Gly
1               5                   10

<210> SEQ ID NO 562
<211> LENGTH: 15
<212> TYPE: PRT
<213> ORGANISM: Homo sapiens

<400> SEQUENCE: 562

Leu Pro Ser Gln Ala Phe Glu Tyr Ile Leu Tyr Asn Lys Gly Ile
1               5                   10                  15

<210> SEQ ID NO 563
<211> LENGTH: 16
<212> TYPE: PRT
<213> ORGANISM: Homo sapiens

<400> SEQUENCE: 563

Leu Pro Ser Gln Ala Phe Glu Tyr Ile Leu Tyr Asn Lys Gly Ile Met
1               5                   10                  15

<210> SEQ ID NO 564
<211> LENGTH: 17
<212> TYPE: PRT
<213> ORGANISM: Homo sapiens

<400> SEQUENCE: 564

Leu Pro Ser Gln Ala Phe Glu Tyr Ile Leu Tyr Asn Lys Gly Ile Met
1               5                   10                  15

Gly

<210> SEQ ID NO 565
<211> LENGTH: 13
<212> TYPE: PRT
<213> ORGANISM: Homo sapiens

<400> SEQUENCE: 565

Met Asn Gly Tyr Phe Leu Ile Glu Arg Gly Lys Asn Met
1               5                   10

<210> SEQ ID NO 566
<211> LENGTH: 12
<212> TYPE: PRT
<213> ORGANISM: Homo sapiens

<400> SEQUENCE: 566

Asn Gly Tyr Phe Leu Ile Glu Arg Gly Lys Asn Met
1               5                   10

<210> SEQ ID NO 567
<211> LENGTH: 13
<212> TYPE: PRT
<213> ORGANISM: Homo sapiens

<400> SEQUENCE: 567

Pro Ser Gln Ala Phe Glu Tyr Ile Leu Tyr Asn Lys Gly
1               5                   10

<210> SEQ ID NO 568
<211> LENGTH: 14
<212> TYPE: PRT
<213> ORGANISM: Homo sapiens

<400> SEQUENCE: 568

Pro Ser Gln Ala Phe Glu Tyr Ile Leu Tyr Asn Lys Gly Ile
1               5                   10

```
<210> SEQ ID NO 569
<211> LENGTH: 15
<212> TYPE: PRT
<213> ORGANISM: Homo sapiens

<400> SEQUENCE: 569

Pro Ser Gln Ala Phe Glu Tyr Ile Leu Tyr Asn Lys Gly Ile Met
1               5                   10                  15

<210> SEQ ID NO 570
<211> LENGTH: 13
<212> TYPE: PRT
<213> ORGANISM: Homo sapiens

<400> SEQUENCE: 570

Glu Gly Val Gln Tyr Ser Tyr Ser Leu Phe His Leu Met
1               5                   10

<210> SEQ ID NO 571
<211> LENGTH: 14
<212> TYPE: PRT
<213> ORGANISM: Homo sapiens

<400> SEQUENCE: 571

Glu Gly Val Gln Tyr Ser Tyr Ser Leu Phe His Leu Met Leu
1               5                   10

<210> SEQ ID NO 572
<211> LENGTH: 12
<212> TYPE: PRT
<213> ORGANISM: Homo sapiens

<400> SEQUENCE: 572

Gly Val Gln Tyr Ser Tyr Ser Leu Phe His Leu Met
1               5                   10

<210> SEQ ID NO 573
<211> LENGTH: 13
<212> TYPE: PRT
<213> ORGANISM: Homo sapiens

<400> SEQUENCE: 573

Gly Val Gln Tyr Ser Tyr Ser Leu Phe His Leu Met Leu
1               5                   10

<210> SEQ ID NO 574
<211> LENGTH: 15
<212> TYPE: PRT
<213> ORGANISM: Homo sapiens

<400> SEQUENCE: 574

Ser Ile Ile Ser Ile His Pro Lys Ile Gln Glu His Gln Pro Arg
1               5                   10                  15

<210> SEQ ID NO 575
<211> LENGTH: 13
<212> TYPE: PRT
<213> ORGANISM: Homo sapiens

<400> SEQUENCE: 575

Ser Ser Ile Arg Thr Ser Thr Asn Ser Gln Val Asp Lys
1               5                   10
```

```
<210> SEQ ID NO 576
<211> LENGTH: 12
<212> TYPE: PRT
<213> ORGANISM: Homo sapiens

<400> SEQUENCE: 576

Val Leu Val Gly Tyr Lys Ala Val Tyr Arg Ile Ser
1               5                   10

<210> SEQ ID NO 577
<211> LENGTH: 14
<212> TYPE: PRT
<213> ORGANISM: Homo sapiens

<400> SEQUENCE: 577

Tyr Ser Ser Ile Arg Thr Ser Thr Asn Ser Gln Val Asp Lys
1               5                   10

<210> SEQ ID NO 578
<211> LENGTH: 18
<212> TYPE: PRT
<213> ORGANISM: Homo sapiens

<400> SEQUENCE: 578

Gly Gly Gly Tyr Gly Ser Gly Gly Ser Gly Gly Tyr Gly Ser Arg
1               5                   10                  15

Arg Phe

<210> SEQ ID NO 579
<211> LENGTH: 12
<212> TYPE: PRT
<213> ORGANISM: Homo sapiens

<400> SEQUENCE: 579

Gly Gly Ser Phe Gly Gly Arg Ser Ser Gly Ser Pro
1               5                   10

<210> SEQ ID NO 580
<211> LENGTH: 13
<212> TYPE: PRT
<213> ORGANISM: Homo sapiens

<400> SEQUENCE: 580

Lys Gly Gly Ser Phe Gly Gly Arg Ser Ser Gly Ser Pro
1               5                   10

<210> SEQ ID NO 581
<211> LENGTH: 25
<212> TYPE: PRT
<213> ORGANISM: Homo sapiens

<400> SEQUENCE: 581

Ser Gly Gln Gln Gln Ser Asn Tyr Gly Pro Met Lys Gly Gly Ser Phe
1               5                   10                  15

Gly Gly Arg Ser Ser Gly Ser Pro Tyr
            20                  25

<210> SEQ ID NO 582
<211> LENGTH: 23
<212> TYPE: PRT
<213> ORGANISM: Homo sapiens

<400> SEQUENCE: 582

Ser Gly Ser Pro Tyr Gly Gly Gly Tyr Gly Ser Gly Gly Gly Ser Gly
```

```
                1               5                   10                  15

Gly Tyr Gly Ser Arg Arg Phe
            20

<210> SEQ ID NO 583
<211> LENGTH: 21
<212> TYPE: PRT
<213> ORGANISM: Homo sapiens

<400> SEQUENCE: 583

Ser Pro Tyr Gly Gly Tyr Gly Ser Gly Gly Ser Gly Tyr
1               5                   10                  15

Gly Ser Arg Arg Phe
            20

<210> SEQ ID NO 584
<211> LENGTH: 19
<212> TYPE: PRT
<213> ORGANISM: Homo sapiens

<400> SEQUENCE: 584

Tyr Gly Gly Gly Tyr Gly Ser Gly Gly Ser Gly Gly Tyr Gly Ser
1               5                   10                  15

Arg Arg Phe

<210> SEQ ID NO 585
<211> LENGTH: 12
<212> TYPE: PRT
<213> ORGANISM: Homo sapiens

<400> SEQUENCE: 585

Gly Asn Arg Ile Asn Glu Phe Ser Ile Ser Ser Phe
1               5                   10

<210> SEQ ID NO 586
<211> LENGTH: 14
<212> TYPE: PRT
<213> ORGANISM: Homo sapiens

<400> SEQUENCE: 586

His Gly Asn Gln Ile Thr Ser Asp Lys Val Gly Arg Lys Val
1               5                   10

<210> SEQ ID NO 587
<211> LENGTH: 14
<212> TYPE: PRT
<213> ORGANISM: Homo sapiens

<400> SEQUENCE: 587

Ile Pro Pro Val Asn Thr Asn Leu Glu Asn Leu Tyr Leu Gln
1               5                   10

<210> SEQ ID NO 588
<211> LENGTH: 13
<212> TYPE: PRT
<213> ORGANISM: Homo sapiens

<400> SEQUENCE: 588

Leu Gln Val Leu Arg Leu Asp Gly Asn Glu Ile Lys Arg
1               5                   10

<210> SEQ ID NO 589
<211> LENGTH: 14
```

```
<212> TYPE: PRT
<213> ORGANISM: Homo sapiens

<400> SEQUENCE: 589

Leu Gln Val Leu Arg Leu Asp Gly Asn Glu Ile Lys Arg Ser
1               5                  10

<210> SEQ ID NO 590
<211> LENGTH: 15
<212> TYPE: PRT
<213> ORGANISM: Homo sapiens

<400> SEQUENCE: 590

Leu Gln Val Leu Arg Leu Asp Gly Asn Glu Ile Lys Arg Ser Ala
1               5                  10                  15

<210> SEQ ID NO 591
<211> LENGTH: 16
<212> TYPE: PRT
<213> ORGANISM: Homo sapiens

<400> SEQUENCE: 591

Leu Arg Glu Leu His Leu Asp His Asn Gln Ile Ser Arg Val Pro Asn
1               5                  10                  15

<210> SEQ ID NO 592
<211> LENGTH: 14
<212> TYPE: PRT
<213> ORGANISM: Homo sapiens

<400> SEQUENCE: 592

Leu Tyr Val Arg Leu Ser His Asn Ser Leu Thr Asn Asn Gly
1               5                  10

<210> SEQ ID NO 593
<211> LENGTH: 14
<212> TYPE: PRT
<213> ORGANISM: Homo sapiens

<400> SEQUENCE: 593

Val Pro Ser Arg Met Lys Tyr Val Tyr Phe Gln Asn Asn Gln
1               5                  10

<210> SEQ ID NO 594
<211> LENGTH: 16
<212> TYPE: PRT
<213> ORGANISM: Homo sapiens

<400> SEQUENCE: 594

Val Pro Ser Arg Met Lys Tyr Val Tyr Phe Gln Asn Asn Gln Ile Thr
1               5                  10                  15

<210> SEQ ID NO 595
<211> LENGTH: 17
<212> TYPE: PRT
<213> ORGANISM: Homo sapiens

<400> SEQUENCE: 595

Val Pro Ser Arg Met Lys Tyr Val Tyr Phe Gln Asn Asn Gln Ile Thr
1               5                  10                  15

Ser

<210> SEQ ID NO 596
<211> LENGTH: 12
```

-continued

<212> TYPE: PRT
<213> ORGANISM: Homo sapiens

<400> SEQUENCE: 596

Trp Ile Ala Leu His Gly Asn Gln Ile Thr Ser Asp
1               5                   10

<210> SEQ ID NO 597
<211> LENGTH: 13
<212> TYPE: PRT
<213> ORGANISM: Homo sapiens

<400> SEQUENCE: 597

Trp Ile Ala Leu His Gly Asn Gln Ile Thr Ser Asp Lys
1               5                   10

<210> SEQ ID NO 598
<211> LENGTH: 15
<212> TYPE: PRT
<213> ORGANISM: Homo sapiens

<400> SEQUENCE: 598

Ala Asp Asp Asn Val Ser Phe Arg Trp Glu Ala Leu Gly Asn Thr
1               5                   10                  15

<210> SEQ ID NO 599
<211> LENGTH: 16
<212> TYPE: PRT
<213> ORGANISM: Homo sapiens

<400> SEQUENCE: 599

Ala Asp Asp Asn Val Ser Phe Arg Trp Glu Ala Leu Gly Asn Thr Leu
1               5                   10                  15

<210> SEQ ID NO 600
<211> LENGTH: 17
<212> TYPE: PRT
<213> ORGANISM: Homo sapiens

<400> SEQUENCE: 600

Asp Ala Asp Asp Asn Val Ser Phe Arg Trp Glu Ala Leu Gly Asn Thr
1               5                   10                  15
Leu

<210> SEQ ID NO 601
<211> LENGTH: 14
<212> TYPE: PRT
<213> ORGANISM: Homo sapiens

<400> SEQUENCE: 601

Asp Asp Asn Val Ser Phe Arg Trp Glu Ala Leu Gly Asn Thr
1               5                   10

<210> SEQ ID NO 602
<211> LENGTH: 15
<212> TYPE: PRT
<213> ORGANISM: Homo sapiens

<400> SEQUENCE: 602

Asp Asp Asn Val Ser Phe Arg Trp Glu Ala Leu Gly Asn Thr Leu
1               5                   10                  15

<210> SEQ ID NO 603
<211> LENGTH: 13

```
<212> TYPE: PRT
<213> ORGANISM: Homo sapiens

<400> SEQUENCE: 603

Asp Asn Val Ser Phe Arg Trp Glu Ala Leu Gly Asn Thr
1               5                   10

<210> SEQ ID NO 604
<211> LENGTH: 14
<212> TYPE: PRT
<213> ORGANISM: Homo sapiens

<400> SEQUENCE: 604

Asp Asn Val Ser Phe Arg Trp Glu Ala Leu Gly Asn Thr Leu
1               5                   10

<210> SEQ ID NO 605
<211> LENGTH: 15
<212> TYPE: PRT
<213> ORGANISM: Homo sapiens

<400> SEQUENCE: 605

Asp Asn Val Ser Phe Arg Trp Glu Ala Leu Gly Asn Thr Leu Ser
1               5                   10                  15

<210> SEQ ID NO 606
<211> LENGTH: 16
<212> TYPE: PRT
<213> ORGANISM: Homo sapiens

<400> SEQUENCE: 606

Asp Thr Gly Ser Tyr Arg Ala Gln Ile Ser Thr Lys Thr Ser Ala Lys
1               5                   10                  15

<210> SEQ ID NO 607
<211> LENGTH: 17
<212> TYPE: PRT
<213> ORGANISM: Homo sapiens

<400> SEQUENCE: 607

Asp Thr Gly Ser Tyr Arg Ala Gln Ile Ser Thr Lys Thr Ser Ala Lys
1               5                   10                  15

Leu

<210> SEQ ID NO 608
<211> LENGTH: 13
<212> TYPE: PRT
<213> ORGANISM: Homo sapiens

<400> SEQUENCE: 608

Asp Thr Ile Thr Ile Tyr Ser Thr Ile Asn His Ser Lys
1               5                   10

<210> SEQ ID NO 609
<211> LENGTH: 17
<212> TYPE: PRT
<213> ORGANISM: Homo sapiens

<400> SEQUENCE: 609

Glu Asp Thr Gly Ser Tyr Arg Ala Gln Ile Ser Thr Lys Thr Ser Ala
1               5                   10                  15

Lys
```

```
<210> SEQ ID NO 610
<211> LENGTH: 15
<212> TYPE: PRT
<213> ORGANISM: Homo sapiens

<400> SEQUENCE: 610

Glu Asn Asp Thr Ile Thr Ile Tyr Ser Thr Ile Asn His Ser Lys
1               5                   10                  15

<210> SEQ ID NO 611
<211> LENGTH: 20
<212> TYPE: PRT
<213> ORGANISM: Homo sapiens

<400> SEQUENCE: 611

Glu Asn Asp Thr Ile Thr Ile Tyr Ser Thr Ile Asn His Ser Lys Glu
1               5                   10                  15

Ser Lys Pro Thr
            20

<210> SEQ ID NO 612
<211> LENGTH: 14
<212> TYPE: PRT
<213> ORGANISM: Homo sapiens

<400> SEQUENCE: 612

Gly Ser Tyr Arg Ala Gln Ile Ser Thr Lys Thr Ser Ala Lys
1               5                   10

<210> SEQ ID NO 613
<211> LENGTH: 12
<212> TYPE: PRT
<213> ORGANISM: Homo sapiens

<400> SEQUENCE: 613

Asn Asp Thr Ile Thr Ile Tyr Ser Thr Ile Asn His
1               5                   10

<210> SEQ ID NO 614
<211> LENGTH: 13
<212> TYPE: PRT
<213> ORGANISM: Homo sapiens

<400> SEQUENCE: 614

Asn Asp Thr Ile Thr Ile Tyr Ser Thr Ile Asn His Ser
1               5                   10

<210> SEQ ID NO 615
<211> LENGTH: 14
<212> TYPE: PRT
<213> ORGANISM: Homo sapiens

<400> SEQUENCE: 615

Asn Asp Thr Ile Thr Ile Tyr Ser Thr Ile Asn His Ser Lys
1               5                   10

<210> SEQ ID NO 616
<211> LENGTH: 13
<212> TYPE: PRT
<213> ORGANISM: Homo sapiens

<400> SEQUENCE: 616

Asn Val Ser Phe Arg Trp Glu Ala Leu Gly Asn Thr Leu
1               5                   10
```

```
<210> SEQ ID NO 617
<211> LENGTH: 18
<212> TYPE: PRT
<213> ORGANISM: Homo sapiens

<400> SEQUENCE: 617

Ser Pro Thr Asn Asn Thr Val Tyr Ala Ser Val Thr His Ser Asn Arg
1               5                   10                  15

Glu Thr

<210> SEQ ID NO 618
<211> LENGTH: 15
<212> TYPE: PRT
<213> ORGANISM: Homo sapiens

<400> SEQUENCE: 618

Thr Gly Ser Tyr Arg Ala Gln Ile Ser Thr Lys Thr Ser Ala Lys
1               5                   10                  15

<210> SEQ ID NO 619
<211> LENGTH: 18
<212> TYPE: PRT
<213> ORGANISM: Homo sapiens

<400> SEQUENCE: 619

Thr Pro Arg Glu Asn Asp Thr Ile Thr Ile Tyr Ser Thr Ile Asn His
1               5                   10                  15

Ser Lys

<210> SEQ ID NO 620
<211> LENGTH: 23
<212> TYPE: PRT
<213> ORGANISM: Homo sapiens

<400> SEQUENCE: 620

Thr Pro Arg Glu Asn Asp Thr Ile Thr Ile Tyr Ser Thr Ile Asn His
1               5                   10                  15

Ser Lys Glu Ser Lys Pro Thr
            20

<210> SEQ ID NO 621
<211> LENGTH: 12
<212> TYPE: PRT
<213> ORGANISM: Homo sapiens

<400> SEQUENCE: 621

Val Ser Phe Arg Trp Glu Ala Leu Gly Asn Thr Leu
1               5                   10

<210> SEQ ID NO 622
<211> LENGTH: 15
<212> TYPE: PRT
<213> ORGANISM: Homo sapiens

<400> SEQUENCE: 622

Ala Pro Ile His Phe Thr Ile Glu Lys Leu Glu Leu Asn Glu Lys
1               5                   10                  15

<210> SEQ ID NO 623
<211> LENGTH: 13
<212> TYPE: PRT
<213> ORGANISM: Homo sapiens
```

```
<400> SEQUENCE: 623

Asp Ala Gln Phe Glu Val Ile Lys Gly Gln Thr Ile Glu
1               5                   10

<210> SEQ ID NO 624
<211> LENGTH: 15
<212> TYPE: PRT
<213> ORGANISM: Homo sapiens

<400> SEQUENCE: 624

Asp Ala Gln Phe Glu Val Ile Lys Gly Gln Thr Ile Glu Val Arg
1               5                   10                  15

<210> SEQ ID NO 625
<211> LENGTH: 15
<212> TYPE: PRT
<213> ORGANISM: Homo sapiens

<400> SEQUENCE: 625

Glu Ser Tyr Phe Ile Pro Glu Val Arg Ile Tyr Asp Ser Gly Thr
1               5                   10                  15

<210> SEQ ID NO 626
<211> LENGTH: 12
<212> TYPE: PRT
<213> ORGANISM: Homo sapiens

<400> SEQUENCE: 626

Ile Pro Glu Val Arg Ile Tyr Asp Ser Gly Thr Tyr
1               5                   10

<210> SEQ ID NO 627
<211> LENGTH: 14
<212> TYPE: PRT
<213> ORGANISM: Homo sapiens

<400> SEQUENCE: 627

Lys Asp Lys Ala Ile Val Ala His Asn Arg His Gly Asn Lys
1               5                   10

<210> SEQ ID NO 628
<211> LENGTH: 15
<212> TYPE: PRT
<213> ORGANISM: Homo sapiens

<400> SEQUENCE: 628

Lys Asp Lys Ala Ile Val Ala His Asn Arg His Gly Asn Lys Ala
1               5                   10                  15

<210> SEQ ID NO 629
<211> LENGTH: 14
<212> TYPE: PRT
<213> ORGANISM: Homo sapiens

<400> SEQUENCE: 629

Asn Phe Val Ile Leu Glu Phe Pro Val Glu Glu Gln Asp Arg
1               5                   10

<210> SEQ ID NO 630
<211> LENGTH: 15
<212> TYPE: PRT
<213> ORGANISM: Homo sapiens

<400> SEQUENCE: 630
```

Ser Gln Pro Arg Ile Ser Tyr Asp Ala Gln Phe Glu Val Ile Lys
1               5                   10                  15

<210> SEQ ID NO 631
<211> LENGTH: 16
<212> TYPE: PRT
<213> ORGANISM: Homo sapiens

<400> SEQUENCE: 631

Ser Gln Pro Arg Ile Ser Tyr Asp Ala Gln Phe Glu Val Ile Lys Gly
1               5                   10                  15

<210> SEQ ID NO 632
<211> LENGTH: 14
<212> TYPE: PRT
<213> ORGANISM: Homo sapiens

<400> SEQUENCE: 632

Tyr Asp Ala Gln Phe Glu Val Ile Lys Gly Gln Thr Ile Glu
1               5                   10

<210> SEQ ID NO 633
<211> LENGTH: 14
<212> TYPE: PRT
<213> ORGANISM: Homo sapiens

<400> SEQUENCE: 633

Gly Asn Pro Ala Tyr Arg Ser Phe Ser Asn Ser Leu Ser Gln
1               5                   10

<210> SEQ ID NO 634
<211> LENGTH: 16
<212> TYPE: PRT
<213> ORGANISM: Homo sapiens

<400> SEQUENCE: 634

Gly Pro Pro Gly Glu Ala Gly Tyr Lys Ala Phe Ser Ser Leu Leu Ala
1               5                   10                  15

<210> SEQ ID NO 635
<211> LENGTH: 18
<212> TYPE: PRT
<213> ORGANISM: Homo sapiens

<400> SEQUENCE: 635

Gly Pro Pro Gly Glu Ala Gly Tyr Lys Ala Phe Ser Ser Leu Leu Ala
1               5                   10                  15

Ser Ser

<210> SEQ ID NO 636
<211> LENGTH: 19
<212> TYPE: PRT
<213> ORGANISM: Homo sapiens

<400> SEQUENCE: 636

Gly Pro Pro Gly Glu Ala Gly Tyr Lys Ala Phe Ser Ser Leu Leu Ala
1               5                   10                  15

Ser Ser Ala

<210> SEQ ID NO 637
<211> LENGTH: 23
<212> TYPE: PRT
<213> ORGANISM: Homo sapiens -continued

<400> SEQUENCE: 637

Gly Pro Pro Gly Glu Ala Gly Tyr Lys Ala Phe Ser Ser Leu Leu Ala
1               5                   10                  15

Ser Ser Ala Val Ser Pro Glu
            20

<210> SEQ ID NO 638
<211> LENGTH: 24
<212> TYPE: PRT
<213> ORGANISM: Homo sapiens

<400> SEQUENCE: 638

Gly Pro Pro Gly Glu Ala Gly Tyr Lys Ala Phe Ser Ser Leu Leu Ala
1               5                   10                  15

Ser Ser Ala Val Ser Pro Glu Lys
            20

<210> SEQ ID NO 639
<211> LENGTH: 16
<212> TYPE: PRT
<213> ORGANISM: Homo sapiens

<400> SEQUENCE: 639

Gly Tyr Lys Ala Phe Ser Ser Leu Leu Ala Ser Ser Ala Val Ser Pro
1               5                   10                  15

<210> SEQ ID NO 640
<211> LENGTH: 17
<212> TYPE: PRT
<213> ORGANISM: Homo sapiens

<400> SEQUENCE: 640

Gly Tyr Lys Ala Phe Ser Ser Leu Leu Ala Ser Ser Ala Val Ser Pro
1               5                   10                  15

Glu

<210> SEQ ID NO 641
<211> LENGTH: 15
<212> TYPE: PRT
<213> ORGANISM: Homo sapiens

<400> SEQUENCE: 641

Lys Ala Phe Ser Ser Leu Leu Ala Ser Ser Ala Val Ser Pro Glu
1               5                   10                  15

<210> SEQ ID NO 642
<211> LENGTH: 13
<212> TYPE: PRT
<213> ORGANISM: Homo sapiens

<400> SEQUENCE: 642

Asn Pro Ala Tyr Arg Ser Phe Ser Asn Ser Leu Ser Gln
1               5                   10

<210> SEQ ID NO 643
<211> LENGTH: 15
<212> TYPE: PRT
<213> ORGANISM: Homo sapiens

<400> SEQUENCE: 643

Ser Arg Asp Asp Phe Gln Glu Gly Arg Glu Gly Ile Val Ala Arg
1               5                   10                  15

<210> SEQ ID NO 644
<211> LENGTH: 13
<212> TYPE: PRT
<213> ORGANISM: Homo sapiens

<400> SEQUENCE: 644

Ser Ser Ser Ser Phe His Pro Ala Pro Gly Asn Ala Gln
1               5                   10

<210> SEQ ID NO 645
<211> LENGTH: 12
<212> TYPE: PRT
<213> ORGANISM: Homo sapiens

<400> SEQUENCE: 645

Val Ala Arg Leu Thr Glu Ser Leu Phe Leu Asp Leu
1               5                   10

<210> SEQ ID NO 646
<211> LENGTH: 14
<212> TYPE: PRT
<213> ORGANISM: Homo sapiens

<400> SEQUENCE: 646

Val Ala Arg Leu Thr Glu Ser Leu Phe Leu Asp Leu Leu Gly
1               5                   10

<210> SEQ ID NO 647
<211> LENGTH: 13
<212> TYPE: PRT
<213> ORGANISM: Homo sapiens

<400> SEQUENCE: 647

Val Ile Ala Gly Asn Pro Ala Tyr Arg Ser Phe Ser Asn
1               5                   10

<210> SEQ ID NO 648
<211> LENGTH: 19
<212> TYPE: PRT
<213> ORGANISM: Homo sapiens

<400> SEQUENCE: 648

Val Pro Gln Pro Glu Pro Glu Thr Trp Glu Gln Ile Leu Arg Arg Asn
1               5                   10                  15

Val Leu Gln

<210> SEQ ID NO 649
<211> LENGTH: 14
<212> TYPE: PRT
<213> ORGANISM: Homo sapiens

<400> SEQUENCE: 649

Tyr Lys Ala Phe Ser Ser Leu Leu Ala Ser Ser Ala Val Ser
1               5                   10

<210> SEQ ID NO 650
<211> LENGTH: 15
<212> TYPE: PRT
<213> ORGANISM: Homo sapiens

<400> SEQUENCE: 650

Tyr Lys Ala Phe Ser Ser Leu Leu Ala Ser Ser Ala Val Ser Pro
1               5                   10                  15

<210> SEQ ID NO 651
<211> LENGTH: 16
<212> TYPE: PRT
<213> ORGANISM: Homo sapiens

<400> SEQUENCE: 651

Tyr Lys Ala Phe Ser Ser Leu Leu Ala Ser Ser Ala Val Ser Pro Glu
1               5                   10                  15

<210> SEQ ID NO 652
<211> LENGTH: 17
<212> TYPE: PRT
<213> ORGANISM: Homo sapiens

<400> SEQUENCE: 652

Gly Asn Gln Val Phe Ser Tyr Thr Ala Asn Lys Glu Ile Arg Thr Asp
1               5                   10                  15

Asp

<210> SEQ ID NO 653
<211> LENGTH: 14
<212> TYPE: PRT
<213> ORGANISM: Homo sapiens

<400> SEQUENCE: 653

Ile Glu Glu Ile Val Leu Val Asp Asp Ala Ser Glu Arg Asp
1               5                   10

<210> SEQ ID NO 654
<211> LENGTH: 15
<212> TYPE: PRT
<213> ORGANISM: Homo sapiens

<400> SEQUENCE: 654

Ile Glu Glu Ile Val Leu Val Asp Asp Ala Ser Glu Arg Asp Phe
1               5                   10                  15

<210> SEQ ID NO 655
<211> LENGTH: 13
<212> TYPE: PRT
<213> ORGANISM: Homo sapiens

<400> SEQUENCE: 655

Leu Glu Asn Ile Tyr Pro Asp Ser Gln Ile Pro Arg His
1               5                   10

<210> SEQ ID NO 656
<211> LENGTH: 14
<212> TYPE: PRT
<213> ORGANISM: Homo sapiens

<400> SEQUENCE: 656

Leu Glu Asn Ile Tyr Pro Asp Ser Gln Ile Pro Arg His Tyr
1               5                   10

<210> SEQ ID NO 657
<211> LENGTH: 13
<212> TYPE: PRT
<213> ORGANISM: Homo sapiens

<400> SEQUENCE: 657

Asn Gln Val Phe Ser Tyr Thr Ala Asn Lys Glu Ile Arg
1               5                   10

<210> SEQ ID NO 658
<211> LENGTH: 14
<212> TYPE: PRT
<213> ORGANISM: Homo sapiens

<400> SEQUENCE: 658

Asn Gln Val Phe Ser Tyr Thr Ala Asn Lys Glu Ile Arg Thr
1               5                   10

<210> SEQ ID NO 659
<211> LENGTH: 16
<212> TYPE: PRT
<213> ORGANISM: Homo sapiens

<400> SEQUENCE: 659

Asn Gln Val Phe Ser Tyr Thr Ala Asn Lys Glu Ile Arg Thr Asp Asp
1               5                   10                  15

<210> SEQ ID NO 660
<211> LENGTH: 15
<212> TYPE: PRT
<213> ORGANISM: Homo sapiens

<400> SEQUENCE: 660

Val His Ser Val Ile Asn Arg Ser Pro Arg His Met Ile Glu Glu
1               5                   10                  15

<210> SEQ ID NO 661
<211> LENGTH: 12
<212> TYPE: PRT
<213> ORGANISM: Homo sapiens

<400> SEQUENCE: 661

Glu Tyr Val Ser Leu Tyr His Gln Pro Ala Ala Met
1               5                   10

<210> SEQ ID NO 662
<211> LENGTH: 16
<212> TYPE: PRT
<213> ORGANISM: Homo sapiens

<400> SEQUENCE: 662

Ile Lys Ala Glu Tyr Lys Gly Arg Val Thr Leu Lys Gln Tyr Pro Arg
1               5                   10                  15

<210> SEQ ID NO 663
<211> LENGTH: 15
<212> TYPE: PRT
<213> ORGANISM: Homo sapiens

<400> SEQUENCE: 663

Leu Asn Val His Ser Glu Tyr Glu Pro Ser Trp Glu Glu Gln Pro
1               5                   10                  15

<210> SEQ ID NO 664
<211> LENGTH: 14
<212> TYPE: PRT
<213> ORGANISM: Homo sapiens

<400> SEQUENCE: 664

Leu Pro Tyr Leu Phe Gln Met Pro Ala Tyr Ala Ser Ser Ser
1               5                   10

<210> SEQ ID NO 665

```
<211> LENGTH: 15
<212> TYPE: PRT
<213> ORGANISM: Homo sapiens

<400> SEQUENCE: 665

Leu Pro Tyr Leu Phe Gln Met Pro Ala Tyr Ala Ser Ser Ser Lys
1               5                   10                  15

<210> SEQ ID NO 666
<211> LENGTH: 12
<212> TYPE: PRT
<213> ORGANISM: Homo sapiens

<400> SEQUENCE: 666

Asn Phe Ile Lys Ala Glu Tyr Lys Gly Arg Val Thr
1               5                   10

<210> SEQ ID NO 667
<211> LENGTH: 13
<212> TYPE: PRT
<213> ORGANISM: Homo sapiens

<400> SEQUENCE: 667

Thr Asn Phe Ile Lys Ala Glu Tyr Lys Gly Arg Val Thr
1               5                   10

<210> SEQ ID NO 668
<211> LENGTH: 14
<212> TYPE: PRT
<213> ORGANISM: Homo sapiens

<400> SEQUENCE: 668

Thr Thr Asn Phe Ile Lys Ala Glu Tyr Lys Gly Arg Val Thr
1               5                   10

<210> SEQ ID NO 669
<211> LENGTH: 17
<212> TYPE: PRT
<213> ORGANISM: Homo sapiens

<400> SEQUENCE: 669

Val Thr Leu Asn Val His Ser Glu Tyr Glu Pro Ser Trp Glu Glu Gln
1               5                   10                  15

Pro

<210> SEQ ID NO 670
<211> LENGTH: 19
<212> TYPE: PRT
<213> ORGANISM: Homo sapiens

<400> SEQUENCE: 670

Tyr Pro Arg Lys Asn Leu Phe Leu Val Glu Val Thr Gln Leu Thr Glu
1               5                   10                  15

Ser Asp Ser

<210> SEQ ID NO 671
<211> LENGTH: 20
<212> TYPE: PRT
<213> ORGANISM: Homo sapiens

<400> SEQUENCE: 671

Tyr Pro Arg Lys Asn Leu Phe Leu Val Glu Val Thr Gln Leu Thr Glu
1               5                   10                  15
```

Ser Asp Ser Gly
            20

<210> SEQ ID NO 672
<211> LENGTH: 12
<212> TYPE: PRT
<213> ORGANISM: Homo sapiens

<400> SEQUENCE: 672

Ala Asp Leu Ser Ser Phe Lys Ser Gln Glu Leu Asn
1               5                   10

<210> SEQ ID NO 673
<211> LENGTH: 14
<212> TYPE: PRT
<213> ORGANISM: Homo sapiens

<400> SEQUENCE: 673

Ala Asp Leu Ser Ser Phe Lys Ser Gln Glu Leu Asn Glu Arg
1               5                   10

<210> SEQ ID NO 674
<211> LENGTH: 15
<212> TYPE: PRT
<213> ORGANISM: Homo sapiens

<400> SEQUENCE: 674

Ala Asp Leu Ser Ser Phe Lys Ser Gln Glu Leu Asn Glu Arg Asn
1               5                   10                  15

<210> SEQ ID NO 675
<211> LENGTH: 16
<212> TYPE: PRT
<213> ORGANISM: Homo sapiens

<400> SEQUENCE: 675

Ala Asp Leu Ser Ser Phe Lys Ser Gln Glu Leu Asn Glu Arg Asn Glu
1               5                   10                  15

<210> SEQ ID NO 676
<211> LENGTH: 17
<212> TYPE: PRT
<213> ORGANISM: Homo sapiens

<400> SEQUENCE: 676

Ala Asp Leu Ser Ser Phe Lys Ser Gln Glu Leu Asn Glu Arg Asn Glu
1               5                   10                  15

Ala

<210> SEQ ID NO 677
<211> LENGTH: 19
<212> TYPE: PRT
<213> ORGANISM: Homo sapiens

<400> SEQUENCE: 677

Ala Glu Gln Gln Arg Leu Lys Ser Gln Asp Leu Glu Leu Ser Trp Asn
1               5                   10                  15

Leu Asn Gly

<210> SEQ ID NO 678
<211> LENGTH: 15
<212> TYPE: PRT
<213> ORGANISM: Homo sapiens

```
<400> SEQUENCE: 678

Glu Gln Gln Arg Leu Lys Ser Gln Asp Leu Glu Leu Ser Trp Asn
1               5                   10                  15

<210> SEQ ID NO 679
<211> LENGTH: 14
<212> TYPE: PRT
<213> ORGANISM: Homo sapiens

<400> SEQUENCE: 679

Ile Ser Gln Glu Leu Glu Glu Leu Arg Ala Glu Gln Gln Arg
1               5                   10

<210> SEQ ID NO 680
<211> LENGTH: 16
<212> TYPE: PRT
<213> ORGANISM: Homo sapiens

<400> SEQUENCE: 680

Ile Ser Gln Glu Leu Glu Glu Leu Arg Ala Glu Gln Gln Arg Leu Lys
1               5                   10                  15

<210> SEQ ID NO 681
<211> LENGTH: 12
<212> TYPE: PRT
<213> ORGANISM: Homo sapiens

<400> SEQUENCE: 681

Lys Gly Thr Lys Gln Trp Val His Ala Arg Tyr Ala
1               5                   10

<210> SEQ ID NO 682
<211> LENGTH: 15
<212> TYPE: PRT
<213> ORGANISM: Homo sapiens

<400> SEQUENCE: 682

Gln Ala Asp Leu Ser Ser Phe Lys Ser Gln Glu Leu Asn Glu Arg
1               5                   10                  15

<210> SEQ ID NO 683
<211> LENGTH: 15
<212> TYPE: PRT
<213> ORGANISM: Homo sapiens

<400> SEQUENCE: 683

Ser Trp Asn Leu Asn Gly Leu Gln Ala Asp Leu Ser Ser Phe Lys
1               5                   10                  15

<210> SEQ ID NO 684
<211> LENGTH: 14
<212> TYPE: PRT
<213> ORGANISM: Homo sapiens

<400> SEQUENCE: 684

Thr Gly Ser Trp Ile Gly Leu Arg Asn Leu Asp Leu Lys Gly
1               5                   10

<210> SEQ ID NO 685
<211> LENGTH: 23
<212> TYPE: PRT
<213> ORGANISM: Homo sapiens

<400> SEQUENCE: 685
```

```
Phe Gly Asn Tyr Asn Asn Gln Ser Ser Asn Phe Gly Pro Met Lys Gly
1               5                   10                  15

Gly Asn Phe Gly Gly Arg Ser
            20
```

<210> SEQ ID NO 686
<211> LENGTH: 23
<212> TYPE: PRT
<213> ORGANISM: Homo sapiens

<400> SEQUENCE: 686

```
Phe Gly Pro Met Lys Gly Gly Asn Phe Gly Gly Arg Ser Ser Gly Pro
1               5                   10                  15

Tyr Gly Gly Gly Gly Gln Tyr
            20
```

<210> SEQ ID NO 687
<211> LENGTH: 15
<212> TYPE: PRT
<213> ORGANISM: Homo sapiens

<400> SEQUENCE: 687

```
Gly Pro Met Lys Gly Gly Asn Phe Gly Gly Arg Ser Ser Gly Pro
1               5                   10                  15
```

<210> SEQ ID NO 688
<211> LENGTH: 13
<212> TYPE: PRT
<213> ORGANISM: Homo sapiens

<400> SEQUENCE: 688

```
Gly Pro Tyr Gly Gly Gly Gly Gln Tyr Phe Ala Lys Pro
1               5                   10
```

<210> SEQ ID NO 689
<211> LENGTH: 12
<212> TYPE: PRT
<213> ORGANISM: Homo sapiens

<400> SEQUENCE: 689

```
Lys Gly Gly Asn Phe Gly Gly Arg Ser Ser Gly Pro
1               5                   10
```

<210> SEQ ID NO 690
<211> LENGTH: 15
<212> TYPE: PRT
<213> ORGANISM: Homo sapiens

<400> SEQUENCE: 690

```
Asn Asp Phe Gly Asn Tyr Asn Asn Gln Ser Ser Asn Phe Gly Pro
1               5                   10                  15
```

<210> SEQ ID NO 691
<211> LENGTH: 14
<212> TYPE: PRT
<213> ORGANISM: Homo sapiens

<400> SEQUENCE: 691

```
Ser Gly Pro Tyr Gly Gly Gly Gly Gln Tyr Phe Ala Lys Pro
1               5                   10
```

<210> SEQ ID NO 692
<211> LENGTH: 15
<212> TYPE: PRT

<213> ORGANISM: Homo sapiens

<400> SEQUENCE: 692

Asp Ala Gly Ser Tyr Lys Ala Gln Ile Asn Gln Arg Asn Phe Glu
1               5                   10                  15

<210> SEQ ID NO 693
<211> LENGTH: 17
<212> TYPE: PRT
<213> ORGANISM: Homo sapiens

<400> SEQUENCE: 693

Asp Ala Gly Ser Tyr Lys Ala Gln Ile Asn Gln Arg Asn Phe Glu Val
1               5                   10                  15

Thr

<210> SEQ ID NO 694
<211> LENGTH: 14
<212> TYPE: PRT
<213> ORGANISM: Homo sapiens

<400> SEQUENCE: 694

Asp Gly Glu Leu Ile Arg Thr Gln Pro Gln Arg Leu Pro Gln
1               5                   10

<210> SEQ ID NO 695
<211> LENGTH: 13
<212> TYPE: PRT
<213> ORGANISM: Homo sapiens

<400> SEQUENCE: 695

Gly Glu Leu Ile Arg Thr Gln Pro Gln Arg Leu Pro Gln
1               5                   10

<210> SEQ ID NO 696
<211> LENGTH: 16
<212> TYPE: PRT
<213> ORGANISM: Homo sapiens

<400> SEQUENCE: 696

Asn Pro Ser Asp Gly Glu Leu Ile Arg Thr Gln Pro Gln Arg Leu Pro
1               5                   10                  15

<210> SEQ ID NO 697
<211> LENGTH: 17
<212> TYPE: PRT
<213> ORGANISM: Homo sapiens

<400> SEQUENCE: 697

Asn Pro Ser Asp Gly Glu Leu Ile Arg Thr Gln Pro Gln Arg Leu Pro
1               5                   10                  15

Gln

<210> SEQ ID NO 698
<211> LENGTH: 18
<212> TYPE: PRT
<213> ORGANISM: Homo sapiens

<400> SEQUENCE: 698

Asn Pro Ser Asp Gly Glu Leu Ile Arg Thr Gln Pro Gln Arg Leu Pro
1               5                   10                  15

Gln Leu

```
<210> SEQ ID NO 699
<211> LENGTH: 15
<212> TYPE: PRT
<213> ORGANISM: Homo sapiens

<400> SEQUENCE: 699

Ala Ser Asn Asp Met Tyr His Ser Arg Ala Leu Gln Val Val Arg
1               5                   10                  15

<210> SEQ ID NO 700
<211> LENGTH: 16
<212> TYPE: PRT
<213> ORGANISM: Homo sapiens

<400> SEQUENCE: 700

Ala Ser Asn Asp Met Tyr His Ser Arg Ala Leu Gln Val Val Arg Ala
1               5                   10                  15

<210> SEQ ID NO 701
<211> LENGTH: 15
<212> TYPE: PRT
<213> ORGANISM: Homo sapiens

<400> SEQUENCE: 701

Glu Gly Val Arg Arg Ala Leu Asp Phe Ala Val Gly Glu Tyr Asn
1               5                   10                  15

<210> SEQ ID NO 702
<211> LENGTH: 16
<212> TYPE: PRT
<213> ORGANISM: Homo sapiens

<400> SEQUENCE: 702

Glu Gly Val Arg Arg Ala Leu Asp Phe Ala Val Gly Glu Tyr Asn Lys
1               5                   10                  15

<210> SEQ ID NO 703
<211> LENGTH: 14
<212> TYPE: PRT
<213> ORGANISM: Homo sapiens

<400> SEQUENCE: 703

Ser Asn Asp Met Tyr His Ser Arg Ala Leu Gln Val Val Arg
1               5                   10

<210> SEQ ID NO 704
<211> LENGTH: 13
<212> TYPE: PRT
<213> ORGANISM: Homo sapiens

<400> SEQUENCE: 704

Val Gly Glu Tyr Asn Lys Ala Ser Asn Asp Met Tyr His
1               5                   10

<210> SEQ ID NO 705
<211> LENGTH: 13
<212> TYPE: PRT
<213> ORGANISM: Homo sapiens

<400> SEQUENCE: 705

Val Arg Ala Arg Lys Gln Ile Val Ala Gly Val Asn Tyr
1               5                   10

<210> SEQ ID NO 706
```

<211> LENGTH: 18
<212> TYPE: PRT
<213> ORGANISM: Homo sapiens

<400> SEQUENCE: 706

Val Arg Arg Ala Leu Asp Phe Ala Val Gly Glu Tyr Asn Lys Ala Ser
1               5                   10                  15

Asn Asp

<210> SEQ ID NO 707
<211> LENGTH: 13
<212> TYPE: PRT
<213> ORGANISM: Homo sapiens

<400> SEQUENCE: 707

Val Val Arg Ala Arg Lys Gln Ile Val Ala Gly Val Asn
1               5                   10

<210> SEQ ID NO 708
<211> LENGTH: 14
<212> TYPE: PRT
<213> ORGANISM: Homo sapiens

<400> SEQUENCE: 708

Val Val Arg Ala Arg Lys Gln Ile Val Ala Gly Val Asn Tyr
1               5                   10

<210> SEQ ID NO 709
<211> LENGTH: 14
<212> TYPE: PRT
<213> ORGANISM: Homo sapiens

<400> SEQUENCE: 709

Ala Pro Leu Glu Gly Ala Arg Phe Ala Leu Val Arg Glu Asp
1               5                   10

<210> SEQ ID NO 710
<211> LENGTH: 16
<212> TYPE: PRT
<213> ORGANISM: Homo sapiens

<400> SEQUENCE: 710

Ala Pro Val Glu Leu Ile Leu Ser Asp Glu Thr Leu Pro Ala Pro Glu
1               5                   10                  15

<210> SEQ ID NO 711
<211> LENGTH: 13
<212> TYPE: PRT
<213> ORGANISM: Homo sapiens

<400> SEQUENCE: 711

Glu Leu Ile Leu Ser Asp Glu Thr Leu Pro Ala Pro Glu
1               5                   10

<210> SEQ ID NO 712
<211> LENGTH: 14
<212> TYPE: PRT
<213> ORGANISM: Homo sapiens

<400> SEQUENCE: 712

Leu Ala Pro Leu Glu Gly Ala Arg Phe Ala Leu Val Arg Glu
1               5                   10

<210> SEQ ID NO 713

```
<210> SEQ ID NO 713
<211> LENGTH: 15
<212> TYPE: PRT
<213> ORGANISM: Homo sapiens

<400> SEQUENCE: 713

Leu Ala Pro Leu Glu Gly Ala Arg Phe Ala Leu Val Arg Glu Asp
1               5                   10                  15

<210> SEQ ID NO 714
<211> LENGTH: 16
<212> TYPE: PRT
<213> ORGANISM: Homo sapiens

<400> SEQUENCE: 714

Arg Gly Glu Lys Glu Leu Leu Val Pro Arg Ser Ser Thr Ser Pro Asp
1               5                   10                  15

<210> SEQ ID NO 715
<211> LENGTH: 16
<212> TYPE: PRT
<213> ORGANISM: Homo sapiens

<400> SEQUENCE: 715

Ala Ser Lys Thr Phe Thr Thr Gln Glu Thr Ile Thr Asn Ala Glu Thr
1               5                   10                  15

<210> SEQ ID NO 716
<211> LENGTH: 15
<212> TYPE: PRT
<213> ORGANISM: Homo sapiens

<400> SEQUENCE: 716

Asp Gln His Phe Arg Thr Thr Pro Leu Glu Lys Asn Ala Pro Val
1               5                   10                  15

<210> SEQ ID NO 717
<211> LENGTH: 14
<212> TYPE: PRT
<213> ORGANISM: Homo sapiens

<400> SEQUENCE: 717

Asn Thr Pro Ile Leu Val Asp Gly Lys Asp Val Met Pro Glu
1               5                   10

<210> SEQ ID NO 718
<211> LENGTH: 15
<212> TYPE: PRT
<213> ORGANISM: Homo sapiens

<400> SEQUENCE: 718

Asn Thr Pro Ile Leu Val Asp Gly Lys Asp Val Met Pro Glu Val
1               5                   10                  15

<210> SEQ ID NO 719
<211> LENGTH: 16
<212> TYPE: PRT
<213> ORGANISM: Homo sapiens

<400> SEQUENCE: 719

Asn Thr Pro Ile Leu Val Asp Gly Lys Asp Val Met Pro Glu Val Asn
1               5                   10                  15

<210> SEQ ID NO 720
<211> LENGTH: 15
<212> TYPE: PRT
```

<213> ORGANISM: Homo sapiens

<400> SEQUENCE: 720

Ser Asn Thr Pro Ile Leu Val Asp Gly Lys Asp Val Met Pro Glu
1               5                   10                  15

<210> SEQ ID NO 721
<211> LENGTH: 17
<212> TYPE: PRT
<213> ORGANISM: Homo sapiens

<400> SEQUENCE: 721

Ser Asn Thr Pro Ile Leu Val Asp Gly Lys Asp Val Met Pro Glu Val
1               5                   10                  15

Asn

<210> SEQ ID NO 722
<211> LENGTH: 12
<212> TYPE: PRT
<213> ORGANISM: Homo sapiens

<400> SEQUENCE: 722

Thr Pro Ile Leu Val Asp Gly Lys Asp Val Met Pro
1               5                   10

<210> SEQ ID NO 723
<211> LENGTH: 13
<212> TYPE: PRT
<213> ORGANISM: Homo sapiens

<400> SEQUENCE: 723

Thr Pro Ile Leu Val Asp Gly Lys Asp Val Met Pro Glu
1               5                   10

<210> SEQ ID NO 724
<211> LENGTH: 14
<212> TYPE: PRT
<213> ORGANISM: Homo sapiens

<400> SEQUENCE: 724

Thr Pro Ile Leu Val Asp Gly Lys Asp Val Met Pro Glu Val
1               5                   10

<210> SEQ ID NO 725
<211> LENGTH: 15
<212> TYPE: PRT
<213> ORGANISM: Homo sapiens

<400> SEQUENCE: 725

Thr Pro Ile Leu Val Asp Gly Lys Asp Val Met Pro Glu Val Asn
1               5                   10                  15

<210> SEQ ID NO 726
<211> LENGTH: 15
<212> TYPE: PRT
<213> ORGANISM: Homo sapiens

<400> SEQUENCE: 726

Gly Pro Leu Lys Phe Leu His Gln Asp Ile Asp Ser Gly Gln Gly
1               5                   10                  15

<210> SEQ ID NO 727
<211> LENGTH: 17
<212> TYPE: PRT

<213> ORGANISM: Homo sapiens

<400> SEQUENCE: 727

Gly Pro Leu Lys Phe Leu His Gln Asp Ile Asp Ser Gly Gln Gly Ile
1               5                   10                  15
Arg

<210> SEQ ID NO 728
<211> LENGTH: 13
<212> TYPE: PRT
<213> ORGANISM: Homo sapiens

<400> SEQUENCE: 728

Leu Gly Asp Ile Tyr Phe Lys Leu Phe Arg Ala Ser Gly
1               5                   10

<210> SEQ ID NO 729
<211> LENGTH: 15
<212> TYPE: PRT
<213> ORGANISM: Homo sapiens

<400> SEQUENCE: 729

Thr Gly His Leu Phe Asp Leu Ser Ser Leu Ser Gly Arg Ala Gly
1               5                   10                  15

<210> SEQ ID NO 730
<211> LENGTH: 16
<212> TYPE: PRT
<213> ORGANISM: Homo sapiens

<400> SEQUENCE: 730

Val Pro Ser Pro Val Asp Cys Gln Val Thr Asp Leu Ala Gly Asn Glu
1               5                   10                  15

<210> SEQ ID NO 731
<211> LENGTH: 18
<212> TYPE: PRT
<213> ORGANISM: Homo sapiens

<400> SEQUENCE: 731

Asp Gly Leu Asn Ser Leu Thr Tyr Gln Val Leu Asp Val Gln Arg Tyr
1               5                   10                  15
Pro Leu

<210> SEQ ID NO 732
<211> LENGTH: 14
<212> TYPE: PRT
<213> ORGANISM: Homo sapiens

<400> SEQUENCE: 732

His Pro Val Leu Gln Arg Gln Gln Leu Asp Tyr Gly Ile Tyr
1               5                   10

<210> SEQ ID NO 733
<211> LENGTH: 13
<212> TYPE: PRT
<213> ORGANISM: Homo sapiens

<400> SEQUENCE: 733

Leu Asn Ser Leu Thr Tyr Gln Val Leu Asp Val Gln Arg
1               5                   10

<210> SEQ ID NO 734

```
<211> LENGTH: 15
<212> TYPE: PRT
<213> ORGANISM: Homo sapiens

<400> SEQUENCE: 734

Leu Asn Ser Leu Thr Tyr Gln Val Leu Asp Val Gln Arg Tyr Pro
1               5                   10                  15

<210> SEQ ID NO 735
<211> LENGTH: 16
<212> TYPE: PRT
<213> ORGANISM: Homo sapiens

<400> SEQUENCE: 735

Leu Asn Ser Leu Thr Tyr Gln Val Leu Asp Val Gln Arg Tyr Pro Leu
1               5                   10                  15

<210> SEQ ID NO 736
<211> LENGTH: 13
<212> TYPE: PRT
<213> ORGANISM: Homo sapiens

<400> SEQUENCE: 736

Leu Pro Gln Leu Val Gly Val Ser Thr Pro Leu Gln Gly
1               5                   10

<210> SEQ ID NO 737
<211> LENGTH: 14
<212> TYPE: PRT
<213> ORGANISM: Homo sapiens

<400> SEQUENCE: 737

Leu Pro Gln Leu Val Gly Val Ser Thr Pro Leu Gln Gly Gly
1               5                   10

<210> SEQ ID NO 738
<211> LENGTH: 15
<212> TYPE: PRT
<213> ORGANISM: Homo sapiens

<400> SEQUENCE: 738

Leu Pro Gln Leu Val Gly Val Ser Thr Pro Leu Gln Gly Gly Ser
1               5                   10                  15

<210> SEQ ID NO 739
<211> LENGTH: 16
<212> TYPE: PRT
<213> ORGANISM: Homo sapiens

<400> SEQUENCE: 739

Arg Leu Pro Gln Leu Val Gly Val Ser Thr Pro Leu Gln Gly Gly Ser
1               5                   10                  15

<210> SEQ ID NO 740
<211> LENGTH: 14
<212> TYPE: PRT
<213> ORGANISM: Homo sapiens

<400> SEQUENCE: 740

Ser Pro His Lys Val Ala Ile Ile Ile Pro Phe Arg Asn Arg
1               5                   10

<210> SEQ ID NO 741
<211> LENGTH: 16
<212> TYPE: PRT
```

```
<213> ORGANISM: Homo sapiens

<400> SEQUENCE: 741

Ser Pro His Lys Val Ala Ile Ile Ile Pro Phe Arg Asn Arg Gln Glu
1               5                   10                  15

<210> SEQ ID NO 742
<211> LENGTH: 17
<212> TYPE: PRT
<213> ORGANISM: Homo sapiens

<400> SEQUENCE: 742

Ser Pro His Lys Val Ala Ile Ile Ile Pro Phe Arg Asn Arg Gln Glu
1               5                   10                  15

His

<210> SEQ ID NO 743
<211> LENGTH: 12
<212> TYPE: PRT
<213> ORGANISM: Homo sapiens

<400> SEQUENCE: 743

Ala Ile Val Gln Ala Val Ser Ala His Arg His Arg
1               5                   10

<210> SEQ ID NO 744
<211> LENGTH: 13
<212> TYPE: PRT
<213> ORGANISM: Homo sapiens

<400> SEQUENCE: 744

Ala Arg Asn Phe Glu Arg Asn Lys Ala Ile Lys Val Ile
1               5                   10

<210> SEQ ID NO 745
<211> LENGTH: 15
<212> TYPE: PRT
<213> ORGANISM: Homo sapiens

<400> SEQUENCE: 745

Ala Arg Asn Phe Glu Arg Asn Lys Ala Ile Lys Val Ile Ile Ala
1               5                   10                  15

<210> SEQ ID NO 746
<211> LENGTH: 12
<212> TYPE: PRT
<213> ORGANISM: Homo sapiens

<400> SEQUENCE: 746

Asn Phe Glu Arg Asn Lys Ala Ile Lys Val Ile Ile
1               5                   10

<210> SEQ ID NO 747
<211> LENGTH: 13
<212> TYPE: PRT
<213> ORGANISM: Homo sapiens

<400> SEQUENCE: 747

Asn Phe Glu Arg Asn Lys Ala Ile Lys Val Ile Ile Ala
1               5                   10

<210> SEQ ID NO 748
<211> LENGTH: 12
<212> TYPE: PRT
```

<213> ORGANISM: Homo sapiens

<400> SEQUENCE: 748

Val Ala Ile Val Gln Ala Val Ser Ala His Arg His
1               5                   10

<210> SEQ ID NO 749
<211> LENGTH: 13
<212> TYPE: PRT
<213> ORGANISM: Homo sapiens

<400> SEQUENCE: 749

Val Ala Ile Val Gln Ala Val Ser Ala His Arg His Arg
1               5                   10

<210> SEQ ID NO 750
<211> LENGTH: 14
<212> TYPE: PRT
<213> ORGANISM: Homo sapiens

<400> SEQUENCE: 750

Val Ala Ile Val Gln Ala Val Ser Ala His Arg His Arg Ala
1               5                   10

<210> SEQ ID NO 751
<211> LENGTH: 15
<212> TYPE: PRT
<213> ORGANISM: Homo sapiens

<400> SEQUENCE: 751

Val Ala Ile Val Gln Ala Val Ser Ala His Arg His Arg Ala Arg
1               5                   10                  15

<210> SEQ ID NO 752
<211> LENGTH: 14
<212> TYPE: PRT
<213> ORGANISM: Homo sapiens

<400> SEQUENCE: 752

Glu Glu Val Ile Thr Leu Ile Arg Ser Asn Gln Gln Leu Glu
1               5                   10

<210> SEQ ID NO 753
<211> LENGTH: 15
<212> TYPE: PRT
<213> ORGANISM: Homo sapiens

<400> SEQUENCE: 753

Glu Glu Val Ile Thr Leu Ile Arg Ser Asn Gln Gln Leu Glu Asn
1               5                   10                  15

<210> SEQ ID NO 754
<211> LENGTH: 16
<212> TYPE: PRT
<213> ORGANISM: Homo sapiens

<400> SEQUENCE: 754

Ile Pro Ala Asp Thr Phe Ala Ala Leu Lys Asn Pro Asn Ala Met Leu
1               5                   10                  15

<210> SEQ ID NO 755
<211> LENGTH: 15
<212> TYPE: PRT
<213> ORGANISM: Homo sapiens

<400> SEQUENCE: 755

Leu Lys Gln Leu Leu Ser Asp Lys Gln Gln Lys Arg Gln Ser Gly
1               5                   10                  15

<210> SEQ ID NO 756
<211> LENGTH: 16
<212> TYPE: PRT
<213> ORGANISM: Homo sapiens

<400> SEQUENCE: 756

Leu Lys Gln Leu Leu Ser Asp Lys Gln Gln Lys Arg Gln Ser Gly Gln
1               5                   10                  15

<210> SEQ ID NO 757
<211> LENGTH: 12
<212> TYPE: PRT
<213> ORGANISM: Homo sapiens

<400> SEQUENCE: 757

Thr Pro Ser Tyr Val Ala Phe Thr Asp Thr Glu Arg
1               5                   10

<210> SEQ ID NO 758
<211> LENGTH: 13
<212> TYPE: PRT
<213> ORGANISM: Homo sapiens

<400> SEQUENCE: 758

Thr Pro Ser Tyr Val Ala Phe Thr Asp Thr Glu Arg Leu
1               5                   10

<210> SEQ ID NO 759
<211> LENGTH: 13
<212> TYPE: PRT
<213> ORGANISM: Homo sapiens

<400> SEQUENCE: 759

Glu Gly Leu Tyr Ser Arg Thr Leu Ala Gly Ser Ile Thr
1               5                   10

<210> SEQ ID NO 760
<211> LENGTH: 16
<212> TYPE: PRT
<213> ORGANISM: Homo sapiens

<400> SEQUENCE: 760

Glu Gly Leu Tyr Ser Arg Thr Leu Ala Gly Ser Ile Thr Thr Pro Pro
1               5                   10                  15

<210> SEQ ID NO 761
<211> LENGTH: 13
<212> TYPE: PRT
<213> ORGANISM: Homo sapiens

<400> SEQUENCE: 761

Glu Lys Trp Tyr Ile Pro Asp Pro Thr Gly Lys Phe Asn
1               5                   10

<210> SEQ ID NO 762
<211> LENGTH: 14
<212> TYPE: PRT
<213> ORGANISM: Homo sapiens

<400> SEQUENCE: 762

Gly Ala Ile Ala Ala Ile Asn Ser Ile Gln His Asn Thr Arg
1               5                   10

<210> SEQ ID NO 763
<211> LENGTH: 12
<212> TYPE: PRT
<213> ORGANISM: Homo sapiens

<400> SEQUENCE: 763

Leu Pro Ile Leu Val Pro Ser Ala Lys Lys Ala Ile
1               5                   10

<210> SEQ ID NO 764
<211> LENGTH: 13
<212> TYPE: PRT
<213> ORGANISM: Homo sapiens

<400> SEQUENCE: 764

Leu Pro Ile Leu Val Pro Ser Ala Lys Lys Ala Ile Tyr
1               5                   10

<210> SEQ ID NO 765
<211> LENGTH: 14
<212> TYPE: PRT
<213> ORGANISM: Homo sapiens

<400> SEQUENCE: 765

Leu Pro Ile Leu Val Pro Ser Ala Lys Lys Ala Ile Tyr Met
1               5                   10

<210> SEQ ID NO 766
<211> LENGTH: 15
<212> TYPE: PRT
<213> ORGANISM: Homo sapiens

<400> SEQUENCE: 766

Leu Pro Ile Leu Val Pro Ser Ala Lys Lys Ala Ile Tyr Met Asp
1               5                   10                  15

<210> SEQ ID NO 767
<211> LENGTH: 16
<212> TYPE: PRT
<213> ORGANISM: Homo sapiens

<400> SEQUENCE: 767

Leu Pro Ile Leu Val Pro Ser Ala Lys Lys Ala Ile Tyr Met Asp Asp
1               5                   10                  15

<210> SEQ ID NO 768
<211> LENGTH: 15
<212> TYPE: PRT
<213> ORGANISM: Homo sapiens

<400> SEQUENCE: 768

Val Glu Glu Gly Leu Tyr Ser Arg Thr Leu Ala Gly Ser Ile Thr
1               5                   10                  15

<210> SEQ ID NO 769
<211> LENGTH: 14
<212> TYPE: PRT
<213> ORGANISM: Homo sapiens

<400> SEQUENCE: 769

Trp Glu Lys Trp Tyr Ile Pro Asp Pro Thr Gly Lys Phe Asn
1               5                   10

<210> SEQ ID NO 770
<211> LENGTH: 12
<212> TYPE: PRT
<213> ORGANISM: Homo sapiens

<400> SEQUENCE: 770

Tyr Lys Ile Val Asn Phe Asp Pro Lys Leu Leu Glu
1               5                   10

<210> SEQ ID NO 771
<211> LENGTH: 13
<212> TYPE: PRT
<213> ORGANISM: Homo sapiens

<400> SEQUENCE: 771

Tyr Lys Ile Val Asn Phe Asp Pro Lys Leu Leu Glu Gly
1               5                   10

<210> SEQ ID NO 772
<211> LENGTH: 15
<212> TYPE: PRT
<213> ORGANISM: Homo sapiens

<400> SEQUENCE: 772

Tyr Lys Ile Val Asn Phe Asp Pro Lys Leu Leu Glu Gly Lys Val
1               5                   10                  15

<210> SEQ ID NO 773
<211> LENGTH: 12
<212> TYPE: PRT
<213> ORGANISM: Homo sapiens

<400> SEQUENCE: 773

Leu Pro Glu Phe Tyr Lys Thr Val Ser Pro Ala Leu
1               5                   10

<210> SEQ ID NO 774
<211> LENGTH: 14
<212> TYPE: PRT
<213> ORGANISM: Homo sapiens

<400> SEQUENCE: 774

Val Gly Gln Phe Ile Gln Asp Val Lys Asn Ser Arg Ser Thr
1               5                   10

<210> SEQ ID NO 775
<211> LENGTH: 15
<212> TYPE: PRT
<213> ORGANISM: Homo sapiens

<400> SEQUENCE: 775

Val Gly Gln Phe Ile Gln Asp Val Lys Asn Ser Arg Ser Thr Asp
1               5                   10                  15

<210> SEQ ID NO 776
<211> LENGTH: 14
<212> TYPE: PRT
<213> ORGANISM: Homo sapiens

<400> SEQUENCE: 776

Val Val Gly Gln Phe Ile Gln Asp Val Lys Asn Ser Arg Ser
1               5                   10

<210> SEQ ID NO 777
<211> LENGTH: 15
<212> TYPE: PRT
<213> ORGANISM: Homo sapiens

<400> SEQUENCE: 777

Val Val Gly Gln Phe Ile Gln Asp Val Lys Asn Ser Arg Ser Thr
1               5                   10                  15

<210> SEQ ID NO 778
<211> LENGTH: 16
<212> TYPE: PRT
<213> ORGANISM: Homo sapiens

<400> SEQUENCE: 778

Val Val Gly Gln Phe Ile Gln Asp Val Lys Asn Ser Arg Ser Thr Asp
1               5                   10                  15

<210> SEQ ID NO 779
<211> LENGTH: 17
<212> TYPE: PRT
<213> ORGANISM: Homo sapiens

<400> SEQUENCE: 779

Val Val Gly Gln Phe Ile Gln Asp Val Lys Asn Ser Arg Ser Thr Asp
1               5                   10                  15

Ser

<210> SEQ ID NO 780
<211> LENGTH: 16
<212> TYPE: PRT
<213> ORGANISM: Homo sapiens

<400> SEQUENCE: 780

Asp Asn Gly His Leu Tyr Arg Glu Asp Gln Thr Ser Pro Ala Pro Gly
1               5                   10                  15

<210> SEQ ID NO 781
<211> LENGTH: 18
<212> TYPE: PRT
<213> ORGANISM: Homo sapiens

<400> SEQUENCE: 781

Asp Asn Gly His Leu Tyr Arg Glu Asp Gln Thr Ser Pro Ala Pro Gly
1               5                   10                  15

Leu Arg

<210> SEQ ID NO 782
<211> LENGTH: 16
<212> TYPE: PRT
<213> ORGANISM: Homo sapiens

<400> SEQUENCE: 782

Glu Val Gln Val Phe Ala Pro Ala Asn Ala Leu Pro Ala Arg Ser Glu
1               5                   10                  15

<210> SEQ ID NO 783
<211> LENGTH: 14
<212> TYPE: PRT
<213> ORGANISM: Homo sapiens

<400> SEQUENCE: 783

Gly His Leu Tyr Arg Glu Asp Gln Thr Ser Pro Ala Pro Gly
1               5                   10

<210> SEQ ID NO 784
<211> LENGTH: 15
<212> TYPE: PRT
<213> ORGANISM: Homo sapiens

<400> SEQUENCE: 784

Leu Pro Ala Arg Ser Glu Ala Ala Val Gln Pro Val Ile Gly
1               5                   10                  15

<210> SEQ ID NO 785
<211> LENGTH: 15
<212> TYPE: PRT
<213> ORGANISM: Homo sapiens

<400> SEQUENCE: 785

Asn Gly His Leu Tyr Arg Glu Asp Gln Thr Ser Pro Ala Pro Gly
1               5                   10                  15

<210> SEQ ID NO 786
<211> LENGTH: 16
<212> TYPE: PRT
<213> ORGANISM: Homo sapiens

<400> SEQUENCE: 786

Asn Gly His Leu Tyr Arg Glu Asp Gln Thr Ser Pro Ala Pro Gly Leu
1               5                   10                  15

<210> SEQ ID NO 787
<211> LENGTH: 17
<212> TYPE: PRT
<213> ORGANISM: Homo sapiens

<400> SEQUENCE: 787

Asn Gly His Leu Tyr Arg Glu Asp Gln Thr Ser Pro Ala Pro Gly Leu
1               5                   10                  15

Arg

<210> SEQ ID NO 788
<211> LENGTH: 15
<212> TYPE: PRT
<213> ORGANISM: Homo sapiens

<400> SEQUENCE: 788

Val Phe Ala Pro Ala Asn Ala Leu Pro Ala Arg Ser Glu Ala Ala
1               5                   10                  15

<210> SEQ ID NO 789
<211> LENGTH: 15
<212> TYPE: PRT
<213> ORGANISM: Homo sapiens

<400> SEQUENCE: 789

Val Gln Val Phe Ala Pro Ala Asn Ala Leu Pro Ala Arg Ser Glu
1               5                   10                  15

<210> SEQ ID NO 790
<211> LENGTH: 14
<212> TYPE: PRT
<213> ORGANISM: Homo sapiens

<400> SEQUENCE: 790

Ala Ile Val Val Ser Asp Arg Asp Gly Val Pro Val Ile Lys
1               5                   10

<210> SEQ ID NO 791
<211> LENGTH: 15
<212> TYPE: PRT
<213> ORGANISM: Homo sapiens

<400> SEQUENCE: 791

Gly Leu His Ala Ile Val Val Ser Asp Arg Asp Gly Val Pro Val
1               5                   10                  15

<210> SEQ ID NO 792
<211> LENGTH: 17
<212> TYPE: PRT
<213> ORGANISM: Homo sapiens

<400> SEQUENCE: 792

Gly Leu His Ala Ile Val Val Ser Asp Arg Asp Gly Val Pro Val Ile
1               5                   10                  15

Lys

<210> SEQ ID NO 793
<211> LENGTH: 13
<212> TYPE: PRT
<213> ORGANISM: Homo sapiens

<400> SEQUENCE: 793

His Ala Ile Val Val Ser Asp Arg Asp Gly Val Pro Val
1               5                   10

<210> SEQ ID NO 794
<211> LENGTH: 18
<212> TYPE: PRT
<213> ORGANISM: Homo sapiens

<400> SEQUENCE: 794

Lys Leu Pro Ser Val Glu Gly Leu His Ala Ile Val Val Ser Asp Arg
1               5                   10                  15

Asp Gly

<210> SEQ ID NO 795
<211> LENGTH: 14
<212> TYPE: PRT
<213> ORGANISM: Homo sapiens

<400> SEQUENCE: 795

Leu His Ala Ile Val Val Ser Asp Arg Asp Gly Val Pro Val
1               5                   10

<210> SEQ ID NO 796
<211> LENGTH: 15
<212> TYPE: PRT
<213> ORGANISM: Homo sapiens

<400> SEQUENCE: 796

Leu His Ala Ile Val Val Ser Asp Arg Asp Gly Val Pro Val Ile
1               5                   10                  15

<210> SEQ ID NO 797
<211> LENGTH: 16
<212> TYPE: PRT
<213> ORGANISM: Homo sapiens

<400> SEQUENCE: 797

Leu His Ala Ile Val Val Ser Asp Arg Asp Gly Val Pro Val Ile Lys
1               5                   10                  15

<210> SEQ ID NO 798
<211> LENGTH: 15
<212> TYPE: PRT
<213> ORGANISM: Homo sapiens

<400> SEQUENCE: 798

Leu Pro Ser Val Glu Gly Leu His Ala Ile Val Val Ser Asp Arg
1               5                   10                  15

<210> SEQ ID NO 799
<211> LENGTH: 13
<212> TYPE: PRT
<213> ORGANISM: Homo sapiens

<400> SEQUENCE: 799

Val Pro Val Ile Lys Val Ala Asn Asp Asn Ala Pro Glu
1               5                   10

<210> SEQ ID NO 800
<211> LENGTH: 13
<212> TYPE: PRT
<213> ORGANISM: Homo sapiens

<400> SEQUENCE: 800

Tyr Asn Thr Tyr Gln Val Val Gln Phe Asn Arg Leu Pro
1               5                   10

<210> SEQ ID NO 801
<211> LENGTH: 14
<212> TYPE: PRT
<213> ORGANISM: Homo sapiens

<400> SEQUENCE: 801

Tyr Asn Thr Tyr Gln Val Val Gln Phe Asn Arg Leu Pro Leu
1               5                   10

<210> SEQ ID NO 802
<211> LENGTH: 15
<212> TYPE: PRT
<213> ORGANISM: Homo sapiens

<400> SEQUENCE: 802

Tyr Asn Thr Tyr Gln Val Val Gln Phe Asn Arg Leu Pro Leu Val
1               5                   10                  15

<210> SEQ ID NO 803
<211> LENGTH: 16
<212> TYPE: PRT
<213> ORGANISM: Homo sapiens

<400> SEQUENCE: 803

Tyr Asn Thr Tyr Gln Val Val Gln Phe Asn Arg Leu Pro Leu Val Val
1               5                   10                  15

<210> SEQ ID NO 804
<211> LENGTH: 14
<212> TYPE: PRT
<213> ORGANISM: Homo sapiens

<400> SEQUENCE: 804

Tyr Tyr Asn Thr Tyr Gln Val Val Gln Phe Asn Arg Leu Pro
1               5                   10

```
<210> SEQ ID NO 805
<211> LENGTH: 15
<212> TYPE: PRT
<213> ORGANISM: Homo sapiens

<400> SEQUENCE: 805

Tyr Tyr Asn Thr Tyr Gln Val Val Gln Phe Asn Arg Leu Pro Leu
1               5                   10                  15

<210> SEQ ID NO 806
<211> LENGTH: 16
<212> TYPE: PRT
<213> ORGANISM: Homo sapiens

<400> SEQUENCE: 806

Tyr Tyr Asn Thr Tyr Gln Val Val Gln Phe Asn Arg Leu Pro Leu Val
1               5                   10                  15

<210> SEQ ID NO 807
<211> LENGTH: 13
<212> TYPE: PRT
<213> ORGANISM: Homo sapiens

<400> SEQUENCE: 807

Asp Lys Ile Tyr Phe Met Ala Gly Ser Ser Arg Lys Glu
1               5                   10

<210> SEQ ID NO 808
<211> LENGTH: 20
<212> TYPE: PRT
<213> ORGANISM: Homo sapiens

<400> SEQUENCE: 808

Asp Val Gly Thr Asp Glu Glu Glu Thr Ala Lys Glu Ser Thr Ala
1               5                   10                  15

Glu Lys Asp Glu
            20

<210> SEQ ID NO 809
<211> LENGTH: 15
<212> TYPE: PRT
<213> ORGANISM: Homo sapiens

<400> SEQUENCE: 809

Glu Val Thr Phe Lys Ser Ile Leu Phe Val Pro Thr Ser Ala Pro
1               5                   10                  15

<210> SEQ ID NO 810
<211> LENGTH: 13
<212> TYPE: PRT
<213> ORGANISM: Homo sapiens

<400> SEQUENCE: 810

Lys Ser Glu Lys Phe Ala Phe Gln Ala Glu Val Asn Arg
1               5                   10

<210> SEQ ID NO 811
<211> LENGTH: 14
<212> TYPE: PRT
<213> ORGANISM: Homo sapiens

<400> SEQUENCE: 811

Leu Pro Glu Phe Asp Gly Lys Arg Phe Gln Asn Val Ala Lys
```

```
<210> SEQ ID NO 812
<211> LENGTH: 13
<212> TYPE: PRT
<213> ORGANISM: Homo sapiens

<400> SEQUENCE: 812

Asp Gly Ser Tyr Arg Ile Phe Ser Lys Gly Ala Ser Glu
1               5                   10

<210> SEQ ID NO 813
<211> LENGTH: 12
<212> TYPE: PRT
<213> ORGANISM: Homo sapiens

<400> SEQUENCE: 813

Gly Ser Tyr Arg Ile Phe Ser Lys Gly Ala Ser Glu
1               5                   10

<210> SEQ ID NO 814
<211> LENGTH: 14
<212> TYPE: PRT
<213> ORGANISM: Homo sapiens

<400> SEQUENCE: 814

Ser Asp Gly Ser Tyr Arg Ile Phe Ser Lys Gly Ala Ser Glu
1               5                   10

<210> SEQ ID NO 815
<211> LENGTH: 14
<212> TYPE: PRT
<213> ORGANISM: Homo sapiens

<400> SEQUENCE: 815

Ser Val Lys Lys Met Met Lys Asp Asn Asn Leu Val Arg His
1               5                   10

<210> SEQ ID NO 816
<211> LENGTH: 13
<212> TYPE: PRT
<213> ORGANISM: Homo sapiens

<400> SEQUENCE: 816

Val Lys Lys Met Met Lys Asp Asn Asn Leu Val Arg His
1               5                   10

<210> SEQ ID NO 817
<211> LENGTH: 13
<212> TYPE: PRT
<213> ORGANISM: Homo sapiens

<400> SEQUENCE: 817

Asn Asn Met Arg Ile Phe Gly Glu Ala Ala Glu Lys Asn
1               5                   10

<210> SEQ ID NO 818
<211> LENGTH: 13
<212> TYPE: PRT
<213> ORGANISM: Homo sapiens

<400> SEQUENCE: 818

Val Asp Lys Val Leu Glu Arg Asp Gln Lys Leu Ser Glu
1               5                   10
```

<210> SEQ ID NO 819
<211> LENGTH: 15
<212> TYPE: PRT
<213> ORGANISM: Homo sapiens

<400> SEQUENCE: 819

Val Asp Lys Val Leu Glu Arg Asp Gln Lys Leu Ser Glu Leu Asp
1               5                   10                  15

<210> SEQ ID NO 820
<211> LENGTH: 16
<212> TYPE: PRT
<213> ORGANISM: Homo sapiens

<400> SEQUENCE: 820

Val Asp Lys Val Leu Glu Arg Asp Gln Lys Leu Ser Glu Leu Asp Asp
1               5                   10                  15

<210> SEQ ID NO 821
<211> LENGTH: 17
<212> TYPE: PRT
<213> ORGANISM: Homo sapiens

<400> SEQUENCE: 821

Val Asp Lys Val Leu Glu Arg Asp Gln Lys Leu Ser Glu Leu Asp Asp
1               5                   10                  15

Arg

<210> SEQ ID NO 822
<211> LENGTH: 14
<212> TYPE: PRT
<213> ORGANISM: Homo sapiens

<400> SEQUENCE: 822

Val Leu Glu Arg Asp Gln Lys Leu Ser Glu Leu Asp Asp Arg
1               5                   10

<210> SEQ ID NO 823
<211> LENGTH: 15
<212> TYPE: PRT
<213> ORGANISM: Homo sapiens

<400> SEQUENCE: 823

Ala Thr Arg Ser Ile Gln Val Asp Gly Lys Thr Ile Lys Ala Gln
1               5                   10                  15

<210> SEQ ID NO 824
<211> LENGTH: 16
<212> TYPE: PRT
<213> ORGANISM: Homo sapiens

<400> SEQUENCE: 824

Ala Thr Arg Ser Ile Gln Val Asp Gly Lys Thr Ile Lys Ala Gln Ile
1               5                   10                  15

<210> SEQ ID NO 825
<211> LENGTH: 15
<212> TYPE: PRT
<213> ORGANISM: Homo sapiens

<400> SEQUENCE: 825

Ile Gly Val Glu Phe Ala Thr Arg Ser Ile Gln Val Asp Gly Lys
1               5                   10                  15

<210> SEQ ID NO 826
<211> LENGTH: 12
<212> TYPE: PRT
<213> ORGANISM: Homo sapiens

<400> SEQUENCE: 826

Arg Ser Ile Gln Val Asp Gly Lys Thr Ile Lys Ala
1               5                   10

<210> SEQ ID NO 827
<211> LENGTH: 13
<212> TYPE: PRT
<213> ORGANISM: Homo sapiens

<400> SEQUENCE: 827

Arg Ser Ile Gln Val Asp Gly Lys Thr Ile Lys Ala Gln
1               5                   10

<210> SEQ ID NO 828
<211> LENGTH: 14
<212> TYPE: PRT
<213> ORGANISM: Homo sapiens

<400> SEQUENCE: 828

Arg Ser Ile Gln Val Asp Gly Lys Thr Ile Lys Ala Gln Ile
1               5                   10

<210> SEQ ID NO 829
<211> LENGTH: 14
<212> TYPE: PRT
<213> ORGANISM: Homo sapiens

<400> SEQUENCE: 829

Thr Arg Ser Ile Gln Val Asp Gly Lys Thr Ile Lys Ala Gln
1               5                   10

<210> SEQ ID NO 830
<211> LENGTH: 16
<212> TYPE: PRT
<213> ORGANISM: Homo sapiens

<400> SEQUENCE: 830

Asp Ile Met Arg Val Asn Val Asp Lys Val Leu Glu Arg Asp Gln Lys
1               5                   10                  15

<210> SEQ ID NO 831
<211> LENGTH: 17
<212> TYPE: PRT
<213> ORGANISM: Homo sapiens

<400> SEQUENCE: 831

Asp Ile Met Arg Val Asn Val Asp Lys Val Leu Glu Arg Asp Gln Lys
1               5                   10                  15

Leu

<210> SEQ ID NO 832
<211> LENGTH: 15
<212> TYPE: PRT
<213> ORGANISM: Homo sapiens

<400> SEQUENCE: 832

Ile Met Arg Val Asn Val Asp Lys Val Leu Glu Arg Asp Gln Lys
1               5                   10                  15

```
<210> SEQ ID NO 833
<211> LENGTH: 13
<212> TYPE: PRT
<213> ORGANISM: Homo sapiens

<400> SEQUENCE: 833

Val Asp Lys Val Leu Glu Arg Asp Gln Lys Leu Ser Glu
1               5                   10

<210> SEQ ID NO 834
<211> LENGTH: 15
<212> TYPE: PRT
<213> ORGANISM: Homo sapiens

<400> SEQUENCE: 834

Val Asp Lys Val Leu Glu Arg Asp Gln Lys Leu Ser Glu Leu Asp
1               5                   10                  15

<210> SEQ ID NO 835
<211> LENGTH: 16
<212> TYPE: PRT
<213> ORGANISM: Homo sapiens

<400> SEQUENCE: 835

Val Asp Lys Val Leu Glu Arg Asp Gln Lys Leu Ser Glu Leu Asp Asp
1               5                   10                  15

<210> SEQ ID NO 836
<211> LENGTH: 17
<212> TYPE: PRT
<213> ORGANISM: Homo sapiens

<400> SEQUENCE: 836

Val Asp Lys Val Leu Glu Arg Asp Gln Lys Leu Ser Glu Leu Asp Asp
1               5                   10                  15

Arg

<210> SEQ ID NO 837
<211> LENGTH: 14
<212> TYPE: PRT
<213> ORGANISM: Homo sapiens

<400> SEQUENCE: 837

Val Leu Glu Arg Asp Gln Lys Leu Ser Glu Leu Asp Asp Arg
1               5                   10

<210> SEQ ID NO 838
<211> LENGTH: 15
<212> TYPE: PRT
<213> ORGANISM: Homo sapiens

<400> SEQUENCE: 838

Ala Thr Arg Ser Ile Gln Val Asp Gly Lys Thr Ile Lys Ala Gln
1               5                   10                  15

<210> SEQ ID NO 839
<211> LENGTH: 16
<212> TYPE: PRT
<213> ORGANISM: Homo sapiens

<400> SEQUENCE: 839

Ala Thr Arg Ser Ile Gln Val Asp Gly Lys Thr Ile Lys Ala Gln Ile
1               5                   10                  15
```

```
<210> SEQ ID NO 840
<211> LENGTH: 15
<212> TYPE: PRT
<213> ORGANISM: Homo sapiens

<400> SEQUENCE: 840

Ile Gly Val Glu Phe Ala Thr Arg Ser Ile Gln Val Asp Gly Lys
1               5                   10                  15

<210> SEQ ID NO 841
<211> LENGTH: 12
<212> TYPE: PRT
<213> ORGANISM: Homo sapiens

<400> SEQUENCE: 841

Arg Ser Ile Gln Val Asp Gly Lys Thr Ile Lys Ala
1               5                   10

<210> SEQ ID NO 842
<211> LENGTH: 13
<212> TYPE: PRT
<213> ORGANISM: Homo sapiens

<400> SEQUENCE: 842

Arg Ser Ile Gln Val Asp Gly Lys Thr Ile Lys Ala Gln
1               5                   10

<210> SEQ ID NO 843
<211> LENGTH: 14
<212> TYPE: PRT
<213> ORGANISM: Homo sapiens

<400> SEQUENCE: 843

Arg Ser Ile Gln Val Asp Gly Lys Thr Ile Lys Ala Gln Ile
1               5                   10

<210> SEQ ID NO 844
<211> LENGTH: 14
<212> TYPE: PRT
<213> ORGANISM: Homo sapiens

<400> SEQUENCE: 844

Thr Arg Ser Ile Gln Val Asp Gly Lys Thr Ile Lys Ala Gln
1               5                   10

<210> SEQ ID NO 845
<211> LENGTH: 12
<212> TYPE: PRT
<213> ORGANISM: Homo sapiens

<400> SEQUENCE: 845

Gly Ile Arg Val Ala Pro Val Pro Leu Tyr Asn Ser
1               5                   10

<210> SEQ ID NO 846
<211> LENGTH: 14
<212> TYPE: PRT
<213> ORGANISM: Homo sapiens

<400> SEQUENCE: 846

Gly Ile Arg Val Ala Pro Val Pro Leu Tyr Asn Ser Phe His
1               5                   10

<210> SEQ ID NO 847
```

```
<211> LENGTH: 17
<212> TYPE: PRT
<213> ORGANISM: Homo sapiens

<400> SEQUENCE: 847

Asn Pro Asn Gly Ile Arg Val Ala Pro Val Pro Leu Tyr Asn Ser Phe
1               5                   10                  15

His

<210> SEQ ID NO 848
<211> LENGTH: 17
<212> TYPE: PRT
<213> ORGANISM: Homo sapiens

<400> SEQUENCE: 848

Asp Asp Pro Ala Ile Asp Val Cys Lys Lys Leu Leu Gly Lys Tyr Pro
1               5                   10                  15

Asn

<210> SEQ ID NO 849
<211> LENGTH: 16
<212> TYPE: PRT
<213> ORGANISM: Homo sapiens

<400> SEQUENCE: 849

Asp Lys Gln Pro Tyr Ser Lys Leu Pro Gly Val Ser Leu Leu Lys Pro
1               5                   10                  15

<210> SEQ ID NO 850
<211> LENGTH: 17
<212> TYPE: PRT
<213> ORGANISM: Homo sapiens

<400> SEQUENCE: 850

Asp Lys Gln Pro Tyr Ser Lys Leu Pro Gly Val Ser Leu Leu Lys Pro
1               5                   10                  15

Leu

<210> SEQ ID NO 851
<211> LENGTH: 14
<212> TYPE: PRT
<213> ORGANISM: Homo sapiens

<400> SEQUENCE: 851

His Pro Arg Tyr Tyr Ile Ser Ala Asn Val Thr Gly Phe Lys
1               5                   10

<210> SEQ ID NO 852
<211> LENGTH: 13
<212> TYPE: PRT
<213> ORGANISM: Homo sapiens

<400> SEQUENCE: 852

Ser His Pro Arg Tyr Tyr Ile Ser Ala Asn Val Thr Gly
1               5                   10

<210> SEQ ID NO 853
<211> LENGTH: 15
<212> TYPE: PRT
<213> ORGANISM: Homo sapiens

<400> SEQUENCE: 853

Ser His Pro Arg Tyr Tyr Ile Ser Ala Asn Val Thr Gly Phe Lys
```

```
1               5                   10                  15
```

<210> SEQ ID NO 854
<211> LENGTH: 14
<212> TYPE: PRT
<213> ORGANISM: Homo sapiens

<400> SEQUENCE: 854

```
Thr Ser His Pro Arg Tyr Tyr Ile Ser Ala Asn Val Thr Gly
1               5                   10
```

<210> SEQ ID NO 855
<211> LENGTH: 16
<212> TYPE: PRT
<213> ORGANISM: Homo sapiens

<400> SEQUENCE: 855

```
Thr Ser His Pro Arg Tyr Tyr Ile Ser Ala Asn Val Thr Gly Phe Lys
1               5                   10                  15
```

<210> SEQ ID NO 856
<211> LENGTH: 12
<212> TYPE: PRT
<213> ORGANISM: Homo sapiens

<400> SEQUENCE: 856

```
Ala Asp Ile Phe Val Asp Pro Val Leu His Thr Ala
1               5                   10
```

<210> SEQ ID NO 857
<211> LENGTH: 14
<212> TYPE: PRT
<213> ORGANISM: Homo sapiens

<400> SEQUENCE: 857

```
Ala Asp Ile Phe Val Asp Pro Val Leu His Thr Ala Cys Ala
1               5                   10
```

<210> SEQ ID NO 858
<211> LENGTH: 15
<212> TYPE: PRT
<213> ORGANISM: Homo sapiens

<400> SEQUENCE: 858

```
Asp Pro Gly Ala Asp Tyr Arg Ile Asp Arg Ala Leu Asn Glu Ala
1               5                   10                  15
```

<210> SEQ ID NO 859
<211> LENGTH: 12
<212> TYPE: PRT
<213> ORGANISM: Homo sapiens

<400> SEQUENCE: 859

```
Ile Ala Gln Asp Tyr Lys Val Ser Tyr Ser Leu Ala
1               5                   10
```

<210> SEQ ID NO 860
<211> LENGTH: 13
<212> TYPE: PRT
<213> ORGANISM: Homo sapiens

<400> SEQUENCE: 860

```
Ile Ala Gln Asp Tyr Lys Val Ser Tyr Ser Leu Ala Lys
1               5                   10
```

<210> SEQ ID NO 861
<211> LENGTH: 14
<212> TYPE: PRT
<213> ORGANISM: Homo sapiens

<400> SEQUENCE: 861

Ile Ser Arg Asp Trp Lys Leu Asp Pro Val Leu Tyr Arg Lys
1               5                   10

<210> SEQ ID NO 862
<211> LENGTH: 13
<212> TYPE: PRT
<213> ORGANISM: Homo sapiens

<400> SEQUENCE: 862

Leu Ile Ala Gln Asp Tyr Lys Val Ser Tyr Ser Leu Ala
1               5                   10

<210> SEQ ID NO 863
<211> LENGTH: 14
<212> TYPE: PRT
<213> ORGANISM: Homo sapiens

<400> SEQUENCE: 863

Arg Gln Lys Leu Ile Ala Gln Asp Tyr Lys Val Ser Tyr Ser
1               5                   10

<210> SEQ ID NO 864
<211> LENGTH: 15
<212> TYPE: PRT
<213> ORGANISM: Homo sapiens

<400> SEQUENCE: 864

Arg Gln Lys Leu Ile Ala Gln Asp Tyr Lys Val Ser Tyr Ser Leu
1               5                   10                  15

<210> SEQ ID NO 865
<211> LENGTH: 16
<212> TYPE: PRT
<213> ORGANISM: Homo sapiens

<400> SEQUENCE: 865

Arg Gln Lys Leu Ile Ala Gln Asp Tyr Lys Val Ser Tyr Ser Leu Ala
1               5                   10                  15

<210> SEQ ID NO 866
<211> LENGTH: 17
<212> TYPE: PRT
<213> ORGANISM: Homo sapiens

<400> SEQUENCE: 866

Arg Gln Lys Leu Ile Ala Gln Asp Tyr Lys Val Ser Tyr Ser Leu Ala
1               5                   10                  15

Lys

<210> SEQ ID NO 867
<211> LENGTH: 14
<212> TYPE: PRT
<213> ORGANISM: Homo sapiens

<400> SEQUENCE: 867

Ser Ala Leu Asp Tyr Arg Leu Asp Pro Gln Leu Gln Leu His
1               5                   10

<210> SEQ ID NO 868
<211> LENGTH: 14
<212> TYPE: PRT
<213> ORGANISM: Homo sapiens

<400> SEQUENCE: 868

Ser Lys Ala Asp Ile Phe Val Asp Pro Val Leu His Thr Ala
1               5                   10

<210> SEQ ID NO 869
<211> LENGTH: 15
<212> TYPE: PRT
<213> ORGANISM: Homo sapiens

<400> SEQUENCE: 869

Ser Pro Ser Lys Asn Tyr Ile Leu Ser Val Ile Ser Gly Ser Ile
1               5                   10                  15

<210> SEQ ID NO 870
<211> LENGTH: 17
<212> TYPE: PRT
<213> ORGANISM: Homo sapiens

<400> SEQUENCE: 870

Glu Thr Thr Gln Leu Thr Ala Asp Ser His Pro Ser Tyr His Thr Asp
1               5                   10                  15
Gly

<210> SEQ ID NO 871
<211> LENGTH: 19
<212> TYPE: PRT
<213> ORGANISM: Homo sapiens

<400> SEQUENCE: 871

Ser Gly Glu Ser Leu Tyr His Val Leu Gly Leu Asp Lys Asn Ala Thr
1               5                   10                  15
Ser Asp Asp

<210> SEQ ID NO 872
<211> LENGTH: 14
<212> TYPE: PRT
<213> ORGANISM: Homo sapiens

<400> SEQUENCE: 872

Thr Thr Gln Leu Thr Ala Asp Ser His Pro Ser Tyr His Thr
1               5                   10

<210> SEQ ID NO 873
<211> LENGTH: 15
<212> TYPE: PRT
<213> ORGANISM: Homo sapiens

<400> SEQUENCE: 873

Thr Thr Gln Leu Thr Ala Asp Ser His Pro Ser Tyr His Thr Asp
1               5                   10                  15

<210> SEQ ID NO 874
<211> LENGTH: 16
<212> TYPE: PRT
<213> ORGANISM: Homo sapiens

<400> SEQUENCE: 874

Thr Thr Gln Leu Thr Ala Asp Ser His Pro Ser Tyr His Thr Asp Gly

-continued

```
1               5                   10                  15
```

<210> SEQ ID NO 875
<211> LENGTH: 13
<212> TYPE: PRT
<213> ORGANISM: Homo sapiens

<400> SEQUENCE: 875

```
Ser Val Glu Glu Phe Leu Ser Glu Lys Leu Glu Arg Ile
1               5                   10
```

<210> SEQ ID NO 876
<211> LENGTH: 12
<212> TYPE: PRT
<213> ORGANISM: Homo sapiens

<400> SEQUENCE: 876

```
Val Glu Glu Phe Leu Ser Glu Lys Leu Glu Arg Ile
1               5                   10
```

<210> SEQ ID NO 877
<211> LENGTH: 15
<212> TYPE: PRT
<213> ORGANISM: Homo sapiens

<400> SEQUENCE: 877

```
Asp Leu Ser Ser Ser Ile Leu Ala Gln Ser Arg Glu Arg Val Ala
1               5                   10                  15
```

<210> SEQ ID NO 878
<211> LENGTH: 16
<212> TYPE: PRT
<213> ORGANISM: Homo sapiens

<400> SEQUENCE: 878

```
Glu Lys Gly Val Arg Thr Leu Thr Ala Ala Ala Val Ser Gly Ala Gln
1               5                   10                  15
```

<210> SEQ ID NO 879
<211> LENGTH: 17
<212> TYPE: PRT
<213> ORGANISM: Homo sapiens

<400> SEQUENCE: 879

```
Glu Lys Gly Val Arg Thr Leu Thr Ala Ala Ala Val Ser Gly Ala Gln
1               5                   10                  15

Pro
```

<210> SEQ ID NO 880
<211> LENGTH: 18
<212> TYPE: PRT
<213> ORGANISM: Homo sapiens

<400> SEQUENCE: 880

```
Glu Lys Gly Val Arg Thr Leu Thr Ala Ala Ala Val Ser Gly Ala Gln
1               5                   10                  15

Pro Ile
```

<210> SEQ ID NO 881
<211> LENGTH: 14
<212> TYPE: PRT
<213> ORGANISM: Homo sapiens

<400> SEQUENCE: 881
```

Lys Gly Val Arg Thr Leu Thr Ala Ala Ala Val Ser Gly Ala
1               5                   10

<210> SEQ ID NO 882
<211> LENGTH: 15
<212> TYPE: PRT
<213> ORGANISM: Homo sapiens

<400> SEQUENCE: 882

Lys Gly Val Arg Thr Leu Thr Ala Ala Ala Val Ser Gly Ala Gln
1               5                   10                  15

<210> SEQ ID NO 883
<211> LENGTH: 17
<212> TYPE: PRT
<213> ORGANISM: Homo sapiens

<400> SEQUENCE: 883

Val Gly Pro Phe Ala Pro Gly Ile Thr Glu Lys Ala Pro Glu Lys
1               5                   10                  15

Lys

<210> SEQ ID NO 884
<211> LENGTH: 14
<212> TYPE: PRT
<213> ORGANISM: Homo sapiens

<400> SEQUENCE: 884

Asp Pro Pro Leu Ile Ala Leu Asp Lys Asp Ala Pro Leu Arg
1               5                   10

<210> SEQ ID NO 885
<211> LENGTH: 15
<212> TYPE: PRT
<213> ORGANISM: Homo sapiens

<400> SEQUENCE: 885

Glu Ile Ile Thr Pro Asp Val Pro Phe Thr Val Asp Lys Asp Gly
1               5                   10                  15

<210> SEQ ID NO 886
<211> LENGTH: 14
<212> TYPE: PRT
<213> ORGANISM: Homo sapiens

<400> SEQUENCE: 886

Ile Ile Thr Pro Asp Val Pro Phe Thr Val Asp Lys Asp Gly
1               5                   10

<210> SEQ ID NO 887
<211> LENGTH: 13
<212> TYPE: PRT
<213> ORGANISM: Homo sapiens

<400> SEQUENCE: 887

Pro Pro Leu Ile Ala Leu Asp Lys Asp Ala Pro Leu Arg
1               5                   10

<210> SEQ ID NO 888
<211> LENGTH: 14
<212> TYPE: PRT
<213> ORGANISM: Homo sapiens

<400> SEQUENCE: 888

Thr Asn Val Lys Lys Ser His Lys Ala Thr Val His Ile Gln
1               5                   10

<210> SEQ ID NO 889
<211> LENGTH: 12
<212> TYPE: PRT
<213> ORGANISM: Homo sapiens

<400> SEQUENCE: 889

Asp Asp Asn Ile Lys Thr Tyr Ser Asp His Pro Glu
1               5                   10

<210> SEQ ID NO 890
<211> LENGTH: 13
<212> TYPE: PRT
<213> ORGANISM: Homo sapiens

<400> SEQUENCE: 890

Asp Asp Asn Ile Lys Thr Tyr Ser Asp His Pro Glu Lys
1               5                   10

<210> SEQ ID NO 891
<211> LENGTH: 14
<212> TYPE: PRT
<213> ORGANISM: Homo sapiens

<400> SEQUENCE: 891

Asp Ser Ala Val Phe Phe Glu Gln Gly Thr Thr Arg Ile Gly
1               5                   10

<210> SEQ ID NO 892
<211> LENGTH: 16
<212> TYPE: PRT
<213> ORGANISM: Homo sapiens

<400> SEQUENCE: 892

Gly Asp Lys Val Tyr Val His Leu Lys Asn Leu Ala Ser Arg Pro Tyr
1               5                   10                  15

<210> SEQ ID NO 893
<211> LENGTH: 17
<212> TYPE: PRT
<213> ORGANISM: Homo sapiens

<400> SEQUENCE: 893

Gly Asp Lys Val Tyr Val His Leu Lys Asn Leu Ala Ser Arg Pro Tyr
1               5                   10                  15

Thr

<210> SEQ ID NO 894
<211> LENGTH: 12
<212> TYPE: PRT
<213> ORGANISM: Homo sapiens

<400> SEQUENCE: 894

Val His Leu Lys Asn Leu Ala Ser Arg Pro Tyr Thr
1               5                   10

<210> SEQ ID NO 895
<211> LENGTH: 13
<212> TYPE: PRT
<213> ORGANISM: Homo sapiens

<400> SEQUENCE: 895

Val Tyr Val His Leu Lys Asn Leu Ala Ser Arg Pro Tyr
1               5                   10

<210> SEQ ID NO 896
<211> LENGTH: 14
<212> TYPE: PRT
<213> ORGANISM: Homo sapiens

<400> SEQUENCE: 896

Val Tyr Val His Leu Lys Asn Leu Ala Ser Arg Pro Tyr Thr
1               5                   10

<210> SEQ ID NO 897
<211> LENGTH: 16
<212> TYPE: PRT
<213> ORGANISM: Homo sapiens

<400> SEQUENCE: 897

Val Tyr Val His Leu Lys Asn Leu Ala Ser Arg Pro Tyr Thr Phe His
1               5                   10                  15

<210> SEQ ID NO 898
<211> LENGTH: 12
<212> TYPE: PRT
<213> ORGANISM: Homo sapiens

<400> SEQUENCE: 898

Tyr Val His Leu Lys Asn Leu Ala Ser Arg Pro Tyr
1               5                   10

<210> SEQ ID NO 899
<211> LENGTH: 13
<212> TYPE: PRT
<213> ORGANISM: Homo sapiens

<400> SEQUENCE: 899

Tyr Val His Leu Lys Asn Leu Ala Ser Arg Pro Tyr Thr
1               5                   10

<210> SEQ ID NO 900
<211> LENGTH: 15
<212> TYPE: PRT
<213> ORGANISM: Homo sapiens

<400> SEQUENCE: 900

Tyr Val His Leu Lys Asn Leu Ala Ser Arg Pro Tyr Thr Phe His
1               5                   10                  15

<210> SEQ ID NO 901
<211> LENGTH: 14
<212> TYPE: PRT
<213> ORGANISM: Homo sapiens

<400> SEQUENCE: 901

Ser Asn Leu Ile Lys Leu Ala Gln Lys Val Pro Thr Ala Asp
1               5                   10

<210> SEQ ID NO 902
<211> LENGTH: 12
<212> TYPE: PRT
<213> ORGANISM: Homo sapiens

<400> SEQUENCE: 902

Tyr Asp Thr Arg Thr Ser Ala Leu Ser Ala Lys Ser

-continued

```
<210> SEQ ID NO 903
<211> LENGTH: 14
<212> TYPE: PRT
<213> ORGANISM: Homo sapiens

<400> SEQUENCE: 903

Ala Leu Met Thr Asp Pro Lys Leu Ile Thr Trp Ser Pro Val
1               5                   10

<210> SEQ ID NO 904
<211> LENGTH: 16
<212> TYPE: PRT
<213> ORGANISM: Homo sapiens

<400> SEQUENCE: 904

Asn Asp Val Ala Trp Asn Phe Glu Lys Phe Leu Val Gly Pro Asp Gly
1               5                   10                  15

<210> SEQ ID NO 905
<211> LENGTH: 13
<212> TYPE: PRT
<213> ORGANISM: Homo sapiens

<400> SEQUENCE: 905

Gln Ser Val Tyr Ala Phe Ser Ala Arg Pro Leu Ala Gly
1               5                   10

<210> SEQ ID NO 906
<211> LENGTH: 17
<212> TYPE: PRT
<213> ORGANISM: Homo sapiens

<400> SEQUENCE: 906

Gln Ser Val Tyr Ala Phe Ser Ala Arg Pro Leu Ala Gly Gly Glu Pro
1               5                   10                  15

Val

<210> SEQ ID NO 907
<211> LENGTH: 12
<212> TYPE: PRT
<213> ORGANISM: Homo sapiens

<400> SEQUENCE: 907

Trp Asn Phe Glu Lys Phe Leu Val Gly Pro Asp Gly
1               5                   10

<210> SEQ ID NO 908
<211> LENGTH: 15
<212> TYPE: PRT
<213> ORGANISM: Homo sapiens

<400> SEQUENCE: 908

Asp Val Gly Met Phe Val Ala Leu Thr Lys Leu Gly Gln Pro Asp
1               5                   10                  15

<210> SEQ ID NO 909
<211> LENGTH: 14
<212> TYPE: PRT
<213> ORGANISM: Homo sapiens

<400> SEQUENCE: 909

Val Gly Met Phe Val Ala Leu Thr Lys Leu Gly Gln Pro Asp
```

<210> SEQ ID NO 910
<211> LENGTH: 12
<212> TYPE: PRT
<213> ORGANISM: Homo sapiens

<400> SEQUENCE: 910

Ala Gly Val Phe His Val Glu Lys Asn Gly Arg Tyr
1               5                   10

<210> SEQ ID NO 911
<211> LENGTH: 14
<212> TYPE: PRT
<213> ORGANISM: Homo sapiens

<400> SEQUENCE: 911

Phe Ala Gly Val Phe His Val Glu Lys Asn Gly Arg Tyr Ser
1               5                   10

<210> SEQ ID NO 912
<211> LENGTH: 14
<212> TYPE: PRT
<213> ORGANISM: Homo sapiens

<400> SEQUENCE: 912

Gly Pro Ile Thr Ile Thr Ile Val Asn Arg Asp Gly Thr Arg
1               5                   10

<210> SEQ ID NO 913
<211> LENGTH: 14
<212> TYPE: PRT
<213> ORGANISM: Homo sapiens

<400> SEQUENCE: 913

Asn Gly Arg Tyr Ser Ile Ser Arg Thr Glu Ala Ala Asp Leu
1               5                   10

<210> SEQ ID NO 914
<211> LENGTH: 14
<212> TYPE: PRT
<213> ORGANISM: Homo sapiens

<400> SEQUENCE: 914

Arg Lys Ser Arg Gln Gly Ser Leu Ala Met Glu Glu Leu Lys
1               5                   10

<210> SEQ ID NO 915
<211> LENGTH: 15
<212> TYPE: PRT
<213> ORGANISM: Homo sapiens

<400> SEQUENCE: 915

Arg Arg Lys Ser Arg Gln Gly Ser Leu Ala Met Glu Glu Leu Lys
1               5                   10                  15

<210> SEQ ID NO 916
<211> LENGTH: 15
<212> TYPE: PRT
<213> ORGANISM: Homo sapiens

<400> SEQUENCE: 916

Glu Glu Phe Lys Lys Leu Thr Ser Ile Lys Ile Gln Asn Asp Lys
1               5                   10                  15

<210> SEQ ID NO 917
<211> LENGTH: 13
<212> TYPE: PRT
<213> ORGANISM: Homo sapiens

<400> SEQUENCE: 917

Ile Asn Arg Arg Met Ala Asp Asp Asn Lys Leu Phe Arg
1               5                   10

<210> SEQ ID NO 918
<211> LENGTH: 15
<212> TYPE: PRT
<213> ORGANISM: Homo sapiens

<400> SEQUENCE: 918

Thr Ala Thr Ile Val Met Val Thr Asn Leu Lys Glu Arg Lys Glu
1               5                   10                  15

<210> SEQ ID NO 919
<211> LENGTH: 14
<212> TYPE: PRT
<213> ORGANISM: Homo sapiens

<400> SEQUENCE: 919

Glu Leu Phe Tyr Lys Gly Ile Arg Pro Ala Ile Asn Val Gly
1               5                   10

<210> SEQ ID NO 920
<211> LENGTH: 13
<212> TYPE: PRT
<213> ORGANISM: Homo sapiens

<400> SEQUENCE: 920

Gly Gln Lys Arg Ser Thr Val Ala Gln Leu Val Lys Arg
1               5                   10

<210> SEQ ID NO 921
<211> LENGTH: 15
<212> TYPE: PRT
<213> ORGANISM: Homo sapiens

<400> SEQUENCE: 921

Ser Asp Leu Asp Ala Ala Thr Gln Gln Leu Leu Ser Arg Gly Val
1               5                   10                  15

<210> SEQ ID NO 922
<211> LENGTH: 14
<212> TYPE: PRT
<213> ORGANISM: Homo sapiens

<400> SEQUENCE: 922

Phe Asp Phe Ser Gln Asn Thr Arg Val Pro Arg Leu Pro Glu
1               5                   10

<210> SEQ ID NO 923
<211> LENGTH: 12
<212> TYPE: PRT
<213> ORGANISM: Homo sapiens

<400> SEQUENCE: 923

Gly Asp Ala Pro Ala Ile Leu Phe Asp Lys Glu Phe
1               5                   10

<210> SEQ ID NO 924

```
<211> LENGTH: 13
<212> TYPE: PRT
<213> ORGANISM: Homo sapiens

<400> SEQUENCE: 924

Val Thr His Glu Ile Asp Arg Tyr Thr Ala Ile Ala Tyr
1               5                   10

<210> SEQ ID NO 925
<211> LENGTH: 16
<212> TYPE: PRT
<213> ORGANISM: Homo sapiens

<400> SEQUENCE: 925

Gly Gln Gly Tyr Leu Ile Lys Asp Gly Lys Leu Ile Lys Asn Asn Ala
1               5                   10                  15

<210> SEQ ID NO 926
<211> LENGTH: 15
<212> TYPE: PRT
<213> ORGANISM: Homo sapiens

<400> SEQUENCE: 926

Ile Asp Thr Thr Ser Lys Phe Gly His Gly Arg Phe Gln Thr Met
1               5                   10                  15

<210> SEQ ID NO 927
<211> LENGTH: 19
<212> TYPE: PRT
<213> ORGANISM: Homo sapiens

<400> SEQUENCE: 927

Ile Asp Val Ile Gly Val Thr Lys Gly Lys Gly Tyr Lys Gly Val Thr
1               5                   10                  15

Ser Arg Trp

<210> SEQ ID NO 928
<211> LENGTH: 15
<212> TYPE: PRT
<213> ORGANISM: Homo sapiens

<400> SEQUENCE: 928

Met Gly Pro Leu Lys Lys Asp Arg Ile Ala Lys Glu Glu Gly Ala
1               5                   10                  15

<210> SEQ ID NO 929
<211> LENGTH: 14
<212> TYPE: PRT
<213> ORGANISM: Homo sapiens

<400> SEQUENCE: 929

Ala Ala Lys Tyr Gln Leu Asp Pro Thr Ala Ser Ile Ser Ala
1               5                   10

<210> SEQ ID NO 930
<211> LENGTH: 15
<212> TYPE: PRT
<213> ORGANISM: Homo sapiens

<400> SEQUENCE: 930

Ile Ala Ala Lys Tyr Gln Leu Asp Pro Thr Ala Ser Ile Ser Ala
1               5                   10                  15

<210> SEQ ID NO 931
```

```
<211> LENGTH: 16
<212> TYPE: PRT
<213> ORGANISM: Homo sapiens

<400> SEQUENCE: 931

Ile Ala Ala Lys Tyr Gln Leu Asp Pro Thr Ala Ser Ile Ser Ala Lys
1               5                   10                  15

<210> SEQ ID NO 932
<211> LENGTH: 15
<212> TYPE: PRT
<213> ORGANISM: Homo sapiens

<400> SEQUENCE: 932

Ala Gly Leu Gly Arg Ala Tyr Ala Leu Ala Phe Ala Glu Arg Gly
1               5                   10                  15

<210> SEQ ID NO 933
<211> LENGTH: 14
<212> TYPE: PRT
<213> ORGANISM: Homo sapiens

<400> SEQUENCE: 933

Asp Ala Phe Gly Arg Ile Asp Val Val Val Asn Asn Ala Gly
1               5                   10

<210> SEQ ID NO 934
<211> LENGTH: 13
<212> TYPE: PRT
<213> ORGANISM: Homo sapiens

<400> SEQUENCE: 934

Gly Leu Gly Arg Ala Tyr Ala Leu Ala Phe Ala Glu Arg
1               5                   10

<210> SEQ ID NO 935
<211> LENGTH: 14
<212> TYPE: PRT
<213> ORGANISM: Homo sapiens

<400> SEQUENCE: 935

Gly Leu Gly Arg Ala Tyr Ala Leu Ala Phe Ala Glu Arg Gly
1               5                   10

<210> SEQ ID NO 936
<211> LENGTH: 15
<212> TYPE: PRT
<213> ORGANISM: Homo sapiens

<400> SEQUENCE: 936

Ala Lys Phe Ala Leu Asn Gly Glu Glu Phe Met Asn Phe Asp Leu
1               5                   10                  15

<210> SEQ ID NO 937
<211> LENGTH: 16
<212> TYPE: PRT
<213> ORGANISM: Homo sapiens

<400> SEQUENCE: 937

Ala Lys Phe Ala Leu Asn Gly Glu Glu Phe Met Asn Phe Asp Leu Lys
1               5                   10                  15

<210> SEQ ID NO 938
<211> LENGTH: 13
<212> TYPE: PRT
```

<213> ORGANISM: Homo sapiens

<400> SEQUENCE: 938

Ala Leu Asn Gly Glu Glu Phe Met Asn Phe Asp Leu Lys
1               5                   10

<210> SEQ ID NO 939
<211> LENGTH: 14
<212> TYPE: PRT
<213> ORGANISM: Homo sapiens

<400> SEQUENCE: 939

Lys Phe Ala Leu Asn Gly Glu Glu Phe Met Asn Phe Asp Leu
1               5                   10

<210> SEQ ID NO 940
<211> LENGTH: 14
<212> TYPE: PRT
<213> ORGANISM: Homo sapiens

<400> SEQUENCE: 940

Ser Asp Gly Ser Phe His Ala Ser Ser Leu Thr Val Lys
1               5                   10

<210> SEQ ID NO 941
<211> LENGTH: 17
<212> TYPE: PRT
<213> ORGANISM: Homo sapiens

<400> SEQUENCE: 941

Glu Glu Arg Asn Leu Leu Ser Val Ala Tyr Lys Asn Val Val Gly Ala
1               5                   10                  15
Arg

<210> SEQ ID NO 942
<211> LENGTH: 16
<212> TYPE: PRT
<213> ORGANISM: Homo sapiens

<400> SEQUENCE: 942

Glu Arg Asn Leu Leu Ser Val Ala Tyr Lys Asn Val Val Gly Ala Arg
1               5                   10                  15

<210> SEQ ID NO 943
<211> LENGTH: 14
<212> TYPE: PRT
<213> ORGANISM: Homo sapiens

<400> SEQUENCE: 943

Ile Ala Glu Leu Asp Thr Leu Ser Glu Glu Ser Tyr Lys Asp
1               5                   10

<210> SEQ ID NO 944
<211> LENGTH: 15
<212> TYPE: PRT
<213> ORGANISM: Homo sapiens

<400> SEQUENCE: 944

Ile Ala Glu Leu Asp Thr Leu Ser Glu Glu Ser Tyr Lys Asp Ser
1               5                   10                  15

<210> SEQ ID NO 945
<211> LENGTH: 16
<212> TYPE: PRT

<213> ORGANISM: Homo sapiens

<400> SEQUENCE: 945

Ala Asp Ser Tyr Leu Asp Glu Gly Phe Leu Leu Asp Lys Lys Ile Gly
1               5                   10                  15

<210> SEQ ID NO 946
<211> LENGTH: 13
<212> TYPE: PRT
<213> ORGANISM: Homo sapiens

<400> SEQUENCE: 946

Asp Ser Tyr Leu Asp Glu Gly Phe Leu Leu Asp Lys Lys
1               5                   10

<210> SEQ ID NO 947
<211> LENGTH: 15
<212> TYPE: PRT
<213> ORGANISM: Homo sapiens

<400> SEQUENCE: 947

Asp Ser Tyr Leu Asp Glu Gly Phe Leu Leu Asp Lys Lys Ile Gly
1               5                   10                  15

<210> SEQ ID NO 948
<211> LENGTH: 15
<212> TYPE: PRT
<213> ORGANISM: Homo sapiens

<400> SEQUENCE: 948

Val Asp Asn Ile Ile Lys Ala Ala Pro Arg Lys Arg Val Pro Asp
1               5                   10                  15

<210> SEQ ID NO 949
<211> LENGTH: 13
<212> TYPE: PRT
<213> ORGANISM: Homo sapiens

<400> SEQUENCE: 949

Ser Pro Pro Gln Phe Arg Val Asn Gly Ala Ile Ser Asn
1               5                   10

<210> SEQ ID NO 950
<211> LENGTH: 15
<212> TYPE: PRT
<213> ORGANISM: Homo sapiens

<400> SEQUENCE: 950

Ser Pro Pro Gln Phe Arg Val Asn Gly Ala Ile Ser Asn Phe Glu
1               5                   10                  15

<210> SEQ ID NO 951
<211> LENGTH: 16
<212> TYPE: PRT
<213> ORGANISM: Homo sapiens

<400> SEQUENCE: 951

Ser Pro Pro Gln Phe Arg Val Asn Gly Ala Ile Ser Asn Phe Glu Glu
1               5                   10                  15

<210> SEQ ID NO 952
<211> LENGTH: 17
<212> TYPE: PRT
<213> ORGANISM: Homo sapiens

```
<400> SEQUENCE: 952

Ser Pro Pro Gln Phe Arg Val Asn Gly Ala Ile Ser Asn Phe Glu Glu
1               5                   10                  15

Phe

<210> SEQ ID NO 953
<211> LENGTH: 15
<212> TYPE: PRT
<213> ORGANISM: Homo sapiens

<400> SEQUENCE: 953

Val Gly Lys Met Phe Val Asp Val Tyr Phe Gln Glu Asp Lys Lys
1               5                   10                  15

<210> SEQ ID NO 954
<211> LENGTH: 16
<212> TYPE: PRT
<213> ORGANISM: Homo sapiens

<400> SEQUENCE: 954

Val Gly Lys Met Phe Val Asp Val Tyr Phe Gln Glu Asp Lys Lys Glu
1               5                   10                  15

<210> SEQ ID NO 955
<211> LENGTH: 17
<212> TYPE: PRT
<213> ORGANISM: Homo sapiens

<400> SEQUENCE: 955

Asp Pro Lys Arg Thr Ile Ala Gln Asp Tyr Gly Val Leu Lys Ala Asp
1               5                   10                  15

Glu

<210> SEQ ID NO 956
<211> LENGTH: 18
<212> TYPE: PRT
<213> ORGANISM: Homo sapiens

<400> SEQUENCE: 956

Asp Pro Lys Arg Thr Ile Ala Gln Asp Tyr Gly Val Leu Lys Ala Asp
1               5                   10                  15

Glu Gly

<210> SEQ ID NO 957
<211> LENGTH: 17
<212> TYPE: PRT
<213> ORGANISM: Homo sapiens

<400> SEQUENCE: 957

Pro Lys Arg Thr Ile Ala Gln Asp Tyr Gly Val Leu Lys Ala Asp Glu
1               5                   10                  15

Gly

<210> SEQ ID NO 958
<211> LENGTH: 13
<212> TYPE: PRT
<213> ORGANISM: Homo sapiens

<400> SEQUENCE: 958

Gly Leu Phe Ile Ile Asp Asp Lys Gly Ile Leu Arg Gln
1               5                   10
```

<210> SEQ ID NO 959
<211> LENGTH: 15
<212> TYPE: PRT
<213> ORGANISM: Homo sapiens

<400> SEQUENCE: 959

Gly Leu Phe Ile Ile Asp Asp Lys Gly Ile Leu Arg Gln Ile Thr
1               5                   10                  15

<210> SEQ ID NO 960
<211> LENGTH: 13
<212> TYPE: PRT
<213> ORGANISM: Homo sapiens

<400> SEQUENCE: 960

Arg Gly Leu Phe Ile Ile Asp Asp Lys Gly Ile Leu Arg
1               5                   10

<210> SEQ ID NO 961
<211> LENGTH: 14
<212> TYPE: PRT
<213> ORGANISM: Homo sapiens

<400> SEQUENCE: 961

Arg Gly Leu Phe Ile Ile Asp Asp Lys Gly Ile Leu Arg Gln
1               5                   10

<210> SEQ ID NO 962
<211> LENGTH: 16
<212> TYPE: PRT
<213> ORGANISM: Homo sapiens

<400> SEQUENCE: 962

Arg Gly Leu Phe Ile Ile Asp Asp Lys Gly Ile Leu Arg Gln Ile Thr
1               5                   10                  15

<210> SEQ ID NO 963
<211> LENGTH: 15
<212> TYPE: PRT
<213> ORGANISM: Homo sapiens

<400> SEQUENCE: 963

Gly Asn Thr Val Ile His Leu Asp Gln Ala Leu Ala Arg Met Arg
1               5                   10                  15

<210> SEQ ID NO 964
<211> LENGTH: 14
<212> TYPE: PRT
<213> ORGANISM: Homo sapiens

<400> SEQUENCE: 964

Asn Thr Val Ile His Leu Asp Gln Ala Leu Ala Arg Met Arg
1               5                   10

<210> SEQ ID NO 965
<211> LENGTH: 15
<212> TYPE: PRT
<213> ORGANISM: Homo sapiens

<400> SEQUENCE: 965

Asn Thr Val Ile His Leu Asp Gln Ala Leu Ala Arg Met Arg Glu
1               5                   10                  15

<210> SEQ ID NO 966

```
<211> LENGTH: 15
<212> TYPE: PRT
<213> ORGANISM: Homo sapiens

<400> SEQUENCE: 966

Glu Asn Asn Glu Ile Ile Ser Asn Ile Arg Asp Ser Val Ile Asn
1               5                   10                  15

<210> SEQ ID NO 967
<211> LENGTH: 14
<212> TYPE: PRT
<213> ORGANISM: Homo sapiens

<400> SEQUENCE: 967

Asn Asn Glu Ile Ile Ser Asn Ile Arg Asp Ser Val Ile Asn
1               5                   10

<210> SEQ ID NO 968
<211> LENGTH: 14
<212> TYPE: PRT
<213> ORGANISM: Homo sapiens

<400> SEQUENCE: 968

Ser Pro Thr Val Gln Val Phe Ser Ala Ser Gly Lys Pro Val
1               5                   10

<210> SEQ ID NO 969
<211> LENGTH: 16
<212> TYPE: PRT
<213> ORGANISM: Homo sapiens

<400> SEQUENCE: 969

Ser Ser Pro Thr Val Gln Val Phe Ser Ala Ser Gly Lys Pro Val Glu
1               5                   10                  15

<210> SEQ ID NO 970
<211> LENGTH: 16
<212> TYPE: PRT
<213> ORGANISM: Homo sapiens

<400> SEQUENCE: 970

Ala Glu Pro Asn Tyr His Ser Leu Pro Ser Ala Arg Thr Asp Glu Gln
1               5                   10                  15

<210> SEQ ID NO 971
<211> LENGTH: 15
<212> TYPE: PRT
<213> ORGANISM: Homo sapiens

<400> SEQUENCE: 971

Ser Ser Ile Leu Ala Lys Thr Ala Ser Asn Ile Ile Asp Val Ser
1               5                   10                  15

<210> SEQ ID NO 972
<211> LENGTH: 15
<212> TYPE: PRT
<213> ORGANISM: Homo sapiens

<400> SEQUENCE: 972

Leu Glu Ala Arg Ala Thr Ala Pro Pro Ala Pro Ser Ala Pro Asn
1               5                   10                  15

<210> SEQ ID NO 973
<211> LENGTH: 12
<212> TYPE: PRT
```

```
<213> ORGANISM: Homo sapiens

<400> SEQUENCE: 973

Ala Asp Asp Leu Glu Gly Glu Ala Phe Leu Pro Leu
1               5                   10

<210> SEQ ID NO 974
<211> LENGTH: 13
<212> TYPE: PRT
<213> ORGANISM: Homo sapiens

<400> SEQUENCE: 974

Ala Asp Asp Leu Glu Gly Glu Ala Phe Leu Pro Leu Arg
1               5                   10

<210> SEQ ID NO 975
<211> LENGTH: 14
<212> TYPE: PRT
<213> ORGANISM: Homo sapiens

<400> SEQUENCE: 975

Ala Asp Asp Leu Glu Gly Glu Ala Phe Leu Pro Leu Arg Glu
1               5                   10

<210> SEQ ID NO 976
<211> LENGTH: 14
<212> TYPE: PRT
<213> ORGANISM: Homo sapiens

<400> SEQUENCE: 976

Gly Ala Asp Asp Leu Glu Gly Glu Ala Phe Leu Pro Leu Arg
1               5                   10

<210> SEQ ID NO 977
<211> LENGTH: 15
<212> TYPE: PRT
<213> ORGANISM: Homo sapiens

<400> SEQUENCE: 977

Ala Gly Arg Glu Ile Asn Leu Val Asp Ala His Leu Lys Ser Glu
1               5                   10                  15

<210> SEQ ID NO 978
<211> LENGTH: 17
<212> TYPE: PRT
<213> ORGANISM: Homo sapiens

<400> SEQUENCE: 978

Ala Gly Arg Glu Ile Asn Leu Val Asp Ala His Leu Lys Ser Glu Gln
1               5                   10                  15

Thr

<210> SEQ ID NO 979
<211> LENGTH: 14
<212> TYPE: PRT
<213> ORGANISM: Homo sapiens

<400> SEQUENCE: 979

Gly Arg Glu Ile Asn Leu Val Asp Ala His Leu Lys Ser Glu
1               5                   10

<210> SEQ ID NO 980
<211> LENGTH: 15
<212> TYPE: PRT
```

<213> ORGANISM: Homo sapiens

<400> SEQUENCE: 980

Lys Pro Gly Ile Val Tyr Ala Ser Leu Asn His Ser Val Ile Gly
1               5                   10                  15

<210> SEQ ID NO 981
<211> LENGTH: 16
<212> TYPE: PRT
<213> ORGANISM: Homo sapiens

<400> SEQUENCE: 981

Asn Lys Pro Gly Ile Val Tyr Ala Ser Leu Asn His Ser Val Ile Gly
1               5                   10                  15

<210> SEQ ID NO 982
<211> LENGTH: 16
<212> TYPE: PRT
<213> ORGANISM: Homo sapiens

<400> SEQUENCE: 982

Thr Thr Leu Tyr Val Thr Asp Val Lys Ser Ala Ser Glu Arg Pro Ser
1               5                   10                  15

<210> SEQ ID NO 983
<211> LENGTH: 16
<212> TYPE: PRT
<213> ORGANISM: Homo sapiens

<400> SEQUENCE: 983

Ala Pro Ser Thr Tyr Ala His Leu Ser Pro Ala Lys Thr Pro Pro Pro
1               5                   10                  15

<210> SEQ ID NO 984
<211> LENGTH: 17
<212> TYPE: PRT
<213> ORGANISM: Homo sapiens

<400> SEQUENCE: 984

Ala Pro Ser Thr Tyr Ala His Leu Ser Pro Ala Lys Thr Pro Pro Pro
1               5                   10                  15

Pro

<210> SEQ ID NO 985
<211> LENGTH: 18
<212> TYPE: PRT
<213> ORGANISM: Homo sapiens

<400> SEQUENCE: 985

Ala Pro Ser Thr Tyr Ala His Leu Ser Pro Ala Lys Thr Pro Pro Pro
1               5                   10                  15

Pro Ala

<210> SEQ ID NO 986
<211> LENGTH: 15
<212> TYPE: PRT
<213> ORGANISM: Homo sapiens

<400> SEQUENCE: 986

Arg Asp Asp Leu Tyr Asp Gln Asp Ser Arg Asp Phe Pro Arg
1               5                   10                  15

<210> SEQ ID NO 987

<210> SEQ ID NO 987 (implied continuation)
<211> LENGTH: 14
<212> TYPE: PRT
<213> ORGANISM: Homo sapiens

<400> SEQUENCE: 987

Thr Arg Pro Tyr His Ser Leu Pro Ser Glu Ala Val Phe Ala
1               5                   10

<210> SEQ ID NO 988
<211> LENGTH: 15
<212> TYPE: PRT
<213> ORGANISM: Homo sapiens

<400> SEQUENCE: 988

Thr Arg Pro Tyr His Ser Leu Pro Ser Glu Ala Val Phe Ala Asn
1               5                   10                  15

<210> SEQ ID NO 989
<211> LENGTH: 12
<212> TYPE: PRT
<213> ORGANISM: Homo sapiens

<400> SEQUENCE: 989

Val Ala Val Phe Thr Phe His Asn His Gly Arg Thr
1               5                   10

<210> SEQ ID NO 990
<211> LENGTH: 13
<212> TYPE: PRT
<213> ORGANISM: Homo sapiens

<400> SEQUENCE: 990

Val Ala Val Phe Thr Phe His Asn His Gly Arg Thr Ala
1               5                   10

<210> SEQ ID NO 991
<211> LENGTH: 15
<212> TYPE: PRT
<213> ORGANISM: Homo sapiens

<400> SEQUENCE: 991

Val Ala Val Phe Thr Phe His Asn His Gly Arg Thr Ala Asn Leu
1               5                   10                  15

<210> SEQ ID NO 992
<211> LENGTH: 16
<212> TYPE: PRT
<213> ORGANISM: Homo sapiens

<400> SEQUENCE: 992

Glu Asp Asp Tyr Ile Lys Ser Trp Glu Asp Asn Gln Gln Gly Asp Glu
1               5                   10                  15

<210> SEQ ID NO 993
<211> LENGTH: 16
<212> TYPE: PRT
<213> ORGANISM: Homo sapiens

<400> SEQUENCE: 993

Glu Leu Glu Arg Ile Gln Ile Gln Glu Ala Ala Lys Lys Lys Pro Gly
1               5                   10                  15

<210> SEQ ID NO 994
<211> LENGTH: 13
<212> TYPE: PRT

<213> ORGANISM: Homo sapiens

<400> SEQUENCE: 994

Glu Arg Ile Gln Ile Gln Glu Ala Ala Lys Lys Pro
1               5                   10

<210> SEQ ID NO 995
<211> LENGTH: 14
<212> TYPE: PRT
<213> ORGANISM: Homo sapiens

<400> SEQUENCE: 995

Glu Arg Ile Gln Ile Gln Glu Ala Ala Lys Lys Pro Gly
1               5                   10

<210> SEQ ID NO 996
<211> LENGTH: 15
<212> TYPE: PRT
<213> ORGANISM: Homo sapiens

<400> SEQUENCE: 996

Glu Arg Ile Gln Ile Gln Glu Ala Ala Lys Lys Pro Gly Ile
1               5                   10                  15

<210> SEQ ID NO 997
<211> LENGTH: 15
<212> TYPE: PRT
<213> ORGANISM: Homo sapiens

<400> SEQUENCE: 997

Leu Glu Arg Ile Gln Ile Gln Glu Ala Ala Lys Lys Pro Gly
1               5                   10                  15

<210> SEQ ID NO 998
<211> LENGTH: 12
<212> TYPE: PRT
<213> ORGANISM: Homo sapiens

<400> SEQUENCE: 998

Leu Ser Ser Ile Ser Gln Tyr Ser Gly Lys Ile Lys
1               5                   10

<210> SEQ ID NO 999
<211> LENGTH: 12
<212> TYPE: PRT
<213> ORGANISM: Homo sapiens

<400> SEQUENCE: 999

Ser Pro Ala Lys Asp Ser Leu Ser Phe Glu Asp Phe
1               5                   10

<210> SEQ ID NO 1000
<211> LENGTH: 15
<212> TYPE: PRT
<213> ORGANISM: Homo sapiens

<400> SEQUENCE: 1000

Ser Pro Ala Lys Asp Ser Leu Ser Phe Glu Asp Phe Leu Asp Leu
1               5                   10                  15

<210> SEQ ID NO 1001
<211> LENGTH: 14
<212> TYPE: PRT
<213> ORGANISM: Homo sapiens

```
<400> SEQUENCE: 1001

Ile Asn Ser Arg Phe Pro Ile Pro Ser Ala Thr Asp Pro Asp
1               5                   10

<210> SEQ ID NO 1002
<211> LENGTH: 14
<212> TYPE: PRT
<213> ORGANISM: Homo sapiens

<400> SEQUENCE: 1002

Val Gln His Tyr Glu Leu Leu Asn Gly Gln Ser Val Phe Gly
1               5                   10

<210> SEQ ID NO 1003
<211> LENGTH: 14
<212> TYPE: PRT
<213> ORGANISM: Homo sapiens

<400> SEQUENCE: 1003

Asp Asn Gln Tyr Ala Val Leu Glu Asn Gln Lys Ser Ser His
1               5                   10

<210> SEQ ID NO 1004
<211> LENGTH: 13
<212> TYPE: PRT
<213> ORGANISM: Homo sapiens

<400> SEQUENCE: 1004

Gly Pro Pro Glu Ile Tyr Ser Asp Thr Gln Phe Pro Ser
1               5                   10

<210> SEQ ID NO 1005
<211> LENGTH: 15
<212> TYPE: PRT
<213> ORGANISM: Homo sapiens

<400> SEQUENCE: 1005

Gly Pro Pro Glu Ile Tyr Ser Asp Thr Gln Phe Pro Ser Leu Gln
1               5                   10                  15

<210> SEQ ID NO 1006
<211> LENGTH: 16
<212> TYPE: PRT
<213> ORGANISM: Homo sapiens

<400> SEQUENCE: 1006

Thr Pro Gln Gly Pro Pro Glu Ile Tyr Ser Asp Thr Gln Phe Pro Ser
1               5                   10                  15

<210> SEQ ID NO 1007
<211> LENGTH: 18
<212> TYPE: PRT
<213> ORGANISM: Homo sapiens

<400> SEQUENCE: 1007

Thr Pro Gln Gly Pro Pro Glu Ile Tyr Ser Asp Thr Gln Phe Pro Ser
1               5                   10                  15

Leu Gln

<210> SEQ ID NO 1008
<211> LENGTH: 20
<212> TYPE: PRT
<213> ORGANISM: Homo sapiens
```

-continued

```
<400> SEQUENCE: 1008

Thr Pro Gln Gly Pro Pro Glu Ile Tyr Ser Asp Thr Gln Phe Pro Ser
1               5                   10                  15

Leu Gln Ser Thr
            20

<210> SEQ ID NO 1009
<211> LENGTH: 14
<212> TYPE: PRT
<213> ORGANISM: Homo sapiens

<400> SEQUENCE: 1009

Ala Asn Leu Gln Arg Ala Tyr Ser Leu Ala Lys Glu Gln Arg
1               5                   10

<210> SEQ ID NO 1010
<211> LENGTH: 13
<212> TYPE: PRT
<213> ORGANISM: Homo sapiens

<400> SEQUENCE: 1010

Asn Leu Gln Arg Ala Tyr Ser Leu Ala Lys Glu Gln Arg
1               5                   10

<210> SEQ ID NO 1011
<211> LENGTH: 15
<212> TYPE: PRT
<213> ORGANISM: Homo sapiens

<400> SEQUENCE: 1011

Thr Pro Ser Gly Ile Thr Tyr Asp Arg Lys Asp Ile Glu Glu His
1               5                   10                  15

<210> SEQ ID NO 1012
<211> LENGTH: 14
<212> TYPE: PRT
<213> ORGANISM: Homo sapiens

<400> SEQUENCE: 1012

Val Ser Thr Leu Asn Ser Glu Asp Phe Val Leu Val Ser Arg
1               5                   10

<210> SEQ ID NO 1013
<211> LENGTH: 15
<212> TYPE: PRT
<213> ORGANISM: Homo sapiens

<400> SEQUENCE: 1013

Val Ser Thr Leu Asn Ser Glu Asp Phe Val Leu Val Ser Arg Gln
1               5                   10                  15

<210> SEQ ID NO 1014
<211> LENGTH: 16
<212> TYPE: PRT
<213> ORGANISM: Homo sapiens

<400> SEQUENCE: 1014

Val Ser Thr Leu Asn Ser Glu Asp Phe Val Leu Val Ser Arg Gln Gly
1               5                   10                  15

<210> SEQ ID NO 1015
<211> LENGTH: 14
<212> TYPE: PRT
<213> ORGANISM: Homo sapiens
```

```
<400> SEQUENCE: 1015

Gly Ser Ser Phe Phe Gly Glu Leu Phe Asn Gln Asn Pro Glu
1               5                   10

<210> SEQ ID NO 1016
<211> LENGTH: 15
<212> TYPE: PRT
<213> ORGANISM: Homo sapiens

<400> SEQUENCE: 1016

Ser Gly Ser Ser Phe Phe Gly Glu Leu Phe Asn Gln Asn Pro Glu
1               5                   10                  15

<210> SEQ ID NO 1017
<211> LENGTH: 10
<212> TYPE: PRT
<213> ORGANISM: Homo sapiens

<400> SEQUENCE: 1017

Glu Leu Ala Gly Ile Gly Ile Leu Thr Val
1               5                   10

<210> SEQ ID NO 1018
<211> LENGTH: 9
<212> TYPE: PRT
<213> ORGANISM: Homo sapiens

<400> SEQUENCE: 1018

Tyr Leu Leu Pro Ala Ile Val His Ile
1               5
```

IMMUNOTHERAPY AGAINST SEVERAL TUMORS OF THE BLOOD, IN PARTICULAR CHRONIC LYMPHOID LEUKEMIA (CLL)

CROSS REFERENCE TO RELATED APPLICATIONS

This application is a continuation of U.S. patent application Ser. No. 16/179,677, filed 2 Nov. 2018, which is a continuation of U.S. patent application Ser. No. 16/126,751, filed 10 Sep. 2018, now U.S. Pat. No. 10,167,317, issued 1 Jan. 2019, which is a continuation of U.S. patent application Ser. No. 15/965,212, filed 27 Apr. 2018, now U.S. Pat. No. 10,144,763, issued 4 Dec. 2018, which is a continuation of U.S. patent application Ser. No. 14/743,335, filed 18 Jun. 2015, now U.S. Pat. No. 10,000,533, issued 19 Jun. 2018, which claims priority to U.S. Provisional Application 62/014,849, filed 20 Jun. 2014, British Application No. 1411037.3, filed 20 Jun. 2014, and PCT/EP2015/063566, filed 17 Jun. 2015. Each of these applications is incorporated by reference in its entirety.

REFERENCE TO SEQUENCE LISTING SUBMITTED AS A COMPLIANT ASCII TEXT FILE (.TXT)

A Sequence Listing is submitted herewith as an ASCII compliant text file named "2912919-036005_Sequence_Listing_ST25.txt", created on 15 May 2019, and having a size of 178,249 bytes as permitted under 37 C.F.R. § 1.821(c). The material in the aforementioned text file is hereby incorporated by reference in its entirety.

BACKGROUND

Field of the Invention

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to several novel peptide sequences and their variants derived from HLA class I and HLA class II molecules of human tumor cells that can be used in vaccine compositions for eliciting anti-tumor immune responses.

Description of Related Art

B-cell chronic lymphocytic leukemia (B-CLL), also known as chronic lymphoid leukemia (CLL), is the most common type of leukemia.

Leukemias are cancers of the white blood cells (leukocytes). CLL affects B cell lymphocytes. B cells originate in the bone marrow, develop in the lymph nodes, and normally fight infection by producing antibodies. In CLL, B cells grow out of control and accumulate in the bone marrow and blood, where they crowd out healthy blood cells. CLL is a stage of small lymphocytic lymphoma (SLL), a type of B-cell lymphoma, which presents primarily in the lymph nodes. CLL and SLL are considered the same underlying disease, just with different appearances.

CLL is a disease of adults, but, in rare cases, it can occur in teenagers and occasionally in children (inherited). Most (>75%) people newly diagnosed with CLL are over the age of 50, and the majority are men, with a median age of 70 years at the time of diagnosis. Though less common, CLL sometimes affects people between 30 and 39 years of age. The incidence of CLL increases very quickly with increasing age.

In the United States, during 2012 about 16,060 new cases are expected to be diagnosed, and 4,580 patients are expected to die from CLL.

CLL is very rare in Asian countries, such as Japan and China, and may account for as few as 10 percent of all leukemias in those regions.

In view of the above, there remains a need for new efficacious and safe treatment option for cancers, in particular chronic lymphoid leukemia (CLL) and other cancers of the blood of different phenotypes which improve the well-being of the patients by not using excessive chemotherapeutic agents or other agents that may lead to severe side effects.

SUMMARY

The present invention employs peptides that stimulate the immune system of the patient and act as anti-tumor-agents in a non-invasive fashion.

In a first aspect of the present invention, the present invention relates to a peptide comprising an amino acid sequence selected from the group of SEQ ID NO: 1 to SEQ ID NO: 225, SEQ ID NO: 226 to SEQ ID NO: 542 or SEQ ID NO: 543 to SEQ ID NO: 1016 or a variant sequence thereof which is at least 80%, preferably at least 90%, homologous (preferably at least 80% or at least 90% identical) to SEQ ID NO: 1 to SEQ ID NO: 225 or SEQ ID NO: 543 to SEQ ID NO: 1016, wherein said variant induces T cells cross-reacting with said peptide, or a pharmaceutical acceptable salt thereof, wherein said peptide is not the underlying full-length polypeptide.

The present invention further relates to a peptide of the present invention comprising a sequence that is selected from the group SEQ ID NO: 1 to SEQ ID NO: 225, SEQ ID NO: 226 to SEQ ID NO: 542 or SEQ ID NO: 543 to SEQ ID NO: 1016 or a variant thereof, which is at least 80%, preferably at least 90%, homologous (preferably at least 80% or at least 90% identical) to SEQ ID NO: 1 to SEQ ID NO: 225 or SEQ ID NO: 543 to SEQ ID NO: 1016, wherein said peptide or variant thereof has an overall length for SEQ ID NO: 1 to SEQ ID NO: 225 of between 8 and 100, preferably between 8 and 30, and most preferred of between 8 and 14 amino acids, and for SEQ ID NO: SEQ ID NO: 543 to SEQ ID NO: 1016 of between 12 and 100, preferably between 12 and 30, and most preferred of between 12 to 18 amino acids.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1a-11 depict embodiments as described herein.

FIG. 3a shows the peptides YGYDNVKEY (SEQ ID NO: 21), AVFDGAQVTSK (SEQ ID NO: 82), SSSGLHPPK (SEQ ID NO: 77), ILDEKPVII (SEQ ID NO: 63), YLNKEIEEA (SEQ ID NO: 44), SILEDPPSI (SEQ ID NO: 213), DLDVKKMPL (SEQ ID NO: 78), QLLDQVEQI (SEQ ID NO: 199), AAANIIRTL (SEQ ID NO: 13), SPRP-PLGSSL (SEQ ID NO: 93), APLQRSQSL (SEQ ID NO: 96), SPTSSRTSSL (SEQ ID NO: 26), KPRQSSPQL (SEQ ID NO: 49), and SASVQRADTSL (SEQ ID NO: 113).

FIG. 4c shows the peptides LPSQAFEYILYNKG (SEQ ID NO: 561), RVEYHFLSPYVSPK (SEQ ID NO: 554), NSVIIVDKNGRLV (SEQ ID NO: 552), DIMRVNVDKV-LERDQKL (SEQ ID NO: 831), YKAFSSLLASSAVSPE (SEQ ID NO: 651), and VDKVLERDQKLSELDDR (SEQ ID NO: 821).

DETAILED DESCRIPTION OF A PREFERRED EMBODIMENT

Figure 5A:
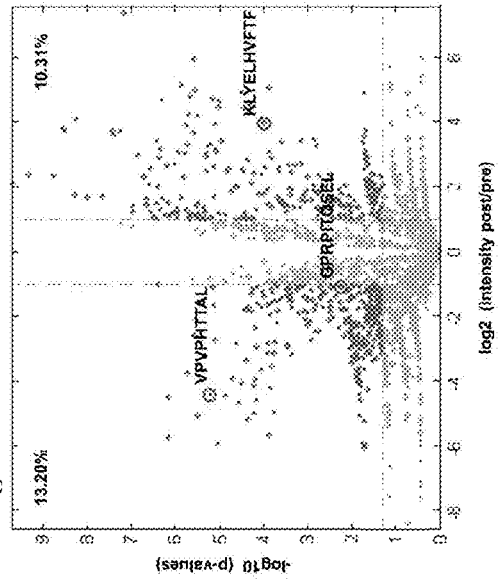
FIG. 5a shows the peptides KITVPASQK (SEQ ID NO: 145), SPRASGSGL (SEQ ID NO: 100), SPTSSRTSSL (SEQ ID NO: 26), SPAPRTAL (SEQ ID NO: 202), TPSS-RPASL (SEQ ID NO: 205), and RPKNLMQTL (SEQ ID NO: 36).

The following tables show the peptides according to the present invention, their respective SEQ ID NO: and the prospective source (underlying) proteins for these peptides. All peptides in Table 1a and 1b bind to HLA A HLA B or HLA C alleles, peptides in Table 2 bind to HLA-DR alleles (MHC class II). The peptides in table 3 are further useful in the diagnosis and/or treatment of CLL, Acute myelogenous leukemia (AML), and other hematological malignancies, which involve an over-expression or over-presentation of the respective underlying polypeptide.

Thus, the present invention relates in particular to a peptide of the present invention comprising a sequence according to SEQ ID NO: 543 to SEQ ID NO: 1016 or a variant thereof, which is at least 80%, preferably at least 90%, homologous (preferably at least 80% or at least 90% identical) to SEQ ID NO: 543 to SEQ ID NO: 1016, wherein said peptide or variant thereof has an overall length of between 12 and 100, preferably between 12 and 30, and most preferred of between 12 to 18 amino acids. The present invention relates in particular to a peptide of the present invention consisting of the sequence according to SEQ ID NO: 543 to SEQ ID NO: 1016.

TABLE 1a

Preferred 49 HLA class I ligandome derived tumor associated antigens (LiTAAs) according to the invention found represented in ≥20% of CLL patient ligandomes (n = 30) and the 225 representing HLA ligands (LiTAPs) annotated with respective HLA restriction.

| SEQ ID NO: | Underlying source protein/HLA ligands | Number of positive CLLs (frequency [%]) | HLA |
|---|---|---|---|
| | APOBEC3D apolipoprotein B mRNA editing enzyme, catalytic polypeptide-like 3D | 13 (43.3) | |
| 1 | AEHPNVTLTI | 1 | B*40 |
| 2 | FLAEHPNVTL | 8 | A*02 |
| 3 | ILYGRSYTW | 1 | A*32 |
| 4 | EVAEFLARH | 2 | A*26 |
| 5 | RHSNVNLTI | 1 | C*07 |
| | CDK14 cyclin-dependent kinase 14 | 12 (40.0) | |

TABLE 1a-continued

Preferred 49 HLA class I ligandome derived tumor associated antigens (LiTAAs) according to the invention found represented in ≥20% of CLL patient ligandomes (n = 30) and the 225 representing HLA ligands (LiTAPs) annotated with respective HLA restriction.

| SEQ ID NO: | Underlying source protein/HLA ligands | Number of positive CLLs (frequency [%]) | HLA |
|---|---|---|---|
| 6 | HPDNVKLFL | 1 | B*35 |
| 7 | ISDTGELKL | 1 | C*05 |
| 8 | KVNGKLVALK | 1 | A*03 |
| 9 | NRLSAQAAL | 1 | B*39 |
| 10 | TPFTAIREA | 1 | B*55 |
| 11 | FGLARAKSV | 6 | B*08 |
| 12 | KIADFGLAR | 1 | A*03 |
| | RASGRF1 Ras protein-specific guanine nucleotide-releasing factor 1 | 12 (40.0) | B*35 A*02, B*13, |
| 13 | AAANIIRTL | 8 | B*51 |
| 14 | GRFKNLREAL | 1 | B*27 |
| 15 | MSPFSKATL | 2 | C*14 |
| 16 | QEDPGDNQITL | 1 | B*40 |
| 17 | SPFSKATL | 2 | B*08, B*07 |
| | CDCA7L cell division cycle associated 7-like | 11 (36.7) | |
| 18 | DALLKRTM | 1 | B*08 |
| 19 | GEDVRSALL | 3 | B*40 |
| 20 | KFAEEFYSF | 2 | A*24 |
| 21 | YGYDNVKEY | 7 | C*03, C*12 |
| | CELSR1 cadherin, EGF LAG seven-pass G-type receptor 1 | 11 (36.7) | |
| 22 | LEVEERTKPV | 1 | B*44 |
| 23 | RDSPINANLRY | 1 | B*40 |
| 24 | RPFVIVTA | 1 | B*55 |
| 25 | RPIINTPMV | 1 | B*55 |
| 26 | SPTSSRTSSL | 7 | B*07 |
| 27 | ATSAPLVSR | 1 | A*11 |
| | AKAP2 A kinase (PRKA) anchor protein 2 | 11 (36.7) | |
| 28 | AELRSTASLL | 1 | B*40 |
| 29 | APASSHERASM | 2 | B*07 |
| 30 | ASRQAPPHI | 1 | A*30 |
| 31 | AVKKNPGIAA | 2 | A*02 |
| 32 | EEHLESHKKY | 2 | B*44 |
| 33 | GEFTSARAV | 1 | B*49 |
| 34 | GQSTPRLFSI | 1 | B*13 |
| 35 | LVDDPLEY | 1 | A*01 |
| 36 | RPKNLMQTL | 3 | B*07 |
| 37 | RQAPPHIEL | 2 | B*13 |
| 38 | SEAAELRSTA | 1 | B*50 |
| | CTDP1 CTD phosphatase, subunit 1 | 11 (36.7) | |
| 39 | AAVRIGSVL | 2 | A*02, B*13 |
| 40 | ERAGVVREL | 1 | C*07 |
| 41 | GAAVRIGSVL | 1 | A*02 |
| 42 | KLYELHVFTF | 1 | A*32 |
| 43 | LYELHVFTF | 2 | A*24, A*23 |
| 44 | YLNKEIEEA | 6 | A*02 |
| | DNMBP dynamin binding protein | 10 [33.3] | |
| 45 | DELPKFHQY | 2 | B*18 |
| 46 | DVTGQFPSSF | 1 | A*26 |
| 47 | EHSRVLQQL | 2 | B*39:01 |
| 48 | IKVSKQLL | 1 | B*08 |
| 49 | KPRQSSPQL | 3 | B*07 |
| 50 | KQLLAALEI | 1 | B*13 |
| 51 | RRKDLVLKY | 2 | B*27 |
| 52 | RTRDYASLPPK | 1 | A*03 |
| | TAGAP T-cell activation RhoGTPase activating protein | 10 (33.3) | |
| 53 | APGSVLPRAL | 3 | B*07 |
| 54 | DIKEHPLL | 1 | B*08 |
| 55 | DSAGPQDAR | 1 | A*68 |
| 56 | FQYAKESYI | 1 | B*13 |
| 57 | KVLSWPFLM | 1 | A*32 |
| 58 | LENDQSLSF | 1 | B*44 |
| 59 | SPSRQPQV | 1 | B*07 |
| 60 | SRHQSFTTK | 3 | B*27 |

TABLE 1a-continued

Preferred 49 HLA class I ligandome derived tumor associated antigens (LiTAAs) according to the invention found represented in ≥20% of CLL patient ligandomes (n = 30) and the 225 representing HLA ligands (LiTAPs) annotated with respective HLA restriction.

| SEQ ID NO: | Underlying source protein/HLA ligands | Number of positive CLLs (frequency [%]) | HLA |
|---|---|---|---|
| 61 | SSHNASKTL | 2 | C*12 |
|  | ABCA6 ATP-binding cassette, sub-family A (ABC1), member 6 | 10 (33.3) |  |
| 62 | EEIDTTMRW | 1 | B*44 |
| 63 | ILDEKPVII | 5 | A*02 |
| 64 | LPQEPRTSL | 2 | B*07 |
| 65 | LTYKLPVA | 1 | B*57 |
| 66 | NEMELAHSSF | 2 | B*18 |
| 67 | REFPEANFEL | 1 | B*40 |
| 68 | THHIPDAKL | 1 | B*38 |
| 69 | TVKENLSLF | 1 | A*26 |
| 70 | VLLKKAVL | 1 | B*08 |
|  | DMXL1 Dmx-like 1 | 10 (33.3) |  |
| 71 | HLKSIPVSL | 2 | B*08, B*07 |
| 72 | KVWYNVENW | 1 | A*32 |
| 73 | LPAYRAQLL | 1 | B*07 |
| 74 | LSEQTSVPL | 1 | A*02 |
| 75 | SLNQWLVSF | 1 | A*32 |
| 76 | SMTSLAQKI | 1 | A*02 |
| 77 | SSSGLHPPK | 2 | A*03, A*11, A*68 |
|  | PARP3 poly (ADP-ribose) polymerase family, member 3 | 10 (33.3) |  |
| 78 | DLDVKKMPL | 4 | B*08 |
| 79 | FYTVIPHNF | 3 | A*24 |
| 80 | HHINTDNPSL | 2 | B*39 |
| 81 | RVGEVGQSK | 2 | A*03 |
|  | TP53I11 tumor protein p53 inducible protein 11 | 8 (26.7) |  |
| 82 | AVFDGAQVTSK | 7 | A*03, A*11 |
| 83 | SQTDLVSRL | 1 | B*15 |
|  | B4GALT1 UDP-Gal:betaGlcNAc beta 1,4-galactosyltransferase, polypeptide 1 | 8 (26.7) |  |
| 84 | VPVPHTTAL | 7 | B*07 |
| 85 | YQVLDVQRY | 1 | B*15 |
|  | IRF9 interferon regulatory factor 9 | 8 (26.7) |  |
| 86 | APFQGDQRSL | 2 | B*07 |
| 87 | DVAEPYKVY | 1 | A*26 |
| 88 | IVSGQPGTQK | 3 | A*03 |
| 89 | TPEQQAAIL | 1 | B*35 |
| 90 | VELFRTAYF | 1 | B*37 |
|  | KDM2B lysine (K)-specific demethylase 2B | 8 (26.7) |  |
| 91 | EHADDDPSL | 1 | B*38 |
| 92 | SEESVKSTTL | 2 | B*40 |
| 93 | SPRPPLGSSL | 4 | B*07 |
| 94 | SPWWRSSL | 1 | B*07 |
| 95 | VYTPVDSLVF | 1 | A*24 |
|  | TBC1D22A TBC1 domain family, member 22A | 8 (26.7) |  |
| 96 | APLQRSQSL | 6 | B*07, B*08 |
| 97 | DEVHQDTY | 1 | B*18 |
| 98 | LPHSATVTL | 1 | B*07 |
|  | ZNF296 zinc finger protein 296 | 8 (26.7) |  |
| 99 | SEAPEAPLL | 1 | B*40 |
| 100 | SPRASGSGL | 6 | B*07 |
| 101 | VVGPAAEAK | 2 | A*03 |
|  | BACH2 BTB and CNC homology 1, basic leucine zipper transcription factor 2 | 8 (26.7) |  |
| 102 | FSITKSVEL | 4 | A*02 |
| 103 | GQTKNDLVV | 1 | B*13 |
| 104 | LSQEVCRD | 2 | n.a. |
| 105 | RDIQSPEQI | 1 | B*40 |
| 106 | REDNSSNSL | 1 | B*40 |
| 107 | TEHQEPGL | 2 | B*40 |
| 108 | TKNDLVVSL | 1 | B*39 |
|  | PRR12 proline rich 12 | 8 (26.7) |  |
| 109 | AEEAGGTRL | 1 | B*40 |
| 110 | ENVNKKDY | 1 | A*26 |
| 111 | GLDPNKPPEL | 4 | A*02 |
| 112 | RPAGEPYNRKTL | 2 | B*07 |
|  | ZFAND5 zinc finger, AN1-type domain 5 | 7 (23.3) |  |
| 113 | SASVQRADTSL | 5 | C*03 |
| 114 | YGNPRTNGM | 2 | B*08 |
|  | ATP5G1 ATP synthase, H+ transporting, mitochondrial Fo complex, subunit C1 | 7 (23.3) |  |
| 115 | LIRPVSASF | 3 | B*07 |
| 116 | SPVNSSKQPSY | 3 | B*35 |
| 117 | QLFSYAILGF | 1 | A*32 |
|  | DMD dystrophin | 7 (23.3) |  |
| 118 | DEHLLIQHY | 2 | B*18 |
| 119 | KQVASSTGF | 1 | B*15 |
| 120 | RDFGPASQHFL | 1 | B*40 |
| 121 | RQLGEVASF | 2 | A*32 |
| 122 | TEAETTANVL | 1 | B*40 |
| 123 | GYLPVQTVL | 1 | A*24 |
|  | ARID5B AT rich interactive domain 5B (MRF1-like) | 7 (23.3) |  |
| 124 | GQKEALLKY | 1 | B*15 |
| 125 | KPSEERKTI | 1 | B*07 |
| 126 | KQTPKVLVV | 1 | B*13 |
| 127 | SVIQHVQSF | 1 | A*26 |
| 128 | TPIERIPYL | 3 | B*51 |
|  | ZNF638 zinc finger protein 638 | 7 (23.3) |  |
| 129 | AEVEKNETV | 1 | B*40 |
| 130 | EVKEEIPLV | 1 | B*08 |
| 131 | KPTSARSGL | 2 | B*07 |
| 132 | KYIETTPLTI | 1 | A*24 |
| 133 | SEIKTSIEV | 1 | B*40 |
| 134 | SVKPTSATK | 4 | A*03 |
| 135 | YPNKGVGQA | 1 | B*55 |
|  | DDX46 DEAD (Asp-Glu-Ala-Asp) box polypeptide 46 | 7 (23.3) |  |
| 136 | ISMKILNSL | 2 | A*02 |
| 137 | KTIAFLLPMF | 1 | A*32 |
| 138 | RDSIINDF | 2 | B*37 |
| 139 | SVKGGGGNEK | 1 | A*03 |
| 140 | GIAKTGSGK | 1 | A*03 |
|  | RRM2B ribonucleotide reductase M2 B (TP53 inducible) | 7 (23.3) |  |
| 141 | AETTDNVFTL | 1 | B*40 |
| 142 | SEYQRFAVM | 3 | B*37, B*40, B*49 |
| 143 | TFGERVVAF | 1 | A*24 |
| 144 | NENLVERF | 2 | B*18 |
|  | BLNK B-cell linker | 7 (23.3) |  |
| 145 | KITVPASQK | 1 | A*03 |
| 146 | KITVPASQKL | 7 | A*02 |
| 147 | VPASQKLRQL | 2 | B*07 |
|  | HSH2D hematopoietic SH2 domain containing | 7 (23.3) |  |
| 148 | HVGYTLSYK | 1 | A*03 |
| 149 | KLPLPLPPRL | 3 | C*14 |
| 150 | KPIEPRREL | 1 | B*07 |
| 151 | SHSHVGYTL | 3 | B*38, B*39 |
|  | ERP44 endoplasmic reticulum protein 44 | 7 (23.3) |  |
| 152 | APSEYRYTL | 1 | B*07 |
| 153 | APSEYRYTLL | 3 | B*07 |
| 154 | EIFQNEVAR | 1 | A*68 |

TABLE 1a-continued

Preferred 49 HLA class I ligandome derived tumor associated antigens (LiTAAs) according to the invention found represented in ≥20% of CLL patient ligandomes (n = 30) and the 225 representing HLA ligands (LiTAPs) annotated with respective HLA restriction.

| SEQ ID NO: | Underlying source protein/HLA ligands | Number of positive CLLs (frequency [%]) | HLA |
|---|---|---|---|
| 155 | KDVLIPGKL | 1 | B*40 |
| 156 | VPLVREITF | 2 | B*08 |
|  | METTL7A methyltransferase like 7A | 7 (23.3) |  |
| 157 | DPNPNFEKF | 1 | B*35 |
| 158 | IQAPLSWEL | 1 | B*13 |
| 159 | VIYNEQMASK | 3 | A*03 |
| 160 | VLRPGGAFY | 2 | B*15 |
|  | ELP3 elongator acetyltransferase complex subunit 3 | 7 (23.3) |  |
| 161 | EDPDQDILI | 1 | B*18 |
| 162 | HGNLRELAL | 3 | B*08 |
| 163 | KLYPTLVIR | 4 | A*03 |
| 164 | SEETFRFEL | 1 | B*40 |
|  | NLRP2 NLR family, pyrin domain containing 2 | 6 (20.0) |  |
| 165 | ELNKLLEEI | 3 | A*02 |
| 166 | IPFSNPRVL | 2 | B*07 |
| 167 | LLDEGAKLLY | 2 | A*01 |
| 168 | SPADAHRNL | 1 | B*07 |
|  | ZC3H12D zinc finger CCCH-type containing 12D | 6 (20.0) |  |
| 169 | AELERQAVL | 1 | B*37 |
| 170 | GRVPGPLSL | 1 | B*27 |
| 171 | SDLARLILL | 1 | B*27 |
| 172 | TPIREQHVL | 3 | B*35 |
|  | NELFE negative elongation factor complex member E | 6 (20.0) |  |
| 173 | APRKGNTL | 1 | B*07 |
| 174 | EEEEALQKKF | 1 | B*44 |
| 175 | KENLVDGF | 2 | B*37 |
| 176 | VYKENLVDGF | 2 | A*23, A*24 |
|  | ATP6V1C1 ATPase, H+ transporting, lysosomal 42 kDa, V1 subunit C1 | 6 (20.0) |  |
| 177 | TLLVVVPKL | 6 | A*02 |
|  | HLA-DMA major histocompatibility complex, class II, DM alpha | 6 (20.0) |  |
| 178 | HEIDRYTAI | 1 | B*40 |
| 179 | VFTLKPLEF | 3 | A*23, A*24 |
| 180 | YWVPRNAL | 2 | B*08 |
|  | TUFM Tu translation elongation factor, mitochondrial | 6 (20.0) |  |
| 181 | IGVEHVVVY | 5 | C*12 |
| 182 | RDKPHVNV | 1 | B*37 |
|  | EIF6 eukaryotic translation initiation factor 6 | 6 (20.0) |  |
| 183 | ADVLKVEVF | 2 | B*37 |
| 184 | IPVVHASI | 1 | B*51 |
| 185 | RDSLIDSLT | 1 | B*40 |
| 186 | TVADQVLVGSY | 2 | A*26 |
|  | CKAP4 cytoskeleton-associated protein 4 | 6 (20.0) |  |
| 187 | AADTERLAL | 1 | A*02 |
| 188 | DMKAKVASL | 2 | B*08 |
| 189 | HVLEEVQQV | 2 | B*13 |
| 190 | KEAADTERL | 1 | B*40 |
| 191 | RISEVLQKL | 1 | A*02 |
| 192 | TEVRELVSL | 2 | B*40 |
|  | COBLL1 cordon-bleu WH2 repeat protein-like 1 | 6 (20.0) |  |
| 193 | AIRSGEAAAK | 2 | A*03 |
| 194 | APNPAPKEL | 4 | B*07 |
| 195 | RQSLLTAI | 1 | B*13 |
| 196 | SPEQTLSPL | 1 | B*35 |
| 197 | TEHQVPSSV | 1 | B*40 |
| 198 | TTYKIVPPK | 1 | A*03 |
|  | TMED4 transmembrane emp24 protein transport domain containing 4 | 6 (20.0) |  |
| 199 | QLLDQVEQI | 4 | A*02 |
| 200 | DETMVIGNY | 1 | B*18 |
| 201 | RQYGSEGRFTF | 1 | B*37 |
|  | TNFRSF13C tumor necrosis factor receptor superfamily, member 13C | 6 (20.0) |  |
| 202 | SPAPRTAL | 6 | B*07 |
|  | UBL7 ubiquitin-like 7 | 6 (20.0) |  |
| 203 | GPRPITQSEL | 6 | B*07 |
| 204 | KPEPVDKVA | 1 | B*07 |
| 205 | TPSSRPASL | 4 | B*07 |
|  | CXorf21 chromosome X open reading frame 21 | 6 (20.0) |  |
| 206 | DETQVRSLY | 2 | B*18 |
| 207 | KEEETNSVATL | 1 | B*40 |
| 208 | LEQKVVELY | 2 | B*18 |
| 209 | NPISNAVLNEY | 1 | B*35 |
| 210 | SIKEKSSL | 1 | B*08 |
| 211 | TEITEISTPSL | 1 | B*40 |
|  | ASUN asunder spermatogenesis regulator | 6 (20.0) |  |
| 212 | GRLNSVNNR | 1 | B*27 |
| 213 | SILEDPPSI | 3 | A*02 |
| 214 | TPRTNNIEL | 2 | B*07 |
|  | RSL24D1 ribosomal L24 domain containing 1 | 6 (20.0) |  |
| 215 | DAMKRVEEI | 3 | B*08 |
| 216 | DIKEVKQNI | 3 | B*08 |
| 217 | GPIYPGHGM | 1 | B*07 |
|  | Q9UII5, ZNF107 zinc finger protein 107 | 6 (20.0) |  |
| 218 | GDYGRAFNL | 2 | B*37 |
| 219 | TRHKIVHTK | 2 | B*27 |
| 220 | RIHTGEKPYK | 1 | A*03 |
| 221 | KAFNWFSTL | 1 | A*32 |
|  | TRAF3IP3 TRAF3 interacting protein 3 | 6 (20.0) |  |
| 222 | QSTQRSLAL | 2 | B*08 |
| 223 | RDLQMNQALRF | 1 | B*40 |
| 224 | RELESQLHVL | 2 | B*40 |
| 225 | SEAEKLTLV | 1 | B*40 |

TABLE 1b

Additional peptides according to the invention for CLL - MHC class I

| SEQ ID NO: | Amino acid sequence | HLA |
|---|---|---|
| 226 | AAAKPVATK | A*03, A*11 |
| 227 | ATYHGSFSTK | A*03, A*11 |
| 228 | FMYDRPLRL | A*02 |
| 229 | FRVGNVQEL |  |
| 230 | GVAPFTIAR | A*03, A*11, A*68 |
| 231 | KMKPLDGSALY | A*30 |
| 232 | KPAPAKPVA | B*55 |
| 233 | KPVAAKPAA | n.a. |
| 234 | KQFGVAPFTI | B*13 |
| 235 | QEELVKISL | B*40:01 |
| 236 | RQLGTVQQVI | B*13 |
| 237 | RQLINALQI | B*13, A*32 |
| 238 | RVIGGLLAGQTY | B*15:01 |
| 239 | SENAFYLSP | n.a. |

TABLE 1b-continued

Additional peptides according to the invention for CLL - MHC class I

| SEQ ID NO: | Amino acid sequence | HLA |
|---|---|---|
| 240 | SQAPVLDAI | B*13 |
| 241 | STRYPPPAV | A*30 |
| 242 | TEDTLKVYL | B*40:01, B*52 |
| 243 | VAAKPVATK | A*03 |
| 244 | VQRVVESL | B*08 |
| 245 | VRNPSVVVK | B*27 |
| 246 | GESEVAIKI | B*49, B*52 |
| 247 | LIYSVGLLLA | A*02 |
| 248 | SAYPHQLSF | A*32 |
| 249 | SVIGVFITK | A*03, A*11, A*68 |
| 250 | AELGNSVQLI | B*49 |
| 251 | ANMTVTRI | n.a |
| 252 | ARISNVEFY | C*07 |
| 253 | AVFIGNQQF | B*15:01 |
| 254 | DIELQAENI | A*02 |
| 255 | DSYTVRVSV | B*51 |
| 256 | DVKIFVNTI | B*51 |
| 257 | EIIPKYGSI | A*25 |
| 258 | EQSKIFIHR | n.a |
| 259 | FVDVGLYQY | A*03 |
| 260 | GHTSTISTL | B*39 |
| 261 | GRIEYVEVF | C*07 |
| 262 | GTSIIPFQK | A*11 |
| 263 | HPFLRGIGY | B*35 |
| 264 | IPVEIHTA | B*55 |
| 265 | KIFVNTIAY | B*15:01 |
| 266 | LPEDKVRIAY | B*35 |
| 267 | LPFSEGLTV | B*51 |
| 268 | LPWANKVTI | B*51 |
| 269 | PWANKVTI | n.a. |
| 270 | QAYNRAVTI | B*51 |
| 271 | RSFPQKMAY | B*15:01 |
| 272 | RYPIHWHLL | C*07 |
| 273 | SPQNLRLML | B*07 |
| 274 | SYFSSPTQR | B*27 |
| 275 | VQIKSSLI | B*13 |
| 276 | VYIGHTSTI | C*07 |
| 277 | YHVPGTGESY | C*07 |
| 278 | ATNGDLASR | A*31 |
| 279 | GLHAEVTGVGY | B*15:01 |
| 280 | HVSSTSSSF | A*32 |
| 281 | LQADLQNGL | B*13 |
| 282 | SELPVSEVA | B*45 |
| 283 | SQTKSVFEI | B*13 |
| 284 | THIFTSDGL | B*39 |
| 285 | VIYFPPLQK | A*11 |
| 286 | YPFSSEQKW | B*35 |
| 287 | GQYFGELAL | B*13 |
| 288 | RIIVKNNAK | n.a. |
| 289 | RRIIVKNNAK | B*27 |
| 290 | SFGELALMY | n.a. |
| 291 | AFNAPVINR | B*27 |
| 292 | IMKRNIATY | B*15:01 |
| 293 | KVVDVIGTK | A*11 |
| 294 | LPFLKSLEF | B*07, B*35 |
| 295 | RLKVVDVIGTK | A*03 |
| 296 | TPRAATITA | B*07, B*51, B*55 |
| 297 | KPSEKIQVL | B*07 |
| 298 | VPYPVTTTV | B*35 |
| 299 | ASFPPFVEK | B*15 |
| 300 | AFIHISTAY | A*29 |
| 301 | ATFEKIPFER | A*11 |
| 302 | KLFEKVKEV | A*02 |
| 303 | SQMPKLEAF | B*15:01 |
| 304 | AVLGQHHNY | A*03 |
| 305 | GPPAHKPR | n.a. |
| 306 | RVYDVLVLK | A*03, A*11 |
| 307 | LPRPQGITV | B*07 |
| 308 | VLYVGSKTK | A*03 |
| 309 | KTKEQVTNV | A*11 |
| 310 | MPVDPDNEAY | B*35 |
| 311 | AEKTKQGVA | B*40 |
| 312 | DIADFFTTR | A*68 |
| 313 | HSYLQRQSV | C*12 |
| 314 | KEVTLIEEL | B*40:01 |
| 315 | REDGPGVAL | B*40:01 |
| 316 | REDPLPPGL | B*40:01 |
| 317 | SLFGGSQGLRK | A*03 |
| 318 | AEFQRLKQA | B*50 |
| 319 | EVIDGVPGKW | A*25 |
| 320 | IPKAPGKII | B*07, B*08, B*55 |
| 321 | SHNGSAIRY | A*32 |
| 322 | TEVTVVGDKL | B*40:01 |
| 323 | YASVVVKRY | A*28 |
| 324 | ATDLALYIK | A*11 |
| 325 | AYHNWRHAF | C*07 |
| 326 | EPLNIKDAY | B*35 |
| 327 | KIAATIISF | B*15:01 |
| 328 | KIFLHIHGL | B*71 |
| 329 | LEVILKKI | n.a. |
| 330 | SEHPLAQLY | B*44 |
| 331 | VPSAQTLKI | B*51 |
| 332 | AEYRSYVA | B*45 |
| 333 | ALAPGRGTLY | A*24 |
| 334 | GPRGTQAAL | B*07 |
| 335 | IEDPGTLHI | B*49 |
| 336 | IEDPGTLHIW | B*44 |
| 337 | RPIPIAVKY | B*35 |
| 338 | VEKLLTNW | n.a. |
| 339 | FLDPDIGGVAV | A*02 |
| 340 | HTAPPENKTW | A*30 |
| 341 | LLDTPVKTQY | A*01 |
| 342 | NAVKDFTSF | A*03, A*11 |
| 343 | SGLLQIKKL | n.a. |
| 344 | YHDKNIVLL | B*39 |
| 345 | SVDPKNYPK | A*11, A*03 |
| 346 | AVGLVLPAK | A*11 |
| 347 | AVGLVLPAKL | n.a. |
| 348 | ALLEVLSQK | A*03 |
| 349 | HEKQDTLVA | B*45 |
| 350 | KELELQIGM | B*40:01, B*52 |
| 351 | MYSDVWKQL | A*24 |
| 352 | RELQDEKAEL | B*40:01 |
| 353 | RITDVLDQK | A*11 |
| 354 | EVIKITGLK | A*68 |
| 355 | HHVDITKKL | B*39 |
| 356 | LPFNVKVSV | B*51 |
| 357 | TLPRVLEI | B*51 |
| 358 | TVDLPKSPK | A*11 |
| 359 | AEHGLLLTA | B*45 |
| 360 | AQAGALLQV | B*13 |
| 361 | DGGFVLKV | B*51 |
| 362 | IVYPSGKVY | B*15:01 |
| 363 | KLDNQVSKV | A*02 |
| 364 | SENVKLFSA | B*45 |
| 365 | VQKLQNII | |
| 366 | FSTPHGLEV | B*51 |
| 367 | KRFHQKSDM | B*27 |
| 368 | KTFGHAVSL | A*32 |
| 369 | SSNLITHSR | A*31 |
| 370 | GVIDGHIYAV | A*02 |
| 371 | IEPAKETTTNV | B*40:01, B*44 |
| 372 | NAPPSEVLL | n.a. |
| 373 | SIEPAKETTTNV | A*02 |
| 374 | AQSQHNQSL | B*13 |
| 375 | AQSRTNPQV | B*13 |
| 376 | KMHDKVFAY | A*03 |
| 377 | TAKAPLSTV | B*51 |

TABLE 1b-continued

Additional peptides according to the invention for CLL - MHC class I

| SEQ ID NO: | Amino acid sequence | HLA |
|---|---|---|
| 378 | IPTRTVAI | B*51 |
| 379 | NHDRKHAV | B*39 |
| 380 | NNHDRKHAV | B*08 |
| 381 | TPGGTRIIY | B*35 |
| 382 | EHWPSPETF | A*68 |
| 383 | EIITNTLSF | A*25 |
| 384 | EVRGALMSAF | A*25 |
| 385 | IPRPILVLL | B*07 |
| 386 | LPNKNRDEL | B*07 |
| 387 | QRIPAGAVL | B*27 |
| 388 | AEGPAGGFMVV | B*49 |
| 389 | AYYRDAEAY | C*07 |
| 390 | QVNRPLTMR | A*03 |
| 391 | RHSPVFQVY | A*32 |
| 392 | SLPVPNSAY | B*15:01 |
| 393 | TLGPPGTAHLY | B*15:01 |
| 394 | IEPAKETTTNV | B*40:01, B*44 |
| 395 | NAPPSEVLL | n.a. |
| 396 | SIEPAKETTTNV | A*02 |
| 397 | DLYSGLNQR | A*68 |
| 398 | KAKAKPVTR | A*31 |
| 399 | AVLDKAMKAK | A*03 |
| 400 | LELSTPLKI | B*49 |
| 401 | LPLNLDTKY | B*35 |
| 402 | TVIYRIQAL | A*02 |
| 403 | DAHIYLNHI | B*51 |
| 404 | NHIEPLKIQL | B*39 |
| 405 | AYRPAVHPR | B*27 |
| 406 | LRAPLEHEL | n.a. |
| 407 | RLFMVLLLK | A*03 |
| 408 | RSPDVLKDF | B*15:01 |
| 409 | ETAPGVHKR | A*68 |
| 410 | LYHGYIYTY | A*24 |
| 411 | GQHVATQHF | B*15:01 |
| 412 | LNGQLPNL | n.a. |
| 413 | LPFPDETHERY | B*35 |
| 414 | LPHNTHRVV | B*51 |
| 415 | VVFDSPRNR | A*03 |
| 416 | YPLGRILI | B*51 |
| 417 | KEFAEFVTS | B*50 |
| 418 | VMLDVPIRL | A*02 |
| 419 | VPMTPLRTV | B*51 |
| 420 | QIDYKTLVL | B*13 |
| 421 | VEDPTIVRI | B*40:01, B*44, B*52 |
| 422 | IPYQDLPHL | B*07 |
| 423 | DTPFLTGHGR | A*68 |
| 424 | EFYRALYI | |
| 425 | RYYPQILTNK | |
| 426 | KAYERHVL | B*08 |
| 427 | LPSEFHDY | B*35 |
| 428 | SLYAHPIEH | A*03 |
| 429 | LVREPGSQA | B*08 |
| 430 | RLAGPGSEKY | B*15:01 |
| 431 | SPGAGRNSVL | B*07 |
| 432 | SVQSDQGYISR | A*11 |
| 433 | GVRPPAPSL | B*13 |
| 434 | IFSEKPVFV | n.a. |
| 435 | KASNLLLGF | B*58 |
| 436 | KRYIFADAY | n.a. |
| 437 | RNLQLSLPR | A*31 |
| 438 | EASEPVALR | A*68 |
| 439 | RPKVPDQSV | B*07, B*08, B*35 |
| 440 | VLYENALKL | A*02 |
| 441 | EVLDKSQTNY | A*25 |
| 442 | MPSPIPAKY | B*35 |
| 443 | YGIENFTSV | B*51 |
| 444 | ARAAQVFFL | B*27 |
| 445 | EHIVPNAEL | B*39 |
| 446 | EAFEFVKQR | A*68 |
| 447 | NHFEGHYQY | n.a. |
| 448 | DAYPKNPHL | B*51 |
| 449 | DVNIKSTER | A*68 |
| 450 | HINSIKSVF | A*31 |
| 451 | YESEKVGVA | B*50 |
| 452 | ENAPTTVSR | A*68 |
| 453 | RFPHLLAHTY | C*14 |
| 454 | TLDGSLHAV | A*02 |
| 455 | RTVLKNLSLLK | A*03 |
| 456 | FEAKVQAI | B*49 |
| 457 | FFEAKVQAI | C*12 |
| 458 | KELQSTFK | n.a. |
| 459 | NVSSRFEEEI | A*02 |
| 460 | EVWNNLGTTK | A*68 |
| 461 | MIFRSGSLI | n.a. |
| 462 | NHALPLPGF | B*39 |
| 463 | ASVFGTMPLK | A*11 |
| 464 | REFPDRLVGY | B*44 |
| 465 | SVFGTMPLK | A*11 |
| 466 | DEMRFVTQI | n.a. |
| 467 | ETVHFATTQW | A*25 |
| 468 | LPPPATQI | B*51 |
| 469 | LARDLYAF | C*03, C*12 |
| 470 | LPGIGLSTSL | B*53 |
| 471 | MEVILPML | n.a. |
| 472 | AILDYILAK | A*03 |
| 473 | KIASQLSKL | A*02 |
| 474 | KVTSTTTVK | A*03, A*11 |
| 475 | YNTLLPYTF | n.a. |
| 476 | FLDPRPLTV | A*02 |
| 477 | SAFADRPAF | C*03 |
| 478 | AAVPVIISR | A*68 |
| 479 | EEIGKVAAA | B*45 |
| 480 | FLKDLVASV | A*02 |
| 481 | VIISRALEL | C*03 |
| 482 | APRTTGTPRTSL | B*07 |
| 483 | ESVGGSPQTK | A*68 |
| 484 | IPKDKAIL | B*08 |
| 485 | LPAYGRTTL | B*07 |
| 486 | HQAAIVSKI | B*13 |
| 487 | QAAIVSKI | B*51 |
| 488 | RQKMPEDGL | B*13 |
| 489 | SVQKSSGVK | A*11 |
| 490 | DSIGSTVSSER | A*68 |
| 491 | LPYNNKDRDAL | B*07 |
| 492 | IYDEIQQEM | C*14 |
| 493 | AQAKGLIQV | B*13 |
| 494 | EVSSEIYQW | A*25 |
| 495 | KWNPVPLSY | A*29 |
| 496 | NRLLAQQSL | B*27 |
| 497 | APRPVAVAV | B*07 |
| 498 | FYRETVQVGR | A*33 |
| 499 | LLAPRPVAV | A*02 |
| 500 | GLAALVILK | A*03 |
| 501 | KIQEVFSSY | B*15:01 |
| 502 | ASLDKFLSH | A*11 |
| 503 | ALYATKTLR | A*03 |
| 504 | MEYVISRI | n.a. |
| 505 | VPVGRQPII | B*51 |
| 506 | KLLIGVIAAV | A*02 |
| 507 | LPSLIKLD | n.a. (B*51!!) |
| 508 | PSLIKLDL | n.a. |
| 509 | ARNKELIGK | B*27 |
| 510 | AVKSNAAAY | B*15:01 |
| 511 | EVIIPHSGW | A*25 |
| 512 | SVKEQEAQF | B*15:01 |
| 513 | APRGLEPIAI | B*07 |
| 514 | GRFGGVITI | B*27 |
| 515 | PVAGFFINR | A*68 |
| 516 | TPKTPSRDA | B*08, B*55 |
| 517 | VLFGGKVSGA | A*02 |
| 518 | AEHIESRTL | B*40, B*44 |
| 519 | DQYPYLKSV | C*12 |

TABLE 1b-continued

Additional peptides according to the invention for CLL - MHC class I

| SEQ ID NO: | Amino acid sequence | HLA |
|---|---|---|
| 520 | IARNLTQQL | B*07 |
| 521 | IESRTLAIA | B*50 |
| 522 | MTSALPIIQK | A*11 |
| 523 | SLLTSSKGQLQK | A*03 |
| 524 | TSALPIIQK | A*11, A*03 |
| 525 | VRLGSLSTK | B*27 |
| 526 | RINEFSISSF | B*15 |
| 527 | DEKQQHIVY | B*18 |
| 528 | DEVYQVTVY | B*18 |
| 529 | GEISEKAKL | B*40 |
| 530 | YTMKEVLFY | A*03 |
| 531 | SQLTTLSFY | B*15 |
| 532 | LEKQLIEL | B*44 |
| 533 | ELTLGEFLK | A*68, A*33 |
| 534 | LTLGEFLK | A*68 |
| 535 | LTLGEFLKL | A*02 |
| 536 | TLGEFLKL | A*02 |
| 537 | ITARPVLW | B*58 |
| 538 | KLMSPKLYVW | A*32 |
| 539 | KVSAVTLAY | A*03 |
| 540 | VEGSGELFRW | B*44 |
| 541 | RPKSNIVL | B*07 |
| 542 | RPKSNIVLL | B*07 |

TABLE 1c

Additional peptides according to the invention for CLL - MHC class II

| SEQ ID NO: | Amino acid sequence | MHC |
|---|---|---|
| 543 | GEPLSYTRFSLARQ | class II |
| 544 | GEPLSYTRFSLARQVD | class II |
| 545 | GEPLSYTRFSLARQVDG | class II |
| 546 | GGEPLSYTRFSLARQVD | class II |
| 547 | GGEPLSYTRFSLARQVDG | class II |
| 548 | NPGGYVAYSKAATVTG | class II |
| 549 | NPGGYVAYSKAATVTGK | class II |
| 550 | NPGGYVAYSKAATVTGKL | class II |
| 551 | NSVIIVDKNGRL | class II |
| 552 | NSVIIVDKNGRLV | class II |
| 553 | NSVIIVDKNGRLVY | class II |
| 554 | RVEYHFLSPYVSPK | class II |
| 555 | RVEYHFLSPYVSPKE | class II |
| 556 | RVEYHFLSPYVSPKESPF | class II |
| 557 | SPFRHVFWGSGSHTL | class II |
| 558 | SVIIVDKNGRLV | class II |
| 559 | VEYHFLSPYVSPK | class II |
| 560 | VEYHFLSPYVSPKE | class II |
| 561 | LPSQAFEYILYNKG | class II |
| 562 | LPSQAFEYILYNKGI | class II |
| 563 | LPSQAFEYILYNKGIM | class II |
| 564 | LPSQAFEYILYNKGIMG | class II |
| 565 | MNGYFLIERGKNM | class II |
| 566 | NGYFLIERGKNM | class II |
| 567 | PSQAFEYILYNKG | class II |
| 568 | PSQAFEYILYNKGI | class II |
| 569 | PSQAFEYILYNKGIM | class II |
| 570 | EGVQYSYSLFHLM | class II |
| 571 | EGVQYSYSLFHLML | class II |
| 572 | GVQYSYSLFHLM | class II |
| 573 | GVQYSYSLFHLML | class II |
| 574 | SIISIHPKIQEHQPR | class II |
| 575 | SSIRTSTNSQVDK | class II |
| 576 | VLVGYKAVYRIS | class II |
| 577 | YSSIRTSTNSQVDK | class II |
| 578 | GGGYGSGGGSGGYGSRRF | class II |
| 579 | GGSFGGRSSGSP | class II |
| 580 | KGGSFGGRSSGSP | class II |
| 581 | SGQQQSNYGPMKGGSFGGRSSGSPY | class II |
| 582 | SGSPYGGGYGSGGGSGGYGSRRF | class II |
| 583 | SPYGGGYGSGGGSGGYGSRRF | class II |

TABLE 1c-continued

Additional peptides according to the invention for CLL - MHC class II

| SEQ ID NO: | Amino acid sequence | MHC |
|---|---|---|
| 584 | YGGGYGSGGGSGGYGSRRF | class II |
| 585 | GNRINEFSISSF | class II |
| 586 | HGNQITSDKVGRKV | class II |
| 587 | IPPVNTNLENLYLQ | class II |
| 588 | LQVLRLDGNEIKR | class II |
| 589 | LQVLRLDGNEIKRS | class II |
| 590 | LQVLRLDGNEIKRSA | class II |
| 591 | LRELHLDHNQISRVPN | class II |
| 592 | LYVRLSHNSLTNNG | class II |
| 593 | VPSRMKYVYFQNNQ | class II |
| 594 | VPSRMKYVYFQNNQIT | class II |
| 595 | VPSRMKYVYFQNNQITS | class II |
| 596 | WIALHGNQITSD | class II |
| 597 | WIALHGNQITSDK | class II |
| 598 | ADDNVSFRWEALGNT | class II |
| 599 | ADDNVSFRWEALGNTL | class II |
| 600 | DADDNVSFRWEALGNTL | class II |
| 601 | DDNVSFRWEALGNT | class II |
| 602 | DDNVSFRWEALGNTL | class II |
| 603 | DNVSFRWEALGNT | class II |
| 604 | DNVSFRWEALGNTL | class II |
| 605 | DNVSFRWEALGNTLS | class II |
| 606 | DTGSYRAQISTKTSAK | class II |
| 607 | DTGSYRAQISTKTSAKL | class II |
| 608 | DTITIYSTINHSK | class II |
| 609 | EDTGSYRAQISTKTSAK | class II |
| 610 | ENDTITIYSTINHSK | class II |
| 611 | ENDTITIYSTINHSKESKPT | class II |
| 612 | GSYRAQISTKTSAK | class II |
| 613 | NDTITIYSTINH | class II |
| 614 | NDTITIYSTINHS | class II |
| 615 | NDTITIYSTINHSK | class II |
| 616 | NVSFRWEALGNTL | class II |
| 617 | SPTNNTVYASVTHSNRET | class II |
| 618 | TGSYRAQISTKTSAK | class II |
| 619 | TPRENDTITIYSTINHSK | class II |
| 620 | TPRENDTITIYSTINHSKESKPT | class II |
| 621 | VSFRWEALGNTL | class II |
| 622 | APIHFTIEKLELNEK | class II |
| 623 | DAQFEVIKGQTIE | class II |
| 624 | DAQFEVIKGQTIEVR | class II |
| 625 | ESYFIPEVRIYDSGT | class II |
| 626 | IPEVRIYDSGTY | class II |
| 627 | KDKAIVAHNRHGNK | class II |
| 628 | KDKAIVAHNRHGNKA | class II |
| 629 | NFVILEFPVEEQDR | class II |
| 630 | SQPRISYDAQFEVIK | class II |
| 631 | SQPRISYDAQFEVIKG | class II |
| 632 | YDAQFEVIKGQTIE | class II |
| 633 | GNPAYRSFSNSLSQ | class II |
| 634 | GPPGEAGYKAFSSLLA | class II |
| 635 | GPPGEAGYKAFSSLLASS | class II |
| 636 | GPPGEAGYKAFSSLLASSA | class II |
| 637 | GPPGEAGYKAFSSLLASSAVSPE | class II |
| 638 | GPPGEAGYKAFSSLLASSAVSPEK | class II |
| 639 | GYKAFSSLLASSAVSP | class II |
| 640 | GYKAFSSLLASSAVSPE | class II |
| 641 | KAFSSLLASSAVSPE | class II |
| 642 | NPAYRSFSNSLSQ | class II |
| 643 | SRDDFQEGREGIVAR | class II |
| 644 | SSSSFHPAPGNAQ | class II |
| 645 | VARLTESLFLDL | class II |
| 646 | VARLTESLFLDLLG | class II |
| 647 | VIAGNPAYRSFSN | class II |
| 648 | VPQPEPETWEQILRRNVLQ | class II |
| 649 | YKAFSSLLASSAVS | class II |
| 650 | YKAFSSLLASSAVSP | class II |
| 651 | YKAFSSLLASSAVSPE | class II |
| 652 | GNQVFSYTANKEIRTDD | class II |
| 653 | IEEIVLVDDASERD | class II |
| 654 | IEEIVLVDDASERDF | class II |
| 655 | LENIYPDSQIPRH | class II |
| 656 | LENIYPDSQIPRHY | class II |
| 657 | NQVFSYTANKEIR | class II |
| 658 | NQVFSYTANKEIRT | class II |
| 659 | NQVFSYTANKEIRTDD | class II |

TABLE 1c-continued

Additional peptides according to the invention for CLL - MHC class II

| SEQ ID NO: | Amino acid sequence | MHC |
|---|---|---|
| 660 | VHSVINRSPRHMIEE | class II |
| 661 | EYVSLYHQPAAM | class II |
| 662 | IKAEYKGRVTLKQYPR | class II |
| 663 | LNVHSEYEPSWEEQP | class II |
| 664 | LPYLFQMPAYASSS | class II |
| 665 | LPYLFQMPAYASSSK | class II |
| 666 | NFIKAEYKGRVT | class II |
| 667 | TNFIKAEYKGRVT | class II |
| 668 | TTNFIKAEYKGRVT | class II |
| 669 | VTLNVHSEYEPSWEEQP | class II |
| 670 | YPRKNLFLVEVTQLTESDS | class II |
| 671 | YPRKNLFLVEVTQLTESDSG | class II |
| 672 | ADLSSFKSQELN | class II |
| 673 | ADLSSFKSQELNER | class II |
| 674 | ADLSSFKSQELNERN | class II |
| 675 | ADLSSFKSQELNERNE | class II |
| 676 | ADLSSFKSQELNERNEA | class II |
| 677 | AEQQRLKSQDLELSWNLNG | class II |
| 678 | EQQRLKSQDLELSWN | class II |
| 679 | ISQELEELRAEQQR | class II |
| 680 | ISQELEELRAEQQRLK | class II |
| 681 | KGTKQWVHARYA | class II |
| 682 | QADLSSFKSQELNER | class II |
| 683 | SWNLNGLQADLSSFK | class II |
| 684 | TGSWIGLRNLDLKG | class II |
| 685 | FGNYNNQSSNFGPMKGGNFGGRS | class II |
| 686 | FGPMKGGNFGGRSSGPYGGGGQY | class II |
| 687 | GPMKGGNFGGRSSGP | class II |
| 688 | GPYGGGGQYFAKP | class II |
| 689 | KGGNFGGRSSGP | class II |
| 690 | NDFGNYNNQSSNFGP | class II |
| 691 | SGPYGGGGQYFAKP | class II |
| 692 | DAGSYKAQINQRNFE | class II |
| 693 | DAGSYKAQINQRNFEVT | class II |
| 694 | DGELIRTQPQRLPQ | class II |
| 695 | GELIRTQPQRLPQ | class II |
| 696 | NPSDGELIRTQPQRLP | class II |
| 697 | NPSDGELIRTQPQRLPQ | class II |
| 698 | NPSDGELIRTQPQRLPQL | class II |
| 699 | ASNDMYHSRALQVVR | class II |
| 700 | ASNDMYHSRALQVVRA | class II |
| 701 | EGVRRALDFAVGEYN | class II |
| 702 | EGVRRALDFAVGEYNK | class II |
| 703 | SNDMYHSRALQVVR | class II |
| 704 | VGEYNKASNDMYH | class II |
| 705 | VRARKQIVAGVNY | class II |
| 706 | VRRALDFAVGEYNKASND | class II |
| 707 | VVRARKQIVAGVN | class II |
| 708 | VVRARKQIVAGVNY | class II |
| 709 | APLEGARFALVRED | class II |
| 710 | APVELILSDETLPAPE | class II |
| 711 | ELILSDETLPAPE | class II |
| 712 | LAPLEGARFALVRE | class II |
| 713 | LAPLEGARFALVRED | class II |
| 714 | RGEKELLVPRSSTSPD | class II |
| 715 | ASKTFTTQETITNAET | class II |
| 716 | DQHFRTTPLEKNAPV | class II |
| 717 | NTPILVDGKDVMPE | class II |
| 718 | NTPILVDGKDVMPEV | class II |
| 719 | NTPILVDGKDVMPEVN | class II |
| 720 | SNTPILVDGKDVMPE | class II |
| 721 | SNTPILVDGKDVMPEVN | class II |
| 722 | TPILVDGKDVMP | class II |
| 723 | TPILVDGKDVMPE | class II |
| 724 | TPILVDGKDVMPEV | class II |
| 725 | TPILVDGKDVMPEVN | class II |
| 726 | GPLKFLHQDIDSGQG | class II |
| 727 | GPLKFLHQDIDSGQGIR | class II |
| 728 | LGDIYFKLFRASG | class II |
| 729 | TGHLFDLSSLSGRAG | class II |
| 730 | VPSPVDCQVTDLAGNE | class II |
| 731 | DGLNSLTYQVLDVQRYPL | class II |
| 732 | HPVLQRQQLDYGIY | class II |
| 733 | LNSLTYQVLDVQR | class II |
| 734 | LNSLTYQVLDVQRYP | class II |
| 735 | LNSLTYQVLDVQRYPL | class II |
| 736 | LPQLVGVSTPLQG | class II |
| 737 | LPQLVGVSTPLQGG | class II |
| 738 | LPQLVGVSTPLQGGS | class II |
| 739 | RLPQLVGVSTPLQGGS | class II |
| 740 | SPHKVAIIPFRNR | class II |
| 741 | SPHKVAIIPFRNRQE | class II |
| 742 | SPHKVAIIPFRNRQEH | class II |
| 743 | AIVQAVSAHRRH | class II |
| 744 | ARNFERNKAIKVI | class II |
| 745 | ARNFERNKAIKVIIA | class II |
| 746 | NFERNKAIKVII | class II |
| 747 | NFERNKAIKVIIA | class II |
| 748 | VAIVQAVSAHRH | class II |
| 749 | VAIVQAVSAHRHR | class II |
| 750 | VAIVQAVSAHRHRA | class II |
| 751 | VAIVQAVSAHRHRAR | class II |
| 752 | EEVITLIRSNQQLE | class II |
| 753 | EEVITLIRSNQQLEN | class II |
| 754 | IPADTFAALKNPNAML | class II |
| 755 | LKQLLSDKQQKRQSG | class II |
| 756 | LKQLLSDKQQKRQSGQ | class II |
| 757 | TPSYVAFTDTER | class II |
| 758 | TPSYVAFTDTERL | class II |
| 759 | EGLYSRTLAGSIT | class II |
| 760 | EGLYSRTLAGSITPP | class II |
| 761 | EKWYIPDPTGKFN | class II |
| 762 | GAIAAINSIQHNTR | class II |
| 763 | LPILVPSAKKAI | class II |
| 764 | LPILVPSAKKAIY | class II |
| 765 | LPILVPSAKKAIYM | class II |
| 766 | LPILVPSAKKAIYMD | class II |
| 767 | LPILVPSAKKAIYMDD | class II |
| 768 | VEEGLYSRTLAGSIT | class II |
| 769 | WEKWYIPDPTGKFN | class II |
| 770 | YKIVNFDPKLLE | class II |
| 771 | YKIVNFDPKLLEG | class II |
| 772 | YKIVNFDPKLLEGKV | class II |
| 773 | LPEFYKTVSPAL | class II |
| 774 | VGQFIQDVKNSRST | class II |
| 775 | VGQFIQDVKNSRSTD | class II |
| 776 | VVGQFIQDVKNSRS | class II |
| 777 | VVGQFIQDVKNSRST | class II |
| 778 | VVGQFIQDVKNSRSTD | class II |
| 779 | VVGQFIQDVKNSRSTDS | class II |
| 780 | DNGHLYREDQTSPAPG | class II |
| 781 | DNGHLYREDQTSPAPGLR | class II |
| 782 | EVQVFAPANALPARSE | class II |
| 783 | GHLYREDQTSPAPG | class II |
| 784 | LPARSEAAAVQPVIG | class II |
| 785 | NGHLYREDQTSPAPG | class II |
| 786 | NGHLYREDQTSPAPGL | class II |
| 787 | NGHLYREDQTSPAPGLR | class II |
| 788 | VFAPANALPARSEAA | class II |
| 789 | VQVFAPANALPARSE | class II |
| 790 | AIVVSDRDGVPVIK | class II |
| 791 | GLHAIVVSDRDGVPV | class II |
| 792 | GLHAIVVSDRDGVPVIK | class II |
| 793 | HAIVVSDRDGVPV | class II |
| 794 | KLPSVEGLHAIVVSDRDG | class II |
| 795 | LHAIVVSDRDGVPV | class II |
| 796 | LHAIVVSDRDGVPVI | class II |
| 797 | LHAIVVSDRDGVPVIK | class II |
| 798 | LPSVEGLHAIVVSDR | class II |
| 799 | VPVIKVANDNAPE | class II |
| 800 | YNTYQVVQFNRLP | class II |
| 801 | YNTYQVVQFNRLPL | class II |
| 802 | YNTYQVVQFNRLPLV | class II |
| 803 | YNTYQVVQFNRLPLVV | class II |
| 804 | YYNTYQVVQFNRLP | class II |
| 805 | YYNTYQVVQFNRLPL | class II |
| 806 | YYNTYQVVQFNRLPLV | class II |
| 807 | DKIYFMAGSSRKE | class II |
| 808 | DVGTDEEEETAKESTAEKDE | class II |
| 809 | EVTFKSILFVPTSAP | class II |
| 810 | KSEKFAFQAEVNR | class II |
| 811 | LPEFDGKRFQNVAK | class II |

TABLE 1c-continued

Additional peptides according to the invention for CLL - MHC class II

| SEQ ID NO: | Amino acid sequence | MHC |
|---|---|---|
| 812 | DGSYRIFSKGASE | class II |
| 813 | GSYRIFSKGASE | class II |
| 814 | SDGSYRIFSKGASE | class II |
| 815 | SVKKMMKDNNLVRH | class II |
| 816 | VKKMMKDNNLVRH | class II |
| 817 | NNMRIFGEAAEKN | class II |
| 818 | VDKVLERDQKLSE | class II |
| 819 | VDKVLERDQKLSELD | class II |
| 820 | VDKVLERDQKLSELDD | class II |
| 821 | VDKVLERDQKLSELDDR | class II |
| 822 | VLERDQKLSELDDR | class II |
| 823 | ATRSIQVDGKTIKAQ | class II |
| 824 | ATRSIQVDGKTIKAQI | class II |
| 825 | IGVEFATRSIQVDGK | class II |
| 826 | RSIQVDGKTIKA | class II |
| 827 | RSIQVDGKTIKAQ | class II |
| 828 | RSIQVDGKTIKAQI | class II |
| 829 | TRSIQVDGKTIKAQ | class II |
| 830 | DIMRVNVDKVLERDQK | class II |
| 831 | DIMRVNVDKVLERDQKL | class II |
| 832 | IMRVNVDKVLERDQK | class II |
| 833 | VDKVLERDQKLSE | class II |
| 834 | VDKVLERDQKLSELD | class II |
| 835 | VDKVLERDQKLSELDD | class II |
| 836 | VDKVLERDQKLSELDDR | class II |
| 837 | VLERDQKLSELDDR | class II |
| 838 | ATRSIQVDGKTIKAQ | class II |
| 839 | ATRSIQVDGKTIKAQI | class II |
| 840 | IGVEFATRSIQVDGK | class II |
| 841 | RSIQVDGKTIKA | class II |
| 842 | RSIQVDGKTIKAQ | class II |
| 843 | RSIQVDGKTIKAQI | class II |
| 844 | TRSIQVDGKTIKAQ | class II |
| 845 | GIRVAPVPLYNS | class II |
| 846 | GIRVAPVPLYNSFH | class II |
| 847 | NPNGIRVAPVPLYNSFH | class II |
| 848 | DDPAIDVCKKLLGKYPN | class II |
| 849 | DKQPYSKLPGVSLLKP | class II |
| 850 | DKQPYSKLPGVSLLKPL | class II |
| 851 | HPRYYISANVTGFK | class II |
| 852 | SHPRYYISANVTG | class II |
| 853 | SHPRYYISANVTGFK | class II |
| 854 | TSHPRYYISANVTG | class II |
| 855 | TSHPRYYISANVTGFK | class II |
| 856 | ADIFVDPVLHTA | class II |
| 857 | ADIFVDPVLHTACA | class II |
| 858 | DPGADYRIDRALNEA | class II |
| 859 | IAQDYKVSYSLA | class II |
| 860 | IAQDYKVSYSLAK | class II |
| 861 | ISRDWKLDPVLYRK | class II |
| 862 | LIAQDYKVSYSLA | class II |
| 863 | RQKLIAQDYKVSYS | class II |
| 864 | RQKLIAQDYKVSYSL | class II |
| 865 | RQKLIAQDYKVSYSLA | class II |
| 866 | RQKLIAQDYKVSYSLAK | class II |
| 867 | SALDYRLDPQLQLH | class II |
| 868 | SKADIFVDPVLHTA | class II |
| 869 | SPSKNYILSVISGSI | class II |
| 870 | ETTQLTADSHPSYHTDG | class II |
| 871 | SGESLYHVLGLDKNATSDD | class II |
| 872 | TTQLTADSHPSYHT | class II |
| 873 | TTQLTADSHPSYHTD | class II |
| 874 | TTQLTADSHPSYHTDG | class II |
| 875 | SVEEFLSEKLERI | class II |
| 876 | VEEFLSEKLERI | class II |
| 877 | DLSSSILAQSRERVA | class II |
| 878 | EKGVRTLTAAAVSGAQ | class II |
| 879 | EKGVRTLTAAAVSGAQP | class II |
| 880 | EKGVRTLTAAAVSGAQPI | class II |
| 881 | KGVRTLTAAAVSGA | class II |
| 882 | KGVRTLTAAAVSGAQ | class II |
| 883 | VGPFAPGITEKAPEEKK | class II |
| 884 | DPPLIALDKDAPLR | class II |
| 885 | EIITPDVPFTVDKDG | class II |
| 886 | IITPDVPFTVDKDG | class II |
| 887 | PPLIALDKDAPLR | class II |
| 888 | TNVKKSHKATVHIQ | class II |
| 889 | DDNIKTYSDHPE | class II |
| 890 | DDNIKTYSDHPEK | class II |
| 891 | DSAVFFEQGTTRIG | class II |
| 892 | GDKVYVHLKNLASRPY | class II |
| 893 | GDKVYVHLKNLASRPYT | class II |
| 894 | VHLKNLASRPYT | class II |
| 895 | VYVHLKNLASRPY | class II |
| 896 | VYVHLKNLASRPYT | class II |
| 897 | VYVHLKNLASRPYTFH | class II |
| 898 | YVHLKNLASRPY | class II |
| 899 | YVHLKNLASRPYT | class II |
| 900 | YVHLKNLASRPYTFH | class II |
| 901 | SNLIKLAQKVPTAD | class II |
| 902 | YDTRTSALSAKS | class II |
| 903 | ALMTDPKLITWSPV | class II |
| 904 | NDVAWNFEKFLVGPDG | class II |
| 905 | QSVYAFSARPLAG | class II |
| 906 | QSVYAFSARPLAGGEPV | class II |
| 907 | WNFEKFLVGPDG | class II |
| 908 | DVGMFVALTKLGQPD | class II |
| 909 | VGMFVALTKLGQPD | class II |
| 910 | AGVFHVEKNGRY | class II |
| 911 | FAGVFHVEKNGRYS | class II |
| 912 | GPITITIVNRDGTR | class II |
| 913 | NGRYSISRTEAADL | class II |
| 914 | RKSRQGSLAMEELK | class II |
| 915 | RRKSRQGSLAMEELK | class II |
| 916 | EEFKKLTSIKIQNDK | class II |
| 917 | INRRMADDNKLFR | class II |
| 918 | TATIVMVTNLKERKE | class II |
| 919 | ELFYKGIRPAINVG | class II |
| 920 | GQKRSTVAQLVKR | class II |
| 921 | SDLDAATQQLLSRGV | class II |
| 922 | FDFSQNTRVPRLPE | class II |
| 923 | GDAPAILFDKEF | class II |
| 924 | VTHEIDRYTAIAY | class II |
| 925 | GQGYLIKDGKLIKNNA | class II |
| 926 | IDTTSKFGHGRFQTM | class II |
| 927 | IDVIGVTKGKGYKGVTSRW | class II |
| 928 | MGPLKKDRIAKEEGA | class II |
| 929 | AAKYQLDPTASISA | class II |
| 930 | IAAKYQLDPTASISA | class II |
| 931 | IAAKYQLDPTASISAK | class II |
| 932 | AGLGRAYALAFAERG | class II |
| 933 | DAFGRIDVVVNNAG | class II |
| 934 | GLGRAYALAFAER | class II |
| 935 | GLGRAYALAFAERG | class II |
| 936 | AKFALNGEEFMNFDL | class II |
| 937 | AKFALNGEEFMNFDLK | class II |
| 938 | ALNGEEFMNFDLK | class II |
| 939 | KFALNGEEFMNFDL | class II |
| 940 | SDGSFHASSSLTVK | class II |
| 941 | EERNLLSVAYKNVVGAR | class II |
| 942 | ERNLLSVAYKNVVGAR | class II |
| 943 | IAELDTLSEESYKD | class II |
| 944 | IAELDTLSEESYKDS | class II |
| 945 | ADSYLDEGFLLDKKIG | class II |
| 946 | DSYLDEGFLLDKK | class II |
| 947 | DSYLDEGFLLDKKIG | class II |
| 948 | VDNIIKAAPRKRVPD | class II |
| 949 | SPPQFRVNGAISN | class II |
| 950 | SPPQFRVNGAISNFE | class II |
| 951 | SPPQFRVNGAISNFEE | class II |
| 952 | SPPQFRVNGAISNFEEF | class II |
| 953 | VGKMFVDVYFQEDKK | class II |
| 954 | VGKMFVDVYFQEDKKE | class II |
| 955 | DPKRTIAQDYGVLKADE | class II |
| 956 | DPKRTIAQDYGVLKADEG | class II |
| 957 | PKRTIAQDYGVLKADEG | class II |
| 958 | GLFIIDDKGILRQ | class II |
| 959 | GLFIIDDKGILRQIT | class II |
| 960 | RGLFIIDDKGILR | class II |
| 961 | RGLFIIDDKGILRQ | class II |
| 962 | RGLFIIDDKGILRQIT | class II |
| 963 | GNTVIHLDQALARMR | class II |

TABLE 1c-continued

Additional peptides according to the invention for CLL - MHC class II

| SEQ ID NO: | Amino acid sequence | MHC |
|---|---|---|
| 964 | NTVIHLDQALARMR | class II |
| 965 | NTVIHLDQALARMRE | class II |
| 966 | ENNEIISNIRDSVIN | class II |
| 967 | NNEIISNIRDSVIN | class II |
| 968 | SPTVQVFSASGKPV | class II |
| 969 | SSPTVQVFSASGKPVE | class II |
| 970 | AEPNYHSLPSARTDEQ | class II |
| 971 | SSILAKTASNIIDVS | class II |
| 972 | LEARATAPPAPSAPN | class II |
| 973 | ADDLEGEAFLPL | class II |
| 974 | ADDLEGEAFLPLR | class II |
| 975 | ADDLEGEAFLPLRE | class II |
| 976 | GADDLEGEAFLPLR | class II |
| 977 | AGREINLVDAHLKSE | class II |
| 978 | AGREINLVDAHLKSEQT | class II |
| 979 | GREINLVDAHLKSE | class II |
| 980 | KPGIVYASLNHSVIG | class II |
| 981 | NKPGIVYASLNHSVIG | class II |
| 982 | TTLYVTDVKSASERPS | class II |
| 983 | APSTYAHLSPAKTPPP | class II |
| 984 | APSTYAHLSPAKTPPPP | class II |
| 985 | APSTYAHLSPAKTPPPPA | class II |
| 986 | RDDLYDQDDSRDFPR | class II |
| 987 | TRPYHSLPSEAVFA | class II |
| 988 | TRPYHSLPSEAVFAN | class II |
| 989 | VAVFTFHNHGRT | class II |
| 990 | VAVFTFHNHGRTA | class II |
| 991 | VAVFTFHNHGRTANL | class II |
| 992 | EDDYIKSWEDNQQGDE | class II |
| 993 | ELERIQIQEAAKKKPG | class II |
| 994 | ERIQIQEAAKKKP | class II |
| 995 | ERIQIQEAAKKKPG | class II |
| 996 | ERIQIQEAAKKKPGI | class II |
| 997 | LERIQIQEAAKKKPG | class II |
| 998 | LSSISQYSGKIK | class II |
| 999 | SPAKDSLSFEDF | class II |
| 1000 | SPAKDSLSFEDFLDL | class II |
| 1001 | INSRFPIPSATDPD | class II |
| 1002 | VQHYELLNGQSVFG | class II |
| 1003 | DNQYAVLENQKSSH | class II |
| 1004 | GPPEIYSDTQFPS | class II |
| 1005 | GPPEIYSDTQFPSLQ | class II |
| 1006 | TPQGPPEIYSDTQFPS | class II |
| 1007 | TPQGPPEIYSDTQFPSLQ | class II |
| 1008 | TPQGPPEIYSDTQFPSLQST | class II |
| 1009 | ANLQRAYSLAKEQR | class II |
| 1010 | NLQRAYSLAKEQR | class II |
| 1011 | TPSGITYDRKDIEEH | class II |
| 1012 | VSTLNSEDFVLVSR | class II |
| 1013 | VSTLNSEDFVLVSRQ | class II |
| 1014 | VSTLNSEDFVLVSRQG | class II |
| 1015 | GSSFFGELFNQNPE | class II |
| 1016 | SGSSFFGELFNQNPE | class II |

TABLE 2

Peptides according to the invention suitable for the (combined) treatment of CLL and/or AML

| SEQ ID NO: | Amino acid sequence |
|---|---|
| 710 | APVELILSDETLPAPE |
| 878 | EKGVRTLTAAAVSGAQ |
| 879 | EKGVRTLTAAAVSGAQP |
| 533 | ELTLGEFLK |
| 476 | FLDPRPLTV |
| 892 | GDKVYVHLKNLASRPY |
| 111 | GLDPNKPPEL |
| 178 | HEIDRYTAI |
| 181 | IGVEHVVVY |
| 184 | IPVVHASI |
| 882 | KGVRTLTAAAVSGAQ |
| 363 | KLDNQVSKV |
| 42 | KLYELHVFTF |
| 163 | KLYPTLVIR |
| 137 | KTIAFLLPMF |
| 713 | LAPLEGARFALVRED |
| 532 | LEKQLIEL |
| 734 | LNSLTYQVLDVQRYP |
| 736 | LPQLVGVSTPLQG |
| 737 | LPQLVGVSTPLQGG |
| 738 | LPQLVGVSTPLQGGS |
| 534 | LTLGEFLK |
| 535 | LTLGEFLKL |
| 914 | RKSRQGSLAMEELK |
| 739 | RLPQLVGVSTPLQGGS |
| 477 | SAFADRPAF |
| 164 | SEETFRFEL |
| 364 | SENVKLFSA |
| 531 | SQLTTLSFY |
| 536 | TLGEFLKL |
| 186 | TVADQVLGSY |
| 179 | VFTLKPLEF |
| 159 | VIYNEQMASK |
| 365 | VQKLQNII |
| 895 | VYVHLKNLASRPY |
| 44 | YLNKEIEEA |
| 180 | YWVPRNAL |

Thus, particularly preferred is at least one peptide according to the present invention selected from the group consisting of SEQ ID NO: 710, 878, 879, 533, 476, 892, 111, 178, 181, 184, 882, 363, 42, 163, 137, 713, 532, 734, 736, 737, 738, 534, 535, 914, 739, 477, 164, 364, 531, 536, 186, 179, 159, 365, 895, 44, and 180, and the use thereof in the treatment of AML and/or CML as described herein.

The present invention furthermore relates to the peptides according to the present invention for use in the treatment of CLLAML As shown in the following table 3, many of the peptides according to the present invention can also be used in other cancerous and proliferative indications.

TABLE 3

Peptides according to the present invention and their specific uses in other proliferative diseases, optionally in other organs.

| Seq ID | Sequence | Tissue and disease |
|---|---|---|
| 1 | AEHPNVTLTI | colon or rectum, spleen, non-Hodgkin's lymphoma |
| 2 | FLAEHPNVTL | colon or rectum, spleen, non-Hodgkin's lymphoma |
| 3 | ILYGRSYTW | stomach, adenocarcinoma, skin, squamous cell carcinoma |
| 4 | EVAEFLARH | colon or rectum, spleen, non-Hodgkin's lymphoma |
| 5 | RHSNVNLTI | colon or rectum, spleen, non-Hodgkin's lymphoma |

TABLE 3-continued

Peptides according to the present invention and their specific uses in other proliferative diseases, optionally in other organs.

| Seq ID | Sequence | Tissue and disease |
|---|---|---|
| 6 | HPDNVKLFL | pancreas, adenocarcinoma, non-Hodgkin's lymphoma, small lymphocytic type |
| 7 | ISDTGELKL | pancreas, adenocarcinoma, non-Hodgkin's lymphoma, small lymphocytic type |
| 8 | KVNGKLVALK | pancreas, adenocarcinoma, non-Hodgkin's lymphoma, small lymphocytic type |
| 9 | NRLSAQAAL | pancreas, adenocarcinoma, non-Hodgkin's lymphoma, small lymphocytic type |
| 10 | TPFTAIREA | pancreas, adenocarcinoma, non-Hodgkin's lymphoma, small lymphocytic type |
| 11 | FGLARAKSV | kidney, clear cell renal cell carcinoma, brain, glioblastoma, liver, hepatocellular carcinoma |
| 12 | KIADFGLAR | liver, hepatocellular carcinoma, adrenal gland, adrenal cortical carcinoma |
| 13 | AAANIIRTL | liver, hepatocellular carcinoma, adrenal gland, adrenal cortical carcinoma |
| 14 | GRFKNLREAL | liver, hepatocellular carcinoma, adrenal gland, adrenal cortical carcinoma |
| 15 | MSPFSKATL | liver, hepatocellular carcinoma, adrenal gland, adrenal cortical carcinoma |
| 16 | QEDPGDNQITL | liver, hepatocellular carcinoma, adrenal gland, adrenal cortical carcinoma |
| 17 | SPFSKATL | stomach, metastatic, skin, basal cell carcinoma |
| 18 | DALLKRTM | stomach, metastatic, skin, basal cell carcinoma |
| 19 | GEDVRSALL | stomach, metastatic, skin, basal cell carcinoma |
| 20 | KFAEEFYSF | stomach, metastatic, skin, basal cell carcinoma |
| 21 | YGYDNVKEY | lung, non-small cell lung carcinoma, breast, carcinoma |
| 22 | LEVEERTKPV | lung, non-small cell lung carcinoma, breast, carcinoma |
| 23 | RDSPINANLRY | lung, non-small cell lung carcinoma, breast, carcinoma |
| 24 | RPFVIVTA | lung, non-small cell lung carcinoma, breast, carcinoma |
| 25 | RPIINTPMV | lung, non-small cell lung carcinoma, breast, carcinoma |
| 26 | SPTSSRTSSL | stomach, metastatic, lung, neuroendocrine carcinoma (non-small cell type) |
| 27 | ATSAPLVSR | lipoma |
| 28 | AELRSTASLL | lipoma |
| 29 | APASSHERASM | lipoma |
| 30 | ASRQAPPHI | lipoma |
| 31 | AVKKNPGIAA | lipoma |
| 32 | EEHLESHKKY | lipoma |
| 33 | GEFTSARAV | lipoma |
| 34 | GQSTPRLFSI | lipoma |
| 35 | LVDDPLEY | lipoma |
| 36 | RPKNLMQTL | lipoma |
| 37 | RQAPPHIEL | lipoma |
| 38 | SEAAELRSTA | colon, adenoma |
| 39 | AAVRIGSVL | colon, adenoma |
| 40 | ERAGVVREL | colon, adenoma |
| 41 | GAAVRIGSVL | colon, adenoma |
| 42 | KLYELHVFTF | colon, adenoma |
| 43 | LYELHVFTF | colon, adenoma |
| 44 | YLNKEIEEA | stomach, adenocarcinoma, white blood cell s, chronic lymphocytic leukemia |
| 45 | DELPKFHQY | stomach, adenocarcinoma, white blood cell s, chronic lymphocytic leukemia |
| 46 | DVTGQFPSSF | stomach, adenocarcinoma, white blood cell s, chronic lymphocytic leukemia |
| 47 | EHSRVLQQL | stomach, adenocarcinoma, white blood cell s, chronic lymphocytic leukemia |

TABLE 3-continued

Peptides according to the present invention and their specific uses in other proliferative diseases, optionally in other organs.

| Seq ID | Sequence | Tissue and disease |
| --- | --- | --- |
| 48 | IKVSKQLL | stomach, adenocarcinoma, white blood cell s, chronic lymphocytic leukemia |
| 49 | KPRQSSPQL | stomach, adenocarcinoma, white blood cell s, chronic lymphocytic leukemia |
| 50 | KQLLAALEI | stomach, adenocarcinoma, liver, focal nodular hyperplasia |
| 51 | RRKDLVLKY | stomach, adenocarcinoma, white blood cell s, chronic lymphocytic leukemia |
| 52 | RTRDYASLPPK | stomach, adenocarcinoma, lymph node, Hodgkin's disease |
| 53 | APGSVLPRAL | stomach, adenocarcinoma, lymph node, Hodgkin's disease |
| 54 | DIKEHPLL | stomach, adenocarcinoma, lymph node, Hodgkin's disease |
| 55 | DSAGPQDAR | stomach, adenocarcinoma, lymph node, Hodgkin's disease |
| 56 | FQYAKESYI | stomach, adenocarcinoma, lymph node, Hodgkin's disease |
| 57 | KVLSWPFLM | stomach, adenocarcinoma, lymph node, Hodgkin's disease |
| 58 | LENDQSLSF | stomach, adenocarcinoma, lymph node, Hodgkin's disease |
| 59 | SPSRQPQV | stomach, adenocarcinoma, lymph node, Hodgkin's disease |
| 60 | SRHQSFTTK | stomach, adenocarcinoma, lymph node, Hodgkin's disease |
| 61 | SSHNASKTL | liver, hepatocellular carcinoma, lipoma |
| 62 | EEIDTTMRW | liver, hepatocellular carcinoma, lipoma |
| 63 | ILDEKPVII | liver, hepatocellular carcinoma, lipoma |
| 64 | LPQEPRTSL | liver, hepatocellular carcinoma, lipoma |
| 65 | LTYKLPVA | liver, hepatocellular carcinoma, lipoma |
| 66 | NEMELAHSSF | liver, hepatocellular carcinoma, lipoma |
| 67 | REFPEANFEL | liver, hepatocellular carcinoma, lipoma |
| 68 | THHIPDAKL | liver, hepatocellular carcinoma, lipoma |
| 69 | TVKENLSLF | liver, hepatocellular carcinoma, lipoma |
| 70 | VLLKKAVL | kidney, clear cell renal cell carcinoma |
| 71 | HLKSIPVSL | kidney, clear cell renal cell carcinoma, prostate, adenocarcinoma |
| 72 | KVWYNVENW | kidney, clear cell renal cell carcinoma, prostate, adenocarcinoma |
| 73 | LPAYRAQLL | kidney, clear cell renal cell carcinoma, prostate, adenocarcinoma |
| 74 | LSEQTSVPL | kidney, clear cell renal cell carcinoma, prostate, adenocarcinoma |
| 75 | SLNQWLVSF | kidney, clear cell renal cell carcinoma, prostate, adenocarcinoma |
| 76 | SMTSLAQKI | kidney, clear cell renal cell carcinoma, prostate, adenocarcinoma |
| 77 | SSSGLHPPK | stomach, metastatic, kidney, carcinoma |
| 78 | DLDVKKMPL | stomach, metastatic, kidney, carcinoma |
| 79 | FYTVIPHNF | stomach, metastatic, kidney, carcinoma |
| 80 | HHINTDNPSL | stomach, metastatic, kidney, carcinoma |
| 81 | RVGEVGQSK | lung, non-small cell lung carcinoma, kidney, oncocytoma |
| 82 | AVFDGAQVTSK | lung, non-small cell lung carcinoma, kidney, oncocytoma |
| 83 | SQTDLVSRL | kidney, clear cell renal cell carcinoma, endometrium, adenocarcinoma, endometrioid type |
| 84 | VPVPHTTAL | kidney, clear cell renal cell carcinoma, endometrium, adenocarcinoma, endometrioid type |
| 85 | YQVLDVQRY | colon or rectum, breast, mucinous carcinoma |
| 86 | APFQGDQRSL | colon or rectum, breast, mucinous carcinoma |
| 87 | DVAEPYKVY | colon or rectum, breast, mucinous carcinoma |
| 88 | IVSGQPGTQK | colon or rectum, breast, mucinous carcinoma |
| 89 | TPEQQAAIL | colon or rectum, breast, mucinous carcinoma |
| 90 | VELFRTAYF | brain, cancer, kidney, Wilm's tumor |
| 91 | EHADDDPSL | brain, cancer, kidney, Wilm's tumor |

TABLE 3-continued

Peptides according to the present invention and their specific uses in other proliferative diseases, optionally in other organs.

| Seq ID | Sequence | Tissue and disease |
|---|---|---|
| 92 | SEESVKSTTL | brain, cancer, kidney, Wilm's tumor |
| 93 | SPRPPLGSSL | brain, cancer, kidney, Wilm's tumor |
| 94 | SPWWRSSL | brain, cancer, kidney, Wilm's tumor |
| 95 | VYTPVDSLVF | pancreas, adenocarcinoma, kidney, renal cell carcinoma |
| 96 | APLQRSQSL | pancreas, adenocarcinoma, kidney, renal cell carcinoma |
| 97 | DEVHQDTY | pancreas, adenocarcinoma, kidney, renal cell carcinoma |
| 98 | LPHSATVTL | cell carcinoma |
| 99 | SEAPEAPLL | testis, seminoma |
| 100 | SPRASGSGL | testis, seminoma |
| 101 | VVGPAAEAK | testis, seminoma |
| 102 | FSITKSVEL | non-Hodgkin's lymphoma, small lymphocytic type |
| 103 | GQTKNDLVV | non-Hodgkin's lymphoma, small lymphocytic type |
| 104 | LSQEVCRD | non-Hodgkin's lymphoma, small lymphocytic type |
| 105 | RDIQSPEQI | non-Hodgkin's lymphoma, small lymphocytic type |
| 106 | REDNSSNSL | non-Hodgkin's lymphoma, small lymphocytic type |
| 107 | TEHQEPGL | non-Hodgkin's lymphoma, small lymphocytic type |
| 108 | TKNDLVVSL | non-Hodgkin's lymphoma, small lymphocytic type |
| 109 | AEEAGGTRL | breast, carcinoma |
| 110 | ENVNKKDY | breast, carcinoma |
| 111 | GLDPNKPPEL | breast, carcinoma |
| 112 | RPAGEPYNRKTL | breast, carcinoma |
| 113 | SASVQRADTSL | liver, hepatocellular carcinoma, adrenal gland, adrenal cortical adenoma |
| 114 | YGNPRTNGM | stomach, metastatic, breast, carcinoma |
| 115 | LIRPVSASF | esophagus, adenocarcinoma |
| 116 | SPVNSSKQPSY | esophagus, adenocarcinoma |
| 117 | QLFSYAILGF | liver, hepatocellular carcinoma, colon, non-Hodgkin's lymphoma |
| 118 | DEHLLIQHY | liver, hepatocellular carcinoma, parotid gland, pleomorphic adenoma |
| 119 | KQVASSTGF | liver, hepatocellular carcinoma, parotid gland, pleomorphic adenoma |
| 120 | RDFGPASQHFL | liver, hepatocellular carcinoma, parotid gland, pleomorphic adenoma |
| 121 | RQLGEVASF | liver, hepatocellular carcinoma, parotid gland, pleomorphic adenoma |
| 122 | TEAETTANVL | liver, hepatocellular carcinoma, parotid gland, pleomorphic adenoma |
| 123 | GYLPVQTVL | kidney, clear cell renal cell carcinoma, parotid gland, pleomorphic adenoma |
| 124 | GQKEALLKY | liver, hepatocellular carcinoma, synovial sarcoma |
| 125 | KPSEERKTI | liver, hepatocellular carcinoma, synovial sarcoma |
| 126 | KQTPKVLVV | liver, hepatocellular carcinoma, synovial sarcoma |
| 127 | SVIQHVQSF | liver, hepatocellular carcinoma, synovial sarcoma |
| 128 | TPIERIPYL | liver, hepatocellular carcinoma, synovial sarcoma |
| 129 | AEVEKNETV | kidney, clear cell renal cell carcinoma, spleen, non-Hodgkin's lymphoma |
| 130 | EVKEEIPLV | kidney, clear cell renal cell carcinoma, spleen, non-Hodgkin's lymphoma |
| 131 | KPTSARSGL | kidney, clear cell renal cell carcinoma, spleen, non-Hodgkin's lymphoma |
| 132 | KYIETTPLTI | kidney, clear cell renal cell carcinoma, spleen, non-Hodgkin's lymphoma |
| 133 | SEIKTSIEV | kidney, clear cell renal cell carcinoma, spleen, non-Hodgkin's lymphoma |
| 134 | SVKPTSATK | kidney, clear cell renal cell carcinoma, spleen, non-Hodgkin's lymphoma |
| 135 | YPNKGVGQA | kidney, clear cell renal cell carcinoma, spleen, non-Hodgkin's lymphoma |

TABLE 3-continued

Peptides according to the present invention and their specific uses in other proliferative diseases, optionally in other organs.

| Seq ID | Sequence | Tissue and disease |
|---|---|---|
| 136 | ISMKILNSL | lung, non-small cell lung carcinoma, thymus, thymoma, benign |
| 137 | KTIAFLLPMF | lung, non-small cell lung carcinoma, thymus, thymoma, benign |
| 138 | RDSIINDF | lung, non-small cell lung carcinoma, thymus, thymoma, benign |
| 139 | SVKGGGGNEK | lung, non-small cell lung carcinoma, thymus, thymoma, benign |
| 140 | GIAKTGSGK | lung, non-small cell lung carcinoma, thymus, thymoma, benign |
| 141 | AETTDNVFTL | kidney, clear cell renal cell carcinoma, thyroid gland, follicular adenoma |
| 142 | SEYQRFAVM | kidney, clear cell renal cell carcinoma, thyroid gland, follicular adenoma |
| 143 | TFGERVVAF | kidney, clear cell renal cell carcinoma, thyroid gland, follicular adenoma |
| 144 | NENLVERF | stomach, adenocarcinoma, colon, adenocarcinoma |
| 145 | KITVPASQK | stomach, adenocarcinoma, colon, non-Hodgkin's lymphoma |
| 146 | KITVPASQKL | stomach, adenocarcinoma, colon, non-Hodgkin's lymphoma |
| 147 | VPASQKLRQL | stomach, adenocarcinoma, colon, non-Hodgkin's lymphoma |
| 148 | HVGYTLSYK | stomach, adenocarcinoma |
| 149 | KLPLPLPPRL | stomach, adenocarcinoma |
| 150 | KPIEPRREL | stomach, adenocarcinoma |
| 151 | SHSHVGYTL | stomach, adenocarcinoma |
| 152 | APSEYRYTL | colon or rectum, stomach, mucinous adenocarcinoma |
| 153 | APSEYRYTLL | colon or rectum, stomach, mucinous adenocarcinoma |
| 154 | EIFQNEVAR | colon or rectum, stomach, mucinous adenocarcinoma |
| 155 | KDVLIPGKL | colon or rectum, stomach, mucinous adenocarcinoma |
| 156 | VPLVREITF | colon or rectum, stomach, mucinous adenocarcinoma |
| 157 | DPNPNFEKF | liver, hepatocellular carcinoma, cancer, liver, focal nodular hyperplasia |
| 158 | IQAPLSWEL | liver, hepatocellular carcinoma, cancer, liver, focal nodular hyperplasia |
| 159 | VIYNEQMASK | liver, hepatocellular carcinoma, cancer, liver, focal nodular hyperplasia |
| 160 | VLRPGGAFY | liver, hepatocellular carcinoma, cancer, liver, focal nodular hyperplasia |
| 161 | EDPDQDILI | stomach, adenocarcinoma, endometrium, adenocarcinoma, endometrioid |
| 162 | HGNLRELAL | stomach, adenocarcinoma, endometrium, adenocarcinoma, endometrioid |
| 163 | KLYPTLVIR | stomach, adenocarcinoma, endometrium, adenocarcinoma, endometrioid |
| 164 | SEETFRFEL | stomach, adenocarcinoma, endometrium, adenocarcinoma, endometrioid |
| 165 | ELNKLLEEI | stomach, adenocarcinoma, ovary, adenocarcinoma, endometrioid |
| 166 | IPFSNPRVL | stomach, adenocarcinoma, ovary, adenocarcinoma, endometrioid |
| 167 | LLDEGAKLLY | stomach, adenocarcinoma, ovary, adenocarcinoma, endometrioid |
| 168 | SPADAHRNL | stomach, adenocarcinoma, ovary, adenocarcinoma, endometrioid |
| 173 | APRKGNTL | stomach, metastatic, endometrium, Mullerian mixed tumor |
| 174 | EEEEALQKKF | stomach, metastatic, endometrium, Mullerian mixed tumor |
| 175 | KENLVDGF | stomach, metastatic, endometrium, Mullerian mixed tumor |
| 176 | VYKENLVDGF | stomach, metastatic, endometrium, Mullerian mixed tumor |
| 177 | TLLVVVPKL | stomach, adenocarcinoma, bone, giant cell tumor of bone |
| 178 | HEIDRYTAI | kidney, clear cell renal cell carcinoma, non-Hodgkin's lymphoma |

TABLE 3-continued

Peptides according to the present invention and their specific uses in other proliferative diseases, optionally in other organs.

| Seq ID | Sequence | Tissue and disease |
|---|---|---|
| 179 | VFTLKPLEF | kidney, clear cell renal cell carcinoma, non-Hodgkin's lymphoma |
| 180 | YWVPRNAL | kidney, clear cell renal cell carcinoma, non-Hodgkin's lymphoma |
| 181 | IGVEHVVVY | brain, cancer, kidney, oncocytoma |
| 182 | RDKPHVNV | brain, cancer, omentum, leiomyosarcoma |
| 183 | ADVLKVEVF | stomach, adenocarcinoma, colon, adenocarcinoma |
| 184 | IPVVHASI | stomach, adenocarcinoma, colon, adenocarcinoma |
| 185 | RDSLIDSLT | stomach, adenocarcinoma, colon, adenocarcinoma |
| 186 | TVADQVLVGSY | stomach, adenocarcinoma, colon, adenocarcinoma |
| 187 | AADTERLAL | lung, non-small cell lung carcinoma, chondrosarcoma |
| 188 | DMKAKVASL | lung, non-small cell lung carcinoma, chondrosarcoma |
| 189 | HVLEEVQQV | lung, non-small cell lung carcinoma, chondrosarcoma |
| 190 | KEAADTERL | lung, non-small cell lung carcinoma, chondrosarcoma |
| 191 | RISEVLQKL | lung, non-small cell lung carcinoma, chondrosarcoma |
| 192 | TEVRELVSL | lung, non-small cell lung carcinoma, chondrosarcoma |
| 193 | AIRSGEAAAK | liver, hepatocellular carcinoma, pleura, malignant mesothelioma |
| 194 | APNPAPKEL | liver, hepatocellular carcinoma, pleura, malignant mesothelioma |
| 195 | RQSLLTAI | liver, hepatocellular carcinoma, liver, hepatocellular carcinoma, cancer, pleura, malignant mesothelioma |
| 196 | SPEQTLSPL | liver, hepatocellular carcinoma, pleura, malignant mesothelioma |
| 197 | TEHQVPSSV | liver, hepatocellular carcinoma, liver, hepatocellular carcinoma, cancer, pleura, malignant mesothelioma |
| 198 | TTYKIVPPK | liver, hepatocellular carcinoma, liver, hepatocellular carcinoma, cancer, pleura, malignant mesothelioma |
| 199 | QLLDQVEQI | stomach, metastatic thyroid gland, papillary carcinoma |
| 200 | DETMVIGNY | stomach, metastatic, rectum, adenocarcinoma |
| 201 | RQYGSEGRFTF | kidney, clear cell renal cell carcinoma, rectum, adenocarcinoma |
| 203 | GPRPITQSEL | stomach, metastatic, lymph node, non-Hodgkin's lymphoma |
| 204 | KPEPVDKVA | stomach, metastatic, lymph node, non-Hodgkin's lymphoma |
| 205 | TPSSRPASL | stomach, metastatic, lymph node, non-Hodgkin's lymphoma |
| 212 | GRLNSVNNR | kidney, clear cell renal cell carcinoma, leiomyosarcoma |
| 213 | SILEDPPSI | kidney, clear cell renal cell carcinoma, leiomyosarcoma |
| 214 | TPRTNNIEL | kidney, clear cell renal cell carcinoma, leiomyosarcoma |
| 215 | DAMKRVEEI | stomach, adenocarcinoma, ovary, thecoma-fibroma |
| 216 | DIKEVKQNI | stomach, adenocarcinoma, ovary, thecoma-fibroma |
| 217 | GPIYPGHGM | stomach, adenocarcinoma, ovary, thecoma-fibroma |
| 218 | GDYGRAFNL | stomach, metastatic, lymph node, non-Hodgkin's lymphoma |
| 219 | TRHKIVHTK | stomach, metastatic, lymph node, non-Hodgkin's lymphoma |
| 220 | RIHTGEKPYK | colon or rectum, thyroid gland, nodular hyperplasia |
| 221 | KAFNWFSTL | stomach, metastatic, lymph node, non-Hodgkin's lymphoma |

TABLE 3-continued

Peptides according to the present invention and their specific uses in other proliferative diseases, optionally in other organs.

| Seq ID | Sequence | Tissue and disease |
|---|---|---|
| 222 | QSTQRSLAL | liver, hepatocellular carcinoma, uterin cervix, squamous cell carcinoma |
| 223 | RDLQMNQALRF | liver, hepatocellular carcinoma, uterin cervix, squamous cell carcinoma |
| 224 | RELESQLHVL | liver, hepatocellular carcinoma, uterin cervix, squamous cell carcinoma |
| 225 | SEAEKLTLV | liver, hepatocellular carcinoma, uterin cervix, squamous cell carcinoma |
| 226 | AAAKPVATK | pancreas, adenocarcinoma, fibromatosis |
| 227 | ATYHGSFSTK | pancreas, adenocarcinoma, fibromatosis |
| 228 | FMYDRPLRL | pancreas, adenocarcinoma, fibromatosis |
| 229 | FRVGNVQEL | pancreas, adenocarcinoma, fibromatosis |
| 230 | GVAPFTIAR | pancreas, adenocarcinoma, fibromatosis |
| 231 | KMKPLDGSALY | pancreas, adenocarcinoma, fibromatosis |
| 232 | KPAPAKPVA | pancreas, adenocarcinoma, fibromatosis |
| 233 | KPVAAKPAA | pancreas, adenocarcinoma, fibromatosis |
| 234 | KQFGVAPFTI | pancreas, adenocarcinoma, fibromatosis |
| 235 | QEELVKISL | pancreas, adenocarcinoma, fibromatosis |
| 236 | RQLGTVQQVI | pancreas, adenocarcinoma, fibromatosis |
| 237 | RQLINALQI | pancreas, adenocarcinoma, fibromatosis |
| 238 | RVIGGLLAGQTY | pancreas, adenocarcinoma, fibromatosis |
| 239 | SENAFYLSP | pancreas, adenocarcinoma, fibromatosis |
| 240 | SQAPVLDAI | pancreas, adenocarcinoma, fibromatosis |
| 241 | STRYPPPAV | pancreas, adenocarcinoma, fibromatosis |
| 242 | TEDTLKVYL | pancreas, adenocarcinoma, fibromatosis |
| 243 | VAAKPVATK | pancreas, adenocarcinoma, fibromatosis |
| 244 | VQRVVESL | pancreas, adenocarcinoma, fibromatosis |
| 245 | VRNPSVVVK | pancreas, adenocarcinoma, fibromatosis |
| 246 | GESEVAIKI | myometrium, leiomyoma |
| 247 | LIYSVGLLLA | myometrium, leiomyoma |
| 248 | SAYPHQLSF | myometrium, leiomyoma |
| 249 | SVIGVFITK | myometrium, leiomyoma |
| 250 | AELGNSVQLI | liver, hepatocellular carcinoma, thyroid gland, nodular hyperplasia |
| 251 | ANMTVTRI | liver, hepatocellular carcinoma, thyroid gland, nodular hyperplasia |
| 252 | ARISNVEFY | liver, hepatocellular carcinoma, thyroid gland, nodular hyperplasia |
| 253 | AVFIGNQQF | liver, hepatocellular carcinoma, thyroid gland, nodular hyperplasia |
| 254 | DIELQAENI | liver, hepatocellular carcinoma, thyroid gland, nodular hyperplasia |
| 255 | DSYTVRVSV | liver, hepatocellular carcinoma, thyroid gland, nodular hyperplasia |
| 256 | DVKIFVNTI | liver, hepatocellular carcinoma, thyroid gland, nodular hyperplasia |
| 257 | EIIPKYGSI | liver, hepatocellular carcinoma, thyroid gland, nodular hyperplasia |
| 258 | EQSKIFIHR | liver, hepatocellular carcinoma, thyroid gland, nodular hyperplasia |
| 259 | FVDVGLYQY | liver, hepatocellular carcinoma, thyroid gland, nodular hyperplasia |
| 260 | GHTSTISTL | liver, hepatocellular carcinoma, thyroid gland, nodular hyperplasia |
| 261 | GRIEYVEVF | liver, hepatocellular carcinoma, thyroid gland, nodular hyperplasia |
| 262 | GTSIIPFQK | liver, hepatocellular carcinoma, thyroid gland, nodular hyperplasia |
| 263 | HPFLRGIGY | liver, hepatocellular carcinoma, thyroid gland, nodular hyperplasia |
| 264 | IPVEIHTA | liver, hepatocellular carcinoma, thyroid gland, nodular hyperplasia |
| 265 | KIFVNTIAY | liver, hepatocellular carcinoma, thyroid gland, nodular hyperplasia |
| 266 | LPEDKVRIAY | liver, hepatocellular carcinoma, thyroid gland, nodular hyperplasia |
| 267 | LPFSEGLTV | liver, hepatocellular carcinoma, thyroid gland, nodular hyperplasia |
| 268 | LPWANKVTI | liver, hepatocellular carcinoma, thyroid gland, nodular hyperplasia |
| 269 | PWANKVTI | liver, hepatocellular carcinoma, thyroid gland, nodular hyperplasia |
| 270 | QAYNRAVTI | liver, hepatocellular carcinoma, thyroid gland, nodular hyperplasia |

TABLE 3-continued

Peptides according to the present invention and their specific uses in other proliferative diseases, optionally in other organs.

| Seq ID | Sequence | Tissue and disease |
|---|---|---|
| 271 | RSFPQKMAY | liver, hepatocellular carcinoma, thyroid gland, nodular hyperplasia |
| 272 | RYPIHWHLL | liver, hepatocellular carcinoma, thyroid gland, nodular hyperplasia |
| 273 | SPQNLRLML | liver, hepatocellular carcinoma, thyroid gland, nodular hyperplasia |
| 274 | SYFSSPTQR | liver, hepatocellular carcinoma, thyroid gland, nodular hyperplasia |
| 275 | VQIKSSLI | liver, hepatocellular carcinoma, thyroid gland, nodular hyperplasia |
| 276 | VYIGHTSTI | liver, hepatocellular carcinoma, thyroid gland, nodular hyperplasia |
| 277 | YHVPGTGESY | liver, hepatocellular carcinoma, thyroid gland, nodular hyperplasia |
| 278 | ATNGDLASR | pancreas, adenocarcinoma, prostate, benign nodular hyperplasia |
| 279 | GLHAEVTGVGY | pancreas, adenocarcinoma, prostate, benign nodular hyperplasia |
| 280 | HVSSTSSSF | pancreas, adenocarcinoma, prostate, benign nodular hyperplasia |
| 281 | LQADLQNGL | pancreas, adenocarcinoma, prostate, benign nodular hyperplasia |
| 282 | SELPVSEVA | pancreas, adenocarcinoma, prostate, benign nodular hyperplasia |
| 283 | SQTKSVFEI | pancreas, adenocarcinoma, prostate, benign nodular hyperplasia |
| 284 | THIFTSDGL | pancreas, adenocarcinoma, prostate, benign nodular hyperplasia |
| 285 | VIYFPPLQK | pancreas, adenocarcinoma, prostate, benign nodular hyperplasia |
| 286 | YPFSSEQKW | pancreas, adenocarcinoma, prostate, benign nodular hyperplasia |
| 287 | GQYFGELAL | stomach, gastrointestinal stromal tumor (GIST) |
| 288 | RIIVKNNAK | stomach, gastrointestinal stromal tumor (GIST) |
| 289 | RRIIVKNNAK | stomach, gastrointestinal stromal tumor (GIST) |
| 290 | SFGELALMY | stomach, gastrointestinal stromal tumor (GIST) |
| 291 | AFNAPVINR | stomach, gastrointestinal stromal tumor (GIST) |
| 292 | IMKRNIATY | stomach, gastrointestinal stromal tumor (GIST) |
| 293 | KVVDVIGTK | stomach, gastrointestinal stromal tumor (GIST) |
| 294 | LPFLKSLEF | stomach, gastrointestinal stromal tumor (GIST) |
| 295 | RLKVVDVIGTK | stomach, gastrointestinal stromal tumor (GIST) |
| 296 | TPRAATITA | stomach, gastrointestinal stromal tumor (GIST) |
| 297 | KPSEKIQVL | lipoma |
| 298 | VPYPVTTTV | lipoma |
| 299 | ASFPPFVEK | lipoma |
| 300 | AFIHISTAY | colon or rectum, colon, adenocarcinoma |
| 301 | ATFEKIPFER | colon or rectum, colon, adenocarcinoma |
| 302 | KLFEKVKEV | colon or rectum, colon, adenocarcinoma |
| 303 | SQMPKLEAF | colon or rectum, colon, adenocarcinoma |
| 304 | AVLGQHHNY | colon or rectum, colon, adenocarcinoma |
| 305 | GPPAHKPR | spleen, chronic myeloid leukemia |
| 306 | RVYDVLVLK | colon or rectum, colon, adenocarcinoma |
| 307 | LPRPQGITV | liver, hepatocellular carcinoma, liver, focal nodular hyperplasia |
| 308 | VLYVGSKTK | brain, glioblastoma, schwannoma |
| 309 | KTKEQVTNV | brain, glioblastoma, schwannoma |
| 310 | MPVDPDNEAY | brain, glioblastoma, schwannoma |
| 311 | AEKTKQGVA | brain, glioblastoma, schwannoma |
| 312 | DIADFFTTR | kidney, clear cell renal cell carcinoma, adrenal gland, adrenal cortical adenoma |
| 313 | HSYLQRQSV | kidney, clear cell renal cell carcinoma, adrenal gland, adrenal cortical adenoma |
| 314 | KEVTLIEEL | kidney, clear cell renal cell carcinoma, adrenal gland, adrenal cortical adenoma |

TABLE 3-continued

Peptides according to the present invention and their specific uses in other proliferative diseases, optionally in other organs.

| Seq ID | Sequence | Tissue and disease |
|---|---|---|
| 315 | REDGPGVAL | kidney, clear cell renal cell carcinoma, adrenal gland, adrenal cortical adenoma |
| 316 | REDPLPPGL | kidney, clear cell renal cell carcinoma, adrenal gland, adrenal cortical adenoma |
| 317 | SLFGGSQGLRK | kidney, clear cell renal cell carcinoma, adrenal gland, adrenal cortical adenoma |
| 318 | AEFQRLKQA | intramuscular lipoma |
| 319 | EVIDGVPGKW | intramuscular lipoma |
| 320 | IPKAPGKII | intramuscular lipoma |
| 321 | SHNGSAIRY | intramuscular lipoma |
| 322 | TEVTVVGDKL | intramuscular lipoma |
| 323 | YASVVVKRY | intramuscular lipoma |
| 324 | ATDLALYIK | stomach, adenocarcinoma, thyroid gland, papillary carcinoma |
| 325 | AYHNWRHAF | stomach, adenocarcinoma, thyroid gland, papillary carcinoma |
| 326 | EPLNIKDAY | stomach, adenocarcinoma, thyroid gland, papillary carcinoma |
| 327 | KIAATIISF | stomach, adenocarcinoma, thyroid gland, papillary carcinoma |
| 328 | KIFLHIHGL | stomach, adenocarcinoma, thyroid gland, papillary carcinoma |
| 329 | LEVILKKI | stomach, adenocarcinoma, thyroid gland, papillary carcinoma |
| 330 | SEHPLAQLY | stomach, adenocarcinoma, thyroid gland, papillary carcinoma |
| 331 | VPSAQTLKI | stomach, adenocarcinoma, thyroid gland, papillary carcinoma |
| 332 | AEYRSYVA | stomach, metastatic adrenal gland, adrenal cortical carcinoma |
| 333 | ALAPGRGTLY | stomach, metastatic adrenal gland, adrenal cortical carcinoma |
| 334 | GPRGTQAAL | stomach, metastatic adrenal gland, adrenal cortical carcinoma |
| 335 | IEDPGTLHI | stomach, metastatic adrenal gland, adrenal cortical carcinoma |
| 336 | IEDPGTLHIW | stomach, metastatic adrenal gland, adrenal cortical carcinoma |
| 337 | RPIPIAVKY | stomach, metastatic adrenal gland, adrenal cortical carcinoma |
| 338 | VEKLLTNW | stomach, metastatic, pancreas, adenocarcinoma |
| 339 | FLDPDIGGVAV | kidney, clear cell renal cell carcinoma, pancreas, adenocarcinoma |
| 340 | HTAPPENKTW | kidney, clear cell renal cell carcinoma, pancreas, adenocarcinoma |
| 341 | LLDTPVKTQY | kidney, clear cell renal cell carcinoma, pancreas, adenocarcinoma |
| 342 | NAVKDFTSF | kidney, clear cell renal cell carcinoma, pancreas, adenocarcinoma |
| 343 | SGLLQIKKL | kidney, clear cell renal cell carcinoma, pancreas, adenocarcinoma |
| 344 | YHDKNIVLL | kidney, clear cell renal cell carcinoma, pancreas, adenocarcinoma |
| 345 | SVDPKNYPK | pancreas, adenocarcinoma, colon, adenocarcinoma |
| 346 | AVGLVLPAK | liver, hepatocellular carcinoma, cancer, thyroid gland, papillary carcinoma |
| 347 | AVGLVLPAKL | liver, hepatocellular carcinoma, cancer, thyroid gland, papillary carcinoma |
| 348 | ALLEVLSQK | stomach, adenocarcinoma, breast, carcinoma |
| 349 | HEKQDTLVA | kidney, clear cell renal cell carcinoma, spleen, chronic myeloid leukemia |
| 350 | KELELQIGM | kidney, clear cell renal cell carcinoma, spleen, chronic myeloid leukemia |
| 351 | MYSDVWKQL | kidney, clear cell renal cell carcinoma, spleen, chronic myeloid leukemia |
| 352 | RELQDEKAEL | kidney, clear cell renal cell carcinoma, spleen, chronic myeloid leukemia |
| 353 | RITDVLDQK | kidney, clear cell renal cell carcinoma, spleen, chronic myeloid leukemia |

TABLE 3-continued

Peptides according to the present invention and their specific uses in other proliferative diseases, optionally in other organs.

| Seq ID | Sequence | Tissue and disease |
|---|---|---|
| 354 | EVIKITGLK | stomach, adenocarcinoma |
| 355 | HHVDITKKL | stomach, adenocarcinoma, kidney, carcinoma |
| 356 | LPFNVKVSV | stomach, adenocarcinoma, stomach, gastrointestinal stromal tumor (GIST) |
| 357 | TLPRVLEI | stomach, adenocarcinoma, bone, giant cell tumor of bone |
| 358 | TVDLPKSPK | stomach, adenocarcinoma, thyroid gland, nodular hyperplasia |
| 359 | AEHGLLLTA | stomach, metastatic, uterin cervix, adenocarcinoma |
| 360 | AQAGALLQV | stomach, metastatic, uterin cervix, adenocarcinoma |
| 361 | DGGFVLKV | stomach, metastatic, uterin cervix, adenocarcinoma |
| 362 | IVYPSGKVY | stomach, metastatic, uterin cervix, adenocarcinoma |
| 363 | KLDNQVSKV | colon or rectum, prostate, benign nodular hyperplasia |
| 364 | SENVKLFSA | colon or rectum, prostate, benign nodular hyperplasia |
| 365 | VQKLQNII | colon or rectum, prostate, benign nodular hyperplasia |
| 366 | FSTPHGLEV | pancreas, adenocarcinoma, spleen, chronic myeloid leukemia |
| 367 | KRFHQKSDM | pancreas, adenocarcinoma, spleen, chronic myeloid leukemia |
| 368 | KTFGHAVSL | pancreas, adenocarcinoma, spleen, chronic myeloid leukemia |
| 369 | SSNLITHSR | pancreas, adenocarcinoma, spleen, chronic myeloid leukemia |
| 370 | GVIDGHIYAV | stomach, metastatic, leiomyosarcoma |
| 371 | IEPAKETTTNV | pancreas, adenocarcinoma, lung, adenocarcinoma |
| 372 | NAPPSEVLL | pancreas, adenocarcinoma, lung, adenocarcinoma |
| 373 | SIEPAKETTTNV | pancreas, adenocarcinoma, lung, adenocarcinoma |
| 374 | AQSQHNQSL | spleen, extramedullary hematopoiesis |
| 375 | AQSRTNPQV | spleen, extramedullary hematopoiesis |
| 376 | KMHDKVFAY | spleen, extramedullary hematopoiesis |
| 377 | TAKAPLSTV | spleen, extramedullary hematopoiesis |
| 378 | IPTRTVAI | liver, hepatocellular carcinoma, lipoma |
| 379 | NHDRKHAV | liver, hepatocellular carcinoma, lipoma |
| 380 | NNHDRKHAV | liver, hepatocellular carcinoma, lipoma |
| 381 | TPGGTRIIY | liver, hepatocellular carcinoma, breast, carcinoma |
| 382 | EHWPSPETF | bone, non-ossifying fibroma |
| 383 | EIITNTLSF | bone, non-ossifying fibroma |
| 384 | EVRGALMSAF | bone, non-ossifying fibroma |
| 385 | IPRPILVLL | bone, non-ossifying fibroma |
| 386 | LPNKNRDEL | bone, non-ossifying fibroma |
| 387 | QRIPAGAVL | bone, non-ossifying fibroma |
| 388 | AEGPAGGFMVV | pancreas, adenocarcinoma, spleen, chronic myeloid leukemia |
| 389 | AYYRDAEAY | pancreas, adenocarcinoma, spleen, chronic myeloid leukemia |
| 390 | QVNRPLTMR | pancreas, adenocarcinoma, spleen, chronic myeloid leukemia |
| 391 | RHSPVFQVY | pancreas, adenocarcinoma, spleen, chronic myeloid leukemia |
| 392 | SLPVPNSAY | pancreas, adenocarcinoma, spleen, chronic myeloid leukemia |
| 393 | TLGPPGTAHLY | pancreas, adenocarcinoma, spleen, chronic myeloid leukemia |
| 394 | IEPAKETTTNV | pancreas, adenocarcinoma, lung, adenocarcinoma |
| 395 | NAPPSEVLL | pancreas, adenocarcinoma, lung, adenocarcinoma |
| 396 | SIEPAKETTTNV | pancreas, adenocarcinoma, lung, adenocarcinoma |
| 397 | DLYSGLNQR | lymph node, Hodgkin's disease |
| 398 | KAKAKPVTR | lymph node, Hodgkin's disease |

TABLE 3-continued

Peptides according to the present invention and their specific uses in other proliferative diseases, optionally in other organs.

| Seq ID | Sequence | Tissue and disease |
|---|---|---|
| 399 | AVLDKAMKAK | liver, hepatocellular carcinoma, liver, hepatic adenoma |
| 400 | LELSTPLKI | liver, hepatocellular carcinoma, liver, hepatic adenoma |
| 401 | LPLNLDTKY | liver, hepatocellular carcinoma, liver, hepatic adenoma |
| 402 | TVIYRIQAL | liver, hepatocellular carcinoma, liver, hepatic adenoma |
| 403 | DAHIYLNHI | stomach, adenocarcinoma, pancreas, microcystic adenoma |
| 404 | NHIEPLKIQL | stomach, adenocarcinoma, pancreas, microcystic adenoma |
| 405 | AYRPAVHPR | thyroid gland, nodular hyperplasia |
| 406 | LRAPLEHEL | thyroid gland, nodular hyperplasia |
| 407 | RLFMVLLLK | thyroid gland, nodular hyperplasia |
| 408 | RSPDVLKDF | thyroid gland, nodular hyperplasia |
| 409 | ETAPGVHKR | stomach, metastatic, non-Hodgkin's lymphoma |
| 410 | LYHGYIYTY | stomach, metastatic, non-Hodgkin's lymphoma |
| 415 | VVFDSPRNR | liver, hepatocellular carcinoma, pancreas, adenocarcinoma |
| 416 | YPLGRILI | lung, non-small cell lung carcinoma, pancreas, adenocarcinoma |
| 417 | KEFAEFVTS | pancreas, adenocarcinoma, pancreas, adenocarcinoma |
| 418 | VMLDVPIRL | pancreas, adenocarcinoma, pancreas, adenocarcinoma |
| 419 | VPMTPLRTV | liver, hepatocellular carcinoma, cancer, rectum, adenocarcinoma |
| 420 | QIDYKTLVL | stomach, metastatic, leiomyosarcoma |
| 421 | VEDPTIVRI | stomach, metastatic, leiomyosarcoma |
| 422 | IPYQDLPHL | kidney, clear cell renal cell carcinoma, lipoma |
| 423 | DTPFLTGHGR | stomach, adenocarcinoma, bone, non-ossifying fibroma |
| 424 | EFYRALYI | stomach, adenocarcinoma, bone, non-ossifying fibroma |
| 425 | RYYPQILTNK | stomach, adenocarcinoma, bone, non-ossifying fibroma |
| 426 | KAYERHVL | intestines, malignant carcinoid tumor |
| 427 | LPSPEFHDY | intestines, malignant carcinoid tumor |
| 428 | SLYAHPIEH | intestines, malignant carcinoid tumor |
| 429 | LVREPGSQA | kidney, clear cell renal cell carcinoma, lymph node, Hodgkin's disease |
| 430 | RLAGPGSEKY | kidney, clear cell renal cell carcinoma, lymph node, Hodgkin's disease |
| 431 | SPGAGRNSVL | kidney, clear cell renal cell carcinoma, lymph node, Hodgkin's disease |
| 432 | SVQSDQGYISR | kidney, clear cell renal cell carcinoma, lymph node, Hodgkin's disease |
| 433 | GVRPPAPSL | liver, hepatocellular carcinoma, kidney, carcinoma |
| 434 | IFSEKPVFV | liver, hepatocellular carcinoma, kidney, carcinoma |
| 435 | KASNLLLGF | liver, hepatocellular carcinoma, kidney, carcinoma |
| 436 | KRYIFADAY | liver, hepatocellular carcinoma, kidney, carcinoma |
| 437 | RNLQLSLPR | liver, hepatocellular carcinoma, kidney, carcinoma |
| 438 | EASEPVALR | brain, glioblastoma, liver, hepatic adenoma |
| 439 | RPKVPDQSV | brain, glioblastoma, liver, hepatic adenoma |
| 440 | VLYENALKL | spleen, extramedullary hematopoiesis |
| 441 | EVLDKSQTNY | liver, hepatocellular carcinoma, endometrium, hyperplasia |
| 442 | MPSPIPAKY | liver, hepatocellular carcinoma, endometrium, hyperplasia |
| 443 | YGIENFTSV | liver, hepatocellular carcinoma, endometrium, hyperplasia |
| 444 | ARAAQVFFL | colon or rectum, kidney, renal cell carcinoma |

TABLE 3-continued

Peptides according to the present invention and their specific uses in other proliferative diseases, optionally in other organs.

| Seq ID | Sequence | Tissue and disease |
|---|---|---|
| 445 | EHIVPNAEL | colon or rectum, kidney, renal cell carcinoma |
| 446 | EAFEFVKQR | stomach, adenocarcinoma, breast, carcinoma |
| 447 | NHFEGHYQY | stomach, adenocarcinoma, breast, carcinoma |
| 448 | DAYPKNPHL | stomach, adenocarcinoma, liver, hepatocellular carcinoma |
| 449 | DVNIKSTER | stomach, adenocarcinoma, liver, hepatocellular carcinoma |
| 450 | HINSIKSVF | stomach, adenocarcinoma, liver, hepatocellular carcinoma |
| 451 | YESEKVGVA | stomach, adenocarcinoma, liver, hepatocellular carcinoma |
| 452 | ENAPTTVSR | stomach, adenocarcinoma, adrenal gland, adrenal cortical adenoma |
| 453 | RFPHLLAHTY | stomach, adenocarcinoma, adrenal gland, adrenal cortical adenoma |
| 454 | TLDGSLHAV | stomach, adenocarcinoma, adrenal gland, adrenal cortical adenoma |
| 455 | RTVLKNLSLLK | liver, hepatocellular carcinoma, pancreas, microcystic adenoma |
| 456 | FEAKVQAI | stomach, adenocarcinoma, metastatic adenocarcinoma of stomach |
| 457 | FFEAKVQAI | stomach, adenocarcinoma, metastatic adenocarcinoma of stomach |
| 458 | KELQSTFK | stomach, adenocarcinoma, metastatic adenocarcinoma of stomach |
| 459 | NVSSRFEEEI | stomach, adenocarcinoma, metastatic adenocarcinoma of stomach |
| 460 | EVWNNLGTTK | brain, cancer, lymph node, malignant melanoma |
| 461 | MIFRSGSLI | brain, cancer, lymph node, malignant melanoma |
| 462 | NHALPLPGF | brain, cancer, lymph node, malignant melanoma |
| 463 | ASVFGTMPLK | kidney, polycystic kidney disease |
| 464 | REFPDRLVGY | kidney, polycystic kidney disease |
| 465 | SVFGTMPLK | kidney, polycystic kidney disease |
| 466 | DEMRFVTQI | lung, non-small cell lung carcinoma, testis, mixed germ cell tumor |
| 467 | ETVHFATTQW | lung, non-small cell lung carcinoma, testis, mixed germ cell tumor |
| 468 | LPPPATQI | lung, non-small cell lung carcinoma, testis, mixed germ cell tumor |
| 469 | LARDLYAF | liver, hepatocellular carcinoma, neuroblastoma |
| 470 | LPGIGLSTSL | liver, hepatocellular carcinoma, neuroblastoma |
| 471 | MEVILPML | liver, hepatocellular carcinoma, neuroblastoma |
| 472 | AILDYILAK | stomach, metastatic, lung, neuroendocrine carcinoma (non-small cell type) |
| 473 | KIASQLSKL | stomach, metastatic, lung, neuroendocrine carcinoma (non-small cell type) |
| 474 | KVTSTTTVK | stomach, metastatic, lung, neuroendocrine carcinoma (non-small cell type) |
| 475 | YNTLLPYTF | stomach, metastatic, lung, neuroendocrine carcinoma (non-small cell type) |
| 476 | FLDPRPLTV | pancreas, adenocarcinoma, myometrium, leiomyoma |
| 477 | SAFADRPAF | pancreas, adenocarcinoma, myometrium, leiomyoma |
| 478 | AAVPVIISR | lymph node, papillary carcinoma of thyroid |
| 479 | EEIGKVAAA | lymph node, papillary carcinoma of thyroid |
| 480 | FLKDLVASV | lymph node, papillary carcinoma of thyroid |
| 481 | VIISRALEL | lymph node, papillary carcinoma of thyroid |
| 482 | APRTTGTPRTSL | kidney, oncocytoma |
| 483 | ESVGGSPQTK | kidney, oncocytoma |
| 484 | IPKDKAIL | kidney, oncocytoma |
| 485 | LPAYGRTTL | kidney, oncocytoma |
| 486 | HQAAIVSKI | stomach, adenocarcinoma, kidney, angiomyolipoma |

TABLE 3-continued

Peptides according to the present invention and their specific uses in other proliferative diseases, optionally in other organs.

| Seq ID | Sequence | Tissue and disease |
|---|---|---|
| 487 | QAAIVSKI | stomach, adenocarcinoma, kidney, angiomyolipoma |
| 488 | RQKMPEDGL | stomach, adenocarcinoma, kidney, angiomyolipoma |
| 489 | SVQKSSGVK | stomach, adenocarcinoma, kidney, angiomyolipoma |
| 490 | DSIGSTVSSER | stomach, adenocarcinoma |
| 491 | LPYNNKDRDAL | stomach, adenocarcinoma |
| 492 | IYDEIQQEM | colon or rectum, colon, adenoma |
| 493 | AQAKGLIQV | thymus, thymoma, benign |
| 494 | EVSSEIYQW | thymus, thymoma, benign |
| 495 | KWNPVPLSY | thymus, thymoma, benign |
| 496 | NRLLAQQSL | thymus, thymoma, benign |
| 497 | APRPVAVAV | stomach, adenocarcinoma |
| 498 | FYRETVQVGR | stomach, adenocarcinoma |
| 499 | LLAPRPVAV | stomach, adenocarcinoma |
| 500 | GLAALVILK | stomach, adenocarcinoma, neurofibroma |
| 501 | KIQEVFSSY | stomach, adenocarcinoma, neurofibroma |
| 502 | ASLDKFLSH | spleen, chronic myeloid leukemia |
| 503 | ALYATKTLR | colon or rectum, pancreas, microcystic adenoma |
| 504 | MEYVISRI | colon or rectum, pancreas, microcystic adenoma |
| 505 | VPVGRQPII | colon or rectum, pancreas, microcystic adenoma |
| 506 | KLLIGVIAAV | stomach, metastatic, colon, adenocarcinoma |
| 507 | LPSLIKLD | stomach, metastatic, colon, adenocarcinoma |
| 508 | PSLIKLDL | stomach, metastatic, colon, adenocarcinoma |
| 509 | ARNKELIGK | stomach, adenocarcinoma |
| 510 | AVKSNAAAY | stomach, adenocarcinoma |
| 511 | EVIIPHSGW | stomach, adenocarcinoma |
| 512 | SVKEQEAQF | stomach, adenocarcinoma |
| 513 | APRGLEPIAI | liver, hepatocellular carcinoma, liver, focal nodular hyperplasia |
| 514 | GRFGGVITI | liver, hepatocellular carcinoma, liver, focal nodular hyperplasia |
| 518 | AEHIESRTL | kidney, clear cell renal cell carcinoma, liver, focal nodular hyperplasia |
| 519 | DQYPYLKSV | kidney, clear cell renal cell carcinoma, liver, focal nodular hyperplasia |
| 520 | IARNLTQQL | kidney, clear cell renal cell carcinoma, liver, focal nodular hyperplasia |
| 521 | IESRTLAIA | kidney, clear cell renal cell carcinoma, liver, focal nodular hyperplasia |
| 522 | MTSALPIIQK | kidney, clear cell renal cell carcinoma, liver, focal nodular hyperplasia |
| 523 | SLLTSSKGQLQK | kidney, clear cell renal cell carcinoma, liver, focal nodular hyperplasia |
| 524 | TSALPIIQK | kidney, clear cell renal cell carcinoma, liver, focal nodular hyperplasia |
| 525 | VRLGSLSTK | kidney, clear cell renal cell carcinoma, liver, focal nodular hyperplasia |
| 526 | RINEFSISSF | chondrosarcoma |
| 527 | DEKQQHIVY | liver, hepatocellular carcinoma, synovial sarcoma |
| 528 | DEVYQVTVY | liver, hepatocellular carcinoma, synovial sarcoma |
| 529 | GEISEKAKL | liver, hepatocellular carcinoma, synovial sarcoma |
| 530 | YTMKEVLFY | liver, hepatocellular carcinoma, synovial sarcoma |
| 531 | SQLTTLSFY | lung, non-small cell lung carcinoma, omentum, adenocarcinoma |
| 532 | LEKQLIEL | stomach, adenocarcinoma, rectum, adenocarcinoma |
| 533 | ELTLGEFLK | stomach, metastatic, ovary, Mullerian mixed tumor |
| 534 | LTLGEFLK | stomach, metastatic, ovary, Mullerian mixed tumor |
| 535 | LTLGEFLKL | stomach, metastatic, ovary, Mullerian mixed tumor |

TABLE 3-continued

Peptides according to the present invention and their specific uses in other proliferative diseases, optionally in other organs.

| Seq ID | Sequence | Tissue and disease |
|---|---|---|
| 536 | TLGEFLKL | stomach, metastatic, ovary, Mullerian mixed tumor |
| 537 | ITARPVLW | non-Hodgkin's lymphoma |
| 538 | KLMSPKLYVW | non-Hodgkin's lymphoma |
| 539 | KVSAVTLAY | non-Hodgkin's lymphoma |
| 540 | VEGSGELFRW | non-Hodgkin's lymphoma |
| 541 | RPKSNIVL | non-Hodgkin's lymphoma |
| 542 | RPKSNIVLL | non-Hodgkin's lymphoma |
| 543 | GEPLSYTRFSLARQ | lung, non-small cell lung carcinoma, lung, adenocarcinoma |
| 544 | GEPLSYTRFSLARQVD | lung, non-small cell lung carcinoma, lung, adenocarcinoma |
| 545 | GEPLSYTRFSLARQVDG | lung, non-small cell lung carcinoma, lung, adenocarcinoma |
| 546 | GGEPLSYTRFSLARQVD | lung, non-small cell lung carcinoma, lung, adenocarcinoma |
| 547 | GGEPLSYTRFSLARQVDG | lung, non-small cell lung carcinoma, lung, adenocarcinoma |
| 548 | NPGGYVAYSKAATVTG | lung, non-small cell lung carcinoma, lung, adenocarcinoma |
| 549 | NPGGYVAYSKAATVTGK | lung, non-small cell lung carcinoma, lung, adenocarcinoma |
| 550 | NPGGYVAYSKAATVTGKL | lung, non-small cell lung carcinoma, lung, adenocarcinoma |
| 551 | NSVIIVDKNGRL | lung, non-small cell lung carcinoma, lung, adenocarcinoma |
| 552 | NSVIIVDKNGRLV | lung, non-small cell lung carcinoma, lung, adenocarcinoma |
| 553 | NSVIIVDKNGRLVY | lung, non-small cell lung carcinoma, lung, adenocarcinoma |
| 554 | RVEYHFLSPYVSPK | lung, non-small cell lung carcinoma, lung, adenocarcinoma |
| 555 | RVEYHFLSPYVSPKE | lung, non-small cell lung carcinoma, lung, adenocarcinoma |
| 556 | RVEYHFLSPYVSPKESPF | lung, non-small cell lung carcinoma, lung, adenocarcinoma |
| 557 | SPFRHVFWGSGSHTL | lung, non-small cell lung carcinoma, lung, adenocarcinoma |
| 558 | SVIIVDKNGRLV | lung, non-small cell lung carcinoma, lung, adenocarcinoma |
| 559 | VEYHFLSPYVSPK | lung, non-small cell lung carcinoma, lung, adenocarcinoma |
| 560 | VEYHFLSPYVSPKE | lung, non-small cell lung carcinoma, lung, adenocarcinoma |
| 561 | LPSQAFEYILYNKG | lung, non-small cell lung carcinoma, lung, adenocarcinoma |
| 562 | LPSQAFEYILYNKGI | lung, non-small cell lung carcinoma, lung, adenocarcinoma |
| 563 | LPSQAFEYILYNKGIM | lung, non-small cell lung carcinoma, lung, adenocarcinoma |
| 564 | LPSQAFEYILYNKGIMG | lung, non-small cell lung carcinoma, lung, adenocarcinoma |
| 565 | MNGYFLIERGKNM | lung, non-small cell lung carcinoma, lung, adenocarcinoma |
| 566 | NGYFLIERGKNm | lung, non-small cell lung carcinoma, lung, adenocarcinoma |
| 567 | PSQAFEYILYNKG | lung, non-small cell lung carcinoma, lung, adenocarcinoma |
| 568 | PSQAFEYILYNKGI | lung, non-small cell lung carcinoma, lung, adenocarcinoma |
| 569 | PSQAFEYILYNKGIM | lung, non-small cell lung carcinoma, lung, adenocarcinoma |
| 570 | EGVQYSYSLFHLM | stomach, metastatic, stomach, gastrointestinal stromal tumor (GIST) |
| 571 | EGVQYSYSLFHLML | stomach, metastatic, stomach, gastrointestinal stromal tumor (GIST) |
| 572 | GVQYSYSLFHLM | stomach, metastatic, stomach, gastrointestinal stromal tumor (GIST) |
| 573 | GVQYSYSLFHLML | stomach, metastatic, stomach, gastrointestinal stromal tumor (GIST) |
| 574 | SIISIHPKIQEHQPR | stomach, metastatic, stomach, gastrointestinal stromal tumor (GIST) |
| 575 | SSIRTSTNSQVDK | stomach, metastatic, stomach, gastrointestinal stromal tumor (GIST) |

TABLE 3-continued

Peptides according to the present invention and their specific uses in other proliferative diseases, optionally in other organs.

| Seq ID | Sequence | Tissue and disease |
|---|---|---|
| 576 | VLVGYKAVYRIS | stomach, metastatic, stomach, gastrointestinal stromal tumor (GIST) |
| 577 | YSSIRTSTNSQVDK GGGYGSGGGSGGYGSRR | stomach, metastatic, stomach, gastrointestinal stromal tumor (GIST) |
| 578 | F | colon or rectum, thymus, thymoma, malignant |
| 579 | GGSFGGRSSGSP | colon or rectum, thymus, thymoma, malignant |
| 580 | KGGSFGGRSSGSP SGQQQSNYGPMKGGSFG | colon or rectum, thymus, thymoma, malignant |
| 581 | GRSSGSPY SGSPYGGGYGSGGGSGG | colon or rectum, thymus, thymoma, malignant |
| 582 | YGSRRF SPYGGGYGSGGGSGGYG | colon or rectum, thymus, thymoma, malignant |
| 583 | SRRF YGGGYGSGGGSGGYGSR | colon or rectum, thymus, thymoma, malignant |
| 584 | RF | colon or rectum, thymus, thymoma, malignant |
| 585 | GNRINEFSISSF | chondrosarcoma |
| 586 | HGNQITSDKVGRKV | chondrosarcoma |
| 587 | IPPVNTNLENLYLQ | chondrosarcoma |
| 588 | LQVLRLDGNEIKR | chondrosarcoma |
| 589 | LQVLRLDGNEIKRS | chondrosarcoma |
| 590 | LQVLRLDGNEIKRSA | chondrosarcoma |
| 591 | LRELHLDHNQISRVPN | chondrosarcoma |
| 592 | LYVRLSHNSLTNNG | chondrosarcoma |
| 593 | VPSRMKYVYFQNNQ | chondrosarcoma |
| 594 | VPSRMKYVYFQNNQIT | chondrosarcoma |
| 595 | VPSRMKYVYFQNNQITS | chondrosarcoma |
| 596 | WIALHGNQITSD | chondrosarcoma |
| 597 | WIALHGNQITSDK | chondrosarcoma |
| 598 | ADDNVSFRWEALGNT | chondrosarcoma |
| 599 | ADDNVSFRWEALGNTL | colon or rectum |
| 600 | DADDNVSFRWEALGNTL | colon or rectum |
| 601 | DDNVSFRWEALGNT | colon or rectum |
| 602 | DDNVSFRWEALGNTL | colon or rectum |
| 603 | DNVSFRWEALGNT | colon or rectum |
| 604 | DNVSFRWEALGNTL | colon or rectum |
| 605 | DNVSFRWEALGNTLS | colon or rectum |
| 606 | DTGSYRAQISTKTSAK | colon or rectum |
| 607 | DTGSYRAQISTKTSAKL | colon or rectum |
| 608 | DTITIYSTINHSK | colon or rectum |
| 609 | EDTGSYRAQISTKTSAK | colon or rectum |
| 610 | ENDTITIYSTINHSK | colon or rectum |
| 611 | ENDTITIYSTINHSKESKPT | colon or rectum |
| 612 | GSYRAQISTKTSAK | colon or rectum |
| 613 | NDTITIYSTINH | colon or rectum |
| 614 | NDTITIYSTINHS | colon or rectum |
| 615 | NDTITIYSTINHSK | colon or rectum |
| 616 | NVSFRWEALGNTL | colon or rectum |
| 617 | SPTNNTVYASVTHSNRET | colon or rectum |
| 618 | TGSYRAQISTKTSAK | colon or rectum |
| 619 | TPRENDTITIYSTINHSK | colon or rectum |
| 620 | TPRENDTITIYSTINHSKESKPT | colon or rectum |
| 621 | VSFRWEALGNTL | colon or rectum |
| 622 | APIHFTIEKLELNEK | lipoma |
| 623 | DAQFEVIKGQTIE | lipoma |
| 624 | DAQFEVIKGQTIEVR | lipoma |
| 625 | ESYFIPEVRIYDSGT | lipoma |
| 626 | IPEVRIYDSGTY | lipoma |
| 627 | KDKAIVAHNRHGNK | lipoma |
| 628 | KDKAIVAHNRHGNKA | lipoma |
| 629 | NFVILEFPVEEQDR | lipoma |
| 630 | SQPRISYDAQFEVIK | lipoma |
| 631 | SQPRISYDAQFEVIKG | lipoma |
| 632 | YDAQFEVIKGQTIE | lipoma |
| 633 | GNPAYRSFSNSLSQ | colon or rectum, kidney, angiomyolipoma |
| 634 | GPPGEAGYKAFSSLLA | colon or rectum, kidney, angiomyolipoma |
| 635 | GPPGEAGYKAFSSLLASS | colon or rectum, kidney, angiomyolipoma |
| 636 | GPPGEAGYKAFSSLLASSA | colon or rectum, kidney, angiomyolipoma |
| 637 | VSPE GPPGEAGYKAFSSLLASSA | colon or rectum, kidney, angiomyolipoma |

TABLE 3-continued

Peptides according to the present invention and their specific uses in other proliferative diseases, optionally in other organs.

| Seq ID | Sequence | Tissue and disease |
|---|---|---|
| 638 | VSPEK | colon or rectum, kidney, angiomyolipoma |
| 639 | GYKAFSSLLASSAVSP | colon or rectum, kidney, angiomyolipoma |
| 640 | GYKAFSSLLASSAVSPE | colon or rectum, kidney, angiomyolipoma |
| 641 | KAFSSLLASSAVSPE | colon or rectum, kidney, angiomyolipoma |
| 642 | NPAYRSFSNSLSQ | colon or rectum, kidney, angiomyolipoma |
| 643 | SRDDFQEGREGIVAR | colon or rectum, kidney, angiomyolipoma |
| 644 | SSSSFHPAPGNAQ | colon or rectum, kidney, angiomyolipoma |
| 645 | VARLTESLFLDL | colon or rectum, kidney, angiomyolipoma |
| 646 | VARLTESLFLDLLG | colon or rectum, kidney, angiomyolipoma |
| 647 | VIAGNPAYRSFSN | colon or rectum, kidney, angiomyolipoma |
| 648 | VPQPEPETWEQILRRNVLQ | colon or rectum, kidney, angiomyolipoma |
| 649 | YKAFSSLLASSAVS | colon or rectum, kidney, angiomyolipoma |
| 650 | YKAFSSLLASSAVSP | colon or rectum, kidney, angiomyolipoma |
| 651 | YKAFSSLLASSAVSPE | colon or rectum, kidney, angiomyolipoma, |
| 652 | GNQVFSYTANKEIRTDD | colon or rectum, urinary bladder, transitional cell carcinoma |
| 653 | IEEIVLVDDASERD | colon or rectum, urinary bladder, transitional cell carcinoma |
| 654 | IEEIVLVDDASERDF | colon or rectum, urinary bladder, transitional cell carcinoma |
| 655 | LENIYPDSQIPRH | colon or rectum, urinary bladder, transitional cell carcinoma |
| 656 | LENIYPDSQIPRHY | colon or rectum, urinary bladder, transitional cell carcinoma |
| 657 | NQVFSYTANKEIR | colon or rectum, urinary bladder, transitional cell carcinoma |
| 658 | NQVFSYTANKEIRT | colon or rectum, urinary bladder, transitional cell carcinoma |
| 659 | NQVFSYTANKEIRTDD | colon or rectum, urinary bladder, transitional cell carcinoma |
| 660 | VHSVINRSPRHMIEE | colon or rectum, urinary bladder, transitional cell carcinoma |
| 661 | EYVSLYHQPAAM | non-Hodgkin's lymphoma |
| 662 | IKAEYKGRVTLKQYPR | non-Hodgkin's lymphoma |
| 663 | LNVHSEYEPSWEEQP | non-Hodgkin's lymphoma |
| 664 | LPYLFQmPAYASSS | non-Hodgkin's lymphoma |
| 665 | LPYLFQmPAYASSSK | non-Hodgkin's lymphoma |
| 666 | NFIKAEYKGRVT | non-Hodgkin's lymphoma |
| 667 | TNFIKAEYKGRVT | non-Hodgkin's lymphoma |
| 668 | TTNFIKAEYKGRVT | non-Hodgkin's lymphoma |
| 669 | VTLNVHSEYEPSWEEQP | non-Hodgkin's lymphoma |
| 670 | YPRKNLFLVEVTQLTESDS | non-Hodgkin's lymphoma |
| 671 | YPRKNLFLVEVTQLTESDSG | non-Hodgkin's lymphoma |
| 672 | ADLSSFKSQELN | lymph node, papillary carcinoma of thyroid |
| 673 | ADLSSFKSQELNER | lymph node, papillary carcinoma of thyroid |
| 674 | ADLSSFKSQELNERN | lymph node, papillary carcinoma of thyroid |
| 675 | ADLSSFKSQELNERNE | lymph node, papillary carcinoma of thyroid |
| 676 | ADLSSFKSQELNERNEA | lymph node, papillary carcinoma of thyroid |
| 677 | AEQQRLKSQDLELSWNLNG | lymph node, papillary carcinoma of thyroid, metastatic |
| 678 | EQQRLKSQDLELSWN | lymph node, papillary carcinoma of thyroid |
| 679 | ISQELEELRAEQQR | lymph node, papillary carcinoma of thyroid |
| 680 | ISQELEELRAEQQRLK | lymph node, papillary carcinoma of thyroid |
| 681 | KGTKQWVHARYA | lymph node, papillary carcinoma of thyroid |
| 682 | QADLSSFKSQELNER | lymph node, papillary carcinoma of thyroid, metastatic |
| 683 | SWNLNGLQADLSSFK | lymph node, papillary carcinoma of thyroid |
| 684 | TGSWIGLRNLDLKG | lymph node, papillary carcinoma of thyroid |
| 685 | FGGRSFGPMKGGNFGGRSSGPYG | pancreas, adenocarcinoma, thymus, thymoma, malignant |
| 686 | GGGQY | pancreas, adenocarcinoma, thymus, thymoma, malignant |
| 687 | GPMKGGNFGGRSSGP | pancreas, adenocarcinoma, thymus, thymoma, malignant |
| 688 | GPYGGGGQYFAKP | pancreas, adenocarcinoma, thymus, thymoma, malignant |
| 689 | KGGNFGGRSSGP | pancreas, adenocarcinoma, thymus, thymoma, malignant |
| 690 | NDFGNYNNQSSNFGP | pancreas, adenocarcinoma, thymus, thymoma, malignant |

TABLE 3-continued

Peptides according to the present invention and their specific uses in other proliferative diseases, optionally in other organs.

| Seq ID | Sequence | Tissue and disease |
|---|---|---|
| 691 | SGPYGGGGQYFAKP | lung, non-small cell lung carcinoma, lymph node, non-Hodgkin's lymphoma |
| 692 | DAGSYKAQINQRNFE | lung, non-small cell lung carcinoma, lymph node, non-Hodgkin's lymphoma |
| 693 | DAGSYKAQINQRNFEVT | pancreas, adenocarcinoma, intramuscular lipoma |
| 694 | DGELIRTQPQRLPQ | pancreas, adenocarcinoma, intramuscular lipoma |
| 695 | GELIRTQPQRLPQ | pancreas, adenocarcinoma, intramuscular lipoma |
| 696 | NPSDGELIRTQPQRLP | pancreas, adenocarcinoma, intramuscular lipoma |
| 697 | NPSDGELIRTQPQRLPQ | pancreas, adenocarcinoma, intramuscular lipoma |
| 698 | NPSDGELIRTQPQRLPQL | colon or rectum, bone, giant cell tumor of bone |
| 699 | ASNDMYHSRALQVVR | colon or rectum, bone, giant cell tumor of bone |
| 700 | ASNDMYHSRALQVVRA | colon or rectum, bone, giant cell tumor of bone |
| 701 | EGVRRALDFAVGEYN | colon or rectum, bone, giant cell tumor of bone |
| 702 | EGVRRALDFAVGEYNK | colon or rectum, bone, giant cell tumor of bone |
| 703 | SNDMYHSRALQVVR | colon or rectum, bone, giant cell tumor of bone |
| 704 | VGEYNKASNDMYH | colon or rectum, bone, giant cell tumor of bone |
| 705 | VRARKQIVAGVNY | colon or rectum, bone, giant cell tumor of bone |
| 706 | VRRALDFAVGEYNKASND | colon or rectum, bone, giant cell tumor of bone |
| 707 | VVRARKQIVAGVN | colon or rectum, bone, giant cell tumor of bone |
| 708 | VVRARKQIVAGVNY | colon or rectum, bone, giant cell tumor of bone |
| 709 | APLEGARFALVRED | liver, hepatocellular carcinoma |
| 710 | APVELILSDETLPAPE | liver, hepatocellular carcinoma |
| 711 | ELILSDETLPAPE | liver, hepatocellular carcinoma |
| 712 | LAPLEGARFALVRE | liver, hepatocellular carcinoma |
| 713 | LAPLEGARFALVRED | liver, hepatocellular carcinoma |
| 714 | RGEKELLVPRSSTSPD | liver, hepatocellular carcinoma |
| 715 | ASKTFTTQETITNAET | kidney, clear cell renal cell carcinoma, kidney, angiomyolipoma |
| 716 | DQHFRTTPLEKNAPV | kidney, clear cell renal cell carcinoma, kidney, angiomyolipoma |
| 717 | NTPILVDGKDVMPE | kidney, clear cell renal cell carcinoma, kidney, angiomyolipoma |
| 718 | NTPILVDGKDVMPEV | kidney, clear cell renal cell carcinoma, kidney, angiomyolipoma |
| 719 | NTPILVDGKDVMPEVN | kidney, clear cell renal cell carcinoma, kidney, angiomyolipoma |
| 720 | SNTPILVDGKDVMPE | kidney, clear cell renal cell carcinoma, kidney, angiomyolipoma |
| 721 | SNTPILVDGKDVMPEVN | kidney, clear cell renal cell carcinoma, kidney, angiomyolipoma |
| 722 | TPILVDGKDVMP | kidney, clear cell renal cell carcinoma, kidney, angiomyolipoma |
| 723 | TPILVDGKDVMPE | kidney, clear cell renal cell carcinoma, kidney, angiomyolipoma |
| 724 | TPILVDGKDVMPEV | kidney, clear cell renal cell carcinoma, kidney, angiomyolipoma |
| 725 | TPILVDGKDVMPEVN | kidney, clear cell renal cell carcinoma, kidney, angiomyolipoma |
| 726 | GPLKFLHQDIDSGQG | kidney, renal cell carcinoma |
| 727 | GPLKFLHQDIDSGQGIR | kidney, renal cell carcinoma |
| 728 | LGDIYFKLFRASG | kidney, renal cell carcinoma |
| 729 | TGHLFDLSSLSGRAG | kidney, renal cell carcinoma |
| 730 | VPSPVDCQVTDLAGNE | kidney, renal cell carcinoma |
| 731 | DGLNSLTYQVLDVQRYPL | kidney, clear cell renal cell carcinoma, endometrium, adenocarcinoma, endometrioid type |

TABLE 3-continued

Peptides according to the present invention and their specific uses in other proliferative diseases, optionally in other organs.

| Seq ID | Sequence | Tissue and disease |
|---|---|---|
| 732 | HPVLQRQQLDYGIY | kidney, clear cell renal cell carcinoma, endometrium, adenocarcinoma, endometrioid type |
| 733 | LNSLTYQVLDVQR | kidney, clear cell renal cell carcinoma, endometrium, adenocarcinoma, endometrioid type |
| 734 | LNSLTYQVLDVQRYP | kidney, clear cell renal cell carcinoma, endometrium, adenocarcinoma, endometrioid type |
| 735 | LNSLTYQVLDVQRYPL | kidney, clear cell renal cell carcinoma, endometrium, adenocarcinoma, endometrioid type |
| 736 | LPQLVGVSTPLQG | kidney, clear cell renal cell carcinoma, endometrium, adenocarcinoma, endometrioid type |
| 737 | LPQLVGVSTPLQGG | kidney, clear cell renal cell carcinoma, endometrium, adenocarcinoma, endometrioid type |
| 738 | LPQLVGVSTPLQGGS | kidney, clear cell renal cell carcinoma, endometrium, adenocarcinoma, endometrioid type |
| 739 | RLPQLVGVSTPLQGGS | kidney, clear cell renal cell carcinoma, endometrium, adenocarcinoma, endometrioid type |
| 740 | SPHKVAIIIPFRNR | kidney, clear cell renal cell carcinoma, endometrium, adenocarcinoma, endometrioid type |
| 741 | SPHKVAIIIPFRNRQE | kidney, clear cell renal cell carcinoma, endometrium, adenocarcinoma, endometrioid type |
| 742 | SPHKVAIIIPFRNRQEH | kidney, clear cell renal cell carcinoma, endometrium, adenocarcinoma, endometrioid type |
| 743 | AIVQAVSAHRHR | non-Hodgkin's lymphoma, peripheral T cell type |
| 744 | ARNFERNKAIKVI | non-Hodgkin's lymphoma, peripheral T cell type |
| 745 | ARNFERNKAIKVIIA | non-Hodgkin's lymphoma, peripheral T cell type |
| 746 | NFERNKAIKVII | non-Hodgkin's lymphoma, peripheral T cell type |
| 747 | NFERNKAIKVIIA | non-Hodgkin's lymphoma, peripheral T cell type |
| 748 | VAIVQAVSAHRH | non-Hodgkin's lymphoma, peripheral T cell type |
| 749 | VAIVQAVSAHRHR | non-Hodgkin's lymphoma, peripheral T cell type |
| 750 | VAIVQAVSAHRHRA | non-Hodgkin's lymphoma, peripheral T cell type |
| 751 | VAIVQAVSAHRHRAR | non-Hodgkin's lymphoma, peripheral T cell type |
| 752 | EEVITLIRSNQQLE | lung, non-small cell lung carcinoma, pancreas, adenocarcinoma |
| 753 | EEVITLIRSNQQLEN | lung, non-small cell lung carcinoma, pancreas, adenocarcinoma |
| 754 | IPADTFAALKNPNAML | lung, non-small cell lung carcinoma, pancreas, adenocarcinoma |
| 755 | LKQLLSDKQQKRQSG | lung, non-small cell lung carcinoma, pancreas, adenocarcinoma |
| 756 | LKQLLSDKQQKRQSGQ | lung, non-small cell lung carcinoma, pancreas, adenocarcinoma |
| 757 | TPSYVAFTDTER | pancreas, adenocarcinoma, rectum, adenocarcinoma |
| 758 | TPSYVAFTDTERL | pancreas, adenocarcinoma, rectum, adenocarcinoma |
| 759 | EGLYSRTLAGSIT | liver, hepatocellular carcinoma, cancer, thyroid gland, nodular hyperplasia |
| 760 | EGLYSRTLAGSITTPP | liver, hepatocellular carcinoma, cancer, thyroid gland, nodular hyperplasia |
| 761 | EKWYIPDPTGKFN | liver, hepatocellular carcinoma, cancer, thyroid gland, nodular hyperplasia |
| 762 | GAIAAINSIQHNTR | liver, hepatocellular carcinoma, cancer, thyroid gland, nodular hyperplasia |

TABLE 3-continued

Peptides according to the present invention and their specific uses in other proliferative diseases, optionally in other organs.

| Seq ID | Sequence | Tissue and disease |
|---|---|---|
| 763 | LPILVPSAKKAI | liver, hepatocellular carcinoma, cancer, thyroid gland, nodular hyperplasia |
| 764 | LPILVPSAKKAIY | liver, hepatocellular carcinoma, cancer, thyroid gland, nodular hyperplasia |
| 765 | LPILVPSAKKAIYM | liver, hepatocellular carcinoma, cancer, thyroid gland, nodular hyperplasia |
| 766 | LPILVPSAKKAIYMD | liver, hepatocellular carcinoma, cancer, thyroid gland, nodular hyperplasia |
| 767 | LPILVPSAKKAIYMDD | liver, hepatocellular carcinoma, cancer, thyroid gland, nodular hyperplasia |
| 768 | VEEGLYSRTLAGSIT | liver, hepatocellular carcinoma, cancer, thyroid gland, nodular hyperplasia |
| 769 | WEKWYIPDPTGKFN | liver, hepatocellular carcinoma, cancer, thyroid gland, nodular hyperplasia |
| 770 | YKIVNFDPKLLE | liver, hepatocellular carcinoma, cancer, thyroid gland, nodular hyperplasia |
| 771 | YKIVNFDPKLLEG | liver, hepatocellular carcinoma, cancer, thyroid gland, nodular hyperplasia |
| 772 | YKIVNFDPKLLEGKV | liver, hepatocellular carcinoma, cancer, thyroid gland, nodular hyperplasia |
| 773 | LPEFYKTVSPAL | colon or rectum, endometrium, adenocarcinoma, endometrioid type |
| 774 | VGQFIQDVKNSRST | colon or rectum, endometrium, adenocarcinoma endometrioid type |
| 775 | VGQFIQDVKNSRSTD | colon or rectum, endometrium, adenocarcinoma endometrioid type |
| 776 | VVGQFIQDVKNSRS | colon or rectum, endometrium, adenocarcinoma endometrioid type |
| 777 | VVGQFIQDVKNSRST | colon or rectum, endometrium, adenocarcinoma endometrioid type |
| 778 | VVGQFIQDVKNSRSTD | colon or rectum, endometrium, adenocarcinoma endometrioid type |
| 779 | VVGQFIQDVKNSRSTDS | colon or rectum, endometrium, adenocarcinoma, endometrioid type |
| 780 | DNGHLYREDQTSPAPG | pancreas, adenocarcinoma, kidney, angiomyolipoma |
| 781 | DNGHLYREDQTSPAPGLR | pancreas, adenocarcinoma, kidney, angiomyolipoma |
| 782 | EVQVFAPANALPARSE | pancreas, adenocarcinoma, kidney, angiomyolipoma |
| 783 | GHLYREDQTSPAPG | pancreas, adenocarcinoma, kidney, angiomyolipoma |
| 784 | LPARSEAAAVQPVIG | pancreas, adenocarcinoma, kidney, angiomyolipoma |
| 785 | NGHLYREDQTSPAPG | pancreas, adenocarcinoma, kidney, angiomyolipoma |
| 786 | NGHLYREDQTSPAPGL | pancreas, adenocarcinoma, kidney, angiomyolipoma |
| 787 | NGHLYREDQTSPAPGLR | pancreas, adenocarcinoma, kidney, angiomyolipoma |
| 788 | VFAPANALPARSEAA | pancreas, adenocarcinoma, kidney, angiomyolipoma |
| 789 | VQVFAPANALPARSE | pancreas, adenocarcinoma, kidney, angiomyolipoma |
| 790 | AIVVSDRDGVPVIK | stomach, adenocarcinoma, parathyroid gland, adenoma |
| 791 | GLHAIVVSDRDGVPV | stomach, adenocarcinoma, parathyroid gland, adenoma |
| 792 | GLHAIVVSDRDGVPVIK | stomach, adenocarcinoma, parathyroid gland, adenoma |
| 793 | HAIVVSDRDGVPV | stomach, adenocarcinoma, parathyroid gland, adenoma |
| 794 | KLPSVEGLHAIVVSDRDG | stomach, adenocarcinoma, parathyroid gland, adenoma |
| 795 | LHAIVVSDRDGVPV | stomach, adenocarcinoma, parathyroid gland, adenoma |
| 796 | LHAIVVSDRDGVPVI | stomach, adenocarcinoma, parathyroid gland, adenoma |
| 797 | LHAIVVSDRDGVPVIK | stomach, adenocarcinoma, parathyroid gland, adenoma |
| 798 | LPSVEGLHAIVVSDR | stomach, adenocarcinoma, parathyroid gland, adenoma |
| 799 | VPVIKVANDNAPE | stomach, adenocarcinoma, parathyroid gland, adenoma |

TABLE 3-continued

Peptides according to the present invention and their specific uses in other proliferative diseases, optionally in other organs.

| Seq ID | Sequence | Tissue and disease |
|---|---|---|
| 800 | YNTYQVVQFNRLP | stomach, adenocarcinoma, parathyroid gland, adenoma |
| 801 | YNTYQVVQFNRLPL | stomach, adenocarcinoma, parathyroid gland, adenoma |
| 802 | YNTYQVVQFNRLPLV | stomach, adenocarcinoma, parathyroid gland, adenoma |
| 803 | YNTYQVVQFNRLPLVV | stomach, adenocarcinoma, parathyroid gland, adenoma |
| 804 | YYNTYQVVQFNRLP | stomach, adenocarcinoma, parathyroid gland, adenoma |
| 805 | YYNTYQVVQFNRLPL | stomach, adenocarcinoma, parathyroid gland, adenoma |
| 806 | YYNTYQVVQFNRLPLV | stomach, adenocarcinoma, parathyroid gland, adenoma |
| 807 | DKIYFmAGSSRKEDVGTDEEEETAKESTAEKD | liver, hepatocellular carcinoma, thyroid gland, nodular hyperplasia |
| 808 | E | liver, hepatocellular carcinoma, thyroid gland, nodular hyperplasia |
| 809 | EVTFKSILFVPTSAP | liver, hepatocellular carcinoma, thyroid gland, nodular hyperplasia |
| 810 | KSEKFAFQAEVNR | liver, hepatocellular carcinoma, thyroid gland, nodular hyperplasia |
| 811 | LPEFDGKRFQNVAK | liver, hepatocellular carcinoma, thyroid gland, nodular hyperplasia |
| 812 | DGSYRIFSKGASE | colon or rectum, liposarcoma |
| 813 | GSYRIFSKGASE | colon or rectum, liposarcoma |
| 814 | SDGSYRIFSKGASE | colon or rectum, liposarcoma |
| 815 | SVKKMMKDNNLVRH | colon or rectum, liver, hepatocellular carcinoma |
| 816 | VKKMMKDNNLVRH | colon or rectum, liver, hepatocellular carcinoma |
| 817 | NNmRIFGEAAEKN | stomach, adenocarcinoma, thyroid gland, papillary carcinoma |
| 818 | VDKVLERDQKLSE | lung, non-small cell lung carcinoma, lymph node, papillary carcinoma of thyroid |
| 819 | VDKVLERDQKLSELD | lung, non-small cell lung carcinoma, lymph node, papillary carcinoma of thyroid |
| 820 | VDKVLERDQKLSELDD | lung, non-small cell lung carcinoma, lymph node, papillary carcinoma of thyroid |
| 821 | VDKVLERDQKLSELDDR | stomach, adenocarcinoma, lymph node, papillary carcinoma of thyroid |
| 822 | VLERDQKLSELDDR | lung, non-small cell lung carcinoma, lymph node, papillary carcinoma of thyroid |
| 823 | ATRSIQVDGKTIKAQ | stomach, adenocarcinoma, kidney, angiomyolipoma |
| 824 | ATRSIQVDGKTIKAQI | stomach, adenocarcinoma, kidney, angiomyolipoma |
| 825 | IGVEFATRSIQVDGK | stomach, adenocarcinoma, kidney, angiomyolipoma |
| 826 | RSIQVDGKTIKA | stomach, adenocarcinoma, kidney, angiomyolipoma |
| 827 | RSIQVDGKTIKAQ | stomach, adenocarcinoma, kidney, angiomyolipoma |
| 828 | RSIQVDGKTIKAQI | stomach, adenocarcinoma, kidney, angiomyolipoma |
| 829 | TRSIQVDGKTIKAQ | stomach, adenocarcinoma, kidney, angiomyolipoma |
| 830 | DIMRVNVDKVLERDQK | stomach, adenocarcinoma, medullary carcinoma of thyroid origin |
| 831 | DIMRVNVDKVLERDQKL | stomach, adenocarcinoma, medullary carcinoma of thyroid origin |
| 832 | IMRVNVDKVLERDQK | lung, non-small cell lung carcinoma, lymph node, Hodgkin's disease |
| 833 | VDKVLERDQKLSE | lung, non-small cell lung carcinoma, lymph node, papillary carcinoma of thyroid |
| 834 | VDKVLERDQKLSELD | lung, non-small cell lung carcinoma, lymph node, papillary carcinoma of thyroid |
| 835 | VDKVLERDQKLSELDD | lung, non-small cell lung carcinoma, lymph node, papillary carcinoma of thyroid |
| 836 | VDKVLERDQKLSELDDR | stomach, adenocarcinoma, lymph node, papillary carcinoma of thyroid |
| 837 | VLERDQKLSELDDR | lung, non-small cell lung carcinoma, lymph node, papillary carcinoma of thyroid |
| 838 | ATRSIQVDGKTIKAQ | stomach, adenocarcinoma |

TABLE 3-continued

Peptides according to the present invention and their specific uses in other proliferative diseases, optionally in other organs.

| Seq ID | Sequence | Tissue and disease |
|---|---|---|
| 839 | ATRSIQVDGKTIKAQI | stomach, adenocarcinoma, kidney, angiomyolipoma |
| 840 | IGVEFATRSIQVDGK | stomach, adenocarcinoma, kidney, angiomyolipoma |
| 841 | RSIQVDGKTIKA | stomach, adenocarcinoma, kidney, angiomyolipoma |
| 842 | RSIQVDGKTIKAQ | stomach, adenocarcinoma, kidney, angiomyolipoma |
| 843 | RSIQVDGKTIKAQI | stomach, adenocarcinoma, kidney, angiomyolipoma |
| 844 | TRSIQVDGKTIKAQ | stomach, adenocarcinoma, kidney, angiomyolipoma |
| 845 | GIRVAPVPLYNS | lung, non-small cell lung carcinoma, liver, hepatocellular carcinoma |
| 846 | GIRVAPVPLYNSFH | lung, non-small cell lung carcinoma, liver, hepatocellular carcinoma |
| 847 | NPNGIRVAPVPLYNSFH | lung, non-small cell lung carcinoma, liver, hepatocellular carcinoma |
| 848 | DDPAIDVCKKLLGKYPN | kidney, clear cell renal cell carcinoma, pancreas, adenocarcinoma |
| 849 | DKQPYSKLPGVSLLKP | kidney, clear cell renal cell carcinoma, pancreas, adenocarcinoma |
| 850 | DKQPYSKLPGVSLLKPL | kidney, clear cell renal cell carcinoma, pancreas, adenocarcinoma |
| 851 | HPRYYISANVTGFK | kidney, clear cell renal cell carcinoma, pancreas, adenocarcinoma |
| 852 | SHPRYYISANVTG | kidney, clear cell renal cell carcinoma, pancreas, adenocarcinoma |
| 853 | SHPRYYISANVTGFK | kidney, clear cell renal cell carcinoma, pancreas, adenocarcinoma |
| 854 | TSHPRYYISANVTG | kidney, clear cell renal cell carcinoma, pancreas, adenocarcinoma |
| 855 | TSHPRYYISANVTGFK | kidney, clear cell renal cell carcinoma, pancreas, adenocarcinoma |
| 856 | ADIFVDPVLHTA | kidney, renal cell carcinoma |
| 857 | ADIFVDPVLHTACA | kidney, renal cell carcinoma |
| 858 | DPGADYRIDRALNEA | kidney, renal cell carcinoma |
| 859 | IAQDYKVSYSLA | kidney, renal cell carcinoma |
| 860 | IAQDYKVSYSLAK | kidney, renal cell carcinoma |
| 861 | ISRDWKLDPVLYRK | kidney, renal cell carcinoma |
| 862 | LIAQDYKVSYSLA | kidney, renal cell carcinoma |
| 863 | RQKLIAQDYKVSYS | kidney, renal cell carcinoma |
| 864 | RQKLIAQDYKVSYSL | kidney, renal cell carcinoma |
| 865 | RQKLIAQDYKVSYSLA | kidney, renal cell carcinoma |
| 866 | RQKLIAQDYKVSYSLAK | kidney, renal cell carcinoma |
| 867 | SALDYRLDPQLQLH | kidney, renal cell carcinoma |
| 868 | SKADIFVDPVLHTA | kidney, renal cell carcinoma |
| 869 | SPSKNYILSVISGSI | kidney, renal cell carcinoma |
| 870 | ETTQLTADSHPSYHTDG | stomach, metastatic, skin, squamous cell carcinoma |
| 871 | SGESLYHVLGLDKNATSDD | stomach, metastatic, skin, squamous cell carcinoma |
| 872 | TTQLTADSHPSYHT | stomach, metastatic, skin, squamous cell carcinoma |
| 873 | TTQLTADSHPSYHTD | stomach, metastatic, skin, squamous cell carcinoma |
| 874 | TTQLTADSHPSYHTDG | stomach, metastatic, skin, squamous cell carcinoma |
| 875 | SVEEFLSEKLERI | pancreas, adenocarcinoma, liver, hepatic adenoma |
| 876 | VEEFLSEKLERI | pancreas, adenocarcinoma, liver, hepatic adenoma |
| 877 | DLSSSILAQSRERVA | pancreas, adenocarcinoma, bone, giant cell tumor of bone |
| 878 | EKGVRTLTAAAVSGAQ | pancreas, adenocarcinoma, bone, giant cell tumor of bone |
| 879 | EKGVRTLTAAAVSGAQP | pancreas, adenocarcinoma, bone, giant cell tumor of bone |
| 880 | EKGVRTLTAAAVSGAQPI | pancreas, adenocarcinoma, bone, giant cell tumor of bone |
| 881 | KGVRTLTAAAVSGA | pancreas, adenocarcinoma, bone, giant cell tumor of bone |
| 882 | KGVRTLTAAAVSGAQ | pancreas, adenocarcinoma, bone, giant cell tumor of bone |

TABLE 3-continued

Peptides according to the present invention and their specific uses in other proliferative diseases, optionally in other organs.

| Seq ID | Sequence | Tissue and disease |
|---|---|---|
| 883 | VGPFAPGITEKAPEEKK | pancreas, adenocarcinoma, bone, giant cell tumor of bone |
| 884 | DPPLIALDKDAPLR | brain, glioblastoma, parotid gland, pleomorphic adenoma |
| 885 | EIITPDVPFTVDKDG | brain, glioblastoma, parotid gland, pleomorphic adenoma |
| 886 | IITPDVPFTVDKDG | brain, glioblastoma, parotid gland, pleomorphic adenoma |
| 887 | PPLIALDKDAPLR | brain, glioblastoma, parotid gland, pleomorphic adenoma |
| 888 | TNVKKSHKATVHIQ | brain, glioblastoma, parotid gland, pleomorphic adenoma |
| 889 | DDNIKTYSDHPE | kidney, clear cell renal cell carcinoma, liver, hepatocellular carcinoma |
| 890 | DDNIKTYSDHPEK | kidney, clear cell renal cell carcinoma, liver, hepatocellular carcinoma |
| 891 | DSAVFFEQGTTRIG | kidney, clear cell renal cell carcinoma, liver, hepatocellular carcinoma |
| 892 | GDKVYVHLKNLASRPY | kidney, clear cell renal cell carcinoma, liver, hepatocellular carcinoma |
| 893 | GDKVYVHLKNLASRPYT | kidney, clear cell renal cell carcinoma, liver, hepatocellular carcinoma |
| 894 | VHLKNLASRPYT | kidney, clear cell renal cell carcinoma, liver, hepatocellular carcinoma |
| 895 | VYVHLKNLASRPY | kidney, clear cell renal cell carcinoma, liver, hepatocellular carcinoma |
| 896 | VYVHLKNLASRPYT | kidney, clear cell renal cell carcinoma, liver, hepatocellular carcinoma |
| 897 | VYVHLKNLASRPYTFH | kidney, clear cell renal cell carcinoma, liver, hepatocellular carcinoma |
| 898 | YVHLKNLASRPY | kidney, clear cell renal cell carcinoma, liver, hepatocellular carcinoma |
| 899 | YVHLKNLASRPYT | kidney, clear cell renal cell carcinoma, liver, hepatocellular carcinoma |
| 900 | YVHLKNLASRPYTFH | kidney, clear cell renal cell carcinoma, liver, hepatocellular carcinoma |
| 901 | SNLIKLAQKVPTAD | liver, hepatocellular carcinoma |
| 902 | YDTRTSALSAKS | liver, hepatocellular carcinoma |
| 903 | ALMTDPKLITWSPV | bone, non-ossifying fibroma |
| 904 | NDVAWNFEKFLVGPDG | bone, non-ossifying fibroma |
| 905 | QSVYAFSARPLAG | bone, non-ossifying fibroma |
| 906 | QSVYAFSARPLAGGEPV | bone, non-ossifying fibroma |
| 907 | WNFEKFLVGPDG | colon or rectum, bone, non-ossifying fibroma |
| 908 | DVGMFVALTKLGQPD | stomach, adenocarcinoma, uterin cervix, squamous cell carcinoma |
| 909 | VGMFVALTKLGQPD | stomach, adenocarcinoma, uterin cervix, squamous cell carcinoma |
| 910 | AGVFHVEKNGRY | stomach, adenocarcinoma, colon, adenocarcinoma |
| 911 | FAGVFHVEKNGRYS | stomach, adenocarcinoma, colon, adenocarcinoma |
| 912 | GPITITIVNRDGTR | stomach, adenocarcinoma, colon, adenocarcinoma |
| 913 | NGRYSISRTEAADL | stomach, adenocarcinoma, colon, adenocarcinoma |
| 914 | RKSRQGSLAMEELK | rectum, adenocarcinoma |
| 915 | RRKSRQGSLAMEELK | rectum, adenocarcinoma |
| 916 | EEFKKLTSIKIQNDK | brain, glioblastoma, small Intestine, gastrointestinal stromal tumor (GIST) |
| 917 | INRRMADDNKLFR | brain, glioblastoma, small Intestine, gastrointestinal stromal tumor (GIST) |
| 918 | TATIVMVTNLKERKE | brain, glioblastoma, small Intestine, gastrointestinal stromal tumor (GIST) |
| 919 | ELFYKGIRPAINVG | liver, hepatocellular carcinoma, kidney, oncocytoma |
| 920 | GQKRSTVAQLVKR | liver, hepatocellular carcinoma, kidney, oncocytoma |
| 921 | SDLDAATQQLLSRGV | liver, hepatocellular carcinoma, kidney, oncocytoma |
| 922 | FDFSQNTRVPRLPE | kidney, clear cell renal cell carcinoma, non-Hodgkin's lymphoma |
| 923 | GDAPAILFDKEF | kidney, clear cell renal cell carcinoma, non-Hodgkin's lymphoma |

TABLE 3-continued

Peptides according to the present invention and their specific uses in other proliferative diseases, optionally in other organs.

| Seq ID | Sequence | Tissue and disease |
|---|---|---|
| 924 | VTHEIDRYTAIAY | kidney, clear cell renal cell carcinoma, non-Hodgkin's lymphoma |
| 929 | AAKYQLDPTASISA | kidney, oncocytoma |
| 930 | IAAKYQLDPTASISA | kidney, oncocytoma |
| 931 | IAAKYQLDPTASISAK | kidney, oncocytoma |
| 932 | AGLGRAYALAFAERG | liver, hepatocellular carcinoma, hepatic adenoma |
| 933 | DAFGRIDVVVNNAG | liver, hepatocellular carcinoma, hepatic adenoma |
| 934 | GLGRAYALAFAER | liver, hepatocellular carcinoma, hepatic adenoma |
| 935 | GLGRAYALAFAERG | liver, hepatocellular carcinoma, hepatic adenoma |
| 936 | AKFALNGEEFMNFDL | liver, hepatocellular carcinoma, liposarcoma |
| 937 | AKFALNGEEFMNFDLK | liver, hepatocellular carcinoma, liposarcoma |
| 938 | ALNGEEFMNFDLK | liver, hepatocellular carcinoma, liposarcoma |
| 939 | KFALNGEEFMNFDL | liver, hepatocellular carcinoma, liposarcoma |
| 940 | SDGSFHASSSLTVK | liver, hepatocellular carcinoma, liposarcoma |
| 941 | EERNLLSVAYKNVVGAR | colon or rectum, esophagus, adenocarcinoma |
| 942 | ERNLLSVAYKNVVGAR | colon or rectum, esophagus, adenocarcinoma |
| 943 | IAELDTLSEESYKD | colon or rectum, Vulva, squamous cell carcinoma |
| 944 | IAELDTLSEESYKDS | colon or rectum, Vulva, squamous cell carcinoma |
| 945 | ADSYLDEGFLLDKKIG | lung, non-small cell lung carcinoma, ovary, Mullerian mixed tumor |
| 946 | DSYLDEGFLLDKK | lung, non-small cell lung carcinoma, ovary, Mullerian mixed tumor |
| 947 | DSYLDEGFLLDKKIG | lung, non-small cell lung carcinoma, ovary, Mullerian mixed tumor |
| 948 | VDNIIKAAPRKRVPD | lung, non-small cell lung carcinoma, ovary, Mullerian mixed tumor |
| 949 | SPPQFRVNGAISN | colon or rectum, ovary, granulosa cell tumor |
| 950 | SPPQFRVNGAISNFE | colon or rectum, ovary, granulosa cell tumor |
| 951 | SPPQFRVNGAISNFEE | colon or rectum, ovary, granulosa cell tumor |
| 952 | SPPQFRVNGAISNFEEF | colon or rectum, ovary, granulosa cell tumor |
| 953 | VGKMFVDVYFQEDKK | colon or rectum, ovary, granulosa cell tumor |
| 954 | VGKMFVDVYFQEDKKE | colon or rectum, ovary, granulosa cell tumor |
| 955 | DPKRTIAQDYGVLKADE | lung, non-small cell lung carcinoma, thyroid gland, nodular hyperplasia |
| 956 | DPKRTIAQDYGVLKADEG | lung, non-small cell lung carcinoma, thyroid gland, nodular hyperplasia |
| 957 | PKRTIAQDYGVLKADEG | lung, non-small cell lung carcinoma, thyroid gland, nodular hyperplasia |
| 958 | GLFIIDDKGILRQ | lung, non-small cell lung carcinoma, thyroid gland, nodular hyperplasia |
| 959 | GLFIIDDKGILRQIT | lung, non-small cell lung carcinoma, thyroid gland, nodular hyperplasia |
| 960 | RGLFIIDDKGILR | lung, non-small cell lung carcinoma, thyroid gland, nodular hyperplasia |
| 961 | RGLFIIDDKGILRQ | lung, non-small cell lung carcinoma, thyroid gland, nodular hyperplasia |
| 962 | RGLFIIDDKGILRQIT | lung, non-small cell lung carcinoma, thyroid gland, nodular hyperplasia |
| 963 | GNTVIHLDQALARMR | brain, glioblastoma, lung, small cell carcinoma |
| 964 | NTVIHLDQALARMR | brain, glioblastoma, lung, small cell carcinoma |
| 965 | NTVIHLDQALARMRE | brain, glioblastoma, lung, small cell carcinoma |

TABLE 3-continued

Peptides according to the present invention and their specific uses in other proliferative diseases, optionally in other organs.

| Seq ID | Sequence | Tissue and disease |
|---|---|---|
| 966 | ENNEIISNIRDSVIN | stomach, adenocarcinoma, kidney, oncocytoma |
| 967 | NNEIISNIRDSVIN | stomach, adenocarcinoma, kidney, oncocytoma |
| 968 | SPTVQVFSASGKPV | stomach, adenocarcinoma, kidney, oncocytoma |
| 969 | SSPTVQVFSASGKPVE | stomach, adenocarcinoma, kidney, oncocytoma |
| 970 | AEPNYHSLPSARTDEQ | thyroid gland, follicular adenoma |
| 971 | SSILAKTASNIIDVS | thyroid gland, follicular adenoma |
| 973 | ADDLEGEAFLPL | stomach, adenocarcinoma, spleen, chronic myeloid leukemia |
| 974 | ADDLEGEAFLPLR | stomach, adenocarcinoma, spleen, chronic myeloid leukemia |
| 975 | ADDLEGEAFLPLRE | stomach, adenocarcinoma, spleen, chronic myeloid leukemia |
| 976 | GADDLEGEAFLPLR | stomach, adenocarcinoma, spleen, chronic myeloid leukemia |
| 977 | AGREINLVDAHLKSE | lymph node, Hodgkin's disease |
| 978 | AGREINLVDAHLKSEQT | lymph node, Hodgkin's disease |
| 979 | GREINLVDAHLKSE | lymph node, Hodgkin's disease |
| 980 | KPGIVYASLNHSVIG | lymph node, Hodgkin's disease |
| 981 | NKPGIVYASLNHSVIG | lymph node, Hodgkin's disease |
| 982 | TTLYVTDVKSASERPS | lymph node, Hodgkin's disease |
| 983 | APSTYAHLSPAKTPPP | stomach, adenocarcinoma, pancreas, adenocarcinoma |
| 984 | APSTYAHLSPAKTPPPP | stomach, adenocarcinoma, pancreas, adenocarcinoma |
| 985 | APSTYAHLSPAKTPPPPA | stomach, adenocarcinoma, pancreas, adenocarcinoma |
| 986 | RDDLYDQDDSRDFPR | stomach, adenocarcinoma, pancreas, adenocarcinoma |
| 987 | TRPYHSLPSEAVFA | adrenal gland, adrenal cortical adenoma |
| 988 | TRPYHSLPSEAVFAN | adrenal gland, adrenal cortical adenoma |
| 989 | VAVFTFHNHGRT | adrenal gland, adrenal cortical adenoma |
| 990 | VAVFTFHNHGRTA | adrenal gland, adrenal cortical adenoma |
| 991 | VAVFTFHNHGRTANL | adrenal gland, adrenal cortical adenoma |
| 992 | EDDYIKSWEDNQQGDE | brain, glioblastoma, pleura, malignant mesothelioma |
| 993 | ELERIQIQEAAKKKPG | brain, glioblastoma, pleura, malignant mesothelioma |
| 994 | ERIQIQEAAKKKP | brain, glioblastoma, pleura, malignant mesothelioma |
| 995 | ERIQIQEAAKKKPG | brain, glioblastoma, pleura, malignant mesothelioma |
| 996 | ERIQIQEAAKKKPGI | brain, glioblastoma, pleura, malignant mesothelioma |
| 997 | LERIQIQEAAKKKPG | brain, glioblastoma, pleura, malignant mesothelioma |
| 998 | LSSISQYSGKIK | brain, glioblastoma, pleura, malignant mesothelioma |
| 999 | SPAKDSLSFEDF | rectum, adenocarcinoma |
| 1000 | SPAKDSLSFEDFLDL | rectum, adenocarcinoma |
| 1001 | INSRFPIPSATDPD | brain, glioblastoma, brain, oligodendroglioma |
| 1002 | VQHYELLNGQSVFG | brain, glioblastoma, brain, oligodendroglioma |
| 1003 | DNQYAVLENQKSSH | colon or rectum, pleura, malignant mesothelioma |
| 1004 | GPPEIYSDTQFPS | colon or rectum, pleura, malignant mesothelioma |
| 1005 | GPPEIYSDTQFPSLQ | colon or rectum, pleura, malignant mesothelioma |
| 1006 | TPQGPPEIYSDTQFPS | colon or rectum, pleura, malignant mesothelioma |
| 1007 | TPQGPPEIYSDTQFPSLQ | colon or rectum, pleura, malignant mesothelioma |
| 1008 | TPQGPPEIYSDTQFPSLQS T | colon or rectum, pleura, malignant mesothelioma |
| 1009 | ANLQRAYSLAKEQR | kidney, clear cell renal cell carcinoma, adrenal gland, adrenal cortical carcinoma |
| 1010 | NLQRAYSLAKEQR | kidney, clear cell renal cell carcinoma, adrenal gland, adrenal cortical carcinoma |

TABLE 3-continued

Peptides according to the present invention and their specific uses in other proliferative diseases, optionally in other organs.

| Seq ID | Sequence | Tissue and disease |
|---|---|---|
| 1011 | TPSGITYDRKDIEEH | kidney, clear cell renal cell carcinoma, adrenal gland, adrenal cortical carcinoma |
| 1012 | VSTLNSEDFVLVSR | brain, glioblastoma, kidney, angiomyolipoma |
| 1013 | VSTLNSEDFVLVSRQ | brain, glioblastoma, kidney, angiomyolipoma |
| 1014 | VSTLNSEDFVLVSRQG | brain, glioblastoma, kidney, angiomyolipoma |
| 1015 | GSSFFGELFNQNPE | brain, glioblastoma, thyroid gland, papillary carcinoma |
| 1016 | SGSSFFGELFNQNPE | brain, glioblastoma, thyroid gland, papillary carcinoma |

Thus, another aspect of the present invention relates to the use of the peptides according to the present invention for the—preferably combined—treatment of a proliferative disease selected from the group of adrenal cortical adenoma; non-ossifying fibroma; brain cancer and a proliferative disease selected from kidney oncocytoma, kidney Wilm's tumor, lymph node malignant melanoma, and omentum leiomyosarcoma; glioblastoma and a proliferative disease selected from oligodendroglioma, kidney angiomyolipoma, liver hepatic adenoma, liver hepatocellular carcinoma, lung small cell carcinoma, parotid gland pleomorphic adenoma, pleura malignant mesothelioma, schwannoma, small intestine gastrointestinal stromal tumor (GIST), and thyroid gland papillary carcinoma; breast carcinoma; chondrosarcoma; colonal or rectal cancer and a proliferative disease selected from bone giant cell tumor of bone, bone, non-ossifying fibroma, breast mucinous carcinoma, colon adenocarcinoma, colon adenoma, endometrium adenocarcinoma endometrioid type, esophagus adenocarcinoma, kidney angiomyolipoma, kidney renal cell carcinoma, liposarcoma, liver hepatocellular carcinoma, ovary granulosa cell tumor, pancreas microcystic adenoma, pleura malignant mesothelioma, prostate benign nodular hyperplasia, spleen non-Hodgkin's lymphoma, stomach mucinous adenocarcinoma, thymus thymoma, malignant, thyroid gland nodular hyperplasia, urinary bladder, transitional cell carcinoma, and vulva squamous cell carcinoma; colon adenoma; esophagus adenocarcinoma; intestines malignant carcinoid tumor; intramuscular lipoma; kidney clear cell renal cell carcinoma and a proliferative disease selected from adrenal gland, adrenal cortical carcinoma, endometrium adenocarcinoma endometrioid type, endometrium adenocarcinoma endometrioid type, kidney angiomyolipoma leiomyosarcoma, lipoma liver hepatocellular carcinoma, lymph node Hodgkin's disease, non-Hodgkin's lymphoma, pancreas adenocarcinoma, parotid gland pleomorphic adenoma, prostate adenocarcinoma, rectum adenocarcinoma, spleen chronic myeloid leukemia, spleen non-Hodgkin's lymphoma, and thyroid gland follicular adenoma; kidney oncocytoma; kidney polycystic kidney disease; kidney renal cell carcinoma; lipoma; liver hepatocellular carcinoma and a proliferative disease selected from, adrenal gland adrenal cortical adenoma, breast carcinoma, liver focal nodular hyperplasia, cancer rectum adenocarcinoma, cancer thyroid gland, nodular hyperplasia, cancer thyroid gland, papillary carcinoma, colon non-Hodgkin's lymphoma, endometrium hyperplasia, hepatic adenoma, kidney carcinoma, kidney oncocytoma, lipoma, liposarcoma, liver focal nodular hyperplasia, liver hepatic adenoma, pleura malignant mesothelioma, neuroblastoma, pancreas adenocarcinoma, pancreas microcystic adenoma, parotid gland pleomorphic adenoma, pleura malignant mesothelioma, synovial sarcoma, thyroid gland nodular hyperplasia, and uterine cervix squamous cell carcinoma; lung, non-small cell lung carcinoma, and a proliferative disease selected from breast carcinoma, chondrosarcoma, kidney oncocytoma, liver hepatocellular carcinoma, lung adenocarcinoma, lymph node Hodgkin's disease, lymph node non-Hodgkin's lymphoma, lymph node papillary carcinoma of thyroid, omentum adenocarcinoma, ovary Mullerian mixed tumor, pancreas adenocarcinoma, testis mixed germ cell tumor, thymus thymoma benign, and thyroid gland, nodular hyperplasia; lymph node Hodgkin's disease; lymph node papillary carcinoma of thyroid; lymph node papillary carcinoma of thyroid metastatic; myometrium leiomyoma; non-Hodgkin's lymphoma; non-Hodgkin's lymphoma, peripheral T cell type or small lymphocytic type; pancreas adenocarcinoma and a proliferative disease selected from bone giant cell tumor of bone, colon adenocarcinoma, fibromatosis, intramuscular lipoma, kidney angiomyolipoma, kidney renal cell carcinoma, liver hepatic adenoma, lung adenocarcinoma, myometrium leiomyoma, non-Hodgkin's lymphoma small lymphocytic type, pancreas adenocarcinoma, prostate benign nodular hyperplasia, rectum adenocarcinoma, spleen chronic myeloid leukemia, and thymus, thymoma, malignant; rectum adenocarcinoma; spleen chronic myeloid leukemia; spleen extramedullary hematopoiesis; stomach, adenocarcinoma and a proliferative disease selected from, adrenal gland adrenal cortical adenoma, bone giant cell tumor of bone, bone non-ossifying fibroma, breast carcinoma, colon adenocarcinoma, colon non-Hodgkin's lymphoma, endometrium adenocarcinoma endometrioid, kidney angiomyolipoma, kidney carcinoma, kidney oncocytoma, liver, focal nodular hyperplasia, liver hepatocellular carcinoma, lymph node Hodgkin's disease, lymph node papillary carcinoma of thyroid, medullary carcinoma of thyroid origin, metastatic adenocarcinoma of stomach, neurofibroma, ovary thecoma-fibroma, pancreas adenocarcinoma, pancreas microcystic adenoma, parathyroid gland adenoma, rectum adenocarcinoma, skin squamous cell carcinoma, spleen chronic myeloid leukemia, stomach gastrointestinal stromal tumor (GIST), thyroid gland nodular hyperplasia, thyroid gland papillary carcinoma, uterin cervix squamous cell carcinoma, and white blood cells chronic lymphocytic leukemia; stomach gastrointestinal stromal tumor (GIST); stomach cancer metastatic and a proliferative disease selected from adrenal gland adrenal cortical carcinoma, thyroid gland papillary carcinoma, skin, squamous cell carcinoma, breast carcinoma, colon adenocarcinoma, endometrium Mullerian mixed tumor, kidney carcinoma, leiomyosarcoma, lung neuroendocrine carcinoma (non-small cell type), lymph node non-Hodgkin's lymphoma, non-Hodgkin's lymphoma, ovary Mullerian mixed tumor, pancreas adenocarcinoma, rectum adenocarcinoma, skin basal cell carcinoma, stomach gastrointestinal stromal tumor (GIST), and uterine cervix adenocarcinoma; testis seminoma; thymus benign thymoma; thyroid gland follicular adenoma; and thyroid gland nodular hyperplasia.

Another preferred aspect of the present invention relates to the use of the peptides according to the present invention for the—preferably combined—preferred immunotherapy of diseases according to the following table 4.

TABLE 4

Preferred peptides according to the present invention and disease to be treated

| Seq ID | Sequence | Tissue and disease |
|---|---|---|
| 22 | LEVEERTKPV | lung, non-small cell lung carcinoma, breast, carcinoma |
| 23 | RDSPINANLRY | lung, non-small cell lung carcinoma, breast, carcinoma |
| 24 | RPFVIVTA | lung, non-small cell lung carcinoma, breast, carcinoma |
| 25 | RPIINTPMV | lung, non-small cell lung carcinoma, breast, carcinoma |
| 26 | SPTSSRTSSL | lung, non-small cell lung carcinoma, breast, carcinoma |
| 27 | ATSAPLVSR | stomach, metastatic, lung, neuroendocrine carcinoma |
| 114 | YGNPRTNGM | stomach, metastatic, breast, carcinoma |
| 102 | FSITKSVEL | non-Hodgkin's lymphoma, small lymphocytic type |
| 103 | GQTKNDLVV | non-Hodgkin's lymphoma, small lymphocytic type |
| 104 | LSQEVCRD | non-Hodgkin's lymphoma, small lymphocytic type |
| 105 | RDIQSPEQI | non-Hodgkin's lymphoma, small lymphocytic type |
| 106 | REDNSSNSL | non-Hodgkin's lymphoma, small lymphocytic type |
| 107 | TEHQEPGL | non-Hodgkin's lymphoma, small lymphocytic type |
| 108 | TKNDLVVSL | non-Hodgkin's lymphoma, small lymphocytic type |
| 977 | AGREINLVDAHLKSE | lymph node, Hodgkin's disease |
| 979 | GREINLVDAHLKSE | lymph node, Hodgkin's disease |
| 980 | KPGIVYASLNHSVIG | lymph node, Hodgkin's disease |
| 220 | RIHTGEKPYK | colon or rectum, thyroid gland, nodular hyperplasia |
| 53 | APGSVLPRAL | lymph node, Hodgkin's disease |
| 54 | DIKEHPLL | lymph node, Hodgkin's disease |
| 55 | DSAGPQDAR | lymph node, Hodgkin's disease |
| 56 | FQYAKESYI | lymph node, Hodgkin's disease |
| 57 | KVLSWPFLM | lymph node, Hodgkin's disease |
| 58 | LENDQSLSF | lymph node, Hodgkin's disease |
| 59 | SPSRQPQV | lymph node, Hodgkin's disease |
| 60 | SRHQSFTTK | lymph node, Hodgkin's disease |
| 61 | SSHNASKTL | lymph node, Hodgkin's disease |
| 1003 | DNQYAVLENQKSSH | colon or rectum, pleura, malignant mesothelioma, |
| 1004 | GPPEIYSDTQFPS | colon or rectum, pleura, malignant mesothelioma, |
| 1005 | GPPEIYSDTQFPSLQ | colon or rectum, pleura, malignant mesothelioma, |
| 1006 | TPQGPPEIYSDTQFPS | colon or rectum, pleura, malignant mesothelioma, |
| 1007 | TPQGPPEIYSDTQFPSLQ | colon or rectum, pleura, malignant mesothelioma, |
| 1008 | TPQGPPEIYSDTQFPSLQST | colon or rectum, pleura, malignant mesothelioma, |
| 91 | EHADDDPSL | kidney, Wilm's tumor |
| 92 | SEESVKSTTL | kidney, Wilm's tumor |
| 93 | SPRPPLGSSL | kidney, Wilm's tumor |
| 94 | SPWWRSSL | kidney, Wilm's tumor |
| 95 | VYTPVDSLVF | kidney, Wilm's tumor |
| 18 | DALLKRTM | stomach, metastatic, skin, basal cell carcinoma |
| 19 | GEDVRSALL | stomach, metastatic, skin, basal cell carcinoma |
| 20 | KFAEEFYSF | stomach, metastatic, skin, basal cell carcinoma |
| 21 | YGYDNVKEY | stomach, metastatic, skin, basal cell carcinoma |
| 661 | EYVSLYHQPAAM | non-Hodgkin's lymphoma, peripheral T cell type |
| 664 | LPYLFQMPAYASSS | non-Hodgkin's lymphoma, peripheral T cell type |

TABLE 4-continued

Preferred peptides according to the present invention and disease to be treated

| Seq ID | Sequence | Tissue and disease |
|---|---|---|
| 665 | LPYLFQMPAYASSSK | non-Hodgkin's lymphoma, peripheral T cell type |
| 666 | NFIKAEYKGRVT | non-Hodgkin's lymphoma, peripheral T cell type |
| 667 | TNFIKAEYKGRVT | non-Hodgkin's lymphoma, peripheral T cell type |
| 668 | TTNFIKAEYKGRVT | non-Hodgkin's lymphoma, peripheral T cell type |
| 780 | DNGHLYREDQTSPAPG | kidney, angiomyolipoma |
| 781 | DNGHLYREDQTSPAPGLR | kidney, angiomyolipoma |
| 782 | EVQVFAPANALPARSE | kidney, angiomyolipoma |
| 783 | GHLYREDQTSPAPG | kidney, angiomyolipoma |
| 784 | LPARSEAAAVQPVIG | kidney, angiomyolipoma |
| 785 | NGHLYREDQTSPAPG | kidney, angiomyolipoma |
| 786 | NGHLYREDQTSPAPGL | kidney, angiomyolipoma |
| 787 | NGHLYREDQTSPAPGLR | kidney, angiomyolipoma |
| 788 | VFAPANALPARSEAA | kidney, angiomyolipoma |
| 789 | VQVFAPANALPARSE | kidney, angiomyolipoma |
| 178 | HEIDRYTAI | non-Hodgkin's lymphoma, follicular type, |
| 179 | VFTLKPLEF | non-Hodgkin's lymphoma, follicular type, |
| 180 | YWVPRNAL | non-Hodgkin's lymphoma, follicular type, |
| 694 | DGELIRTQPQRLPQ | pancreas, adenocarcinoma, intramuscular lipoma |
| 695 | GELIRTQPQRLPQ | pancreas, adenocarcinoma, intramuscular lipoma |
| 696 | NPSDGELIRTQPQRLP | pancreas, adenocarcinoma, intramuscular lipoma |
| 697 | NPSDGELIRTQPQRLPQ | pancreas, adenocarcinoma, intramuscular lipoma |
| 698 | NPSDGELIRTQPQRLPQL | pancreas, adenocarcinoma, intramuscular lipoma |
| 922 | FDFSQNTRVPRLPE | non-Hodgkin's lymphoma, follicular type |
| 923 | GDAPAILFDKEF | non-Hodgkin's lymphoma, follicular type |
| 924 | VTHEIDRYTAIAY | non-Hodgkin's lymphoma, follicular type |
| 692 | DAGSYKAQINQRNFE | lymph node, non-Hodgkin's lymphoma |
| 693 | DAGSYKAQINQRNFEVT | lymph node, non-Hodgkin's lymphoma |
| 1 | AEHPNVTLTI | spleen, non-Hodgkin's lymphoma |
| 2 | FLAEHPNVTL | spleen, non-Hodgkin's lymphoma |
| 4 | EVAEFLARH | spleen, non-Hodgkin's lymphoma |
| 5 | RHSNVNLTI | spleen, non-Hodgkin's lymphoma |
| 222 | QSTQRSLAL | uterine cervix, squamous cell carcinoma |
| 223 | RDLQMNQALRF | uterine cervix, squamous cell carcinoma |
| 224 | RELESQLHVL | uterine cervix, squamous cell carcinoma |
| 225 | SEAEKLTLV | uterine cervix, squamous cell carcinoma |
| 6 | HPDNVKLFL | pancreas, adenocarcinoma, non-Hodgkin's lymphoma, small lymphocytic type |
| 7 | ISDTGELKL | pancreas, adenocarcinoma, non-Hodgkin's lymphoma, small lymphocytic type |
| 8 | KVNGKLVALK | pancreas, adenocarcinoma, non-Hodgkin's lymphoma, small lymphocytic type |
| 9 | NRLSAQAAL | pancreas, pancreas, adenocarcinoma, non-Hodgkin's lymphoma, small lymphocytic type |
| 10 | TPFTAIREA | pancreas, pancreas, adenocarcinoma, non-Hodgkin's lymphoma, small lymphocytic type |
| 11 | FGLARAKSV | kidney, clear cell renal cell carcinoma, kidney, renal cell carcinoma, clear cell type |
| 12 | KIADFGLAR | brain, glioblastoma, liver, hepatocellular carcinoma |
| 812 | DGSYRIFSKGASE | colon or rectum, liposarcoma |
| 813 | GSYRIFSKGASE | colon or rectum, liposarcoma |
| 814 | SDGSYRIFSKGASE | colon or rectum, liposarcoma |
| 815 | SVKKMMKDNNLVRH | colon or rectum, liver, hepatocellular carcinoma |
| 816 | VKKMMKDNNLVRH | colon or rectum, liver, hepatocellular carcinoma |
| 145 | KITVPASQK | colon, non-Hodgkin's lymphoma |
| 146 | KITVPASQKL | colon, non-Hodgkin's lymphoma |
| 147 | VPASQKLRQL | colon, non-Hodgkin's lymphoma |
| 537 | ITARPVLW | non-Hodgkin's lymphoma, diffuse large B-cell type |
| 538 | KLMSPKLYVW | non-Hodgkin's lymphoma, diffuse large B-cell type |
| 539 | KVSAVTLAY | non-Hodgkin's lymphoma, diffuse large B-cell type |
| 540 | VEGSGELFRW | non-Hodgkin's lymphoma, diffuse large B-cell type |
| 672 | ADLSSFKSQELN | lymph node, papillary carcinoma of thyroid, metastatic |
| 673 | ADLSSFKSQELNER | lymph node, papillary carcinoma of thyroid, metastatic |

TABLE 4-continued

Preferred peptides according to the present invention and disease to be treated

| Seq ID | Sequence | Tissue and disease |
|---|---|---|
| 674 | ADLSSFKSQELNERN | lymph node, papillary carcinoma of thyroid, metastatic |
| 679 | ISQELEELRAEQQR | lymph node, papillary carcinoma of thyroid, metastatic |
| 680 | ISQELEELRAEQQRLK | lymph node, papillary carcinoma of thyroid, metastatic |
| 681 | KGTKQWVHARYA | lymph node, papillary carcinoma of thyroid, metastatic |
| 682 | QADLSSFKSQELNER | lymph node, papillary carcinoma of thyroid, metastatic |
| 684 | TGSWIGLRNLDLKG | lymph node, papillary carcinoma of thyroid, metastatic |
| 743 | AIVQAVSAHRHR | non-Hodgkin's lymphoma, peripheral T cell type |
| 744 | ARNFERNKAIKVI | non-Hodgkin's lymphoma, peripheral T cell type |
| 745 | ARNFERNKAIKVIIA | non-Hodgkin's lymphoma, peripheral T cell type |
| 746 | NFERNKAIKVII | non-Hodgkin's lymphoma, peripheral T cell type |
| 747 | NFERNKAIKVIIA | non-Hodgkin's lymphoma, peripheral T cell type |
| 748 | VAIVQAVSAHRH | non-Hodgkin's lymphoma, peripheral T cell type |
| 749 | VAIVQAVSAHRHR | non-Hodgkin's lymphoma, peripheral T cell type |
| 750 | VAIVQAVSAHRHRA | non-Hodgkin's lymphoma, peripheral T cell type |
| 818 | VDKVLERDQKLSE | lung, non-small cell lung carcinoma, lymph node, papillary carcinoma of thyroid, metastatic |
| 819 | VDKVLERDQKLSELD | lung, non-small cell lung carcinoma, lymph node, papillary carcinoma of thyroid, metastatic |
| 820 | VDKVLERDQKLSELDD | lung, non-small cell lung carcinoma, lymph node, papillary carcinoma of thyroid, metastatic |
| 821 | VDKVLERDQKLSELDDR | stomach, diffuse subtype adenocarcinoma, lymph node, papillary carcinoma of thyroid, metastatic |
| 822 | VLERDQKLSELDDR | lung, non-small cell lung carcinoma, lymph node, papillary carcinoma of thyroid, metastatic |
| 833 | VDKVLERDQKLSE | lung, non-small cell lung carcinoma, lymph node, papillary carcinoma of thyroid, metastatic |
| 834 | VDKVLERDQKLSELD | lung, non-small cell lung carcinoma, lymph node, papillary carcinoma of thyroid, etastatic |
| 835 | VDKVLERDQKLSELDD | lung, non-small cell lung carcinoma, lymph node, papillary carcinoma of thyroid, metastatic |
| 836 | VDKVLERDQKLSELDDR | stomach, diffuse subtype adenocarcinoma, lymph node, papillary carcinoma of thyroid, metastatic |
| 837 | VLERDQKLSELDDR | lung, non-small cell lung carcinoma, lymph node, papillary carcinoma of thyroid, metastatic |
| 848 | DDPAIDVCKKLLGKYPN | kidney, clear cell renal cell carcinoma, pancreas, adenocarcinoma |
| 849 | DKQPYSKLPGVSLLKP | kidney, clear cell renal cell carcinoma, pancreas, adenocarcinoma |
| 850 | DKQPYSKLPGVSLLKPL | kidney, clear cell renal cell carcinoma, pancreas, adenocarcinoma |
| 851 | HPRYYISANVTGFK | kidney, clear cell renal cell carcinoma, pancreas, adenocarcinoma |
| 852 | SHPRYYISANVTG | kidney, clear cell renal cell carcinoma, pancreas, adenocarcinoma |
| 853 | SHPRYYISANVTGFK | kidney, clear cell renal cell carcinoma, pancreas, adenocarcinoma |
| 854 | TSHPRYYISANVTG | kidney, clear cell renal cell carcinoma, pancreas, adenocarcinoma |
| 855 | TSHPRYYISANVTGFK | kidney, clear cell renal cell carcinoma, pancreas, adenocarcinoma |
| 908 | DVGMFVALTKLGQPD | stomach, differentiated subtype adenocarcinoma, uterine cervix, squamous cell carcinoma, |
| 909 | VGMFVALTKLGQPD | stomach, differentiated subtype adenocarcinoma, uterine cervix, squamous cell carcinoma |
| 1015 | GSSFFGELFNQNPE | brain, glioblastoma, thyroid gland, papillary carcinoma |
| 1016 | SGSSFFGELFNQNPE | brain, glioblastoma, thyroid gland, papillary carcinoma |

TABLE 4-continued

Preferred peptides according to the present invention and disease to be treated

| Seq ID | Sequence | Tissue and disease |
|---|---|---|
| 466 | DEMRFVTQI | testis, mixed germ cell tumor |
| 467 | ETVHFATTQW | testis, mixed germ cell tumor |
| 468 | LPPPATQI | testis, mixed germ cell tumor |
| 633 | GNPAYRSFSNSLSQ | kidney, angiomyolipoma |
| 634 | GPPGEAGYKAFSSLLA | kidney, angiomyolipoma |
| 635 | GPPGEAGYKAFSSLLASS | kidney, angiomyolipoma |
| 636 | GPPGEAGYKAFSSLLASSA | kidney, angiomyolipoma |
| 637 | GPPGEAGYKAFSSLLASSAVSPE | kidney, angiomyolipoma |
| 638 | GPPGEAGYKAFSSLLASSAVSPEK | kidney, angiomyolipoma |
| 639 | GYKAFSSLLASSAVSP | kidney, angiomyolipoma |
| 640 | GYKAFSSLLASSAVSPE | kidney, angiomyolipoma |
| 641 | KAFSSLLASSAVSPE | kidney, angiomyolipoma |
| 642 | NPAYRSFSNSLSQ | kidney, angiomyolipoma |
| 643 | SRDDFQEGREGIVAR | kidney, angiomyolipoma |
| 644 | SSSSFHPAPGNAQ | kidney, angiomyolipoma |
| 645 | VARLTESLFLDL | kidney, angiomyolipoma |
| 646 | VARLTESLFLDLLG | kidney, angiomyolipoma |
| 647 | VIAGNPAYRSFSN | kidney, angiomyolipoma |
| 648 | VPQPEPETWEQILRRNVLQ | kidney, angiomyolipoma |
| 649 | YKAFSSLLASSAVS | kidney, angiomyolipoma |
| 650 | YKAFSSLLASSAVSP | kidney, angiomyolipoma |
| 651 | YKAFSSLLASSAVSPE | kidney, angiomyolipoma |
| 992 | EDDYIKSWEDNQQGDE | pleura, malignant mesothelioma |
| 993 | ELERIQIQEAAKKKPG | pleura, malignant mesothelioma |
| 994 | ERIQIQEAAKKKP | pleura, malignant mesothelioma |
| 995 | ERIQIQEAAKKKPG | pleura, malignant mesothelioma |
| 996 | ERIQIQEAAKKKPGI | pleura, malignant mesothelioma |
| 997 | LERIQIQEAAKKKPG | pleura, malignant mesothelioma |
| 998 | LSSISQYSGKIK | pleura, malignant mesothelioma |
| 941 | EERNLLSVAYKNVVGAR | colon or rectum, esophagus, adenocarcinoma, |
| 942 | ERNLLSVAYKNVVGAR | colon or rectum, esophagus, adenocarcinoma, |
| 943 | IAELDTLSEESYKD | colon or rectum, vulva, squamous cell carcinoma, |
| 944 | IAELDTLSEESYKDS | colon or rectum, vulva, squamous cell carcinoma, |
| 218 | GDYGRAFNL | stomach, metastatic, lymph node, non-Hodgkin's lymphoma, small lymphocytic type |
| 219 | TRHKIVHTK | stomach, metastatic, lymph node, non-Hodgkin's lymphoma, small lymphocytic type |
| 221 | KAFNWFSTL | stomach, metastatic, lymph node, non-Hodgkin's lymphoma, small lymphocytic type |
| 541 | RPKSNIVL | non-Hodgkin's lymphoma, diffuse large B-cell type |
| 542 | RPKSNIVLL | non-Hodgkin's lymphoma, diffuse large B-cell type |
| 1001 | INSRFPIPSATDPD | brain, glioblastoma, brain, oligodendroglioma, |
| 1002 | VQHYELLNGQSVFG | brain, glioblastoma, brain, oligodendroglioma, |
| 910 | AGVFHVEKNGRY | stomach, diffuse subtype adenocarcinoma, colon, adenocarcinoma |
| 911 | FAGVFHVEKNGRYS | stomach, diffuse subtype adenocarcinoma, colon, adenocarcinoma |
| 912 | GPITITIVNRDGTR | stomach, diffuse subtype adenocarcinoma, colon, adenocarcinoma |
| 913 | NGRYSISRTEAADL | stomach, diffuse subtype adenocarcinoma, colon, adenocarcinoma |
| 45 | DELPKFHQY | stomach, adenocarcinoma, white blood cells, chronic lymphocytic leukemia |
| 46 | DVTGQFPSSF | white blood cells, chronic lymphocytic leukemia |
| 47 | EHSRVLQQL | white blood cells, chronic lymphocytic leukemia |
| 48 | IKVSKQLL | white blood cells, chronic lymphocytic leukemia |
| 49 | KPRQSSPQL | white blood cells, chronic lymphocytic leukemia |
| 50 | KQLLAALEI | white blood cells, chronic lymphocytic leukemia |
| 51 | RRKDLVLKY | liver, focalnodular hyperplasia |
| 52 | RTRDYASLPPK | white blood cells, chronic lymphocytic leukemia |
| 124 | GQKEALLKY | liver, hepatocellular carcinoma, synovial sarcoma |
| 125 | KPSEERKTI | liver, hepatocellular carcinoma, synovial sarcoma |
| 126 | KQTPKVLVV | liver, hepatocellular carcinoma, synovial sarcoma |

TABLE 4-continued

Preferred peptides according to the present invention and disease to be treated

| Seq ID | Sequence | Tissue and disease |
|---|---|---|
| 127 | SVIQHVQSF | liver, hepatocellular carcinoma, synovial sarcoma |
| 128 | TPIERIPYL | liver, hepatocellular carcinoma, synovial sarcoma |
| 773 | LPEFYKTVSPAL | colon or rectum, endometrium, adenocarcinoma, endometrioid type |
| 774 | VGQFIQDVKNSRST | colon or rectum, endometrium, adenocarcinoma, endometrioid type |
| 775 | VGQFIQDVKNSRSTD | colon or rectum, endometrium, adenocarcinoma, endometrioid type |
| 776 | VVGQFIQDVKNSRS | colon or rectum, endometrium, adenocarcinoma, endometrioid type |
| 777 | VVGQFIQDVKNSRST | colon or rectum, endometrium, adenocarcinoma, endometrioid type |
| 778 | VVGQFIQDVKNSRSTD | colon or rectum, endometrium, adenocarcinoma, endometrioid type |
| 779 | VVGQFIQDVKNSRSTDS | colon or rectum, endometrium, adenocarcinoma, endometrioid type |
| 685 | FGNYNNQSSNFGPMKGGNFGGRS | pancreas, adenocarcinoma, thymus, thymoma, malignant |
| 686 | FGPMKGGNFGGRSSGPYGGGGQY | pancreas, adenocarcinoma, thymus, thymoma, malignant |
| 687 | GPMKGGNFGGRSSGP | pancreas, adenocarcinoma, thymus, thymoma, malignant |
| 688 | GPYGGGGQYFAKP | pancreas, adenocarcinoma, thymus, thymoma, malignant |
| 689 | KGGNFGGRSSGP | pancreas, adenocarcinoma, thymus, thymoma, malignant |
| 690 | NDFGNYNNQSSNFGP | pancreas, adenocarcinoma, thymus, thymoma, malignant |
| 691 | SGPYGGGGQYFAKP | pancreas, adenocarcinoma, thymus, thymoma, malignant |
| 13 | AAANIIRTL | liver, hepatocellular carcinoma, adrenal gland, adrenal cortical carcinoma |
| 14 | GRFKNLREAL | liver, hepatocellular carcinoma, adrenal gland, adrenal cortical carcinoma, |
| 15 | MSPFSKATL | liver, hepatocellular carcinoma, adrenal gland, adrenal cortical carcinoma, |
| 16 | QEDPGDNQITL | liver, hepatocellular carcinoma, adrenal gland, adrenal cortical carcinoma, |
| 17 | SPFSKATL | liver, hepatocellular carcinoma, adrenal gland, adrenal cortical carcinoma, |
| 129 | AEVEKNETV | kidney, clear cell renal cell carcinoma, spleen, non-Hodgkin's lymphoma, follicular type |
| 130 | EVKEEIPLV | kidney, clear cell renal cell carcinoma, spleen, non-Hodgkin's lymphoma, follicular type |
| 131 | KPTSARSGL | kidney, clear cell renal cell carcinoma, spleen, non-Hodgkin's lymphoma, follicular type |
| 132 | KYIETTPLTI | kidney, clear cell renal cell carcinoma, spleen, non-Hodgkin's lymphoma, follicular type |
| 133 | SEIKTSIEV | kidney, clear cell renal cell carcinoma, spleen, non-Hodgkin's lymphoma, follicular type |
| 134 | SVKPTSATK | kidney, clear cell renal cell carcinoma, spleen, non-Hodgkin's lymphoma, follicular type |
| 135 | YPNKGVGQA | kidney, clear cell renal cell carcinoma, spleen, non-Hodgkin's lymphoma, follicular type |
| 966 | ENNEIISNIRDSVIN | stomach, adenocarcinoma, kidney, oncocytoma |
| 967 | NNEIISNIRDSVIN | stomach, adenocarcinoma, kidney, oncocytoma |
| 968 | SPTVQVFSASGKPV | stomach, adenocarcinoma, kidney, oncocytoma |
| 969 | SSPTVQVFSASGKPVE | stomach, adenocarcinoma, kidney, oncocytoma |
| 830 | DIMRVNVDKVLERDQK | stomach, diffuse subtype adenocarcinoma, Medullary carcinoma of thyroid Origin |
| 831 | DIMRVNVDKVLERDQKL | stomach, diffuse subtype adenocarcinoma, medullary carcinoma |
| 832 | IMRVNVDKVLERDQK | lung, non-small cell lung carcinoma, lymph node, Hodgkin's disease |
| 752 | EEVITLIRSNQQLE | pancreas, adenocarcinoma |
| 753 | EEVITLIRSNQQLEN | pancreas, adenocarcinoma |
| 754 | IPADTFAALKNPNAML | pancreas, adenocarcinoma |
| 755 | LKQLLSDKQQKRQSG | pancreas, adenocarcinoma |
| 756 | LKQLLSDKQQKRQSGQ | pancreas, adenocarcinoma |
| 118 | DEHLLIQHY | parotid gland, pleomorphic adenoma |
| 119 | KQVASSTGF | parotid gland, pleomorphic adenoma |
| 120 | RDFGPASQHFL | parotid gland, pleomorphic adenoma |

TABLE 4-continued

Preferred peptides according to the present invention and disease to be treated

| Seq ID | Sequence | Tissue and disease |
|---|---|---|
| 121 | RQLGEVASF | parotid gland, pleomorphic adenoma |
| 122 | TEAETTANVL | parotid gland, pleomorphic adenoma |
| 123 | GYLPVQTVL | kidney, clear cell renal cell carcinoma, parotid gland, pleomorphic adenoma |
| 987 | TRPYHSLPSEAVFA | adrenal gland, adrenal cortical adenoma |
| 988 | TRPYHSLPSEAVFAN | adrenal gland, adrenal cortical adenoma |
| 989 | VAVFTFHNHGRT | adrenal gland, adrenal cortical adenoma |
| 990 | VAVFTFHNHGRTA | adrenal gland, adrenal cortical adenoma |
| 991 | VAVFTFHNHGRTANL | adrenal gland, adrenal cortical adenoma |
| 339 | FLDPDIGGVAV | kidney, clear cell renal cell carcinoma, pancreas, adenocarcinoma |
| 340 | HTAPPENKTW | kidney, clear cell renal cell carcinoma, pancreas, adenocarcinoma |
| 341 | LLDTPVKTQY | kidney, clear cell renal cell carcinoma, pancreas, adenocarcinoma |
| 342 | NAVKDFTSF | kidney, clear cell renal cell carcinoma, pancreas, adenocarcinoma |
| 343 | SGLLQIKKL | kidney, clear cell renal cell carcinoma, pancreas, adenocarcinoma |
| 344 | YHDKNIVLL | kidney, clear cell renal cell carcinoma, pancreas, adenocarcinoma |
| 71 | HLKSIPVSL | kidney, clear cell renal cell carcinoma, prostate, adenocarcinoma |
| 72 | KVWYNVENW | kidney, clear cell renal cell carcinoma, prostate, adenocarcinoma |
| 73 | LPAYRAQLL | kidney, clear cell renal cell carcinoma, prostate, adenocarcinoma |
| 74 | LSEQTSVPL | kidney, clear cell renal cell carcinoma, prostate, adenocarcinoma |
| 75 | SLNQWLVSF | kidney, clear cell renal cell carcinoma, prostate, adenocarcinoma |
| 76 | SMTSLAQKI | kidney, clear cell renal cell carcinoma, prostate, adenocarcinoma |
| 77 | SSSGLHPPK | kidney, clear cell renal cell carcinoma, prostate, adenocarcinoma |
| 578 | GGGYGSGGGSGGYGSRRF | colon or rectum, thymus, thymoma, malignant, |
| 579 | GGSFGGRSSGSP | colon or rectum, thymus, thymoma, malignant |
| 580 | KGGSFGGRSSGSP | colon or rectum, thymus, thymoma, malignant |
| 581 | SGQQQSNYGPMKGGSFGGRSSGSPY | colon or rectum, thymus, thymoma, malignant |
| 582 | SGSPYGGGYGSGGGSGGYGSRRF | colon or rectum, thymus, thymoma, malignant |
| 583 | SPYGGGYGSGGGSGGYGSRRF | colon or rectum, thymus, thymoma, malignant |
| 584 | YGGGYGSGGGSGGYGSRRF | colon or rectum, thymus, thymoma, malignant |
| 84 | VPVPHTTAL | kidney, clear cell renal cell carcinoma, endometrium, adenocarcinoma, endometrioid type |
| 85 | YQVLDVQRY | kidney, clear cell renal cell carcinoma, endometrium, adenocarcinoma, endometrioid type |
| 731 | DGLNSLTYQVLDVQRYPL | kidney, clear cell renal cell carcinoma, endometrium, adenocarcinoma, endometrioid type |
| 732 | HPVLQRQQLDYGIY | kidney, clear cell renal cell carcinoma, endometrium, adenocarcinoma, endometrioid type |
| 733 | LNSLTYQVLDVQR | kidney, clear cell renal cell carcinoma, endometrium, adenocarcinoma, endometrioid type |
| 734 | LNSLTYQVLDVQRYP | kidney, clear cell renal cell carcinoma, endometrium, adenocarcinoma, endometrioid type |
| 735 | LNSLTYQVLDVQRYPL | kidney, clear cell renal cell carcinoma, endometrium, adenocarcinoma, endometrioid type |
| 736 | LPQLVGVSTPLQG | kidney, clear cell renal cell carcinoma, endometrium, adenocarcinoma, endometrioid type |
| 737 | LPQLVGVSTPLQGG | kidney, clear cell renal cell carcinoma, endometrium, adenocarcinoma, endometrioid type |

TABLE 4-continued

Preferred peptides according to the present invention and disease to be treated

| Seq ID | Sequence | Tissue and disease |
|---|---|---|
| 738 | LPQLVGVSTPLQGGS | kidney, clear cell renal cell carcinoma, endometrium, adenocarcinoma, endometrioid type |
| 739 | RLPQLVGVSTPLQGGS | kidney, clear cell renal cell carcinoma, endometrium, adenocarcinoma, endometrioid type |
| 740 | SPHKVAIIIPFRNR | kidney, clear cell renal cell carcinoma, endometrium, adenocarcinoma, endometrioid type |
| 741 | SPHKVAIIIPFRNRQE | kidney, clear cell renal cell carcinoma, endometrium, adenocarcinoma, endometrioid type |
| 742 | SPHKVAIIIPFRNRQEH | kidney, clear cell renal cell carcinoma, endometrium, adenocarcinoma, endometrioid type |
| 527 | DEKQQHIVY | liver, hepatocellular carcinoma, synovial sarcoma |
| 528 | DEVYQVTVY | liver, hepatocellular carcinoma, synovial sarcoma |
| 529 | GEISEKAKL | liver, hepatocellular carcinoma, synovial sarcoma |
| 530 | YTMKEVLFY | liver, hepatocellular carcinoma, synovial sarcoma |
| 203 | GPRPITQSEL | lymph node, non-Hodgkin's lymphoma, marginal zone B-cell type |
| 204 | KPEPVDKVA | lymph node, non-Hodgkin's lymphoma |
| 205 | TPSSRPASL | lymph node, non-Hodgkin's lymphoma |
| 949 | SPPQFRVNGAISN | ovary, granulosa cell tumor |
| 950 | SPPQFRVNGAISNFE | ovary, granulosa cell tumor |
| 951 | SPPQFRVNGAISNFEE | ovary, granulosa cell tumor |
| 952 | SPPQFRVNGAISNFEEF | ovary, granulosa cell tumor |
| 953 | VGKMFVDVYFQEDKK | ovary, granulosa cell tumor |
| 954 | VGKmFVDVYFQEDKKE | ovary, granulosa cell tumor |
| 916 | EEFKKLTSIKIQNDK | brain, glioblastoma, small intestine, gastrointestinal stromal tumor (GIST) |
| 917 | INRRMADDNKLFR | brain, glioblastoma, small intestine, gastrointestinal stromal tumor (GIST) |
| 918 | TATIVMVTNLKERKE | brain, glioblastoma, small intestine, gastrointestinal stromal tumor (GIST) |
| 526 | RINEFSISSF | chondrosarcoma |
| 585 | GNRINEFSISSF | chondrosarcoma |
| 586 | HGNQITSDKVGRKV | chondrosarcoma |
| 587 | IPPVNTNLENLYLQ | chondrosarcoma |
| 588 | LQVLRLDGNEIKR | chondrosarcoma |
| 589 | LQVLRLDGNEIKRS | chondrosarcoma |
| 590 | LQVLRLDGNEIKRSA | chondrosarcoma |
| 592 | LYVRLSHNSLTNNG | chondrosarcoma |
| 596 | WIALHGNQITSD | chondrosarcoma |
| 597 | WIALHGNQITSDK | chondrosarcoma |
| 165 | ELNKLLEEI | ovary, adenocarcinoma |
| 166 | IPFSNPRVL | ovary, adenocarcinoma |
| 167 | LLDEGAKLLY | ovary, adenocarcinoma |
| 168 | SPADAHRNL | ovary, adenocarcinoma |
| 96 | APLQRSQSL | kidney, renal cell carcinoma, clear cell type |
| 97 | DEVHQDTY | kidney, renal cell carcinoma, clear cell type |
| 98 | LPHSATVTL | kidney, renal cell carcinoma, clear cell type |
| 152 | APSEYRYTL | stomach, mucinous adenocarcinoma |
| 153 | APSEYRYTLL | stomach, mucinous adenocarcinoma |
| 154 | EIFQNEVAR | stomach, mucinous adenocarcinoma |
| 155 | KDVLIPGKL | stomach, mucinous adenocarcinoma |
| 156 | VPLVREITF | stomach, mucinous adenocarcinoma |
| 62 | EEIDTTMRW | liver, hepatocellular carcinoma, lipoma |
| 63 | ILDEKPVII | liver, hepatocellular carcinoma, lipoma |
| 64 | LPQEPRTSL | liver, hepatocellular carcinoma, lipoma |
| 65 | LTYKLPVA | liver, hepatocellular carcinoma, lipoma |
| 66 | NEMELAHSSF | liver, hepatocellular carcinoma, lipoma |
| 67 | REFPEANFEL | liver, hepatocellular carcinoma, lipoma |
| 68 | THHIPDAKL | liver, hepatocellular carcinoma, lipoma |
| 69 | TVKENLSLF | liver, hepatocellular carcinoma, lipoma |
| 70 | VLLKKAVL | liver, hepatocellular carcinoma, lipoma |
| 136 | ISMKILNSL | lung, non-small cell lung carcinoma, thymus, thymoma |
| 137 | KTIAFLLPMF | lung, non-small cell lung carcinoma, thymus, thymoma |

TABLE 4-continued

Preferred peptides according to the present invention and disease to be treated

| Seq ID | Sequence | Tissue and disease |
|---|---|---|
| 138 | RDSIINDF | lung, non-small cell lung carcinoma, thymus, thymoma |
| 139 | SVKGGGGNEK | lung, non-small cell lung carcinoma, thymus, thymoma |
| 140 | GIAKTGSGK | lung, non-small cell lung carcinoma, thymus, thymoma |
| 503 | ALYATKTLR | pancreas, microcystic adenoma |
| 504 | MEYVISRI | pancreas, microcystic adenoma |
| 505 | VPVGRQPII | pancreas, microcystic adenoma |
| 278 | ATNGDLASR | pancreas, adenocarcinoma, prostate, benign nodular hyperplasia |
| 279 | GLHAEVTGVGY | pancreas, adenocarcinoma, prostate, benign nodular hyperplasia |
| 280 | HVSSTSSSF | pancreas, adenocarcinoma, prostate, benign nodular hyperplasia |
| 281 | LQADLQNGL | pancreas, adenocarcinoma, prostate, benign nodular hyperplasia |
| 282 | SELPVSEVA | pancreas, adenocarcinoma, prostate, benign nodular hyperplasia |
| 283 | SQTKSVFEI | pancreas, adenocarcinoma, prostate, benign nodular hyperplasia |
| 284 | THIFTSDGL | pancreas, adenocarcinoma, prostate, benign nodular hyperplasia |
| 285 | VIYFPPLQK | pancreas, adenocarcinoma, prostate, benign nodular hyperplasia |
| 286 | YPFSSEQKW | pancreas, adenocarcinoma, prostate, benign nodular hyperplasia |
| 78 | DLDVKKMPL | kidney, carcinoma |
| 79 | FYTVIPHNF | kidney, carcinoma |
| 80 | HHINTDNPSL | kidney, carcinoma |
| 81 | RVGEVGQSK | kidney, carcinoma |
| 28 | AELRSTASLL | lipoma |
| 29 | APASSHERASM | lipoma |
| 30 | ASRQAPPHI | lipoma |
| 31 | AVKKNPGIAA | lipoma |
| 32 | EEHLESHKKY | lipoma |
| 33 | GEFTSARAV | lipoma |
| 34 | GQSTPRLFSI | lipoma |
| 35 | LVDDPLEY | lipoma |
| 36 | RPKNLMQTL | lipoma |
| 37 | RQAPPHIEL | lipoma |
| 38 | SEAAELRSTA | lipoma |
| 490 | DSIGSTVSSER | stomach, adenocarcinoma, signet ring cell type, |
| 491 | LPYNNKDRDAL | stomach, adenocarcinoma, signet ring cell type, |
| 215 | DAMKRVEEI | ovary, thecoma-fibroma |
| 216 | DIKEVKQNI | ovary, thecoma-fibroma |
| 217 | GPIYPGHGM | ovary, thecoma-fibroma |
| 963 | GNTVIHLDQALARMR | lung, small cell carcinoma |
| 964 | NTVIHLDQALARMR | lung, small cell carcinoma |
| 965 | NTVIHLDQALARMRE | lung, small cell carcinoma |
| 187 | AADTERLAL | chondrosarcoma |
| 188 | DMKAKVASL | chondrosarcoma |
| 189 | HVLEEVQQV | chondrosarcoma |
| 190 | KEAADTERL | chondrosarcoma |
| 191 | RISEVLQKL | chondrosarcoma |
| 192 | TEVRELVSL | chondrosarcoma |
| 875 | SVEEFLSEKLERI | liver, hepatic adenoma |
| 876 | VEEFLSEKLERI | liver, hepatic adenoma |
| 973 | ADDLEGEAFLPL | spleen, chronic myeloid leukemia |
| 974 | ADDLEGEAFLPLR | spleen, chronic myeloid leukemia |
| 975 | ADDLEGEAFLPLRE | spleen, chronic myeloid leukemia |
| 976 | GADDLEGEAFLPLR | spleen, chronic myeloid leukemia |
| 141 | AETTDNVFTL | kidney, clear cell renal cell carcinoma, thyroid gland, follicular adenoma |
| 142 | SEYQRFAVM | kidney, clear cell renal cell carcinoma, thyroid gland, follicular adenoma |
| 143 | TFGERVVAF | kidney, clear cell renal cell carcinoma, thyroid gland, follicular adenoma |
| 144 | NENLVERF | stomach, colon, adenocarcinoma, mucinous type |
| 117 | QLFSYAILGF | liver, hepatocellular carcinoma, colon, non-Hodgkin's lymphoma |
| 845 | GIRVAPVPLYNS | lung, non-small cell lung carcinoma, liver, hepatocellular carcinoma |
| 846 | GIRVAPVPLYNSFH | lung, non-small cell lung carcinoma, liver, hepatocellular carcinoma |

TABLE 4-continued

Preferred peptides according to the present invention and disease to be treated

| Seq ID | Sequence | Tissue and disease |
|---|---|---|
| 847 | NPNGIRVAPVPLYNSFH | lung, non-small cell lung carcinoma, liver, hepatocellular carcinoma |
| 478 | AAVPVIISR | lymph node, papillary carcinoma of thyroid, metastatic |
| 479 | EEIGKVAAA | lymph node, papillary carcinoma of thyroid, metastatic |
| 480 | FLKDLVASV | lymph node, papillary carcinoma of thyroid, metastatic |
| 481 | VIISRALEL | lymph node, papillary carcinoma of thyroid, metastatic |
| 420 | QIDYKTLVL | stomach, metastatic, leiomyosarcoma |
| 421 | VEDPTIVRI | stomach, metastatic, leiomyosarcoma |
| 543 | GEPLSYTRFSLARQ | lung, non-small cell lung carcinoma, lung, adenocarcinoma |
| 544 | GEPLSYTRFSLARQVD | lung, non-small cell lung carcinoma, lung, adenocarcinoma |
| 545 | GEPLSYTRFSLARQVDG | lung, non-small cell lung carcinoma, lung, adenocarcinoma |
| 546 | GGEPLSYTRFSLARQVD | lung, non-small cell lung carcinoma, lung, adenocarcinoma |
| 547 | GGEPLSYTRFSLARQVDG | lung, non-small cell lung carcinoma, lung, adenocarcinoma |
| 548 | NPGGYVAYSKAATVTG | lung, non-small cell lung carcinoma, lung, adenocarcinoma |
| 549 | NPGGYVAYSKAATVTGK | lung, non-small cell lung carcinoma, lung, adenocarcinoma |
| 550 | NPGGYVAYSKAATVTGKL | lung, non-small cell lung carcinoma, lung, adenocarcinoma |
| 551 | NSVIIVDKNGRL | lung, non-small cell lung carcinoma, lung, adenocarcinoma |
| 552 | NSVIIVDKNGRLV | lung, non-small cell lung carcinoma, lung, adenocarcinoma |
| 553 | NSVIIVDKNGRLVY | lung, non-small cell lung carcinoma, lung, adenocarcinoma |
| 554 | RVEYHFLSPYVSPK | lung, non-small cell lung carcinoma, lung, adenocarcinoma |
| 555 | RVEYHFLSPYVSPKE | lung, non-small cell lung carcinoma, lung, adenocarcinoma |
| 556 | RVEYHFLSPYVSPKESPF | lung, non-small cell lung carcinoma, lung, adenocarcinoma |
| 557 | SPFRHVFWGSGSHTL | lung, non-small cell lung carcinoma, lung, adenocarcinoma |
| 558 | SVIIVDKNGRLV | lung, non-small cell lung carcinoma, lung, adenocarcinoma |
| 559 | VEYHFLSPYVSPK | lung, non-small cell lung carcinoma, lung, adenocarcinoma |
| 560 | VEYHFLSPYVSPKE | lung, non-small cell lung carcinoma, lung, adenocarcinoma |
| 388 | AEGPAGGFMVV | spleen, chronic myeloid leukemia |
| 389 | AYYRDAEAY | spleen, chronic myeloid leukemia |
| 390 | QVNRPLTMR | spleen, chronic myeloid leukemia |
| 391 | RHSPVFQVY | spleen, chronic myeloid leukemia |
| 392 | SLPVPNSAY | spleen, chronic myeloid leukemia |
| 393 | TLGPPGTAHLY | spleen, chronic myeloid leukemia |
| 308 | VLYVGSKTK | schwannoma |
| 309 | KTKEQVTNV | schwannoma |
| 310 | MPVDPDNEAY | schwannoma |
| 311 | AEKTKQGVA | schwannoma |
| 446 | EAFEFVKQR | stomach, adenocarcinoma, breast, carcinoma |
| 447 | NHFEGHYQY | stomach, adenocarcinoma, breast, carcinoma |

Another more preferred aspect of the present invention relates to the use of the peptides according to the present invention for the—preferably combined—more preferred immunotherapy of diseases according to the following table 5.

TABLE 5

More preferred peptides according to the present invention and diseases to be treated

| Seq ID | Sequence | Tissue and disease |
|---|---|---|
| 22 | LEVEERTKPV | breast, carcinoma |
| 23 | RDSPINANLRY | breast, carcinoma |
| 24 | RPFVIVTA | breast, carcinoma |
| 25 | RPIINTPMV | breast, carcinoma |
| 26 | SPTSSRTSSL | breast, carcinoma |
| 27 | ATSAPLVSR | lung, neuroendocrine carcinoma |
| 114 | YGNPRTNGM | breast, carcinoma |
| 102 | FSITKSVEL | non-Hodgkin's lymphoma, small lymphocytic type |
| 103 | GQTKNDLVV | non-Hodgkin's lymphoma, small lymphocytic type |
| 104 | LSQEVCRD | non-Hodgkin's lymphoma, small lymphocytic type |
| 105 | RDIQSPEQI | non-Hodgkin's lymphoma, small lymphocytic type |
| 106 | REDNSSNSL | non-Hodgkin's lymphoma, small lymphocytic type |
| 107 | TEHQEPGL | non-Hodgkin's lymphoma, small lymphocytic type |
| 108 | TKNDLVVSL | non-Hodgkin's lymphoma, small lymphocytic type |
| 977 | AGREINLVDAHLKSE | lymph node, Hodgkin's disease |
| 978 | AGREINLVDAHLKSEQT | lymph node, Hodgkin's disease |
| 979 | GREINLVDAHLKSE | lymph node, Hodgkin's disease |
| 980 | KPGIVYASLNHSVIG | lymph node, Hodgkin's disease |
| 981 | NKPGIVYASLNHSVIG | lymph node, Hodgkin's disease |
| 982 | TTLYVTDVKSASERPS | lymph node, Hodgkin's disease |
| 220 | RIHTGEKPYK | thyroid gland, nodular hyperplasia |
| 53 | APGSVLPRAL | lymph node, Hodgkin's disease |
| 54 | DIKEHPLL | lymph node, Hodgkin's disease |
| 55 | DSAGPQDAR | lymph node, Hodgkin's disease |
| 56 | FQYAKESYI | lymph node, Hodgkin's disease |
| 57 | KVLSWPFLM | lymph node, Hodgkin's disease |
| 58 | LENDQSLSF | lymph node, Hodgkin's disease |
| 59 | SPSRQPQV | lymph node, Hodgkin's disease |
| 60 | SRHQSFTTK | lymph node, Hodgkin's disease |
| 61 | SSHNASKTL | lymph node, Hodgkin's disease |
| 1003 | DNQYAVLENQKSSH | pleura, malignant mesothelioma |
| 1004 | GPPEIYSDTQFPS | pleura, malignant mesothelioma |
| 1005 | GPPEIYSDTQFPSLQ | pleura, malignant mesothelioma |
| 1006 | TPQGPPEIYSDTQFPS | pleura, malignant mesothelioma |
| 1007 | TPQGPPEIYSDTQFPSLQ | pleura, malignant mesothelioma |
| 1008 | TPQGPPEIYSDTQFPSLQST | pleura, malignant mesothelioma |
| 91 | EHADDDPSL | kidney, Wilm's tumor |
| 92 | SEESVKSTTL | kidney, Wilm's tumor |
| 93 | SPRPPLGSSL | kidney, Wilm's tumor |
| 94 | SPWWRSSL | kidney, Wilm's tumor |
| 95 | VYTPVDSLVF | kidney, Wilm's tumor |
| 18 | DALLKRTM | skin, basal cell carcinoma |
| 19 | GEDVRSALL | skin, basal cell carcinoma |
| 20 | KFAEEFYSF | skin, basal cell carcinoma |
| 21 | YGYDNVKEY | skin, basal cell carcinoma |
| 661 | EYVSLYHQPAAM | non-Hodgkin's lymphoma, peripheral T cell type, |
| 662 | IKAEYKGRVTLKQYPR | non-Hodgkin's lymphoma, peripheral T cell type |
| 663 | LNVHSEYEPSWEEQP | non-Hodgkin's lymphoma, peripheral T cell type |
| 664 | LPYLFQmPAYASSS | non-Hodgkin's lymphoma, peripheral T cell type |
| 665 | LPYLFQmPAYASSSK | non-Hodgkin's lymphoma, peripheral T cell type |
| 666 | NFIKAEYKGRVT | non-Hodgkin's lymphoma, peripheral T cell type |
| 667 | TNFIKAEYKGRVT | non-Hodgkin's lymphoma, peripheral T cell type |
| 668 | TTNFIKAEYKGRVT | non-Hodgkin's lymphoma, peripheral T cell type |
| 669 | VTLNVHSEYEPSWEEQP | non-Hodgkin's lymphoma, peripheral T cell type |
| 670 | YPRKNLFLVEVTQLTESDS | non-Hodgkin's lymphoma, peripheral T cell type |
| 671 | YPRKNLFLVEVTQLTESDSG | non-Hodgkin's lymphoma, peripheral T cell type |
| 780 | DNGHLYREDQTSPAPG | kidney, angiomyolipoma |
| 781 | DNGHLYREDQTSPAPGLR | kidney, angiomyolipoma |
| 782 | EVQVFAPANALPARSE | kidney, angiomyolipoma |
| 783 | GHLYREDQTSPAPG | kidney, angiomyolipoma |
| 784 | LPARSEAAAVQPVIG | kidney, angiomyolipoma |
| 785 | NGHLYREDQTSPAPG | kidney, angiomyolipoma |
| 786 | NGHLYREDQTSPAPGL | kidney, angiomyolipoma |
| 787 | NGHLYREDQTSPAPGLR | kidney, angiomyolipoma |
| 788 | VFAPANALPARSEAA | kidney, angiomyolipoma |
| 789 | VQVFAPANALPARSE | kidney, angiomyolipoma |
| 178 | HEIDRYTAI | non-Hodgkin's lymphoma |
| 179 | VFTLKPLEF | non-Hodgkin's lymphoma |

TABLE 5-continued

More preferred peptides according to the present invention and diseases to be treated

| Seq ID | Sequence | Tissue and disease |
|---|---|---|
| 180 | YWVPRNAL | non-Hodgkin's lymphoma |
| 694 | DGELIRTQPQRLPQ | intramuscular lipoma |
| 695 | GELIRTQPQRLPQ | intramuscular lipoma |
| 696 | NPSDGELIRTQPQRLP | intramuscular lipoma |
| 697 | NPSDGELIRTQPQRLPQ | intramuscular lipoma |
| 698 | NPSDGELIRTQPQRLPQL | intramuscular lipoma |
| 922 | FDFSQNTRVPRLPE | non-Hodgkin's lymphoma |
| 923 | GDAPAILFDKEF | non-Hodgkin's lymphoma |
| 924 | VTHEIDRYTAIAY | non-Hodgkin's lymphoma |
| 692 | DAGSYKAQINQRNFE | lymph node, non-Hodgkin's lymphoma |
| 693 | DAGSYKAQINQRNFEVT | lymph node, non-Hodgkin's lymphoma |
| 1 | AEHPNVTLTI | spleen, non-Hodgkin's lymphoma |
| 2 | FLAEHPNVTL | spleen, non-Hodgkin's lymphoma |
| 4 | EVAEFLARH | spleen, non-Hodgkin's lymphoma |
| 5 | RHSNVNLTI | spleen, non-Hodgkin's lymphoma |
| 222 | QSTQRSLAL | uterine cervix, squamous cell carcinoma |
| 223 | RDLQMNQALRF | uterine cervix, squamous cell carcinoma |
| 224 | RELESQLHVL | uterine cervix, squamous cell carcinoma |
| 225 | SEAEKLTLV | uterine cervix, squamous cell carcinoma |
| 6 | HPDNVKLFL | non-Hodgkin's lymphoma, small lymphocytic type |
| 7 | ISDTGELKL | non-Hodgkin's lymphoma, small lymphocytic type |
| 8 | KVNGKLVALK | non-Hodgkin's lymphoma, small lymphocytic type |
| 9 | NRLSAQAAL | non-Hodgkin's lymphoma, small lymphocytic type |
| 10 | TPFTAIREA | non-Hodgkin's lymphoma, small lymphocytic type |
| 11 | FGLARAKSV | kidney, renal cell carcinoma, clear cell type |
| 12 | KIADFGLAR | liver, hepatocellular carcinoma |
| 812 | DGSYRIFSKGASE | liposarcoma |
| 813 | GSYRIFSKGASE | liposarcoma |
| 814 | SDGSYRIFSKGASE | liposarcoma |
| 815 | SVKKMMKDNNLVRH | liver, hepatocellular carcinoma |
| 816 | VKKMMKDNNLVRH | liver, hepatocellular carcinoma |
| 145 | KITVPASQK | colon, non-Hodgkin's lymphoma |
| 146 | KITVPASQKL | colon, non-Hodgkin's lymphoma |
| 147 | VPASQKLRQL | colon, non-Hodgkin's lymphoma |
| 537 | ITARPVLW | non-Hodgkin's lymphoma, diffuse large B-cell type |
| 538 | KLMSPKLYVW | non-Hodgkin's lymphoma, diffuse large B-cell type |
| 539 | KVSAVTLAY | non-Hodgkin's lymphoma, diffuse large B-cell type |
| 540 | VEGSGELFRW | non-Hodgkin's lymphoma, diffuse large B-cell type |
| 672 | ADLSSFKSQELN | lymph node, papillary carcinoma of thyroid, metastatic |
| 673 | ADLSSFKSQELNER | lymph node, papillary carcinoma of thyroid, metastatic |
| 674 | ADLSSFKSQELNERN | lymph node, papillary carcinoma of thyroid, metastatic |
| 675 | ADLSSFKSQELNERNE | lymph node, papillary carcinoma of thyroid, metastatic |
| 676 | ADLSSFKSQELNERNEA | lymph node, papillary carcinoma of thyroid, metastatic |
| 677 | AEQQRLKSQDLELSWNLNG | lymph node, papillary carcinoma of thyroid, metastatic |
| 678 | EQQRLKSQDLELSWN | lymph node, papillary carcinoma of thyroid, metastatic |
| 679 | ISQELEELRAEQQR | lymph node, papillary carcinoma of thyroid, metastatic |
| 680 | ISQELEELRAEQQRLK | lymph node, papillary carcinoma of thyroid, metastatic |
| 681 | KGTKQWVHARYA | lymph node, papillary carcinoma of thyroid, metastatic |
| 682 | QADLSSFKSQELNER | lymph node, papillary carcinoma of thyroid, metastatic |
| 683 | SWNLNGLQADLSSFK | lymph node, papillary carcinoma of thyroid, metastatic |
| 684 | TGSWIGLRNLDLKG | lymph node, papillary carcinoma of thyroid, metastatic |
| 743 | AIVQAVSAHRHR | non-Hodgkin's lymphoma, peripheral T cell type |
| 744 | ARNFERNKAIKVI | non-Hodgkin's lymphoma, peripheral T cell type |
| 745 | ARNFERNKAIKVIIA | non-Hodgkin's lymphoma, peripheral T cell type |
| 746 | NFERNKAIKVII | non-Hodgkin's lymphoma, peripheral T cell type |
| 747 | NFERNKAIKVIIA | non-Hodgkin's lymphoma, peripheral T cell type |
| 748 | VAIVQAVSAHRH | non-Hodgkin's lymphoma, peripheral T cell type |
| 749 | VAIVQAVSAHRHR | non-Hodgkin's lymphoma, peripheral T cell type |
| 750 | VAIVQAVSAHRHRA | non-Hodgkin's lymphoma, peripheral T cell type |
| 751 | VAIVQAVSAHRHRAR | non-Hodgkin's lymphoma, peripheral T cell type |
| 818 | VDKVLERDQKLSE | lymph node, papillary carcinoma of thyroid, metastatic |

TABLE 5-continued

More preferred peptides according to the present invention and diseases to be treated

| Seq ID | Sequence | Tissue and disease |
|---|---|---|
| 819 | VDKVLERDQKLSELD | lymph node, papillary carcinoma of thyroid, metastatic |
| 820 | VDKVLERDQKLSELDD | lymph node, papillary carcinoma of thyroid, metastatic |
| 821 | VDKVLERDQKLSELDDR | lymph node, papillary carcinoma of thyroid, metastatic |
| 822 | VLERDQKLSELDDR | lymph node, papillary carcinoma of thyroid, metastatic |
| 833 | VDKVLERDQKLSE | lymph node, papillary carcinoma of thyroid, metastatic |
| 834 | VDKVLERDQKLSELD | lymph node, papillary carcinoma of thyroid, metastatic |
| 835 | VDKVLERDQKLSELDD | lymph node, papillary carcinoma of thyroid, metastatic |
| 836 | VDKVLERDQKLSELDDR | lymph node, papillary carcinoma of thyroid, metastatic |
| 837 | VLERDQKLSELDDR | lymph node, papillary carcinoma of thyroid, metastatic |
| 848 | DDPAIDVCKKLLGKYPN | pancreas, adenocarcinoma |
| 849 | DKQPYSKLPGVSLLKP | pancreas, adenocarcinoma |
| 850 | DKQPYSKLPGVSLLKPL | pancreas, adenocarcinoma |
| 851 | HPRYYISANVTGFK | pancreas, adenocarcinoma |
| 852 | SHPRYYISANVTG | pancreas, adenocarcinoma |
| 853 | SHPRYYISANVTGFK | pancreas, adenocarcinoma |
| 854 | TSHPRYYISANVTG | pancreas, adenocarcinoma |
| 855 | TSHPRYYISANVTGFK | pancreas, adenocarcinoma |
| 908 | DVGMFVALTKLGQPD | uterine cervix, squamous cell carcinoma |
| 909 | VGmFVALTKLGQPD | uterine cervix, squamous cell carcinoma |
| 1015 | GSSFFGELFNQNPE | thyroid gland, papillary carcinoma |
| 1016 | SGSSFFGELFNQNPE | thyroid gland, papillary carcinoma |
| 466 | DEMRFVTQI | testis, mixed germ cell tumor |
| 467 | ETVHFATTQW | testis, mixed germ cell tumor |
| 468 | LPPPATQI | testis, mixed germ cell tumor |
| 633 | GNPAYRSFSNSLSQ | kidney, angiomyolipoma |
| 634 | GPPGEAGYKAFSSLLA | kidney, angiomyolipoma |
| 635 | GPPGEAGYKAFSSLLASS | kidney, angiomyolipoma |
| 636 | GPPGEAGYKAFSSLLASSA | kidney, angiomyolipoma |
| 637 | GPPGEAGYKAFSSLLASSAVSPE | kidney, angiomyolipoma |
| 639 | GYKAFSSLLASSAVSP | kidney, angiomyolipoma |
| 640 | GYKAFSSLLASSAVSPE | kidney, angiomyolipoma |
| 641 | KAFSSLLASSAVSPE | kidney, angiomyolipoma |
| 642 | NPAYRSFSNSLSQ | kidney, angiomyolipoma |
| 643 | SRDDFQEGREGIVAR | kidney, angiomyolipoma |
| 644 | SSSSFHPAPGNAQ | kidney, angiomyolipoma |
| 645 | VARLTESLFLDL | kidney, angiomyolipoma |
| 646 | VARLTESLFLDLLG | kidney, angiomyolipoma |
| 647 | VIAGNPAYRSFSN | kidney, angiomyolipoma |
| 648 | VPQPEPETVVEQILRRNVLQ | kidney, angiomyolipoma |
| 649 | YKAFSSLLASSAVS | kidney, angiomyolipoma |
| 650 | YKAFSSLLASSAVSP | kidney, angiomyolipoma |
| 651 | YKAFSSLLASSAVSPE | kidney, angiomyolipoma |
| 992 | EDDYIKSWEDNQQGDE | pleura, malignant mesothelioma |
| 993 | ELERIQIQEAAKKKPG | pleura, malignant mesothelioma |
| 994 | ERIQIQEAAKKKP | pleura, malignant mesothelioma |
| 995 | ERIQIQEAAKKKPG | pleura, malignant mesothelioma |
| 996 | ERIQIQEAAKKKPGI | pleura, malignant mesothelioma |
| 997 | LERIQIQEAAKKKPG | pleura, malignant mesothelioma |
| 998 | LSSISQYSGKIK | pleura, malignant mesothelioma, |
| 941 | EERNLLSVAYKNVVGAR | esophagus, adenocarcinoma |
| 942 | ERNLLSVAYKNVVGAR | esophagus, adenocarcinoma |
| 943 | IAELDTLSEESYKD | vulva, squamous cell carcinoma |
| 944 | IAELDTLSEESYKDS | vulva, squamous cell carcinoma |
| 218 | GDYGRAFNL | stomach, metastatic, lymph node, non-Hodgkin's lymphoma, small lymphocytic type |
| 219 | TRHKIVHTK | stomach, metastatic, lymph node, non-Hodgkin's lymphoma, small lymphocytic type |
| 221 | KAFNWFSTL | stomach, metastatic, lymph node, non-Hodgkin's lymphoma, small lymphocytic type |
| 541 | RPKSNIVL | non-Hodgkin's lymphoma, diffuse large B-cell type |
| 542 | RPKSNIVLL | non-Hodgkin's lymphoma, diffuse large B-cell type |
| 1001 | INSRFPIPSATDPD | brain, glioblastoma, brain, oligodendroglioma, |
| 1002 | VQHYELLNGQSVFG | brain, glioblastoma, brain, oligodendroglioma, |
| 910 | AGVFHVEKNGRY | colon, adenocarcinoma, mucinous type |
| 911 | FAGVFHVEKNGRYS | colon, adenocarcinoma, mucinous type |
| 912 | GPITITIVNRDGTR | colon, adenocarcinoma, mucinous type |

TABLE 5-continued

More preferred peptides according to the present invention and diseases to be treated

| Seq ID | Sequence | Tissue and disease |
|---|---|---|
| 913 | NGRYSISRTEAADL | colon, adenocarcinoma, mucinous type |
| 45 | DELPKFHQY | white blood cells, chronic lymphocytic leukemia |
| 46 | DVTGQFPSSF | white blood cells, chronic lymphocytic leukemia |
| 47 | EHSRVLQQL | white blood cells, chronic lymphocytic leukemia |
| 48 | IKVSKQLL | white blood cells, chronic lymphocytic leukemia |
| 49 | KPRQSSPQL | white blood cells, chronic lymphocytic leukemia |
| 50 | KQLLAALEI | white blood cells, chronic lymphocytic leukemia |
| 51 | RRKDLVLKY | liver, focalnodular hyperplasia |
| 52 | RTRDYASLPPK | white blood cells, chronic lymphocytic leukemia |
| 124 | GQKEALLKY | synovial sarcoma |
| 125 | KPSEERKTI | synovial sarcoma |
| 126 | KQTPKVLVV | synovial sarcoma |
| 127 | SVIQHVQSF | synovial sarcoma |
| 128 | TPIERIPYL | synovial sarcoma |
| 773 | LPEFYKTVSPAL | endometrium, adenocarcinoma, endometrioid type |
| 774 | VGQFIQDVKNSRST | endometrium, adenocarcinoma, endometrioid type |
| 775 | VGQFIQDVKNSRSTD | endometrium, adenocarcinoma, endometrioid type |
| 776 | VVGQFIQDVKNSRS | endometrium, adenocarcinoma, endometrioid type |
| 777 | VVGQFIQDVKNSRST | endometrium, adenocarcinoma, endometrioid type |
| 778 | VVGQFIQDVKNSRSTD | endometrium, adenocarcinoma, endometrioid type |
| 779 | VVGQFIQDVKNSRSTDS | endometrium, adenocarcinoma, endometrioid type |
| 687 | GPMKGGNFGGRSSGP | thymus, thymoma, malignant |
| 688 | GPYGGGGQYFAKP | thymus, thymoma, malignant |
| 689 | KGGNFGGRSSGP | thymus, thymoma, malignant |
| 690 | NDFGNYNNQSSNFGP | thymus, thymoma, malignant |
| 691 | SGPYGGGGQYFAKP | thymus, thymoma, malignant |
| 13 | AAANIIRTL | adrenal gland, adrenal cortical carcinoma |
| 14 | GRFKNLREAL | adrenal gland, adrenal cortical carcinoma |
| 15 | MSPFSKATL | adrenal gland, adrenal cortical carcinoma |
| 16 | QEDPGDNQITL | adrenal gland, adrenal cortical carcinoma |
| 17 | SPFSKATL | adrenal gland, adrenal cortical carcinoma |
| 129 | AEVEKNETV | spleen, non-Hodgkin's lymphoma |
| 130 | EVKEEIPLV | spleen, non-Hodgkin's lymphoma |
| 131 | KPTSARSGL | spleen, non-Hodgkin's lymphoma |
| 132 | KYIETTPLTI | spleen, non-Hodgkin's lymphoma |
| 133 | SEIKTSIEV | spleen, non-Hodgkin's lymphoma |
| 134 | SVKPTSATK | spleen, non-Hodgkin's lymphoma |
| 135 | YPNKGVGQA | spleen, non-Hodgkin's lymphoma |
| 966 | ENNEIISNIRDSVIN | kidney, oncocytoma |
| 967 | NNEIISNIRDSVIN | kidney, oncocytoma |
| 968 | SPTVQVFSASGKPV | kidney, oncocytoma |
| 969 | SSPTVQVFSASGKPVE | kidney, oncocytoma |
| 830 | DIMRVNVDKVLERDQK | Medullary carcinoma of thyroid origin |
| 831 | DIMRVNVDKVLERDQKL | Medullary carcinoma of thyroid origin |
| 832 | IMRVNVDKVLERDQK | lymph node, Hodgkin's disease |
| 752 | EEVITLIRSNQQLE | pancreas, adenocarcinoma, |
| 753 | EEVITLIRSNQQLEN | pancreas, adenocarcinoma, |
| 754 | IPADTFAALKNPNAML | pancreas, adenocarcinoma |
| 755 | LKQLLSDKQQKRQSG | pancreas, adenocarcinoma |
| 756 | LKQLLSDKQQKRQSGQ | pancreas, adenocarcinoma |
| 339 | FLDPDIGGVAV | pancreas, adenocarcinoma |
| 340 | HTAPPENKTW | pancreas, adenocarcinoma |
| 341 | LLDTPVKTQY | pancreas, adenocarcinoma |
| 342 | NAVKDFTSF | pancreas, adenocarcinoma |
| 343 | SGLLQIKKL | pancreas, adenocarcinoma |
| 344 | YHDKNIVLL | pancreas, adenocarcinoma |
| 71 | HLKSIPVSL | prostate, adenocarcinoma |
| 72 | KVWYNVENW | prostate, adenocarcinoma |
| 73 | LPAYRAQLL | prostate, adenocarcinoma |
| 74 | LSEQTSVPL | prostate, adenocarcinoma |
| 75 | SLNQWLVSF | prostate, adenocarcinoma |
| 76 | SMTSLAQKI | prostate, adenocarcinoma |
| 77 | SSSGLHPPK | prostate, adenocarcinoma |
| 578 | GGGYGSGGGSGGYGSRRF | thymus, thymoma, malignant |
| 579 | GGSFGGRSSGSP | thymus, thymoma, malignant |
| 580 | KGGSFGGRSSGSP | thymus, thymoma, malignant |
| 583 | SPYGGGYGSGGGSGGYGSRRF | thymus, thymoma, malignant |
| 584 | YGGGYGSGGGSGGYGSRRF | thymus, thymoma, malignant |
| 84 | VPVPHTTAL | endometrium, adenocarcinoma |
| 85 | YQVLDVQRY | endometrium, adenocarcinoma |
| 731 | DGLNSLTYQVLDVQRYPL | endometrium, adenocarcinoma |
| 732 | HPVLQRQQLDYGIY | endometrium, adenocarcinoma |
| 733 | LNSLTYQVLDVQR | endometrium, adenocarcinoma |
| 734 | LNSLTYQVLDVQRYP | endometrium, adenocarcinoma |
| 735 | LNSLTYQVLDVQRYPL | endometrium, adenocarcinoma |

TABLE 5-continued

More preferred peptides according to the present invention and diseases to be treated

| Seq ID | Sequence | Tissue and disease |
|---|---|---|
| 736 | LPQLVGVSTPLQG | endometrium, adenocarcinoma |
| 737 | LPQLVGVSTPLQGG | endometrium, adenocarcinoma |
| 738 | LPQLVGVSTPLQGGS | endometrium, adenocarcinoma |
| 739 | RLPQLVGVSTPLQGGS | endometrium, adenocarcinoma |
| 740 | SPHKVAIIIPFRNR | endometrium, adenocarcinoma |
| 741 | SPHKVAIIIPFRNRQE | endometrium, adenocarcinoma |
| 742 | SPHKVAIIIPFRNRQEH | endometrium, adenocarcinoma |
| 527 | DEKQQHIVY | synovial sarcoma |
| 528 | DEVYQVTVY | synovial sarcoma |
| 529 | GEISEKAKL | synovial sarcoma |
| 530 | YTMKEVLFY | synovial sarcoma |
| 203 | GPRPITQSEL | lymph node, non-Hodgkin's lymphoma, marginal Zone B-cell type |
| 204 | KPEPVDKVA | lymph node, non-Hodgkin's lymphoma, marginal Zone B-cell type |
| 205 | TPSSRPASL | lymph node, non-Hodgkin's lymphoma, marginal Zone B-cell type |
| 949 | SPPQFRVNGAISN | ovary, granulosa cell tumor |
| 950 | SPPQFRVNGAISNFE | ovary, granulosa cell tumor |
| 951 | SPPQFRVNGAISNFEE | ovary, granulosa cell tumor |
| 952 | SPPQFRVNGAISNFEEF | ovary, granulosa cell tumor |
| 953 | VGKMFVDVYFQEDKK | ovary, granulosa cell tumor |
| 954 | VGKmFVDVYFQEDKKE | ovary, granulosa cell tumor |
| 916 | EEFKKLTSIKIQNDK | small intestine, gastrointestinal stromal tumor (GIST) |
| 917 | INRRMADDNKLFR | small intestine, gastrointestinal stromal tumor (GIST) |
| 918 | TATIVMVTNLKERKE | small intestine, gastrointestinal stromal tumor (GIST) |
| 526 | RINEFSISSF | connective tissues, chondrosarcoma |
| 585 | GNRINEFSISSF | connective tissues, chondrosarcoma |
| 586 | HGNQITSDKVGRKV | connective tissues, chondrosarcoma |
| 587 | IPPVNTNLENLYLQ | connective tissues, chondrosarcoma |
| 588 | LQVLRLDGNEIKR | connective tissues, chondrosarcoma |
| 589 | LQVLRLDGNEIKRS | connective tissues, chondrosarcoma |
| 590 | LQVLRLDGNEIKRSA | connective tissues, chondrosarcoma |
| 591 | LRELHLDHNQISRVPN | connective tissues, chondrosarcoma |
| 592 | LYVRLSHNSLTNNG | connective tissues, chondrosarcoma, |
| 593 | VPSRMKYVYFQNNQ | connective tissues, chondrosarcoma |
| 594 | VPSRMKYVYFQNNQIT | connective tissues, chondrosarcoma |
| 595 | VPSRMKYVYFQNNQITS | connective tissues, chondrosarcoma |
| 596 | WIALHGNQITSD | connective tissues, chondrosarcoma |
| 597 | WIALHGNQITSDK | connective tissues, chondrosarcoma |
| 165 | ELNKLLEEI | ovary, adenocarcinoma, endometrioid type |
| 166 | IPFSNPRVL | ovary, adenocarcinoma, endometrioid type |
| 167 | LLDEGAKLLY | ovary, adenocarcinoma, endometrioid type |
| 168 | SPADAHRNL | ovary, adenocarcinoma, endometrioid type |
| 96 | APLQRSQSL | kidney, renal cell carcinoma, clear cell type |
| 97 | DEVHQDTY | kidney, renal cell carcinoma, clear cell type |
| 98 | LPHSATVTL | kidney, renal cell carcinoma, clear cell type |
| 152 | APSEYRYTL | stomach, mucinous adenocarcinoma |
| 153 | APSEYRYTLL | stomach, mucinous adenocarcinoma |
| 154 | EIFQNEVAR | stomach, mucinous adenocarcinoma |
| 155 | KDVLIPGKL | stomach, mucinous adenocarcinoma |
| 156 | VPLVREITF | stomach, mucinous adenocarcinoma |
| 136 | ISMKILNSL | thymus, thymoma, benign |
| 137 | KTIAFLLPMF | thymus, thymoma, benign |
| 138 | RDSIINDF | thymus, thymoma, benign |
| 139 | SVKGGGGNEK | thymus, thymoma, benign |
| 140 | GIAKTGSGK | thymus, thymoma, benign |
| 503 | ALYATKTLR | pancreas, microcystic adenoma |
| 504 | MEYVISRI | pancreas, microcystic adenoma |
| 505 | VPVGRQPII | pancreas, microcystic adenoma |
| 278 | ATNGDLASR | prostate, benign nodular hyperplasia |
| 279 | GLHAEVTGVGY | prostate, benign nodular hyperplasia |
| 280 | HVSSTSSSF | prostate, benign nodular hyperplasia |
| 281 | LQADLQNGL | prostate, benign nodular hyperplasia |
| 282 | SELPVSEVA | prostate, benign nodular hyperplasia |
| 283 | SQTKSVFEI | prostate, benign nodular hyperplasia |
| 284 | THIFTSDGL | prostate, benign nodular hyperplasia |
| 285 | VIYFPPLQK | prostate, benign nodular hyperplasia |
| 286 | YPFSSEQKW | prostate, benign nodular hyperplasia |
| 963 | GNTVIHLDQALARMR | lung, small cell carcinoma |
| 964 | NTVIHLDQALARMR | lung, small cell carcinoma |
| 965 | NTVIHLDQALARMRE | lung, small cell carcinoma |

TABLE 5-continued

More preferred peptides according to the present invention and diseases to be treated

| Seq ID | Sequence | Tissue and disease |
| --- | --- | --- |
| 187 | AADTERLAL | connective tissues, chondrosarcoma |
| 188 | DMKAKVASL | connective tissues, chondrosarcoma |
| 189 | HVLEEVQQV | connective tissues, chondrosarcoma |
| 190 | KEAADTERL | connective tissues, chondrosarcoma |
| 191 | RISEVLQKL | connective tissues, chondrosarcoma |
| 192 | TEVRELVSL | |
| 973 | ADDLEGEAFLPL | spleen, chronic myeloid leukemia |
| 974 | ADDLEGEAFLPLR | spleen, chronic myeloid leukemia |
| 975 | ADDLEGEAFLPLRE | spleen, chronic myeloid leukemia |
| 976 | GADDLEGEAFLPLR | spleen, chronic myeloid leukemia |
| 141 | AETTDNVFTL | thyroid gland, follicular adenoma |
| 142 | SEYQRFAVM | thyroid gland, follicular adenoma |
| 143 | TFGERVVAF | thyroid gland, follicular adenoma |
| 144 | NENLVERF | stomach, colon, adenocarcinoma, mucinous type |
| 117 | QLFSYAILGF | colon, non-Hodgkin's lymphoma |
| 845 | GIRVAPVPLYNS | lung, non-small cell lung carcinoma, liver, hepatocellular carcinoma |
| 846 | GIRVAPVPLYNSFH | lung, non-small cell lung carcinoma, liver, hepatocellular carcinoma |
| 847 | NPNGIRVAPVPLYNSFH | lung, non-small cell lung carcinoma, liver, hepatocellular carcinoma |
| 478 | AAVPVIISR | lymph node, papillary carcinoma of thyroid, metastatic |
| 479 | EEIGKVAAA | lymph node, papillary carcinoma of thyroid, metastatic |
| 480 | FLKDLVASV | lymph node, papillary carcinoma of thyroid, metastatic |
| 481 | VIISRALEL | lymph node, papillary carcinoma of thyroid, metastatic |
| 420 | QIDYKTLVL | leiomyosarcoma |
| 421 | VEDPTIVRI | leiomyosarcoma |
| 543 | GEPLSYTRFSLARQ | lung, non-small cell lung carcinoma, lung, adenocarcinoma |
| 544 | GEPLSYTRFSLARQVD | lung, non-small cell lung carcinoma, lung, adenocarcinoma |
| 545 | GEPLSYTRFSLARQVDG | lung, non-small cell lung carcinoma, lung, adenocarcinoma |
| 546 | GGEPLSYTRFSLARQVD | lung, non-small cell lung carcinoma, lung, adenocarcinoma |
| 547 | GGEPLSYTRFSLARQVDG | lung, non-small cell lung carcinoma, lung, adenocarcinoma |
| 548 | NPGGYVAYSKAATVTG | lung, non-small cell lung carcinoma, lung, adenocarcinoma |
| 549 | NPGGYVAYSKAATVTGK | lung, non-small cell lung carcinoma, lung, adenocarcinoma |
| 550 | NPGGYVAYSKAATVTGKL | lung, non-small cell lung carcinoma, lung, adenocarcinoma |
| 551 | NSVIIVDKNGRL | lung, non-small cell lung carcinoma, lung, adenocarcinoma |
| 552 | NSVIIVDKNGRLV | lung, non-small cell lung carcinoma, lung, adenocarcinoma |
| 553 | NSVIIVDKNGRLVY | lung, non-small cell lung carcinoma, lung, adenocarcinoma |
| 554 | RVEYHFLSPYVSPK | lung, non-small cell lung carcinoma, lung, adenocarcinoma |
| 555 | RVEYHFLSPYVSPKE | lung, non-small cell lung carcinoma, lung, adenocarcinoma |
| 556 | RVEYHFLSPYVSPKESPF | lung, non-small cell lung carcinoma, lung, adenocarcinoma |
| 557 | SPFRHVFWGSGSHTL | lung, non-small cell lung carcinoma, lung, adenocarcinoma |
| 558 | SVIIVDKNGRLV | lung, non-small cell lung carcinoma, lung, adenocarcinoma |
| 559 | VEYHFLSPYVSPK | lung, non-small cell lung carcinoma, lung, adenocarcinoma |
| 560 | VEYHFLSPYVSPKE | lung, non-small cell lung carcinoma, lung, adenocarcinoma |
| 388 | AEGPAGGFmVV | spleen, chronic myeloid leukemia |
| 389 | AYYRDAEAY | spleen, chronic myeloid leukemia |
| 390 | QVNRPLTMR | spleen, chronic myeloid leukemia |
| 391 | RHSPVFQVY | spleen, chronic myeloid leukemia |
| 392 | SLPVPNSAY | spleen, chronic myeloid leukemia |
| 393 | TLGPPGTAHLY | spleen, chronic myeloid leukemia |
| 308 | VLYVGSKTK | schwannoma |

TABLE 5-continued

More preferred peptides according to the present invention and diseases to be treated

| Seq ID | Sequence | Tissue and disease |
|---|---|---|
| 309 | KTKEQVTNV | schwannoma |
| 310 | MPVDPDNEAY | schwannoma |
| 311 | AEKTKQGVA | schwannoma |
| 446 | EAFEFVKQR | stomach, diffuse subtype adenocarcinoma, breast, carcinoma |
| 447 | NHFEGHYQY | stomach, diffuse subtype adenocarcinoma, breast, carcinoma |

Finally a most preferred aspect of the present invention relates to the use of the peptides according to the present invention for the—preferably combined—most preferred immunotherapy of diseases according to the following table 6.

TABLE 6

Most preferred peptides according to the present invention and diseases to be treated

| Seq ID | Sequence | Tissue and disease |
|---|---|---|
| 22 | LEVEERTKPV | breast, carcinoma |
| 23 | RDSPINANLRY | breast, carcinoma |
| 24 | RPFVIVTA | breast, carcinoma |
| 25 | RPIINTPMV | breast, carcinoma |
| 26 | SPTSSRTSSL | breast, carcinoma |
| 27 | ATSAPLVSR | lung, neuroendocrine carcinoma (non-small cell type) |
| 114 | YGNPRTNGM | breast, carcinoma |
| 102 | FSITKSVEL | non-Hodgkin's lymphoma, small lymphocytic type |
| 103 | GQTKNDLVV | non-Hodgkin's lymphoma, small lymphocytic type |
| 104 | LSQEVCRD | non-Hodgkin's lymphoma, small lymphocytic type |
| 105 | RDIQSPEQI | non-Hodgkin's lymphoma, small lymphocytic type |
| 106 | REDNSSNSL | non-Hodgkin's lymphoma, small lymphocytic type |
| 107 | TEHQEPGL | non-Hodgkin's lymphoma, small lymphocytic type |
| 108 | TKNDLVVSL | non-Hodgkin's lymphoma, small lymphocytic type |
| 977 | AGREINLVDAHLKSE | lymph node, Hodgkin's disease |
| 978 | AGREINLVDAHLKSEQT | lymph node, Hodgkin's disease |
| 979 | GREINLVDAHLKSE | lymph node, Hodgkin's disease |
| 980 | KPGIVYASLNHSVIG | lymph node, Hodgkin's disease |
| 981 | NKPGIVYASLNHSVIG | lymph node, Hodgkin's disease |
| 982 | TTLYVTDVKSASERPS | lymph node, Hodgkin's disease |
| 220 | RIHTGEKPYK | colon or rectum, thyroid gland, nodular hyperplasia |
| 53 | APGSVLPRAL | lymph node, Hodgkin's disease |
| 54 | DIKEHPLL | lymph node, Hodgkin's disease |
| 55 | DSAGPQDAR | lymph node, Hodgkin's disease |
| 56 | FQYAKESYI | lymph node, Hodgkin's disease |
| 57 | KVLSWPFLM | lymph node, Hodgkin's disease |
| 58 | LENDQSLSF | lymph node, Hodgkin's disease |
| 59 | SPSRQPQV | lymph node, Hodgkin's disease |
| 60 | SRHQSFTTK | lymph node, Hodgkin's disease |
| 61 | SSHNASKTL | lymph node, Hodgkin's disease |
| 1003 | DNQYAVLENQKSSH | pleura, malignant mesothelioma |
| 1004 | GPPEIYSDTQFPS | pleura, malignant mesothelioma |
| 1005 | GPPEIYSDTQFPSLQ | pleura, malignant mesothelioma |
| 1006 | TPQGPPEIYSDTQFPS | pleura, malignant mesothelioma |
| 1007 | TPQGPPEIYSDTQFPSLQ | pleura, malignant mesothelioma |
| 1008 | TPQGPPEIYSDTQFPSLQST | pleura, malignant mesothelioma |
| 661 | EYVSLYHQPAAM | non-Hodgkin's lymphoma, peripheral T cell type |
| 662 | IKAEYKGRVTLKQYPR | non-Hodgkin's lymphoma, peripheral T cell type |
| 663 | LNVHSEYEPSWEEQP | non-Hodgkin's lymphoma, peripheral T cell type |

TABLE 6-continued

Most preferred peptides according to the present invention and diseases to be treated

| Seq ID | Sequence | Tissue and disease |
| --- | --- | --- |
| 664 | LPYLFQMPAYASSS | non-Hodgkin's lymphoma, peripheral T cell type |
| 665 | LPYLFQMPAYASSSK | non-Hodgkin's lymphoma, peripheral T cell type |
| 666 | NFIKAEYKGRVT | non-Hodgkin's lymphoma, peripheral T cell type |
| 667 | TNFIKAEYKGRVT | non-Hodgkin's lymphoma, peripheral T cell type |
| 668 | TTNFIKAEYKGRVT | non-Hodgkin's lymphoma, peripheral T cell type |
| 669 | VTLNVHSEYEPSWEEQP | non-Hodgkin's lymphoma, peripheral T cell type |
| 670 | YPRKNLFLVEVTQLTESDS | non-Hodgkin's lymphoma, peripheral T cell type |
| 671 | YPRKNLFLVEVTQLTESDSG | non-Hodgkin's lymphoma, peripheral T cell type |
| 780 | DNGHLYREDQTSPAPG | kidney, angiomyolipoma |
| 781 | DNGHLYREDQTSPAPGLR | kidney, angiomyolipoma |
| 782 | EVQVFAPANALPARSE | kidney, angiomyolipoma |
| 783 | GHLYREDQTSPAPG | kidney, angiomyolipoma |
| 784 | LPARSEAAVQPVIG | kidney, angiomyolipoma |
| 785 | NGHLYREDQTSPAPG | kidney, angiomyolipoma |
| 786 | NGHLYREDQTSPAPGL | kidney, angiomyolipoma |
| 787 | NGHLYREDQTSPAPGLR | kidney, angiomyolipoma |
| 788 | VFAPANALPARSEAA | kidney, angiomyolipoma |
| 789 | VQVFAPANALPARSE | kidney, angiomyolipoma |
| 222 | QSTQRSLAL | uterine cervix, squamous cell carcinoma |
| 223 | RDLQMNQALRF | uterine cervix, squamous cell carcinoma |
| 224 | RELESQLHVL | uterine cervix, squamous cell carcinoma |
| 225 | SEAEKLTLV | uterine cervix, squamous cell carcinoma |
| 12 | KIADFGLAR | liver, hepatocellular carcinoma |
| 812 | DGSYRIFSKGASE | colon or rectum |
| 813 | GSYRIFSKGASE | colon or rectum |
| 814 | SDGSYRIFSKGASE | colon or rectum |
| 815 | SVKKMMKDNNLVRH | colon or rectum, liver, hepatocellular carcinoma |
| 816 | VKKMMKDNNLVRH | colon or rectum, liver, hepatocellular carcinoma |
| 743 | AIVQAVSAHRHR | non-Hodgkin's lymphoma, peripheral T cell type |
| 744 | ARNFERNKAIKVI | non-Hodgkin's lymphoma, peripheral T cell type |
| 745 | ARNFERNKAIKVIIA | non-Hodgkin's lymphoma, peripheral T cell type |
| 746 | NFERNKAIKVII | non-Hodgkin's lymphoma, peripheral T cell type |
| 747 | NFERNKAIKVIIA | non-Hodgkin's lymphoma, peripheral T cell type |
| 748 | VAIVQAVSAHRH | non-Hodgkin's lymphoma, peripheral T cell type |
| 749 | VAIVQAVSAHRHR | non-Hodgkin's lymphoma, peripheral T cell type |
| 750 | VAIVQAVSAHRHRA | non-Hodgkin's lymphoma, peripheral T cell type |
| 751 | VAIVQAVSAHRHRAR | non-Hodgkin's lymphoma, peripheral T cell type |
| 818 | VDKVLERDQKLSE | lymph node, papillary carcinoma of thyroid, metastatic |
| 819 | VDKVLERDQKLSELD | lymph node, papillary carcinoma of thyroid, metastatic |
| 820 | VDKVLERDQKLSELDD | lymph node, papillary carcinoma of thyroid, metastatic |
| 821 | VDKVLERDQKLSELDDR | lymph node, papillary carcinoma of thyroid, metastatic |
| 822 | VLERDQKLSELDDR | lymph node, papillary carcinoma of thyroid, metastatic |
| 833 | VDKVLERDQKLSE | lymph node, papillary carcinoma of thyroid, metastatic |
| 834 | VDKVLERDQKLSELD | lymph node, papillary carcinoma of thyroid, metastatic |
| 835 | VDKVLERDQKLSELDD | lymph node, papillary carcinoma of thyroid, metastatic |
| 836 | VDKVLERDQKLSELDDR | lymph node, papillary carcinoma of thyroid, metastatic |

TABLE 6-continued

Most preferred peptides according to the present invention and diseases to be treated

| Seq ID | Sequence | Tissue and disease |
|---|---|---|
| 837 | VLERDQKLSELDDR | lymph node, papillary carcinoma of thyroid, metastatic |
| 908 | DVGMFVALTKLGQPD | uterine cervix, squamous cell carcinoma |
| 909 | VGmFVALTKLGQPD | uterine cervix, squamous cell carcinoma |
| 218 | GDYGRAFNL | lymph node, non-Hodgkin's lymphoma, small lymphocytic type |
| 219 | TRHKIVHTK | lymph node, non-Hodgkin's lymphoma, small lymphocytic type |
| 221 | KAFNWFSTL | lymph node, non-Hodgkin's lymphoma, small lymphocytic type |
| 541 | RPKSNIVL | non-Hodgkin's lymphoma, diffuse large B-cell type |
| 542 | RPKSNIVLL | non-Hodgkin's lymphoma, diffuse large B-cell type |
| 752 | EEVITLIRSNQQLE | pancreas, adenocarcinoma |
| 753 | EEVITLIRSNQQLEN | pancreas, adenocarcinoma |
| 754 | IPADTFAALKNPNAML | pancreas, adenocarcinoma |
| 755 | LKQLLSDKQQKRQSG | pancreas, adenocarcinoma |
| 756 | LKQLLSDKQQKRQSGQ | pancreas, adenocarcinoma |
| 71 | HLKSIPVSL | prostate, adenocarcinoma |
| 72 | KVWYNVENW | prostate, adenocarcinoma |
| 73 | LPAYRAQLL | prostate, adenocarcinoma |
| 74 | LSEQTSVPL | prostate, adenocarcinoma |
| 75 | SLNQWLVSF | prostate, adenocarcinoma |
| 76 | SMTSLAQKI | prostate, adenocarcinoma |
| 77 | SSSGLHPPK | prostate, adenocarcinoma |
| 527 | DEKQQHIVY | synovial sarcoma |
| 528 | DEVYQVTVY | synovial sarcoma |
| 529 | GEISEKAKL | synovial sarcoma |
| 530 | YTMKEVLFY | synovial sarcoma |
| 165 | ELNKLLEEI | ovary, adenocarcinoma, endometrioid type |
| 166 | IPFSNPRVL | ovary, adenocarcinoma, endometrioid type |
| 167 | LLDEGAKLLY | ovary, adenocarcinoma, endometrioid type |
| 168 | SPADAHRNL | ovary, adenocarcinoma, endometrioid type |
| 96 | APLQRSQSL | kidney, renal cell carcinoma, clear cell type |
| 97 | DEVHQDTY | kidney, renal cell carcinoma, clear cell type |
| 98 | LPHSATVTL | kidney, renal cell carcinoma, clear cell type |
| 278 | ATNGDLASR | prostate, benign nodular hyperplasia |
| 279 | GLHAEVTGVGY | prostate, benign nodular hyperplasia |
| 280 | HVSSTSSSF | prostate, benign nodular hyperplasia |
| 281 | LQADLQNGL | prostate, benign nodular hyperplasia |
| 282 | SELPVSEVA | prostate, benign nodular hyperplasia |
| 283 | SQTKSVFEI | prostate, benign nodular hyperplasia |
| 284 | THIFTSDGL | prostate, benign nodular hyperplasia |
| 285 | VIYFPPLQK | prostate, benign nodular hyperplasia |
| 286 | YPFSSEQKW | prostate, benign nodular hyperplasia |
| 973 | ADDLEGEAFLPL | spleen, chronic myeloid leukemia |
| 974 | ADDLEGEAFLPLR | spleen, chronic myeloid leukemia |
| 975 | ADDLEGEAFLPLRE | spleen, chronic myeloid leukemia |
| 976 | GADDLEGEAFLPLR | spleen, chronic myeloid leukemia |
| 141 | AETTDNVFTL | thyroid gland, follicular adenoma |
| 142 | SEYQRFAVM | thyroid gland, follicular adenoma |
| 143 | TFGERVVAF | thyroid gland, follicular adenoma |
| 144 | NENLVERF | colon, adenocarcinoma, mucinous type |
| 845 | GIRVAPVPLYNS | liver, hepatocellular carcinoma |
| 846 | GIRVAPVPLYNSFH | liver, hepatocellular carcinoma |
| 847 | NPNGIRVAPVPLYNSFH | liver, hepatocellular carcinoma |
| 478 | AAVPVIISR | lymph node, papillary carcinoma of thyroid, metastatic |
| 479 | EEIGKVAAA | lymph node, papillary carcinoma of thyroid, metastatic |
| 480 | FLKDLVASV | lymph node, papillary carcinoma of thyroid, metastatic |
| 481 | VIISRALEL | lymph node, papillary carcinoma of thyroid, metastatic |
| 420 | QIDYKTLVL | leiomyosarcoma |
| 421 | VEDPTIVRI | leiomyosarcoma |
| 543 | GEPLSYTRFSLARQ | lung, non-small cell lung carcinoma, lung, adenocarcinoma |
| 544 | GEPLSYTRFSLARQVD | lung, non-small cell lung carcinoma, lung, adenocarcinoma |
| 545 | GEPLSYTRFSLARQVDG | lung, non-small cell lung carcinoma, lung, adenocarcinoma |
| 546 | GGEPLSYTRFSLARQVD | lung, non-small cell lung carcinoma, lung, adenocarcinoma |

TABLE 6-continued

Most preferred peptides according to the present invention and diseases to be treated

| Seq ID | Sequence | Tissue and disease |
|---|---|---|
| 547 | GGEPLSYTRFSLARQVDG | lung, non-small cell lung carcinoma, lung, adenocarcinoma |
| 548 | NPGGYVAYSKAATVTG | lung, non-small cell lung carcinoma, lung, adenocarcinoma |
| 549 | NPGGYVAYSKAATVTGK | lung, non-small cell lung carcinoma, lung, adenocarcinoma |
| 550 | NPGGYVAYSKAATVTGKL | lung, non-small cell lung carcinoma, lung, adenocarcinoma |
| 551 | NSVIIVDKNGRL | lung, non-small cell lung carcinoma, lung, adenocarcinoma |
| 552 | NSVIIVDKNGRLV | lung, non-small cell lung carcinoma, lung, adenocarcinoma |
| 553 | NSVIIVDKNGRLVY | lung, non-small cell lung carcinoma, lung, adenocarcinoma |
| 554 | RVEYHFLSPYVSPK | lung, non-small cell lung carcinoma, lung, adenocarcinoma |
| 555 | RVEYHFLSPYVSPKE | lung, non-small cell lung carcinoma, lung, adenocarcinoma |
| 556 | RVEYHFLSPYVSPKESPF | lung, non-small cell lung carcinoma, lung, adenocarcinoma |
| 557 | SPFRHVFWGSGSHTL | lung, non-small cell lung carcinoma, lung, adenocarcinoma |
| 558 | SVIIVDKNGRLV | lung, non-small cell lung carcinoma, lung, adenocarcinoma |
| 559 | VEYHFLSPYVSPK | lung, non-small cell lung carcinoma, lung, adenocarcinoma |
| 560 | VEYHFLSPYVSPKE | lung, non-small cell lung carcinoma, lung, adenocarcinoma |

B4GALT1 encodes a type II membrane-bound glycoprotein that appears to have exclusive specificity for the donor substrate UDP-galactose (RefSeq). B4GALT1 was shown to be up-regulated in a variety of highly metastatic cell lines such as human lung cancer and ovarian cancer cell lines and was described as a valuable candidate biomarker of invasive phenotype of colorectal cancer (Poeta et al., 2012; Zhou et al., 2012).

CP encodes a metalloprotein that binds most of the copper in plasma and is involved in the peroxidation of Fe(II) transferrin to Fe(III) transferrin (RefSeq).

CST3 encodes a member of the cystatin superfamily, which encompasses proteins that contain multiple cystatin-like sequences (RefSeq).

CTSH encodes a lysosomal cysteine proteinase, which is important in the overall degradation of lysosomal proteins (RefSeq). CTSH expression is increased in pathologic conditions including breast carcinoma, melanoma, gliomas, colorectal carcinoma and prostate carcinoma. CTSH-mediated processing of talin is thought to promote cancer cell progression by affecting integrin activation and adhesion strength (Jevnikar et al., 2013).

DNAJC5 encodes a member of the J protein family. J proteins function in many cellular processes by regulating the ATPase activity of 70 kDa heat shock proteins (RefSeq).

FAIM3 also known as TOSO encodes an Fc receptor for IgM (RefSeq). FAIM3 was identified as being over-expressed and associated with anti-apoptotic characteristics in chronic lymphocytic leukemia and it is regulated by B-cell receptor activation. These studies show that FAIM3 could be used as a prognostic marker for high-risk chronic lymphocytic leukemia (Pallasch et al., 2008; Yi et al., 2011; Yu et al., 2011).

FCER2 encodes a B-cell specific antigen and a low-affinity receptor for IgE. It has essential roles in B cell growth and differentiation, and the regulation of IgE production (RefSeq).

FMOD encodes a member of the family of small interstitial proteoglycans. The encoded protein possesses a central region containing leucine-rich repeats with 4 keratan sulfate chains, flanked by terminal domains containing disulphide bonds (RefSeq). FMOD was shown to be highly over-expressed in chronic lymphocytic leukemia cells. Hence, FMOD might serve as potential tumor-associated antigen in chronic lymphocytic leukemia (Mayr et al., 2005).

GALNT1 encodes a member of the UDP-N-acetyl-alpha-D-galactosamine:polypeptide N-acetylgalactosaminyltransferase (GalNAc-T) family of enzymes (RefSeq). Studies have revealed that GALNT1 expression correlates with the degree of proliferation and recurrence in human breast cancer, ovarian cancer and bladder carcinoma. The latter suggests the use of GALNT1 as a clinical prognostic marker in human bladder carcinoma (Ding et al., 2012).

GLT8D1 encodes a member of the glycosyltransferase family (RefSeq). Studies revealed that GLT8D1 was ubiquitously up-regulated in the majority of human cancers, such as brain, liver, breast, lung, stomach, pancreas, colon, kidney, bladder, prostate and testis. GLT8D1-induced differentially methylated genes have strong potential as epigenetic biomarkers for early cancer screening, diagnostic, prognostic and therapeutic interventions (Teh et al., 2012).

GPI encodes a member of the glucose phosphate isomerase protein family (RefSeq). The GPI gene has been identified to be hypoxia inducible in human pancreatic cancer. The use of GPI inhibitors such as erythrose-4-phosphate diminishes the migratory and invasive capacities in bi-dimensional cultures of several breast cancer cell lines, suggesting that GPI inhibition could be a selective strategy to block tumor metastasis (Yoon et al., 2001; Gallardo-Perez et al., 2014).

GPX1 encodes a member of the glutathione peroxidase family (RefSeq). The GPX1 rs1050450 C>T polymorphism was associated with an increased risk of bladder cancer, but not prostate cancer. High expression of GPX1 in breast cancer cells of patients correlated with a worse clinical outcome and reduced overall survival of patients who underwent chemotherapy, implying that GPX1 could be used as a prognostic marker for these patients (Jardim et al., 2013; Men et al., 2014).

TFRC encodes the transferrin receptor and it is located on chromosome 3q29 (RefSeq). The expression rate of TFRC in oral squamous cell carcinoma was significantly higher than that in dysplasia, suggesting that oral squamous cell carcinoma disease progression might be related to TFRC expression. Anti-TFRC antibody blocked the interaction between transferrin and TFRC and, consequently, iron uptake. The resulting iron deprivation inhibited cell growth and induced apoptosis (Nagai et al., 2014).

UGCG encodes an enzyme that catalyzes the first glycosylation step in the biosynthesis of glycosphingolipids, which are membrane components containing lipid and sugar moieties (RefSeq). Studies have shown that UGCG is overexpressed in leukemia, breast cancer, renal cell cancer and papillary thyroid carcinomas. UGCG up-regulates MDR1 expression through activation of cSrc and beta-catenin signaling (Zhang et al., 2013; Liu et al., 2010).

The present invention furthermore relates to the peptides according to the present invention that have the ability to bind to a molecule of the human major histocompatibility complex (MHC) class-I or -II.

The present invention further relates to the peptides according to the present invention wherein said peptides (each) consist or consist essentially of an amino acid sequence according to SEQ ID NO: 1 to SEQ ID NO: 225, SEQ ID NO: 226 to SEQ ID NO: 542 or SEQ ID NO: 543 to SEQ ID NO: 1016.

A peptide consisting essentially of the amino acid sequence as indicated can have one or two non-anchor amino acids (see below regarding the anchor motif) exchanged without that the ability to bind to a molecule of the human major histocompatibility complex (MHC) class-I or -II is substantially changed or is negatively affected, compared to the non-modified peptide. In another peptide consisting essentially of the amino acid sequence, one or two amino acids are exchanged with their conservative exchange partners (see herein below as well) without that the ability to bind to a molecule of the human major histocompatibility complex (MHC) class-I or -II is substantially changed or is negatively affected, compared to the non-modified peptide.

The present invention further relates to the peptides according to the present invention, wherein said peptide is modified and/or includes non-peptide bonds.

The present invention further relates to the peptides according to the present invention, wherein said peptide is part of a fusion protein, in particular fused to the N-terminal amino acids of the HLA-DR antigen-associated invariant chain (Ii), or fused to (or into the sequence of) an antibody, such as, for example, an antibody that is specific for dendritic cells.

The present invention further relates to a nucleic acid, encoding the peptides according to the present invention.

The present invention further relates to the nucleic acid according to the present invention that is DNA, cDNA, PNA, RNA or combinations thereof.

The present invention further relates to an expression vector capable of expressing and/or presenting a nucleic acid according to the present invention.

The present invention further relates to a peptide according to the present invention according to SEQ ID NO: 1 to SEQ ID NO: 225, SEQ ID NO: 226 to SEQ ID NO: 542 or SEQ ID NO: 543 to SEQ ID NO: 1016, a nucleic acid according to the present invention or an expression vector according to the present invention for use in medicine.

The present invention further relates to antibodies according to the present invention that are specific for a peptide according to SEQ ID NO: 1 to SEQ ID NO: 225, SEQ ID NO: 226 to SEQ ID NO: 542 or SEQ ID NO: 543 to SEQ ID NO: 1016, and methods of making them.

The present invention further relates to T-cell receptors (TCR), in particular soluble TCR (sTCRs) targeting the peptides according to SEQ ID NO: 1 to SEQ ID NO: 225, SEQ ID NO: 226 to SEQ ID NO: 542 or SEQ ID NO: 543 to SEQ ID NO: 1016 and/or complexes of said peptides according to the present invention with MHC, and methods of making them.

The present invention further relates to a host cell comprising a nucleic acid according to the present invention or an expression vector as described before.

The present invention further relates to the host cell according to the present invention that is an antigen presenting cell.

The present invention further relates to the host cell according to the present invention wherein the antigen presenting cell is a dendritic cell.

The present invention further relates to a method of producing a peptide according to the present invention, the method comprising culturing the host cell according to the present invention, and isolating the peptide from the host cell or its culture medium.

The present invention further relates to an in vitro method for producing activated cytotoxic T lymphocytes (CTL), the method comprising contacting in vitro CTL with antigen loaded human class I or II MHC molecules expressed on the surface of a suitable antigen-presenting cell for a period of time sufficient to activate said CTL in an antigen specific manner, wherein said antigen is any peptide according to the present invention.

The present invention further relates to the method according to the present invention, wherein the antigen is loaded onto class I or II MHC molecules expressed on the surface of a suitable antigen-presenting cell by contacting a sufficient amount of the antigen with an antigen-presenting cell.

The present invention further relates to the method according to the present invention, wherein the antigen-presenting cell comprises an expression vector capable of expressing said peptide containing SEQ ID NO: 1 to SEQ ID NO: 225, SEQ ID NO: 527 to SEQ ID NO: 551 or SEQ ID NO: 552 to SEQ ID NO: 1016, or said variant amino acid sequence.

The present invention further relates to activated cytotoxic T lymphocytes (CTL), produced by the method according to the present invention, which selectively recognize a cell which aberrantly expresses a polypeptide comprising an amino acid sequence according to the present invention.

The present invention further relates to a method of killing target cells in a patient which target cells aberrantly express a polypeptide comprising any amino acid sequence according to the present invention, the method comprising administering to the patient an effective number of cytotoxic T lymphocytes (CTL) as according to the present invention.

The present invention further relates to the use of any peptide described, a nucleic acid according to the present invention, an expression vector according to the present invention, a cell according to the present invention, or an activated cytotoxic T lymphocyte according to the present invention as a medicament or in the manufacture of a medicament.

The present invention further relates to a use according to the present invention, wherein said medicament is a vaccine.

The present invention further relates to a use according to the present invention, wherein the medicament is active against cancer.

The present invention further relates to a use according to the present invention, wherein said cancer cells are cells of haematological malignancies, such as, CLL or AML cells.

The present invention further relates to particular marker proteins and biomarkers based on the peptides according to the present invention that can be used in the diagnosis and/or prognosis of haematological malignancies, in particular chronic lymphoid leukemia (CLL) cells.

Further, the present invention relates to the use of these novel targets for cancer treatment.

Further, the present invention relates to a method for producing a personalized anti-cancer vaccine for an individual patient using a database ("warehouse") of pre-screened tumour associated peptides.

Stimulation of an immune response is dependent upon the presence of antigens recognised as foreign by the host immune system. The discovery of the existence of tumor associated antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognising and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognise Class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

There are two classes of MHC-molecules: MHC class I molecules that can be found on most cells having a nucleus. MHC molecules are composed of an alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed. Complexes of peptide and MHC class I molecules are recognized by CD8-positive cytotoxic T-lymphocytes bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells. The identification of CD4-positive T-cell epitopes derived from tumor associated antigens (TAA) is of great importance for the development of pharmaceutical products for triggering anti-tumor immune responses (Gnjatic S, et al. Survey of naturally occurring CD4+ T cell responses against NY-ESO-1 in cancer patients: correlation with antibody responses. Proc Natl Acad Sci USA. 2003 Jul. 22; 100(15):8862-7). At the tumor site, T helper cells, support a CTL friendly cytokine milieu Mortara L, et al. CIITA-induced MHC class II expression in mammary adenocarcinoma leads to a Th1 polarization of the tumor microenvironment, tumor rejection, and specific antitumor memory. Clin Cancer Res. 2006 Jun. 1; 12(11 Pt 1):3435-43) and attract effector cells, e.g. CTLs, NK cells, macrophages, granulocytes (Hwang M L, et al. Cognate memory CD4+ T cells generated with dendritic cell priming influence the expansion, trafficking, and differentiation of secondary CD8+ T cells and enhance tumor control. J Immunol. 2007 Nov. 1; 179(9):5829-38).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have surprisingly been found to express MHC class II molecules (Dengjel J, et al. Unexpected abundance of HLA class II presented peptides in primary renal cell carcinomas. Clin Cancer Res. 2006 Jul. 15; 12(14 Pt 1):4163-70).

It was shown in mammalian animal models, e.g., mice, that even in the absence of CTL effector cells (i.e., CD8-positive T lymphocytes), CD4-positive T cells are sufficient for inhibiting manifestation of tumors via inhibition of angiogenesis by secretion of interferon-gamma (IFNγ).

Additionally, it was shown that CD4-positive T cells recognizing peptides from tumor-associated antigens presented by HLA class II molecules can counteract tumor progression via the induction of antibody (Ab) responses.

In contrast to tumor-associated peptides binding to HLA class I molecules, only a small number of class II ligands of tumor associated antigens (TAA) have been described to date.

Since the constitutive expression of HLA class II molecules is usually limited to cells of the immune system, the possibility of isolating class II peptides directly from primary tumors was not considered possible. However, Dengjel et al. were successful in identifying a number of MHC Class II epitopes directly from tumors (WO 2007/028574, EP 1 760 088 B1; (Dengjel et al., 2006).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

Since both types of response, CD8 and CD4 dependent, contribute jointly and synergistically to the anti-tumor effect, the identification and characterization of tumor-associated antigens recognized by either CD8+ CTLs (ligand: MHC class I molecule+peptide epitope) or by CD4-positive T-helper cells (ligand: MHC class II molecule+peptide epitope) is important in the development of tumor vaccines.

The present invention also relates to two new and very useful MHC class II peptides (according to SEQ ID NO: 543 to SEQ ID NO: 1016). These peptides are particularly useful in the diagnosis and/or treatment of CLL and other cancers over-expressing and/or over—presenting the antigens the peptides are derived from respectively, such as AML.

The present invention also relates to so-called length variants of the inventive MHC class II peptides according to SEQ ID NO: 543 to SEQ ID NO: 1016.

The length variants are generally N- and/or C-terminally extended (between 1 and 5, preferably 1 to 10 amino acids) or N- and/or C-terminally shortened (between 1 and 5 amino acids) peptides, which still can bind to MHC, and elicit a cellular immune response as described herein. As is known in the state of the art, peptides binding to class II proteins are not constrained in size and can vary from 11 to 30 amino acids in length. The peptide binding groove in the MHC class II molecules is open at both ends, which enables binding of peptides with relatively longer length. Though the "core" nine residues long segment contributes the most to the recognition of the peptide, the flanking regions are also important for the specificity of the peptide to the class II allele (see, for example, Meydan C, et al., Prediction of peptides binding to MHC class I and II alleles by temporal motif mining. BMC Bioinformatics. 2013; 14 Suppl 2: S13). Using the many software tools as available (e.g. as described above), the person of skill in the art will be able to identify the binding motif, and thus identify the possibilities for extensions and/or deletions of the MHC class II peptides according to Table 1c, in order to create length variants.

For a peptide to trigger (elicit) a cellular immune response, it must bind to an MHC-molecule. This process is dependent on the allele of the MHC-molecule and specific polymorphisms of the amino acid sequence of the peptide. MHC-class-1-binding peptides are usually 8-12 amino acid residues in length and usually contain two conserved residues ("anchors") in their sequence that interact with the corresponding binding groove of the MHC-molecule. In this way each MHC allele has a "binding motif" determining which peptides can bind specifically to the binding groove.

In the MHC class I dependent immune reaction, peptides not only have to be able to bind to certain MHC class I molecules being expressed by tumor cells, they also have to be recognized by T cells bearing specific T cell receptors (TCR).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated antigens comprises the following major groups:

a) Cancer-testis antigens: The first TAAs ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

b) Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

c) Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

d) Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

e) TAAs arising from abnormal post-translational modifications: Such TAAs may arise from proteins which are neither specific nor overexpressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

f) Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or—associated antigens, and to be used in a therapy, particular prerequisites must be fulfilled. The antigen should be expressed mainly by tumor cells and not or in comparably small amounts by normal healthy tissues or in another preferred embodiment the peptide should be over-presented by tumor cells as compared to normal healthy tissues. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, downstream targets of the proteins directly causative for a transformation may be upregulated and thus may be indirectly tumor-associated. Such indirect tumor-associated antigens may also be targets of a vaccination approach (Singh-Jasuja et al., 2004). In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. In a very preferred embodiment of the invention it is therefore important to select only those over- or selectively presented peptides against which a functional and/or a proliferating T cell can be found. Such a functional T cell is defined as a T cell, which upon stimulation with a specific antigen can be clonally expanded and is able to execute effector functions ("effector T cell").

In case of TCRs and antibodies according to the invention the immunogenicity of the underlying peptides is secondary. For TCRs and antibodies according to the invention the presentation is the determining factor.

T-helper cells play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

The inventors identified a novel category of ligandome-derived tumor-associated antigens (LiTAAs), which were frequently and exclusively detected in CLL patients. Specific immune recognition of the corresponding HLA ligands (LiTAPs) was observed exclusively in CLL patients, remarkably showing a direct correlation with the frequency of HLA restricted presentation. Furthermore, retrospective survival analysis of 33 CLL patients indicated a potential association of LiTAP-specific immune responses with improved overall survival in CLL patients.

Uses against further cancers are disclosed in the following description of the proteins of the peptides according to the invention.

As used herein and except as noted otherwise all terms are defined as given below.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 and in case of MHC class II peptides they can be as long as 15, 16, 17, 18, 19 or 20 amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts.

The term "peptide" shall include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 15 amino acids in length.

The term "the peptides of the present invention" shall include the peptides consisting of or comprising a peptide as defined above according to SEQ ID NO: 1 to SEQ ID NO: 225, SEQ ID NO: 527 to SEQ ID NO: 551 or SEQ ID NO: 552 to SEQ ID NO: 1016.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response. In another aspect, the immunogen can be the peptide, the complex of the peptide with MHC, oligopeptide, and/or protein that is used to raise specific antibodies or TCRs against it.

A class I T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In humans there are three different genetic loci that encode MHC class I molecules (the MHC-molecules of the human are also designated human leukocyte antigens (HLA)): HLA-A, HLA-B, and HLA-C. HLA-A*01, HLA-A*02, and HLA-B*07 are examples of different MHC class I alleles that can be expressed from these loci.

TABLE 7

Expression frequencies F of HLA*A02 and the most frequent HLA-DR serotypes. Frequencies are deduced from haplotype frequencies $G_f$ within the American population adapted from Mori et al. (Mori M, et al. HLA gene and haplotype frequencies in the North American population: the National Marrow Donor Program Donor Registry. Transplantation. 1997 Oct. 15; 64(7): 1017-27) employing the Hardy-Weinberg formula F = $1 - (1 - G_f)^2$. Combinations of A*02 with certain HLA-DR alleles might be enriched or less frequent than expected from their single frequencies due to linkage disequilibrium. For details refer to Chanock et al. (S. J. Chanock, et al (2004) HLA-A, -B, -Cw, -DQA1 and DRB1 in an African American population from Bethesda, USA Human Immunology, 65: 1223-1235).

| | Expression frequencies of HLA*02 and HLA-DR serotypes within North American subpopulations | | | |
|---|---|---|---|---|
| HLA Allele | Caucasian American | African American | Asian American | Latin American |
| A*02 | 49.1% | 34.1% | 43.2% | 48.3% |
| DR1 | 19.4% | 13.2% | 6.8% | 15.3% |
| DR2 | 28.2% | 29.8% | 33.8% | 21.2% |

TABLE 7-continued

Expression frequencies F of HLA*A02 and the most frequent HLA-DR serotypes. Frequencies are deduced from haplotype frequencies $G_f$ within the American population adapted from Mori et al. (Mori M, et al. HLA gene and haplotype frequencies in the North American population: the National Marrow Donor Program Donor Registry. Transplantation. 1997 Oct. 15; 64(7): 1017-27) employing the Hardy-Weinberg formula $F = 1 - (1 - G_f)^2$. Combinations of A*02 with certain HLA-DR alleles might be enriched or less frequent than expected from their single frequencies due to linkage disequilibrium. For details refer to Chanock et al. (S. J. Chanock, et al (2004) HLA-A, -B, -Cw, -DQA1 and DRB1 in an African American population from Bethesda, USA Human Immunology, 65: 1223-1235).

Expression frequencies of HLA*02 and HLA-DR serotypes within North American subpopulations

| HLA Allele | Caucasian American | African American | Asian American | Latin American |
|---|---|---|---|---|
| DR3 | 20.6% | 24.8% | 9.2% | 15.2% |
| DR4 | 30.7% | 11.1% | 28.6% | 36.8% |
| DR5 | 23.3% | 31.1% | 30.0% | 20.0% |
| DR6 | 26.7% | 33.7% | 25.1% | 31.1% |
| DR7 | 24.8% | 19.2% | 13.4% | 20.2% |
| DR8 | 5.7% | 12.1% | 12.7% | 18.6% |
| DR9 | 2.1% | 5.8% | 18.6% | 2.1% |

Therefore, for therapeutic and diagnostic purposes a peptide that binds with appropriate affinity to several different HLA class II receptors is highly desirable. A peptide binding to several different HLA class II molecules is called a promiscuous binder.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence. The term "coding region" refers to that portion of a gene which either naturally or normally codes for the expression product of that gene in its natural genomic environment, i.e., the region coding in vivo for the native expression product of the gene.

The coding region can be from a non-mutated ("normal"), mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence coding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding (or encoding) for a peptide" refers to a nucleotide sequence coding for the peptide including artificial (man-made) start and stop codons compatible for the biological system the sequence is going to be expressed by.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present invention, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=$100[1-(C/R)]$ wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference and (iiii) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the Percent Identity as calculated above is about equal to or greater than a specified minimum Percent Identity then the Compared Sequence has the specified minimum Percent Identity to the Reference Sequence even though alignments may exist in which the herein above calculated Percent Identity is less than the specified Percent Identity.

The original (unmodified) peptides as disclosed herein can be modified by the substitution of one or more residues at different, possibly selective, sites within the peptide chain, if not otherwise stated. Preferably those substitutions are located at the end of the amino acid chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would simultaneously be substituted.

The peptides of the invention can be elongated by up to four amino acids, that is 1, 2, 3 or 4 amino acids can be added to either end in any combination between 4:0 and 0:4.

| Combinations of the elongations according to the invention can be depicted from table 8: | |
| --- | --- |
| C-terminus | N-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |
| N-terminus | C-terminus |
| 4 | 0 |
| 3 | 0 or 1 |
| 2 | 0 or 1 or 2 |
| 1 | 0 or 1 or 2 or 3 |
| 0 | 0 or 1 or 2 or 3 or 4 |

The amino acids for the elongation can be the peptides of the original sequence of the protein or any other amino acid. The elongation can be used to enhance the stability or solubility of the peptides.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation.

Preferably, when the CTLs specific for a peptide according to the present invention are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than 4 residues from the reference peptide, as long as they have substantially identical antigenic activity.

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defences against cancer. CD8-positive T-cells in particular, which recognize class I molecules of the major histocompatibility complex (MHC)-bearing peptides of usually 8 to 12 residues derived from proteins or defect ribosomal products (DRIPS) located in the cytosols, play an important role in this response. The MHC-molecules of the human are also designated as human leukocyte-antigens (HLA).

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

Since both types of response, CD8 and CD4 dependent, contribute jointly and synergistically to the anti-tumor effect, the identification and characterization of tumor-associated antigens recognized by either CD8-positive CTLs (MHC class I molecule) or by CD4-positive CTLs (MHC class II molecule) is important in the development of tumor vaccines. It is therefore an object of the present invention, to provide compositions of peptides that contain peptides binding to MHC complexes of either class.

Considering the severe side-effects and expense associated with treating cancer better prognosis and diagnostic methods are desperately needed. Therefore, there is a need to identify other factors representing biomarkers for cancer in general and CLL in particular. Furthermore, there is a need to identify factors that can be used in the treatment of cancer in general and CLL in particular.

The present invention provides peptides that are useful in treating cancers/tumors, preferably CLL that over- or exclusively present the peptides of the invention. These peptides were shown by mass spectrometry to be naturally presented by HLA molecules on primary human CLL samples.

The source gene/protein (also designated "full-length protein" or "underlying protein") from which the peptides are derived were shown to be highly overexpressed in diseased (e.g. cancerous) compared with normal tissues. "Normal tissues" in relation to this invention shall particularly mean a blood sample from a healthy donor and sub-populations of blood cells, especially white blood cells, (see example 2, and FIGS. 2a-2f) demonstrating a high degree of tumor association of the source genes. Moreover, the peptides themselves are strongly over-presented on tumor tissue—"tumor tissue" in relation to this invention shall mean a blood sample from a patient suffering from CLL and sub-populations of blood cells, especially white blood cells, but not on normal tissues (see example 3 and FIGS. 3a-3e).

HLA-bound peptides can be recognized by the immune system, specifically T lymphocytes/T cells. T cells can destroy the cells presenting the recognized HLA/peptide complex, e.g. cells presenting the peptides of the present invention that are derived from their underlying proteins.

The peptides of the present invention have been shown to be capable of stimulating T cell responses and/or are over-presented and thus can be used for the production of antibodies and/or TCRs, in particular sTCRs, according to the present invention (see example 4 and FIG. 4a-4g). Furthermore, the peptides when complexed with the respective MHC can be used for the production of antibodies and/or TCRs, in particular sTCRs, according to the present invention, as well. Respective methods are well known to the person of skill, and can be found in the respective literature as well. Thus, the peptides of the present invention are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues in comparable copy numbers, preventing the risk of undesired autoimmune reactions against normal cells in the patient.

A "pharmaceutical composition" is a composition suitable for administration to a human being in a medical setting. Preferably, said pharmaceutical composition is sterile and produced according to the GMP guidelines.

The pharmaceutical compositions comprise the peptides either in the free form or in the form of a pharmaceutically acceptable salt (see also above). As used herein, "a pharmaceutically acceptable salt" refers to a derivative of the disclosed peptides wherein the peptide is modified by making acid or base salts of the agent. For example, acid salts are prepared from the free base (typically wherein the neutral form of the drug has a neutral —NH$_2$ group) involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methane sulfonic acid, ethane sulfonic acid, p-toluenesulfonic acid, salicylic acid, and the like, as well as inorganic acids, e.g., hydrochloric acid, hydrobromic acid, sulfuric acid, nitric acid phosphoric acid and the like. Conversely, preparation of basic salts of acid moieties which may be present on a peptide are prepared using a pharmaceutically acceptable base such as sodium hydroxide, potassium hydroxide, ammonium hydroxide, calcium hydroxide, trimethylamine or the like.

In an especially preferred embodiment, the pharmaceutical compositions comprise the peptides as salts of acetic acid (acetates), trifluoro acetates or hydrochloric acid (chlorides).

In addition to being useful for treating cancer, the peptides of the present invention are also useful as diagnostics. Since the peptides were generated from CLL (leukimea) cells and since it was determined that these peptides are not or at lower levels present in normal tissues (such as white blood cells), these peptides can be used to diagnose the presence of a cancer.

The presence of claimed peptides in blood samples can assist a pathologist in diagnosis of cancer. Detection of certain peptides by means of antibodies, mass spectrometry or other methods known in the art can tell the pathologist that the sample is malignant or generally diseased, or can be used as a biomarker for CLL. Presence of groups of peptides can enable classification or sub-classification of diseased tissues.

The detection of peptides on diseased tissue specimen can enable the decision about the benefit of therapies involving the immune system, especially if T-lymphocytes are known or expected to be involved in the mechanism of action. Loss of MHC expression is a well described mechanism by which infected of malignant cells escape immuno-surveillance. Thus, presence of peptides shows that this mechanism is not exploited by the analyzed cells.

The peptides of the present invention might be used to analyze lymphocyte responses against those peptides such as T cell responses or antibody responses against the peptide or the peptide complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against peptides can be considered in the assessment of side effects. Monitoring of lymphocyte responses might also be a valuable tool for follow-up examinations of transplantation therapies, e.g. for the detection of graft versus host and host versus graft diseases.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Therefore, it is a further aspect of the invention to provide a method for producing a recombinant antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically binding to said human major histocompatibility complex (MHC) class I or II being complexed with said HLA-restricted antigen.

It is a further aspect of the invention to provide an antibody that specifically binds to a human major histocompatibility complex (MHC) class I or II being complexed with a HLA-restricted antigen, wherein the antibody preferably is a polyclonal antibody, monoclonal antibody, bi-specific antibody and/or a chimeric antibody.

Yet another aspect of the present invention then relates to a method of producing said antibody specifically binding to a human major histocompatibility complex (MHC) class I or II being complexed with a HLA-restricted antigen, the method comprising: immunizing a genetically engineered non-human mammal comprising cells expressing said human major histocompatibility complex (MHC) class I or II with a soluble form of a MHC class I or II molecule being complexed with said HLA-restricted antigen; isolating mRNA molecules from antibody producing cells of said non-human mammal; producing a phage display library displaying protein molecules encoded by said mRNA molecules; and isolating at least one phage from said phage display library, said at least one phage displaying said antibody specifically bindable to said human major histocompatibility complex (MHC) class I or II being complexed with said HLA-restricted antigen. Respective methods for producing such antibodies and single chain class I major histocompatibility complexes, as well as other tools for the production of these antibodies are disclosed in WO 03/068201, WO 2004/084798, WO 01/72768, WO 03/070752, and Cohen C J, et al. Recombinant antibodies with MHC-restricted, peptide-specific, T-cell receptor-like specificity: new tools to study antigen presentation and TCR-peptide-MHC interactions. J Mol Recognit. 2003 September-October; 16(5):324-32.; Denkberg G, et al. Selective targeting of melanoma and APCs using a recombinant antibody with TCR-like specificity directed toward a melanoma differentiation antigen. J Immunol. 2003 Sep. 1; 171(5):2197-207; and Cohen C J, et al. Direct phenotypic analysis of human MHC class I antigen presentation: visualization, quantitation, and in situ detection of human viral epitopes using peptide-specific, MHC-restricted human recombinant antibodies. J Immunol. 2003 Apr. 15; 170(8): 4349-61, which for the purposes of the present invention are all explicitly incorporated by reference in their entireties.

Preferably, the antibody is binding with a binding affinity of below 20 nanomolar, preferably of below 10 nanomolar, to the complex, which is regarded as "specific" in the context of the present invention.

It is a further aspect of the invention to provide a method for producing a soluble T-cell receptor recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, Liddy N, et al. Monoclonal TCR-redirected tumor cell killing. Nat Med 2012 June; 18(6):980-987). For the purpose of stabilization of T-cell receptors during phage display and in case of practical use as drug, alpha and beta chain can be linked e.g. by non-native disulfide bonds, other covalent bonds (single-chain T-cell receptor), or by dimerization domains (see Boulter J M, et al. Stable, soluble T-cell receptor molecules for crystallization and therapeutics. Protein Eng 2003 September; 16(9):707-711.; Card K F, et al. A soluble single-chain T-cell receptor IL-2 fusion protein retains MHC-restricted peptide specificity and IL-2 bioactivity. Cancer Immunol Immunother 2004 April; 53(4):345-357; and Willcox B E, et al. Production of soluble alphabeta T-cell receptor heterodimers suitable for biophysical analysis of ligand binding. Protein Sci 1999 November; 8 (11): 2418-2423). The T-cell receptor can be linked to toxins, drugs, cytokines (see US 2013/0115191), domains recruiting effector cells such as an anti-CD3 domain, etc., in order to execute particular functions on target cells. Moreover, it could be expressed in T cells used for adoptive transfer.

Further information can be found in WO 2004/033685A1 and WO 2004/074322A1. A combination of sTCRs is described in WO 2012/056407A1. Further methods for the production are disclosed in WO 2013/057586A1.

In addition, they can be used to verify a pathologist's diagnosis of a cancer based on a biopsied sample.

In order to select over-presented peptides, a presentation profile is calculated showing the median sample presentation as well as replicate variation. The profile juxtaposes samples of the tumor entity of interest to a baseline of normal tissue samples. Each of these profiles can then be consolidated into an over-presentation score by calculating the p-value of a Linear Mixed-Effects Model (J. Pinheiro, et al. The nlme Package: Linear and Nonlinear Mixed Effects Models. 2007) adjusting for multiple testing by False Discovery Rate (Y. Benjamini and Y. Hochberg. Controlling the False Discovery Rate: A Practical and Powerful Approach to Multiple Testing. Journal of the Royal Statistical Society. Series B (Methodological), Vol. 57 (No. 1):289-300, 1995).

For the identification and relative quantitation of HLA ligands by mass spectrometry, HLA molecules from shock-frozen tissue samples were purified and HLA-associated peptides were isolated. The isolated peptides were separated and sequences were identified by online nano-electrospray-ionization (nanoESI) liquid chromatography-mass spectrometry (LC-MS) experiments. The resulting peptide sequences were verified by comparison of the fragmentation pattern of natural TUMAPs recorded from CLL samples with the fragmentation patterns of corresponding synthetic reference peptides of identical sequences. Since the peptides were directly identified as ligands of HLA molecules of primary tumors, these results provide direct evidence for the natural processing and presentation of the identified peptides on primary cancer tissue obtained from CLL patients.

The discovery pipeline XPRESIDENT® v2.1 (see, for example, US 2013-0096016, which is hereby incorporated by reference in its entirety) allows the identification and selection of relevant over-presented peptide vaccine candidates based on direct relative quantitation of HLA-restricted peptide levels on cancer tissues in comparison to several different non-cancerous tissues and organs. This was achieved by the development of label-free differential quantitation using the acquired LC-MS data processed by a proprietary data analysis pipeline, combining algorithms for sequence identification, spectral clustering, ion counting, retention time alignment, charge state deconvolution and normalization.

Presentation levels including error estimates for each peptide and sample were established. Peptides exclusively presented on tumor tissue and peptides over-presented in tumor versus non-cancerous tissues and organs have been identified.

HLA-peptide complexes from CLL tissue samples were purified and HLA-associated peptides were isolated and analysed by LC-MS (see examples). All TUMAPs contained in the present application were identified with this approach on primary CLL samples confirming their presentation on primary CLL.

All TUMAPs contained in the application at hand were identified with this approach on primary CLL samples confirming their presentation on primary CLL.

TUMAPs identified on multiple CLL tumor and normal tissues were quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a bar plot, called presentation profile. The presentation profile consolidates different analysis methods like protein database search, spectral clustering, charge state deconvolution (decharging) and retention time alignment and normalization.

The present invention therefore relates to a peptide comprising a sequence that is selected from the group consisting of SEQ ID NO: 1 to SEQ ID NO: 225, SEQ ID NO: 527 to SEQ ID NO: 551 or SEQ ID NO: 552 to SEQ ID NO: 1016 or a variant thereof which is at least 90% homologous (preferably identical) to SEQ ID NO: 1 to SEQ ID NO: 225, SEQ ID NO: 527 to SEQ ID NO: 551 or SEQ ID NO: 552 to SEQ ID NO: 1016 or a variant thereof that induces T cells cross-reacting with said peptide, wherein said peptide is not the underlying full-length polypeptide.

The present invention further relates to a peptide comprising a sequence that is selected from the group consisting of SEQ ID NO: 1 to SEQ ID NO: 225, SEQ ID NO: 527 to SEQ ID NO: 551 or SEQ ID NO: 552 to SEQ ID NO: 1024 or a variant thereof which is at least 90% homologous (preferably identical) to SEQ ID NO: 1 to SEQ ID NO: 225, SEQ ID NO: 527 to SEQ ID NO: 551 or SEQ ID NO: 552 to SEQ ID NO: 1016, wherein said peptide or variant has an overall length of between 8 and 100, preferably between 8 and 30, and most preferred between 8 and 14 amino acids.

The present invention further relates to the peptides according to the invention that have the ability to bind to a molecule of the human major histocompatibility complex (MHC) class-I or -II.

The present invention further relates to the peptides according to the invention wherein the peptide consists or consists essentially of an amino acid sequence according to SEQ ID NO: 1 to SEQ ID NO: 225, SEQ ID NO: 527 to SEQ ID NO: 551 or SEQ ID NO: 552 to SEQ ID NO: 1016.

The present invention further relates to the peptides according to the invention, wherein the peptide is (chemically) modified and/or includes non-peptide bonds.

The present invention further relates to the peptides according to the invention, wherein the peptide is part of a fusion protein, in particular comprising N-terminal amino acids of the HLA-DR antigen-associated invariant chain (Ii), or wherein the peptide is fused to (or into) an antibody, such as, for example, an antibody that is specific for dendritic cells.

The present invention further relates to a nucleic acid, encoding the peptides according to the invention, provided that the peptide is not the full human protein.

The present invention further relates to the nucleic acid according to the invention that is DNA, cDNA, PNA, RNA or combinations thereof.

The present invention further relates to an expression vector capable of expressing a nucleic acid according to the invention.

The present invention further relates to a peptide according to the invention, a nucleic acid according to the invention or an expression vector according to the invention for use in medicine.

The present invention further relates to a host cell comprising a nucleic acid according to the invention or an expression vector according to the invention.

The present invention further relates to the host cell according to the invention that is an antigen presenting cell.

The present invention further relates to the host cell according to the invention wherein the antigen presenting cell is a dendritic cell.

The present invention further relates to a method for producing a peptide according to the invention, the method comprising culturing the host cell described, and isolating the peptide from the host cell or its culture medium.

The present invention further relates to an in vitro method for producing activated cytotoxic T lymphocytes (CTL), the method comprising contacting in vitro CTL with antigen loaded human class I or II MHC molecules expressed on the surface of a suitable antigen-presenting cell for a period of time sufficient to activate said CTL in an antigen specific manner, wherein said antigen is any peptide according to the invention.

The present invention further relates to the method as described, wherein said antigen is loaded onto class I or II MHC molecules expressed on the surface of a suitable antigen-presenting cell by contacting a sufficient amount of the antigen with an antigen-presenting cell.

The present invention further relates to the method according to the invention, wherein the antigen-presenting cell comprises an expression vector capable of expressing said peptide containing SEQ ID NO: 1 to SEQ ID NO: 225, SEQ ID NO: 527 to SEQ ID NO: 551 or SEQ ID NO: 552 to SEQ ID NO: 1016 or said variant amino acid sequence.

The present invention further relates to activated cytotoxic T lymphocytes (CTL), produced by the method according to the invention, which selectively recognise a cell which aberrantly expresses a polypeptide comprising an amino acid sequence described.

The present invention further relates to a method of killing target cells in a patient which target cells aberrantly express a polypeptide comprising any amino acid sequence according to the invention, the method comprising administering to the patient an effective number of cytotoxic T lymphocytes (CTL) according to the invention.

The present invention further relates to the use of any peptide according to the invention, a nucleic acid according to the invention, an expression vector according to the invention, a cell according to the invention, or an activated cytotoxic T lymphocyte according to the invention as a medicament or in the manufacture of a medicament.

The present invention further relates to a use according to the invention, wherein the medicament is a vaccine.

The present invention further relates to a use according to the invention, wherein the medicament is active against cancer.

The present invention further relates to a use according to the invention, wherein said cancer cells are CLL cells or other non solid tumor cells.

The present invention further relates to particular marker proteins and biomarkers that can be used in the prognosis of CLL.

Further, the present invention relates to the use of the novel targets as described in accordance with the present invention for cancer treatment.

The term "antibody" or "antibodies" is used herein in a broad sense and includes both polyclonal and monoclonal antibodies. In addition to intact or "full" immunoglobulin molecules, also included in the term "antibodies" are fragments or polymers of those immunoglobulin molecules and humanized versions of immunoglobulin molecules, so long as they exhibit any of the desired properties (e.g., specific binding of an CLL marker polypeptide, delivery of a toxin to an CLL (leukimea) cells expressing a CLL marker gene at an increased level, and/or inhibiting the activity of a CLL marker polypeptide) according to the invention.

Whenever possible, the antibodies of the invention may be purchased from commercial sources. The antibodies of the invention may also be generated using well-known methods. The skilled artisan will understand that either full length CLL marker polypeptides or fragments thereof may be used to generate the antibodies of the invention. A polypeptide to be used for generating an antibody of the invention may be partially or fully purified from a natural source, or may be produced using recombinant DNA techniques.

For example, a cDNA encoding a peptide according to the present invention, such as a peptide according to SEQ ID NO: 1 to SEQ ID NO: 225, SEQ ID NO: 226 to SEQ ID NO: 542 or SEQ ID NO: 543 to SEQ ID NO: 1016 polypeptide, or a variant or fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically bind the CLL marker polypeptide used to generate the antibody according to the invention.

One of skill in the art will realize that the generation of two or more different sets of monoclonal or polyclonal antibodies maximizes the likelihood of obtaining an antibody with the specificity and affinity required for its intended use (e.g., ELISA, immunohistochemistry, in vivo imaging, immunotoxin therapy). The antibodies are tested for their desired activity by known methods, in accordance with the purpose for which the antibodies are to be used (e.g., ELISA, immunohistochemistry, immunotherapy, etc.; for further guidance on the generation and testing of antibodies, see, e.g., Harlow and Lane, Antibodies: A Laboratory Manual, Cold Spring Harbor Laboratory Press, Cold Spring Harbor, N.Y., 1988, new $2^{nd}$ edition 2013). For example, the antibodies may be tested in ELISA assays or Western blots. After their initial in vitro characterization, antibodies intended for therapeutic or in vivo diagnostic use are tested according to known clinical testing methods.

The term "monoclonal antibody" as used herein refers to an antibody obtained from a substantially homogeneous population of antibodies, i.e.; the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired antagonistic activity (U.S. Pat. No. 4,816,567, which is hereby incorporated in its entirety).

Monoclonal antibodies of the invention may be prepared using hybridoma methods. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 and U.S. Pat. No. 4,342,566. Papain digestion of antibodies typically produces two identical antigen binding fragments, called Fab fragments, each with a single antigen binding site, and a residual Fc fragment. Pepsin treatment yields a a F(ab')2 fragment and a pFc' fragment.

The antibody fragments, whether attached to other sequences or not, can also include insertions, deletions, substitutions, or other selected modifications of particular regions or specific amino acids residues, provided the activity of the fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody fragment.

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework (FR) residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region gene in chimeric and germ-line mutant mice results in complete inhibition of endogenous antibody production. Transfer of the human germ-line immunoglobulin gene array in such germ-line mutant mice will result in the production of human antibodies upon antigen challenge. Human antibodies can also be produced in phage display libraries.

Antibodies of the invention are preferably administered to a subject in a pharmaceutically acceptable carrier. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., intravenous, intraperitoneal, subcutaneous, intramuscular), or by other methods such as infusion that ensure its delivery to the bloodstream in an effective form. The antibodies may also be administered by intratumoral or peritumoral routes, to exert local as well as systemic therapeutic effects. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. A typical daily dosage of the antibody used alone might range from about 1 (μg/kg to up to 100 mg/kg of body weight or more per day, depending on the factors mentioned above. Following administration of an antibody for treating CLL, the efficacy of the therapeutic antibody can be assessed in various ways well known to the skilled practitioner. s secondary to CLL Because the peptides as mentioned in the Tables above (specifically the ones associated with CLL) of the invention and thus their underlying polypeptides are highly expressed in CLL, and are expressed at rather to extremely low levels in normal cells, the inhibition of a protein selected from the group consisting of APOBEC3D, CDK14, RASGRF1, CDCA7L, CELSR1, AKAP2, CTDP1, DNMBP, TAGAP, ABCA6, DMXL1, PARP3, TP53111, B4GALT1, IRF9, KDM2B, TBC1D22A, ZNF296, BACH2, PRR12, ZFAND5, ATP5G1, DMD, ARID5B, ZNF638, DDX46, RRM2B, BLNK, HSH2D, ERP44, METTL7A, ELP3, NLRP2, ZC3H12D, NELFE, ATP6V1C1, HLA-DMA, TUFM, EIF6, CKAP4, COBLL1, TMED4, TNFRSF13C, UBL7, CXorf21, ASUN, SL24D1, and TRAF3IP3 expression or of the activity thereof may be preferably integrated into a therapeutic strategy for treating or preventing CLL.

The principle of antisense therapy is based on the hypothesis that sequence-specific suppression of gene expression (via transcription or translation) may be achieved by intracellular hybridization between genomic DNA or mRNA and a complementary antisense species. The formation of such a hybrid nucleic acid duplex interferes with transcription of the target tumor antigen-encoding genomic DNA, or processing/transport/translation and/or stability of the target tumor antigen mRNA.

Antisense nucleic acids can be delivered by a variety of approaches. For example, antisense oligonucleotides or antisense RNA can be directly administered (e.g., by intravenous injection) to a subject in a form that allows uptake into tumor cells. Alternatively, viral or plasmid vectors that encode antisense RNA (or RNA fragments) can be introduced into cells in vivo. Antisense effects can also be induced by sense sequences; however, the extent of phenotypic changes is highly variable. Phenotypic changes induced by effective antisense therapy are assessed according to changes in, e.g., target mRNA levels, target protein levels, and/or target protein activity levels.

In a specific example, inhibition of CLL marker function by antisense gene therapy may be accomplished by direct administration of antisense lung tumor marker RNA to a subject. The antisense tumor marker RNA may be produced and isolated by any standard technique, but is most readily produced by in vitro transcription using an antisense tumor marker cDNA under the control of a high efficiency promoter (e.g., the T7 promoter). Administration of anti-sense tumor marker RNA to cells can be carried out by any of the methods for direct nucleic acid administration described below.

An alternative strategy for inhibiting the function of a protein selected from the group consisting of APOBEC3D, CDK14, RASGRF1, CDCA7L, CELSR1, AKAP2, CTDP1, DNMBP, TAGAP, ABCA6, DMXL1, PARP3, TP53111, B4GALT1, IRF9, KDM2B, TBC1D22A, ZNF296, BACH2, PRR12, ZFAND5, ATP5G1, DMD, ARID5B, ZNF638, DDX46, RRM2B, BLNK, HSH2D, ERP44, METTL7A, ELP3, NLRP2, ZC3H12D, NELFE, ATP6V1C1, HLA-DMA, TUFM, EIF6, CKAP4, COBLL1, TMED4, TNFRSF13C, UBL7, CXorf21, ASUN, SL24D1, and TRAF3IP3 using gene therapy involves intracellular expression of an anti-protein antibody or a portion of an anti-protein antibody. For example, the gene (or gene fragment) encoding a monoclonal antibody that specifically binds to a protein selected from the group consisting of APOBEC3D, CDK14, RASGRF1, CDCA7L, CELSR1, AKAP2, CTDP1, DNMBP, TAGAP, ABCA6, DMXL1, PARP3, TP53111, B4GALT1, IRF9, KDM2B, TBC1D22A, ZNF296, BACH2, PRR12, ZFAND5, ATP5G1, DMD, ARID5B, ZNF638, DDX46, RRM2B, BLNK, HSH2D, ERP44, METTL7A, ELP3, NLRP2, ZC3H12D, NELFE, ATP6V1C1, HLA-DMA, TUFM, EIF6, CKAP4, COBLL1, TMED4, TNFRSF13C, UBL7, CXorf21, ASUN, SL24D1, and TRAF3IP3 and inhibits its biological activity is placed under the transcriptional control of a specific (e.g., tissue- or tumor-specific) gene regulatory sequence, within a nucleic acid expression vector. The vector is then administered to the subject such that it is taken up by CLL cells or other cells, which then secrete the anti-protein antibody, and thereby block biological activity of the respective polypeptide. Preferably, proteins are present on the cellular surface of CLL cancer cells.

In the methods described above, which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for inhibition of CLL tumor marker protein expression. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis., US), as well as other liposomes developed according to procedures standard in the art. In addition, the nucleic acid or vector of this invention can be delivered in vivo by electroporation, the technology for which is available from Genetronics, Inc. (San Diego, US) as well as by means of a SONOPORATION machine (ImaRx Pharmaceutical Corp., Tucson, Ariz., US).

As one example, vector delivery can be via a viral system, such as a retroviral vector system that can package a recombinant retroviral genome. The recombinant retrovirus can then be used to infect and thereby deliver to the infected cells antisense nucleic acid that inhibits expression of a protein selected from the group consisting of APOBEC3D, CDK14, RASGRF1, CDCA7L, CELSR1, AKAP2, CTDP1, DNMBP, TAGAP, ABCA6, DMXL1, PARP3, TP53111, B4GALT1, IRF9, KDM2B, TBC1D22A, ZNF296, BACH2, PRR12, ZFAND5, ATP5G1, DMD, ARID5B, ZNF638, DDX46, RRM2B, BLNK, HSH2D, ERP44, METTL7A, ELP3, NLRP2, ZC3H12D, NELFE, ATP6V1C1, HLA-DMA, TUFM, EIF6, CKAP4, COBLL1, TMED4, TNFRSF13C, UBL7, CXorf21, ASUN, SL24D1, and TRAF3IP3. The exact method of introducing the altered nucleic acid into mammalian cells is, of course, not limited to the use of retroviral vectors. Other techniques are widely available for this procedure including the use of adenoviral vectors, adeno-associated viral (AAV) vectors, lentiviral vectors, pseudotyped retroviral vectors. Physical transduction techniques can also be used, such as liposome delivery and receptor-mediated and other endocytosis mechanisms. This invention can be used in conjunction with any of these or other commonly used gene transfer methods.

The antibodies may also be used for in vivo diagnostic assays. Generally, the antibody is labeled with a radionucleotide (such as $^{111}$In, $^{99}$Tc, $^{14}$C, $^{131}$I, $^{3}$H, $^{32}$P or $^{35}$S) so that the tumor can be localized using immunoscintiography. In one embodiment, antibodies or fragments thereof bind to the extracellular domains of two or more targets of a protein selected from the group consisting of APOBEC3D, CDK14, RASGRF1, CDCA7L, CELSR1, AKAP2, CTDP1, DNMBP, TAGAP, ABCA6, DMXL1, PARP3, TP53I11, B4GALT1, IRF9, KDM2B, TBC1D22A, ZNF296, BACH2, PRR12, ZFAND5, ATP5G1, DMD, ARID5B, ZNF638, DDX46, RRM2B, BLNK, HSH2D, ERP44, METTL7A, ELP3, NLRP2, ZC3H12D, NELFE, ATP6V1C1, HLA-DMA, TUFM, EIF6, CKAP4, COBLL1, TMED4, TNFRSF13C, UBL7, CXorf21, ASUN, SL24D1, and TRAF3IP3, and the affinity value (Kd) is less than $1 \times 10$ μM.

Antibodies for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies may be directly or indirectly labeled with said probes. Attachment of probes to the antibodies includes covalent attachment of the probe, incorporation of the probe into the antibody, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

The present invention thus provides a peptide comprising a sequence that is selected from the group of consisting of SEQ ID NO: 1 to SEQ ID NO: 225, SEQ ID NO: 226 to SEQ ID NO: 542 or SEQ ID NO: 543 to SEQ ID NO: 1016 or a variant thereof which is 90% homologous to SEQ ID NO: 1 to SEQ ID NO: 225, SEQ ID NO: 226 to SEQ ID NO: 542 or SEQ ID NO: 543 to SEQ ID NO: 1016, or a variant thereof that will induce T cells cross-reacting with said peptide.

The peptides of the invention have the ability to bind to a molecule of the human major histocompatibility complex (MHC) class-I and/or class II.

In the present invention, the term "homologous" refers to the degree of identity (see Percent Identity above) between sequences of two amino acid sequences, i.e. peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other analysis tools are provided by public databases.

A person skilled in the art will be able to assess, whether T cells induced by a variant of a specific peptide will be able to cross-react with the peptide itself (Fong L, et al. Altered peptide ligand vaccination with Flt3 ligand expanded dendritic cells for tumor immunotherapy. Proc Natl Acad Sci USA. 2001 Jul. 17; 98(15):8809-14; Zaremba S, et al. Identification of an enhancer agonist cytotoxic T lymphocyte peptide from human carcinoembryonic antigen. Cancer Res. 1997 Oct. 15; 57(20):4570-7; Colombetti S, et al. Impact of orthologous melan-A peptide immunizations on the anti-self melan-A/HLA-A2 T cell cross-reactivity. J Immunol. 2006 Jun. 1; 176(11):6560-7; Appay V, et al. Decreased specific CD8+ T cell cross-reactivity of antigen recognition following vaccination with Melan-A peptide. Eur J Immunol. 2006 July; 36(7):1805-14).

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence in consisting of SEQ ID NO: 1 to SEQ ID NO: 225, SEQ ID NO: 226 to SEQ ID NO: 542 or SEQ ID NO: 543 to SEQ ID NO: 1016. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated CTL.

These CTL can subsequently cross-react with cells and kill cells that express a polypeptide that contains the natural amino acid sequence of the cognate peptide as defined in the aspects of the invention. As can be derived from the scientific literature (Godkin A, et al. Use of eluted peptide sequence data to identify the binding characteristics of peptides to the insulin-dependent diabetes susceptibility allele HLA-DQ8 (DQ 3.2). Int Immunol. 1997 June; 9(6): 905-11) and databases (Rammensee H. et al. SYFPEITHI: database for MHC ligands and peptide motifs. Immunogenetics. 1999 November; 50(3-4):213-9), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus, one skilled in the art would be able to modify the amino acid sequences set forth in SEQ ID NO: 1 to SEQ ID NO: 225, SEQ ID NO: 226 to SEQ ID NO: 542 or SEQ ID NO: 543 to SEQ ID NO: 1016, by maintaining the known anchor residues, and would be able to determine whether such variants maintain the ability to bind MHC class I or II molecules. The variants of the present invention retain the ability to bind to the TCR of activated CTL, which can subsequently cross-react with— and kill cells that express a polypeptide containing the natural amino acid sequence of the cognate peptide as defined in the aspects of the invention.

The amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide), which includes the amino acid sequences or a portion or variant thereof as given.

Longer peptides may also be suitable. It is also possible, that MHC class I epitopes, although usually between 8 and 11 amino acids long, are generated by peptide processing from longer peptides or proteins that include the actual epitope. It is preferred that the residues that flank the actual epitope are residues that do not substantially affect proteolytic cleavage necessary to expose the actual epitope during processing.

Accordingly, the present invention also provides peptides and variants of MHC class I epitopes wherein the peptide or variant has an overall length of between 8 and 100, preferably between 8 and 30, and most preferred between 8 and 14, namely 8, 9, 10, 11, 12, 13, 14 amino acids, in case of the class II binding peptides the length can also be 15, 16, 17, 18, 19, 20, 21 or 22 amino acids.

Of course, the peptide or variant according to the present invention will have the ability to bind to a molecule of the human major histocompatibility complex (MHC) class I. Binding of a peptide or a variant to a MHC complex may be tested by methods known in the art.

In a particularly preferred embodiment of the invention the peptide consists or consists essentially of an amino acid sequence according to SEQ ID NO: 1 to SEQ ID NO: 225, SEQ ID NO: 226 to SEQ ID NO: 542 or SEQ ID NO: 543 to SEQ ID NO: 1016.

"Consisting essentially of" shall mean that a peptide according to the present invention, in addition to the sequence according to any of SEQ ID NO: 1 to SEQ ID NO: 225, SEQ ID NO: 226: to SEQ ID NO: 542 or SEQ ID NO: 543 to SEQ ID NO: 1016 or a variant thereof contains additional N- and/or C-terminally located stretches of amino acids that are not necessarily forming part of the peptide that functions as an epitope for MHC molecules epitope.

Nevertheless, these stretches can be important to provide an efficient introduction of the peptide according to the present invention into the cells. In one embodiment of the present invention, the peptide is a fusion protein which comprises, for example, the 80 N-terminal amino acids of the HLA-DR antigen-associated invariant chain (p33, in the following "Ii") as derived from the NCBI, GenBank Accession number X00497. In other fusions, the peptides of the present invention can be fused to an antibody as described herein, or a functional part thereof, in particular into a sequence of an antibody, so as to be specifically targeted by said antibody, or, for example, to or into an antibody that is specific for dendritic cells.

In addition, the peptide or variant may be modified further to improve stability and/or binding to MHC molecules in order to elicit a stronger immune response. Methods for such an optimization of a peptide sequence are well known in the art and include, for example, the introduction of reverse peptide bonds or non-peptide bonds.

In a reverse peptide bond amino acid residues are not joined by peptide (—CO—NH—) linkages but the peptide bond is reversed. Such retro-inverso peptidomimetics may be made using methods known in the art, for example such as those described in Meziere et al (1997) J. Immunol. 159, 3230-3237, incorporated herein by reference. This approach involves making pseudopeptides containing changes involving the backbone, and not the orientation of side chains. Meziere et al (1997) show that for MHC binding and T helper cell responses, these pseudopeptides are useful. Retro-inverse peptides, which contain NH—CO bonds instead of CO—NH peptide bonds, are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—. U.S. Pat. No. 4,897, 445 provides a method for the solid phase synthesis of non-peptide bonds (—CH$_2$—NH) in polypeptide chains which involves polypeptides synthesized by standard procedures and the non-peptide bond synthesized by reacting an amino aldehyde and an amino acid in the presence of NaCNBH$_3$.

Peptides comprising the sequences described above may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxycarbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well-known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich provide information on specific reagents.

Selective reduction of disulfide bonds in proteins is also common. Disulfide bonds can be formed and oxidized during the heat treatment of biopharmaceuticals.

Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue.

For example, diethylpyrocarbonate is a reagent for the modification of histidyl residues in proteins. Histidine can also be modified using 4-hydroxy-2-nonenal.

The reaction of lysine residues and other a-amino groups is, for example, useful in binding of peptides to surfaces or the cross-linking of proteins/peptides. Lysine is the site of attachment of poly(ethylene)glycol and the major site of modification in the glycosylation of proteins.

Methionine residues in proteins can be modified with e.g. iodoacetamide, bromoethylamine, and chloramine T.

Tetranitromethane and N-acetylimidazole can be used for the modification of tyrosyl residues. Cross-linking via the formation of dityrosine can be accomplished with hydrogen peroxide/copper ions.

Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole).

Successful modification of therapeutic proteins and peptides with PEG is often associated with an extension of circulatory half-life while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesized by the Fmoc-polyamide mode of solid-phase peptide synthesis as disclosed by Lukas et al. (Solid-phase peptide synthesis under continuous-flow conditions. Proc Natl Acad Sci USA. May 1981; 78(5): 2791-2795) and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethandithiol, phenol, anisole and water, the exact choice depending on the constituent amino acids of the peptide being synthesized. Also a combination of solid phase and solution phase methodologies for the synthesis of peptides is possible (see, for example, Bruckdorfer et al., 2004, and the references as cited therein).

Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (for example a polynucleotide) encoding a peptide or peptide variant of the invention. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the invention employs the polymerase chain reaction as disclosed by Saiki R K, et al. (Diagnosis of sickle cell anemia and beta-thalassemia with enzymatically amplified DNA and nonradioactive allele-specific oligonucleotide probes. N Engl J Med. 1988 Sep. 1; 319(9):537-41). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. Nos. 4,440,859, 4,530,901, 4,582,800, 4,677,063, 4,678,751, 4,704,362, 4,710,463, 4,757,006, 4,766,075, and 4,810,648.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the preprotrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the invention are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well-known methods that typically depend on the type of vector used. With regard to transformation of prokaryotic host cells, see, for example, Cohen et al (1972) Proc. Natl. Acad. Sci. USA 69, 2110, and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well-known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules. Thus, the current invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Small E J, et al. Placebo-controlled phase III trial of immunologic therapy with sipuleucel-T (APC8015) in patients with metastatic, asymptomatic hormone refractory prostate cancer. J Clin Oncol. 2006 Jul. 1; 24(19):3089-94. Rini et al. Combination immunotherapy with prostatic acid phosphatase pulsed antigen-presenting cells (provenge) plus bevacizumab in patients with serologic progression of prostate cancer after definitive local therapy. Cancer. 2006 Jul. 1; 107(1):67-74).

A further aspect of the invention provides a method of producing a peptide or its variant, the method comprising culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g. between 50 μg and 1.5 mg, preferably 125 μg to 500 μg, of peptide or DNA may be given and will depend on the respective peptide or DNA. Dosages of this range were successfully used in previous trials (Walter et al Nature Medicine 18, 1254-1261 (2012)).

Another aspect of the present invention includes an in vitro method for producing activated T cells, the method comprising contacting in vitro T cells with antigen loaded human MHC molecules expressed on the surface of a suitable antigen-presenting cell for a period of time sufficient to activate the T cell in an antigen specific manner, wherein the antigen is a peptide according to the invention. Preferably a sufficient amount of the antigen is used with an antigen-presenting cell.

Preferably the mammalian cell lacks or has a reduced level or function of the TAP peptide transporter. Suitable cells that lack the TAP peptide transporter include T2, RMA-S and Drosophila cells. TAP is the transporter associated with antigen processing.

The human peptide loading deficient cell line T2 is available from the American Type Culture Collection, 12301 Parklawn Drive, Rockville, Md. 20852, USA under Catalogue No CRL 1992; the Drosophila cell line Schneider line 2 is available from the ATCC under Catalogue No CRL 19863; the mouse RMA-S cell line is described in Karre et al 1985 (Ljunggren, H.-G., and K. Karre. 1985. J. Exp. Med. 162:1745).

Preferably, the host cell before transfection expresses substantially no MHC class I molecules. It is also preferred that the stimulator cell expresses a molecule important for providing a co-stimulatory signal for T-cells such as any of B7.1, B7.2, ICAM-1 and LFA 3. The nucleic acid sequences of numerous MHC class I molecules and of the co-stimulator molecules are publicly available from the GenBank and EMBL databases.

In case of a MHC class I epitope being used as an antigen, the T cells are CD8-positive CTLs.

If an antigen-presenting cell is transfected to express such an epitope, preferably the cell comprises an expression vector capable of expressing a peptide containing SEQ ID NO: 1 to SEQ ID NO: 225, SEQ ID NO: 226 to SEQ ID NO: 542 or SEQ ID NO: 543 to SEQ ID NO: 1016, or a variant amino acid sequence thereof.

A number of other methods may be used for generating CTL in vitro. For example, autologous tumor-infiltrating lymphocytes can be used in the generation of CTL. Plebanski et al (1995) (Induction of peptide-specific primary cytotoxic T lymphocyte responses from human peripheral blood. Eur J Immunol. 1995 June; 25(6):1783-7) make use of autologous peripheral blood lymphocytes (PLBs) in the preparation of CTL. Furthermore, the production of autologous CTL by pulsing dendritic cells with peptide or polypeptide, or via infection with recombinant virus is possible. Also, B cells can be used in the production of autologous CTL. In addition, macrophages pulsed with peptide or polypeptide, or infected with recombinant virus, may be used in the preparation of autologous CTL. S. Walter et al. 2003 (Cutting edge: predetermined avidity of human CD8 T cells expanded on calibrated MHC/anti-CD28-coated microspheres. J Immunol. 2003 Nov. 15; 171(10):4974-8) describe the in vitro priming of T cells by using artificial antigen presenting cells (aAPCs), which is also a suitable way for generating T cells against the peptide of choice. In the present invention, aAPCs were generated by the coupling of preformed MHC:peptide complexes to the surface of polystyrene particles (microbeads) by biotin:streptavidin biochemistry. This system permits the exact control of the MHC density on aAPCs, which allows to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based systems often require the addition of appropriate soluble factors, e. g. cytokines, like interleukin-12.

Allogeneic cells may also be used in the preparation of T cells and a method is described in detail in WO 97/26328, incorporated herein by reference. For example, in addition to Drosophila cells and T2 cells, other cells may be used to present antigens such as CHO cells, baculovirus-infected insect cells, bacteria, yeast, vaccinia-infected target cells. In addition plant viruses may be used (see, for example, Porta et al. (1994) Development of cowpea mosaic virus as a high-yielding system for the presentation of foreign peptides. Virology. 1994 Aug. 1; 202(2):949-55) which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells, which are produced by the above method, will selectively recognize a cell that aberrantly expresses a polypeptide that comprises an amino acid sequence of SEQ ID NO: 1 to SEQ ID NO: 225, SEQ ID NO: 226 to SEQ ID NO: 542 or SEQ ID NO: 543 to SEQ ID NO: 1016.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease that can be readily tested for, and detected.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the present invention may be used as active ingredients of a therapeutic composition. Thus, the invention also provides a method of killing target cells in a patient whose target cells aberrantly express a polypeptide comprising an amino acid sequence of the invention, the method comprising administering to the patient an effective number of T cells as defined above.

By "aberrantly expressed" the inventors also mean that the polypeptide is over-expressed compared to normal levels of expression or that the gene is silent in the tissue from which the tumor is derived but in the tumor it is expressed. By "over-expressed" the inventors mean that the polypeptide is present at a level at least 1.2-fold of that present in normal tissue; preferably at least 2-fold, and more preferably at least 5-fold or 10-fold the level present in normal tissue.

T cells may be obtained by methods known in the art, e.g. those described above.

Protocols for this so-called adoptive transfer of T cells are well known in the art. Reviews can be found in: Gattinoni L, et al. Adoptive immunotherapy for cancer: building on success. Nat Rev Immunol. 2006 May; 6(5):383-93. Review. and Morgan R A, et al. Cancer regression in patients after transfer of genetically engineered lymphocytes. Science. 2006 Oct. 6; 314(5796):126-9).

Any molecule of the invention, i.e. the peptide, nucleic acid, antibody, expression vector, cell, activated CTL, T-cell receptor or the nucleic acid encoding it is useful for the treatment of disorders, characterized by cells escaping an immune response. Therefore any molecule of the present invention may be used as medicament or in the manufacture of a medicament. The molecule may be used by itself or combined with other molecule(s) of the invention or (a) known molecule(s).

Preferably, the medicament of the present invention is a vaccine. It may be administered directly into the patient, into the affected organ or systemically i.d., i.m., s.c., i.p. and i.v., or applied ex vivo to cells derived from the patient or a human cell line which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker, 1993). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of help provided by CD4 T-helper cells. Thus, for MHC Class I epitopes that stimulate CD8 CTL the fusion partner or sections of a hybrid molecule suitably provide epitopes which stimulate CD4-positive T cells. CD4- and CD8-stimulating epitopes are well known in the art and include those identified in the present invention.

In one aspect, the vaccine comprises at least one peptide having the amino acid sequence set forth SEQ ID No. 1 to SEQ ID No. 1016, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

In another aspect, the vaccine comprises at least one peptide having the amino acid sequence set forth in SEQ ID NO: 1 to SEQ ID NO: 225, SEQ ID NO: 226 to SEQ ID NO: 542 or SEQ ID NO: 543 to SEQ ID NO: 1016, and at least one additional peptide, preferably two to 50, more preferably two to 25, even more preferably two to 20 and most preferably two, three, four, five, six, seven, eight, nine, ten, eleven, twelve, thirteen, fourteen, fifteen, sixteen, seventeen or eighteen peptides. The peptide(s) may be derived from one or more specific TAAs and may bind to MHC class I molecules.

The polynucleotide may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g. (Pascolo et al., Human peripheral blood mononuclear cells transfected with messenger RNA stimulate antigen-specific cytotoxic T-lymphocytes in vitro. Cell Mol Life Sci. 2005 August; 62(15):1755-62). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CTLs and helper-T ($T_H$) cells to an antigen, and would thus be considered useful in the medicament of the present invention. Suitable adjuvants include, but are not limited to, 1018 ISS, aluminium salts, AMPLIVAX®, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA®), resiquimod, ImuFact IMP321, Interleukins as IL-2, IL-13, IL-21, Interferon-alpha or -beta, or pegylated derivatives thereof, IS Patch, ISS, ISCOMATRIX, ISCOMs, JuvImmune®, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel® vector system, poly(lactid coglycolid) [PLG]-based and dextran microparticles, talactoferrin SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Allison and Krummel, 1995 The Yin and Yang of T cell costimulation.Science. 1995 Nov. 10; 270(5238):932-3. Review). Also cytokines may be used. Several cytokines have been directly linked to influencing dendritic cell migration to lymphoid tissues (e.g., TNF-), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha. IFN-beta) (Gabrilovich, 1996 Production of vascular endothelial growth factor by human tumors inhibits the functional maturation of dendritic cells Nat Med. 1996 October; 2(10):1096-103).

CpG immunostimulatory oligonucleotides have also been reported to enhance the effects of adjuvants in a vaccine setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nanoparticles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg, 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and derivates thereof (e.g. AmpliGen®, Hiltonal®, poly-(ICLC), poly(IC-R), poly(I:C12U), non-CpG bacterial DNA or RNA as well as immunoactive small molecules and antibodies such as cyclophosphamide, sunitinib, Bevacizumab®, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4, other antibodies targeting key structures of the immune system (e.g. anti-CD40, anti-TGFbeta, anti-TNFalpha receptor) and SC58175, which may act therapeutically and/or as an adjuvant. The amounts and concentrations of adjuvants and additives useful in the context of the present invention can readily be determined by the skilled artisan without undue experimentation.

Preferred adjuvants are imiquimod, resiquimod, GM-CSF, cyclophosphamide, sunitinib, bevacizumab, interferon-alpha, CpG oligonucleotides and derivates, poly-(I:C) and derivates, RNA, sildenafil, and particulate formulations with PLG or virosomes.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, imiquimod, resiquimod, and interferon-alpha.

In a preferred embodiment, the pharmaceutical composition according to the invention the adjuvant is selected from the group consisting of colony-stimulating factors, such as Granulocyte Macrophage Colony Stimulating Factor (GM-CSF, sargramostim), cyclophosphamide, immiquimod and resiquimod.

In a preferred embodiment of the pharmaceutical composition according to the invention, the adjuvant is cyclophosphamide, imiquimod or resiquimod.

Even more preferred adjuvants are Montanide IMS 1312, Montanide ISA 206, Montanide ISA 50V, Montanide ISA-51, poly-ICLC (Hiltonal®) and anti-CD40 mAB or combinations thereof.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavours, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, $3^{rd}$ Ed., 2000, American Pharmaceutical Association and pharmaceutical press. The composition can be used for a prevention, prophylaxis and/or therapy of adenomateous or cancerous diseases. Exemplary formulations can be found in, for example, EP2112253.

Nevertheless depending on the number and the physicochemical characteristics of the peptides of the invention further research is needed to provide formulations for specific combinations of peptides, especially combinations with more than 20 peptides that are stable for more than 12 to 18 months.

The present invention provides a medicament that useful in treating cancer, in particular AML, Chronic lymphoid leukemia (CLL) and other hematological malignancies.

The present invention is further directed at a kit comprising:

(a) a container containing a pharmaceutical composition as described above, in solution or in lyophilized form;

(b) optionally a second container containing a diluent or reconstituting solution for the lyophilized formulation; and (c) optionally, instructions for (i) use of the solution or (ii) reconstitution and/or use of the lyophilized formulation.

The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contain/s instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, an anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The present formulation is one that is suitable for administration of the peptides by any acceptable route such as oral (enteral), nasal, ophthal, subcutaneous, intradermal, intramuscular, intravenous or transdermal. Preferably the administration is s.c., and most preferably i.d. Administration may be by infusion pump.

Since the peptides of the invention were isolated from CLL, the medicament of the invention is preferably used to treat CLL. In a preferred embodiment, since the peptides of the invention derived from a protein selected from the group consisting of APOBEC3D, CDK14, RASGRF1, CDCA7L, CELSR1, AKAP2, CTDP1, DNMBP, TAGAP, ABCA6, DMXL1, PARP3, TP53111, B4GALT1, IRF9, KDM2B, TBC1D22A, ZNF296, BACH2, PRR12, ZFAND5, ATP5G1, DMD, ARID5B, ZNF638, DDX46, RRM2B, BLNK, HSH2D, ERP44, METTL7A, ELP3, NLRP2, ZC3H12D, NELFE, ATP6V1C1, HLA-DMA, TUFM, EIF6, CKAP4, COBLL1, TMED4, TNFRSF13C, UBL7, CXorf21, ASUN, SL24D1, and TRAF3IP3 were isolated from CLL, and thus the medicament of the invention is preferably used to treat CLL.

The present invention further includes a method for producing a personalized pharmaceutical for an individual patient comprising manufacturing a pharmaceutical composition comprising at least one peptide selected from a warehouse of pre-screened TUMAPs, wherein the at least one peptide used in the pharmaceutical composition is selected for suitability in the individual patient. Preferably, the pharmaceutical composition is a vaccine. The method could also be adapted to produce T cell clones for downstream applications such as TCR isolations.

A "personalized pharmaceutical" shall mean specifically tailored therapies for one individual patient that will only be used for therapy in such individual patient, including actively personalized cancer vaccines and adoptive cellular therapies using autologous patient tissue.

As used herein, the term "warehouse" shall refer to a group of peptides that have been pre-screened for immunogenicity and over-presentation in a particular tumour type. The term "warehouse" is not intended to imply that the particular peptides included in the vaccine have been pre-manufactured and stored in a physical facility, although that possibility is contemplated. It is expressly contemplated that the peptides may be manufactured de novo for each individualized vaccine produced, or may be pre-manufactured and stored.

The warehouse (e.g. in the form of a database) is composed of tumour-associated peptides which were highly overexpressed in the tumour tissue of several HLA-A, HLA-B and HLA-C positive CLL patients analyzed (see tables above). It contains MHC class I and MHC class II peptides. In addition to the tumor associated peptides collected from several GBM tissues, the warehouse may contain an HLA-A*02 and an HLA-A*24 marker peptide. These peptides allow comparison of the magnitude of T-cell immunity induced by TUMAPS in a quantitative manner and hence allow important conclusion to be drawn on the capacity of the vaccine to elicit anti-tumor responses. Secondly, it functions as an important positive control peptide derived from a "non-self" antigen in the case that any vaccine-induced T-cell responses to TUMAPs derived from "self" antigens in a patient are not observed. And thirdly, it may allow conclusions to be drawn, regarding the status of immunocompetence of the patient population.

HLA class I and II TUMAPs for the warehouse are identified by using an integrated functional genomics approach combining gene expression analysis, mass spectrometry, and T-cell immunology. The approach assures that only TUMAPs truly present on a high percentage of tumours but not or only minimally expressed on normal tissue, are chosen for further analysis. For peptide selection, CLL samples from patients and blood from healthy donors were analyzed in a stepwise approach:

1. HLA ligands from the malignant material were identified by mass spectrometry
2. Genome-wide messenger ribonucleic acid (mRNA) expression analysis by microarrays was used to identify genes over-expressed in the malignant tissue (CLL) compared with a range of normal organs and tissues
3. Identified HLA ligands were compared to gene expression data. Peptides encoded by selectively expressed or over-expressed genes as detected in step 2 were considered suitable TUMAP candidates for a multi-peptide vaccine.
4. Literature research was performed in order to identify additional evidence supporting the relevance of the identified peptides as TUMAPs
5. The relevance of over-expression at the mRNA level was confirmed by redetection of selected TUMAPs from step 3 on tumor tissue and lack of (or infrequent) detection on healthy tissues
6. To assess whether an induction of in vivo T-cell responses by the selected peptides may be feasible, in vitro immunogenicity assays were performed using human T cells from healthy donors as well as from CLL patients.

In an aspect, the peptides are pre-screened for immunogenicity before being included in the warehouse. By way of example, and not limitation, the immunogenicity of the peptides included in the warehouse is determined by a method comprising in vitro T-cell priming through repeated stimulations of CD8+ T cells from healthy donors with artificial antigen presenting cells loaded with peptide/MHC complexes and anti-CD28 antibody.

This method is preferred for rare cancers and patients with a rare expression profile. In contrast to multi-peptide cocktails with a fixed composition as currently developed the warehouse allows a significantly higher matching of the actual expression of antigens in the tumour with the vaccine. Selected single or combinations of several "off-the-shelf" peptides will be used for each patient in a multitarget approach. In theory an approach based on selection of e.g. 5 different antigenic peptides from a library of 50 would already lead to approximately 17 million possible drug product (DP) compositions.

In an aspect, the peptides are selected for inclusion in the vaccine based on their suitability for the individual patient based on the method according to the present invention as described herein, and as follows.

The HLA phenotype, transcriptomic and peptidomic data will be gathered from the patient's tumour material and blood samples to identify the most suitable peptides for each patient containing warehouse and patient-unique (ie. mutated) TUMAPs. Those peptides will be chosen, which are selectively or over-expressed in the patients tumor and, where possible, showed strong in vitro immunogenicity if tested with the patients individual PBMCs.

Preferably, the peptides included in the vaccine are identified by a method comprising: (a) identifying tumour-associated peptides (TUMAPs) presented by a tumor sample from the individual patient; (b) comparing the peptides identified in (a) with a warehouse (database) of peptides as described above; and (c) selecting at least one peptide from the warehouse (database) that correlates with a tumour-associated peptide identified in the patient. For example, the TUMAPs presented by the tumor sample are identified by: (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. Preferably, the sequences of MHC ligands are identified by eluting bound peptides from MHC molecules isolated from the tumor sample, and sequencing the eluted ligands. Preferably, the tumor sample and the normal tissue are obtained from the same patient.

In addition to, or as an alternative to, selecting peptides using a warehousing (database) model, TUMAPs may be identified in the patient de novo and then included in the vaccine. As one example, candidate TUMAPs may be identified in the patient by (a1) comparing expression data from the tumor sample to expression data from a sample of normal tissue corresponding to the tissue type of the tumor sample to identify proteins that are over-expressed or aberrantly expressed in the tumor sample; and (a2) correlating the expression data with sequences of MHC ligands bound to MHC class I and/or class II molecules in the tumor sample to identify MHC ligands derived from proteins over-expressed or aberrantly expressed by the tumor. As another example, proteins may be identified containing mutations that are unique to the tumor sample relative to normal corresponding tissue from the individual patient, and TUMAPs can be identified that specifically target the mutation. For example, the genome of the tumour and of corresponding normal tissue can be sequenced by whole genome sequencing: For discovery of non-synonymous mutations in the protein-coding regions of genes, genomic DNA and RNA are extracted from tumour tissues and normal non-mutated genomic germline DNA is extracted from peripheral blood mononuclear cells (PBMCs). The applied NGS approach is confined to the re-sequencing of protein coding regions (exome re-sequencing). For this purpose, exonic DNA from human samples is captured using vendor-supplied target enrichment kits, followed by sequencing with e.g. a HiSeq2000 (Illumina). Additionally, tumour mRNA is sequenced for direct quantification of gene expression and validation that mutated genes are expressed in the patients' tumours. The resultant millions of sequence reads are processed through software algorithms. The output list contains mutations and gene expression. Tumour-specific somatic mutations are determined by comparison with the PBMC-derived germline variations and prioritized. The de novo identified peptides may then be tested for immunogenicity as described above for the warehouse, and candidate TUMAPs possessing suitable immunogenicity are selected for inclusion in the vaccine.

In one exemplary embodiment, the peptides included in the vaccine are identified by: (a) identifying tumour-associated peptides (TUMAPs) presented by a tumor sample from the individual patient by the methods described above; (b) comparing the peptides identified in a) with a warehouse of peptides that have been prescreened for immunogenicity and overrepresentation in tumors as compared to corresponding normal tissue; (c) selecting at least one peptide from the warehouse that correlates with a tumour-associated peptide identified in the patient; and (d) optionally, selecting at least one peptide identified de novo in (a) confirming its immunogenicity.

In one exemplary embodiment, the peptides included in the vaccine are identified by: (a) identifying tumour-associated peptides (TUMAPs) presented by a tumor sample from the individual patient; and (b) selecting at least one peptide identified de novo in (a) and confirming its immunogenicity.

Once the peptides are selected, the vaccine is manufactured.

The vaccine preferably is a liquid formulation consisting of the individual peptides dissolved in 33% DMSO.

Each peptide to be included into a product is dissolved in DMSO. The concentration of the single peptide solutions has to be chosen depending on the number of peptides to be included into the product. The single peptide-DMSO solutions are mixed in equal parts to achieve a solution containing all peptides to be included in the product with a concentration of ~2.5 mg/ml per peptide. The mixed solution is then diluted 1:3 with water for injection to achieve a concentration of 0.826 mg/ml per peptide in 33% DMSO. The diluted solution is filtered through a 0.22 µm sterile filter. The final bulk solution is obtained.

Final bulk solution is filled into vials and stored at −20° C. until use. One vial contains 700 µL solution containing 0.578 mg of each peptide. Of this, 500 µL (approx. 400 pg per peptide) will be applied for intradermal injection.

The present invention will now be described in the following examples that describe preferred embodiments thereof, nevertheless, without being limited thereto. For the purposes of the present invention, all references as cited herein are incorporated by reference in their entireties.

The patent or application file contains at least one drawing executed in color. Copies of this patent or patent application publication with color drawing(s) will be provided by the Office upon request and payment of the necessary fee.

FIGS. 1a-1d show the HLA surface expression of primary CLL samples. (FIG. 1a) HLA class I and (FIG. 1b) HLA class II expression of CD5$^+$CD19$^+$ CLL cells compared to autologous CD5$^-$CD19$^+$ B cells in 7 primary CLL samples. Data are expressed as mean±s.d. of triplicate experiments. (FIG. 1c) Mean HLA class I and (FIG. 1d) HLA class II expression CD5$^+$CD19$^+$ CLL cells compared to autologous CD5$^-$CD19$^+$ B cells (n=7). * P<0.01 Abbreviations: UPN, uniform patient number FIGS. 2a-2f show the identification of a novel category of tumor-associated antigens by HLA ligandome profiling. (FIG. 2a) Overlap of HLA class I ligand source proteins of primary CLL samples (n=30) and HV PBMC (n=30). (FIG. 2b) Comparative profiling of HLA class I ligand source proteins based on the frequency of HLA restricted representation in CLL and HV PBMC ligandomes. Frequencies [%] of CLL patients/HVs positive for HLA restricted presentation of the respective source protein (x-axis) are indicated on the y-axis. The box on the left-hand side highlights the subset of source proteins showing CLL-exclusive representation in >20% of patients (LiTAAs: ligandome-derived tumor-associated antigens). (FIG. 2c) Representation of published CLL-associated antigens in HLA class I ligandomes. Bars indicate relative representation [%] of respective antigens by HLA class I ligands in CLL and HV PBMC. Dashed lines separate the antigens into three groups according to their degree of CLL-association. (FIG. 2d) Source protein overlaps of CLL samples from different stages of disease (Binet A (n=9), Binet B (n=7), Binet C (n=14)). (FIG. 2e) Heatmap analysis of the representation frequencies [%] of LiTAAs across different disease stages (Binet A-C, as in (FIG. 2d)) (FIG. 2f) Heatmap analysis of LiTAA representation [%] on primary CLL samples with del17p (n=5) and without del17p (n=25). Abbreviations: CLL, chronic lymphocytic leukemia; HV, healthy volunteer FIGS. 3a-3e show that LiTAAs are specifically recognized by CLL patient immune responses. (FIG. 3a) HLA class I LiTAAs and corresponding LiTAPs (3 HLA-A*03, 5 HLA-A*02, 5 HLA-B*07) functionally evaluated in IFNγ ELISPOT assays. Absolute numbers and frequencies of peptide-specific immune recognition by CLL patient PBMC are summarized in the right hand column. (FIG. 3b) Example of A*03 LiTAPs evaluated in ELISPOT using HV PBMC as a control. An EBV epitope mix containing 4 frequently recognized peptides ( . . . ) was used as positive control, HIV GAG$_{18-26}$ A*03 peptide served as negative control. (FIG. 3c) Example of ELISPOT assays using HLA-A*03 LiTAPs (n=3) on PBMC of 3 different CLL patients. Results are shown for immunoreactive LiTAPs. EBV epitope mix served as positive control, HIV GAG$_{18-26}$ A*03 peptide as negative control. (FIG. 3d) Example of HLA-A*03 benign tissue-derived LiBAPs (n=3) tested on CLL patient PBMC as internal control for the target selection strategy. EBV epitope mix served as positive control, HIV GAG 18-26 A*03 peptide as negative control. (FIG. 3e) Scatterplot of the allele-adjusted frequencies of LiTAP presentation in CLL ligandomes (as detected by MS) and the corresponding allele-adjusted frequencies of immune recognition by CLL patient PBMC in IFNγ ELISPOT. Data points are shown for the 14/15 LiTAPs showing immune recognition. Abbreviations: LiTAP, ligandome-derived tumor-associated peptide; HV, healthy volunteer; neg., negative; pos., positive; UPN, uniform patient number; LiBAP, ligandome-derived benign tissue-associated peptide; MS, mass spectrometry.

FIGS. 4a-4g show the identification of additional/synergistic HLA class II LiTAAs and LiTAPs. (FIG. 4a) Overlap of HLA class II ligand source proteins of primary CLL samples (n=20) and HV PBMC (n=13). (FIG. 4b) Comparative profiling of HLA class II ligand source proteins based on the frequency of HLA restricted representation in CLL and HV PBMC ligandomes. Frequencies [%] of CLL patients/HVs positive for HLA restricted presentation of the respective source protein (x-axis) are indicated on the y-axis. The box on the left-hand side highlights the subset of source proteins showing CLL-exclusive representation in >20% of patients (LiTAAs: ligandome-derived tumor-associated antigens). (FIG. 4c) HLA class II LiTAAs and corresponding LiTAPs (n=6) functionally evaluated in IFNγ ELISPOT assays. Absolute numbers and frequencies of peptide-specific immune recognition by CLL patient PBMC are summarized in the right hand column. (FIG. 4d) Example of HLA class II LiTAPs evaluated in ELISPOT using HV PBMC as a control. PHA was used as positive control. FLNA1669-1683 HLA-DR peptide served as negative control. (FIG. 4e) Example of ELISPOT assays using HLA class II LiTAPs (n=6) on PBMC of 3 different CLL patients. Results are shown for immunoreactive LiTAPs. PHA was used as positive control, FLNA1669-1683 HLA-DR peptide served as negative control. (FIG. 4f) Overlap analysis of CLL-exclusive HLA class I and HLA class II ligand source proteins for shared/synergistic vaccine targets. (FIG. 4g) Heatmap analysis of the 132 shared HLA class I/II LiTAAs (identified in (FIG. 4d)). The two source proteins showing representation in ≥20% of both, HLA class I and II CLL patient ligandomes are specified.

Figure 5C:
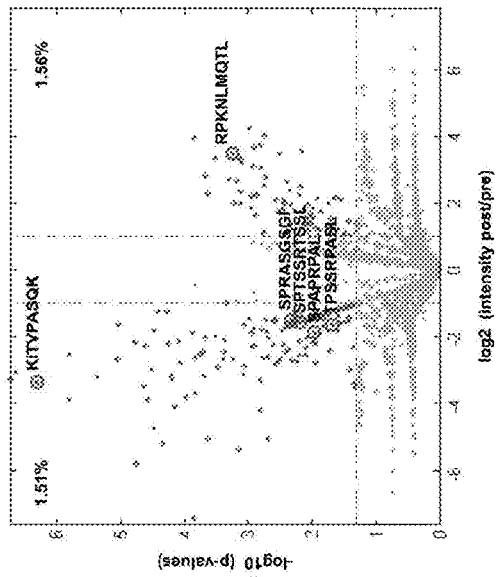
FIG. 5c shows the peptides TFGERVVAF (SEQ ID NO: 143) and KFAEEFYSF (SEQ ID NO: 20).
Figure 5B:
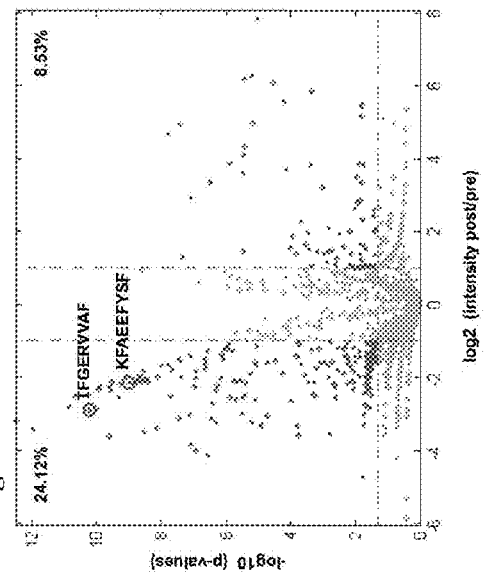
FIG. 5b shows the peptides VPVPHTTAL (SEQ ID NO: 84), GPRPITQSEL (SEQ ID NO: 203), and KLYELHVFTF (SEQ ID NO: 42).

FIGS. 5a-5c show the longitudinal HLA class I ligandome analysis of CLL patients undergoing chemo-/immunotherapy. Volcano-Plots of the relative abundances of ligands in the HLA class I ligandomes of patients after treatment compared to their respective abundance prior to therapy (ratio post therapy/pre therapy). Dashed lines indicate the thresholds for significant changes in abundance (>2-fold ratio, p<0.05), with significantly up-regulated ligands in the upper-right and significantly down-regulated ligands in the upper-left. Frequencies of significantly regulated ligands are specified in the respective quadrants. LiTAPs showing significant regulation over the course of therapy are marked in red and their sequences are specified. (FIG. 5a) Analysis of a CLL patient ligandome prior to therapy and 48 h/24 h after treatment with rituximab/bendamustin (375 mg/m$^2$/90 mg/m$^2$). 1/28 (3.6%) of detectable LiTAPs showed significant changes in abundance. (FIG. 5b) Analysis of a CLL patient ligandome prior to therapy and after the first 7 days of treatment with alemtuzumab (3 doses of alemtuzumab, 10 mg, 20 mg and 30 mg on day 1, 3 and 5; ligandome analysis on day 7). 3/24 (12.5%) of detectable LiTAPs showed significant changes in abundance. (FIG. 5c) Analysis of a CLL patient ligandome prior to therapy and 24 h after treatment with 300 mg ofatumumab. 2/10 (20.0%) of detectable LiTAPs showed significant changes in abundance.

Figure 6B:
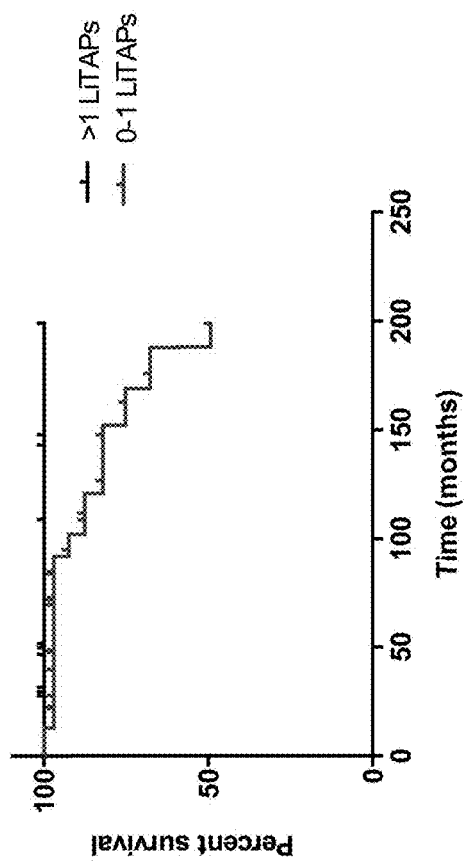
Figure 6A:
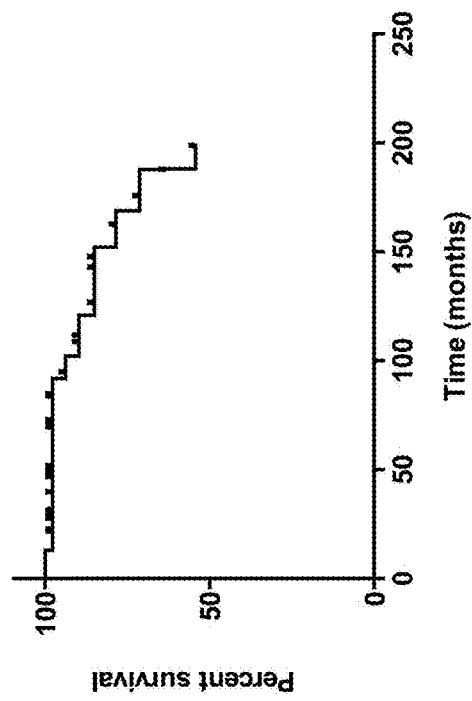

FIGS. 6a and 6b show the retrospective survival analysis of CLL patients with respect to their immune recognition of LiTAPs. (FIG. 6a) Kaplan Meier plot of the overall survival of 44 CLL patients. (FIG. 6b) Overall survival of subjects evaluated for LiTAP-specific immune responses grouped as follows: black, CLL patients showing immune responses to >1 LiTAPs (n=10). Red, CLL patients showing immune reactions to 0-1 LiTAPs (n=34).

Figure 7:
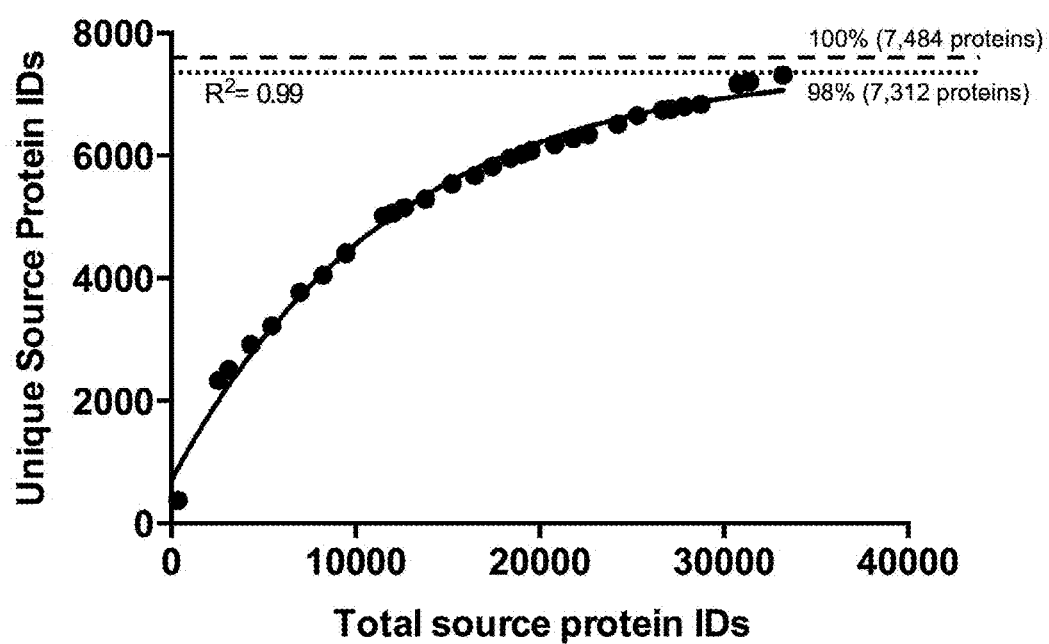

FIG. 7 shows the saturation analysis of HLA class I ligand source protein identifications in CLL patients. Number of unique HLA ligand source protein identifications as a function of total HLA ligand source protein identifications in 30 CLL patients. Exponential regression allowed for the robust calculation ($R^2$=0.9912) of the maximum attainable number of different source protein identifications (dashed line). The dotted line depicts the source proteome coverage achieved in our CLL patient cohort.

Figure 8A:
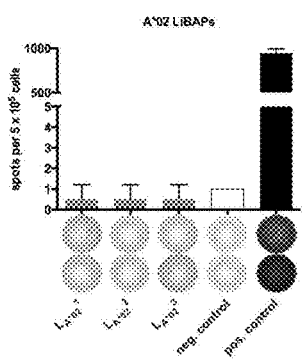
Figure 8B:
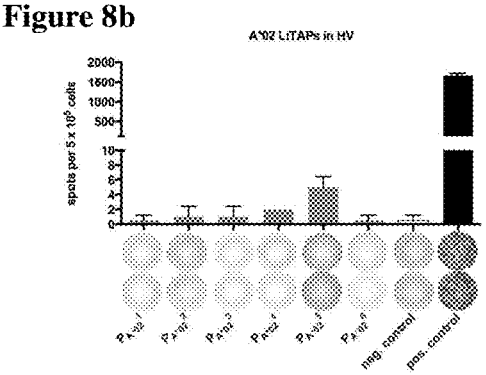
Figure 8C:
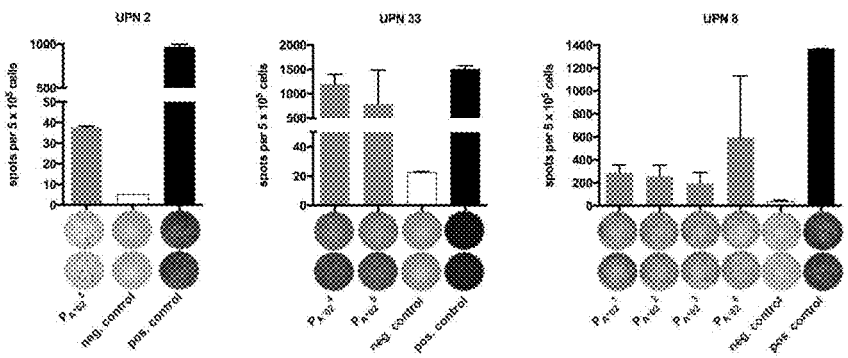
Figure 8D:
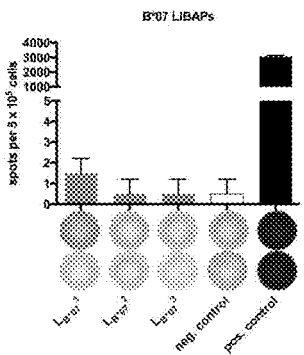
Figure 8E:
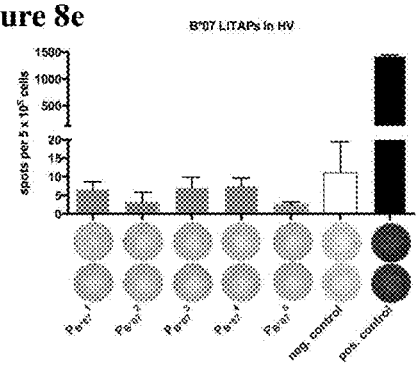
Figure 8F:
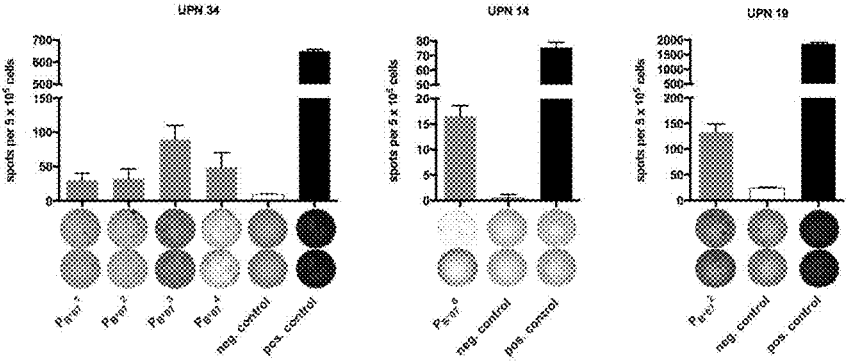
Figure 10B:
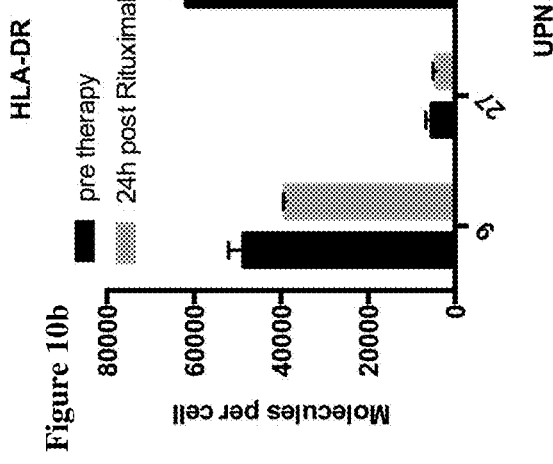
Figure 10A:
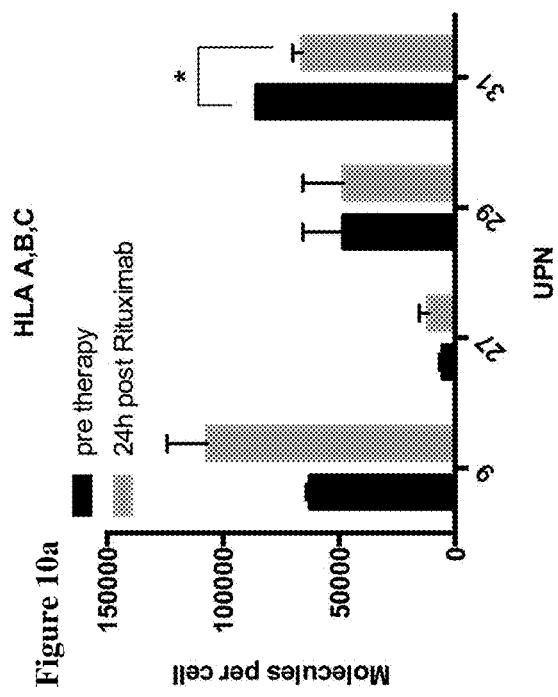
Figure 10C:
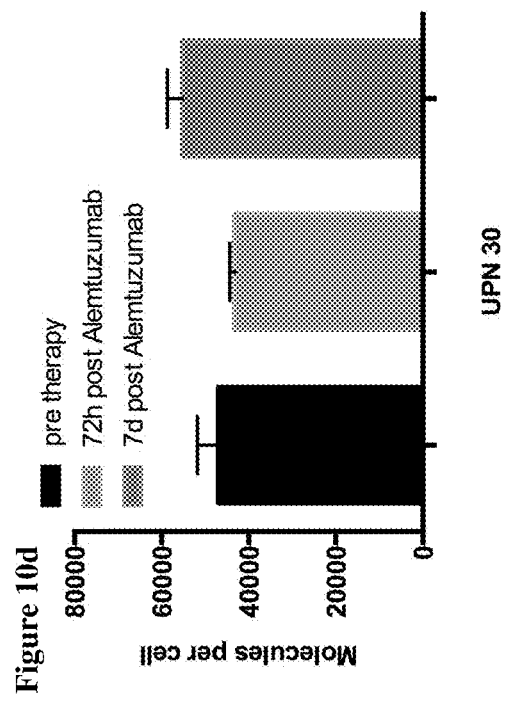
Figure 10D:
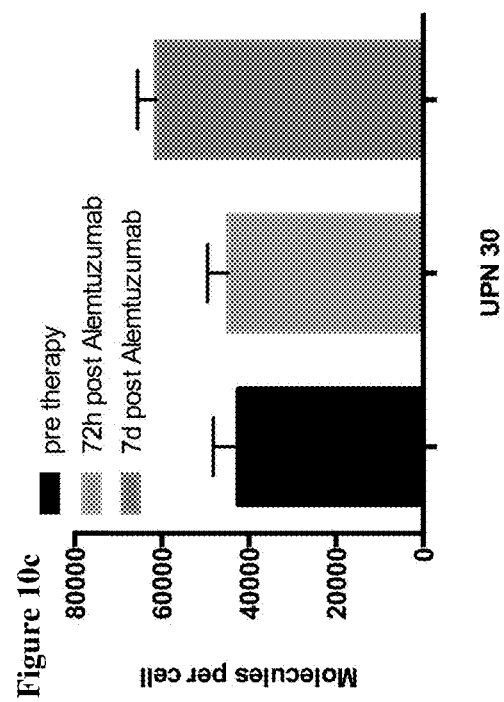

FIGS. 8a-8f show that HLA-A*02 and B*07 LiTAPs are specifically recognized by CLL patient immune responses. (FIG. 8a) Example of HLA-A*02 (n=3) and (FIG. 8d) HLA-B*07 (n=3) benign tissue-derived LiBAPs tested on CLL patient PBMC as internal control for the target selection strategy. EBV epitope mix served as positive control, HIV XX$_{xx-xx}$ A*02 and HIV XX$_{xx-xx}$ HLA-B*07 peptide served as negative control, respectively. (FIG. 8b) Example of HLA-A*02 (n=6) and (FIG. 8e) HLA-B*07 (n=5) LiTAPs evaluated in ELISPOT assays using HV PBMC as a control. Positive and negative controls as described in (FIG. 8a). (FIG. 8c) Example of ELISPOT assays using HLA-A*02 (n=6) and (FIG. 8f) HLA-B*07 (n=5) LiTAPs on PBMC of 3 different HLA-matched CLL patients, each. Results are shown for immunoreactive LiTAPs. Positive and negative controls as described in (FIG. 8a). Abbreviations: LiBAP, ligandome-derived benign tissue-associated peptide; LiTAP, ligandome-derived tumor-associated peptide; HV, healthy volunteer; neg., negative; pos., positive; UPN, uniform patient number.

FIGS. 9a and 9b show the intracellular cytokine and tetramer staining of HLA-A*03 LiTAP specific CLL patient T cells. (FIG. 9a) Intracellular staining for IFNγ and TNFα of P$_{A*03}$$^3$ (DMXL1$_{1271-1279}$ SSSGLHPPK (SEQ ID NO: 77) stimulated CLL patient PBMC. PMA/ionomycin served as positive control, HIV GAG$_{18-26}$ A*03 peptide as negative control. (FIG. 9b) Tetramer staining of CLL patient CD8$^+$ T cells with P$_{A*03}$$^3$ (DMXL1$_{1271-1279}$ SSSGLHPPK (SEQ ID NO: 77)) tetramers. As control, tetramer staining with the non-recognized P$_{A*02}$$^1$ (ABCA6$_{1270-1278}$ ILDEKPVII (SEQ ID NO: 63) in the same patient is shown.

FIGS. 10a-10d show the quantification of HLA surface expression on primary CLL cells from patients undergoing chemo-/immunotherapy. HLA surface expression on CD5$^+$ CD19$^+$ CLL cells was quantified by flow cytometry, before and after therapy. Data are expressed as mean±s.d. of triplicate experiments. (FIG. 10a) HLA class I and (FIG. 10b) HLA class II surface expression on primary CLL cells of 4 patients prior to therapy and 24 h after treatment with rituximab. (FIG. 10c) HLA class I and (FIG. 10d) HLA class II surface expression on primary CLL cells of a patient prior to therapy, 72 h (10 mg) and 7 d (60 mg) after treatment with alemtuzumab. *P<0.01 Abbreviations: UPN, uniform patient number; h, hour; d, day.

Figure 11:
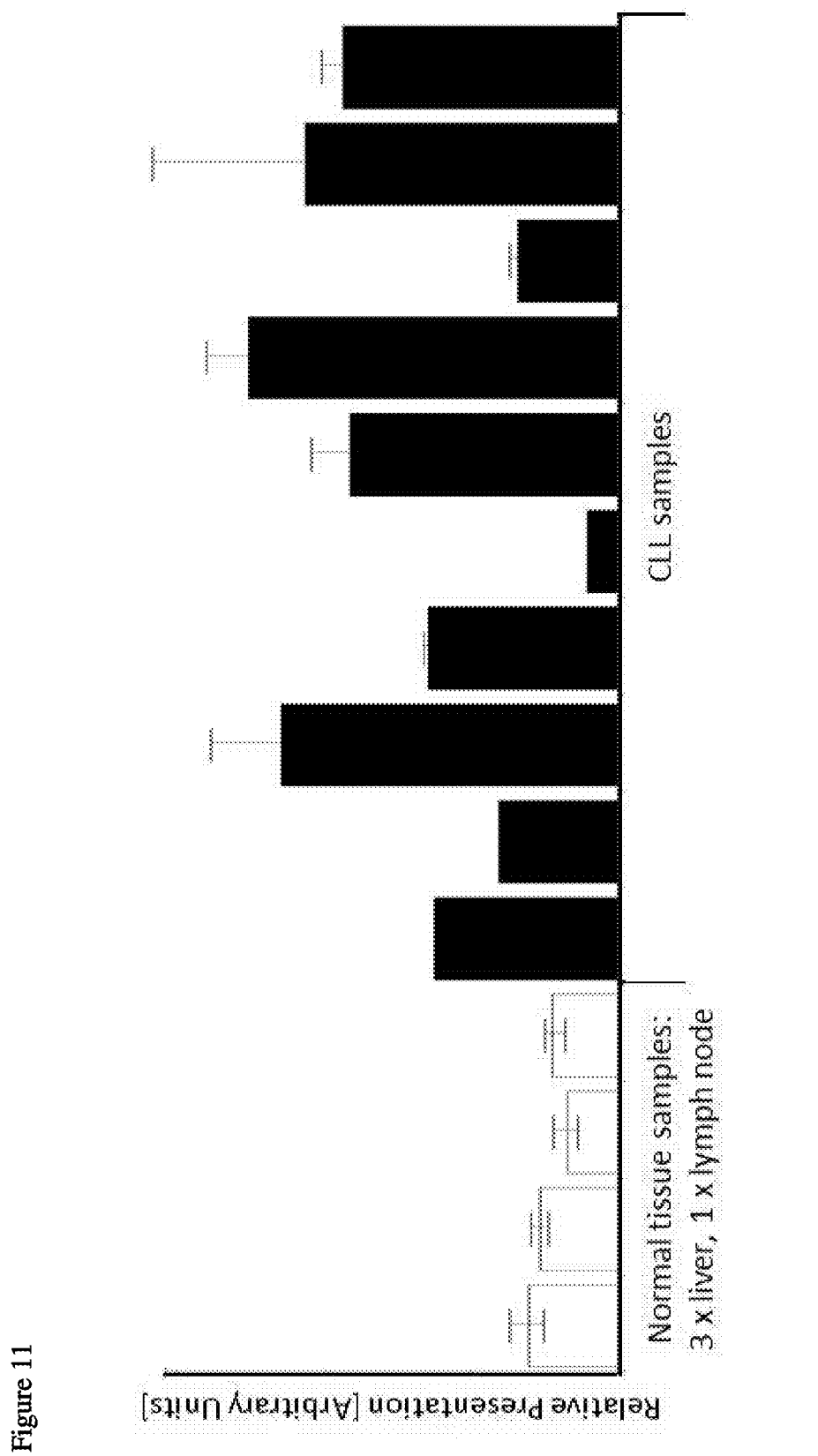

FIG. 11 shows the over-presentation of peptide ILDEKPVII (SEQ ID NO: 63) in normal tissues as compared to CLL samples. Shown are only samples on which the peptide was detected. The test panel included 12 CLL samples and the following normal samples: 1×adipose tissue, 3×adrenal gland, 6×artery, 5×bone marrow, 7×brain, 3×breast, 5×nerve, 13×colon, 7×esophagus, 2×gallbladder, 5×heart, 12×kidney, 20×liver, 44×lung, 3×lymph node, 4×peripheral blood mononuclear cells, 2×ovary, 6×pancreas, 1×peritoneum, 3×pituitary, 2×placenta, 3×pleura, 3×prostate, 6×rectum, 7×salivary gland, 4×skeletal muscle, 5×skin, 3×small intestine, 4×spleen, 5×stomach, 4×testis, 3×thymus, 3×thyroid gland, 3×trachea, 2×ureter, 5×urinary bladder, 2×uterus, 2×vein.

EXAMPLES

Example 1

Identification and Quantitation of Tumor Associated Peptides Presented on the Cell Surface Tissue Samples Patients' tumor samples were provided by University of Tübingen, Tübingen, Germany. Written informed consents of all patients had been given. For ligandome analysis, PBMC from CLL patients (>80% CLL cell frequency) as well as PBMC from healthy volunteers (HVs) were isolated by density gradient centrifugation. Informed consent was obtained in accordance with the Helsinki protocol. This study was performed according to the guidelines of the local ethics committee. HLA typing was carried out by the Department of Hematology and Oncology, Tübingen. Samples were stored at −80° C. until further use.

Quantification of HLA Surface Expression

For comparison with healthy autologous B lymphocytes, quantification of HLA surface expression was performed in patient samples containing at least 0.5% CD5$^-$CD19$^+$ normal B cells. HLA surface expression was analyzed using the QIFIKIT® quantitative flow cytometric assay (Dako) according to the manufacturer's instructions. In brief, triplicates of each sample were stained with the pan-HLA class I specific monoclonal antibody (mAb) W6/32, HLA-DR specific mAb L243 (both produced in house) or IgG isotype control (BioLegend), respectively. Surface marker staining was carried out with directly labeled CD3 (BD), CD5 (BD) and CD19 (BD) antibodies. 7-AAD (BioLegend) was added as viability marker immediately prior to flow cytometric analysis on a FACSCanto Analyzer (BD).

Isolation of HLA Peptides from Tissue Samples

HLA class I and II molecules were isolated employing standard immunoaffinity purification as described previously. In brief, snap-frozen cell pellets were lysed in 10 mM CHAPS/PBS (AppliChem, St. Louis, Mo., USA/Gibco, Carlsbad, Calif., USA) containing 1× protease inhibitor (Complete, Roche, Basel, Switzerland). HLA molecules were single-step purified using the pan-HLA class I specific mAb W6/32 and the pan-HLA class II specific mAb TU39 respectively, covalently linked to CNBr-activated sepharose (GE Healthcare, Chalfont St Giles, UK). HLA:peptide complexes were eluted by repeated addition of 0.2% trifluoroacetic acid (TFA, Merck, Whitehouse Station, N.J., USA). Elution fractions E1-E8 were pooled and free HLA ligands were isolated by ultrafiltration using centrifugal filter units (Amicon, Millipore, Billerica, Mass., USA). HLA ligands were extracted and desalted from the filtrate using ZipTip C18 pipette tips (Millipore). Extracted peptides were eluted in 35 µl of 80% acetonitrile (ACN, Merck)/0.2% TFA, centrifuged to complete dryness and resuspended in 25 µl of 1% ACN/0.05% TFA. Samples were stored at −20° C. until analysis by LC-MS/MS.

Analysis of HLA Ligands by LC-MS/MS

Peptide samples were separated by reversed-phase liquid chromatography (nanoUHPLC, UltiMate 3000 RSLCnano, ThermoFisher, Waltham, Mass., USA) and subsequently analyzed in an on-line coupled LTQ Orbitrap XL hybrid mass spectrometer (ThermoFisher). Samples were analyzed in 5 technical replicates. Sample volumes of 5 µl (sample shares of 20%) were injected onto a 75 µm×2 cm trapping column (Acclaim PepMap RSLC, ThermoFisher) at 4 µl/min for 5.75 min. Peptide separation was subsequently performed at 50° C. and a flow rate of 175 nl/min on a 50 µm×50 cm separation column (Acclaim PepMap RSLC, ThermoFisher) applying a gradient ranging from 2.4-32.0% of ACN over the course of 140 min. Eluting peptides were ionized by nanospray ionization and analyzed in the mass spectrometer implementing a top 5 CID (collision induced dissociation) method generating fragment spectra for the 5 most abundant precursor ions in the survey scans. Resolution was set to 60,000. For HLA class I ligands, the mass range was limited to 400-650 m/z with charge states 2 and 3 permitted for fragmentation. For HLA class II, a mass range of 300-1,500 m/z was analyzed with charge states allowed for fragmentation.

Database Search and Spectral Annotation

For data processing, the software Proteome Discoverer (v1.3, ThermoFisher) was used to integrate the search results of the Mascot search engine (Mascot 2.2.04, Matrix Science) against the human proteome as comprised in the Swiss-Prot database (release: Sep. 27, 2013; 20,279 reviewed protein sequences contained). The search combined data of technical replicates and was not restricted by enzymatic specificity. Precursor mass tolerance was set to 5 ppm, fragment mass tolerance to 0.5 Da. Oxidized methionine was allowed as a dynamic modification. False discovery rates (FDR) were determined by the Percolator algorithm based on processing against a decoy database consisting of the shuffled target database. FDR was set at a target value of q≤0.05 (5% FDR). Peptide-spectrum matches (PSMs) with q≤0.05 were filtered according to additional, orthogonal parameters, to ensure spectral quality and validity. Mascot scores were filtered to ≥20. For HLA class I, peptide lengths were limited to 8-12 amino acids (aa) of length. For HLA class II, peptides were limited to 12-25 aa length. Protein grouping was disabled, allowing for multiple annotations of peptides (e.g. conserved sequences mapping into multiple proteins). For quality control, yield thresholds of ≥300 unique HLA class I ligands and ≥100 unique HLA class II ligands per sample were applied. HLA annotation was performed using SYFPEITHI or an extended in-house database.

Longitudinal Analysis of CLL Patient Ligandomes Over the Course of Therapy

For label-free quantification (LFQ) of the relative HLA ligand abundances over the course of therapy, the injected peptide amounts of paired samples were normalized and LC-MS/MS analysis was performed in 5 technical replicates for each sample.

In brief, relative amounts of substance of paired samples were calculated from average precursor ion intensities determined in dose-finding mass spectrometry runs and adjusted accordingly by dilution. Relative quantification of HLA ligands was performed by calculating the area under the curve of the corresponding precursor extracted ion chromatograms (XIC) using Proteome Discoverer 1.3. The ratios of the mean areas of the individual peptides in the 5 LFQ-MS runs of each sample were calculated and two-tailed t-tests were performed using an in-house Matlab script (v8.2, Mathworks).

Peptide Synthesis

The automated peptide synthesizer EPS221 (Abimed) was used to synthesize peptides using the 9-fluorenylmethyl-oxycarbonyl/tert-butyl (Fmoc/tBu) strategy as described. Synthetic peptides were used for validation of LC-MS/MS identifications as well as for functional experiments.

Amplification of Peptide-Specific T Cells

PBMC from CLL patients and healthy volunteers were cultured in RPMI1640 medium (Gibco) supplemented with 10% pooled human serum (PHS, produced in-house), 100 mM β-mercaptoethanol (Roth, Karlsruhe, Germany) and 1% penicillin/streptomycin (GE). For CD8$^+$ T cell stimulation, PBMC were thawed and pulsed with 1 µg/ml per peptide. Peptide-pulsed PBMC (5-6×10$^6$ cells/ml) were cultured at 37° C. and 5% CO$_2$ for 12 days. On day 0 and day 1.5 ng/ml IL-4 (R&D Systems, Minneapolis, Minn., USA) and 5 ng/ml IL-7 (Promokine, Heidelberg, Germany) were added to the culture medium. On days 3, 5, 7 and 9, 2 ng/ml IL-2 (R&D Systems) were added to the culture medium. Peptide-stimulated PBMC were functionally characterized by ELISPOT assays on day 12 and by intracellular cytokine staining on day 13 respectively. For CD4$^+$ T-cell stimulation, culture was performed as described for CD8$^+$ T cells with 2 modifications: pulsing was carried out with 10 µg/ml of HLA class II peptide and no IL-4 and IL-7 was added.

IFN-γ ELISPOT Assay

IFN-γ ELISPOT assays were carried out as described previously (33). In brief, 96-well nitrocellulose plates (Millipore) were coated with 1 mg/ml IFN-γ mAb (Mabtech, Cincinnati, Ohio, USA) and incubated over night at 4° C. Plates were blocked with 10% PHS for 2 h at 37° C. 5×10$^5$ cells/well of pre-stimulated PBMC were pulsed with 1 µg/ml (HLA class I) or 2.5 µg/ml (HLA class II) peptide and incubated for 24-26 h. Readout was performed according to manufacturer's instructions. Spots were counted using an ImmunoSpot S5 analyzer (CTL, Shaker Heights, Ohio, USA). T cell responses were considered to be positive when >15 spots/well were counted and the mean spot count per well was at least 3-fold higher than the mean number of spots in the negative control wells (according to the cancer immunoguiding program (CIP) guidelines).

Intracellular IFN-γ and TNF-α Staining

The frequency and functionality of peptide-specific CD8+ T cells was analyzed by intracellular IFN-γ and TNF-α staining. PBMC were pulsed with 1 μg/ml of individual peptide and incubated in the presence of 10 μg/ml Brefeldin A (Sigma, St. Louis, Mo., USA) and 10 μg/ml GolgiStop (BD) for 6-8 h. Cells were labeled using Cytofix/Cytoperm (BD), CD8-PECy7 (Beckman Coulter, Fullerton, Calif., USA), CD4-APC (BD Bioscience), TNF-α-PE (Beckman Coulter) and IFN-γ-FITC (BD). Samples were analyzed on a FACS Canto II.

The frequency of peptide-specific CD8+ T cells was determined by staining with anti-CD8 and HLA:peptide-tetramer-PE Results Primary CLL Cells Display No Loss or Down-Regulation of HLA Expression Compared to Autologous Normal B Cells HLA loss or down-regulation in malignancies may pose a major limitation for T cell based immunotherapy. Therefore, as a first step, the inventors determined the HLA expression levels on CD19+CD5+ CLL cells compared to autologous CD19+CD5-B lymphocytes. HLA surface levels were quantified by flow cytometry in a panel of 7 CLL patients. HLA surface expression levels revealed patient-individual heterogeneity with total HLA class I molecule counts ranging from ~42,500-288,500 molecules/cell on CLL cells and 32,000-256,500 molecules/cell on normal B cells. Patient individual analysis of HLA surface expression in triplicates revealed small, albeit significant differences in expression levels ($P<0.01$) for 4/7 patients (FIG. 1a). HLA-DR expression ranged from ~29,000-100,500 on CLL cells and ~19,500-79,500 on B cells. Minor differences in HLA-DR levels ($P<0.01$) were detected for 5/7 patients. Statistical analysis of mean HLA surface expression on CLL cells compared to normal B cells showed no significant differences in HLA class I and II expression (FIGS. 1c, 1d). Taken together, these data demonstrate high levels of HLA class I and II expression on CLL cells without evidence of HLA loss or down-regulation compared to normal B cells.

LC-MS/MS Identifies a Vast Array of Naturally Presented HLA Class I & II Ligands Mapping the HLA class I ligandomes of 30 CLL patients, the inventors were able to identify a total of 18,844 different peptides representing 7,377 source proteins, attaining >95% of maximum attainable coverage (FIG. 7). The numbers of different peptides identified per patient ranged from 345-2,497 (mean 1,131). Overall, peptides restricted by more than 30 different HLA-A and -B alleles (covering >99% of the Caucasian population_ENREF_27) were identified in this study. In the HV cohort of 30 PBMC donors, a total of 17,322 unique peptides representing 7,180 different source proteins were identified (>90% coverage). The HLA allele distribution in the HV cohort covered 100% of HLA-A and >80% of HLA-B alleles in the CLL patient cohort.

Analysis of the HLA class II ligandomes was performed for 20 CLL patients. A total of 5,059 unique peptides representing 1,486 source proteins was identified. The HLA class II HV cohort of 13 PBMC donors yielded 2,046 different peptides representing 756 source proteins.

Comparative Profiling of HLA Class I Ligandomes Reveals a Multitude of CLL-Associated Antigens In order to identify novel CLL-associated antigens, the inventors compared the HLA ligand source proteomes of the CLL and HV cohorts. Overlap analysis of HLA source proteins revealed 2,148 proteins (29.1% of the mapped CLL source proteome) to be exclusively represented in the HLA ligandome of CLL (FIG. 2a). With the aim of designing a broadly applicable off-the-shelf peptide vaccine, the inventors subsequently prioritized the selection of potential targets according to the following criteria:

CLL-exclusivity was defined as paramount criterion, followed by ranking of antigens according to frequency of representation in CLL ligandomes (FIG. 2b). Our platform highlighted 49 source proteins (0.7% of the CLL source proteome) represented by 225 different HLA ligands showing CLL-exclusive representation in ≥20% of CLL patients. Applying the same antigen ranking strategy to HV PBMC exclusive antigens, a set of 71 ligandome-derived benign tissue-associated antigens (LiBAAs) and the 298 corresponding ligands (LiBAPs) were identified for use as internal control in immunological assays.

Apart from broadly represented CLL-LiTAAs suited for the design of off-the-shelf vaccines, a second panel of 2,099 CLL-exclusive antigens with representation frequencies <20% was identified by our platform. These targets lend themselves as repositories for more individualized therapeutic approaches.

Detection of Naturally Presented HLA Class I Ligands Derived from Established CLL-Associated Antigens by LC-MS/MS Alongside the identification of novel CLL-associated antigens, a secondary approach focused on the ranking of the few established CLL-antigens within the present dataset of naturally presented HLA ligands. The inventors were able to identify 28 different HLA ligands representing 8 described CLL-associated antigens. Of note, only Fibromodulin ($FMOD_{324-333}$, RINEFSISSF, HLA-A*23 (SEQ ID NO: 526) showed CLL-exclusive representation, ranking at #437 of CLL-antigens in the present dataset, due to low frequency of representation in the CLL patient cohort. The remaining seven antigens showed representation, both on CLL and HV PBMC, thus failing to fulfill the paramount criterion of CLL-exclusivity. However, for CD19, CD20, RHAMM and PRAME, CLL-associated overrepresentation of varying degrees was detected (FIG. 2c).

Comparative Ligandome Profiling Identifies LiTAAs Shared Among Different Disease Stages and Risk Strata In order to assess the applicability of the novel targets across different stages of disease, the inventors performed subset-specific ligandome profiling comparing patients in disease stages Binet A (n=9), B (n=7) and C (n=14). Overlap analysis of the 2,148 CLL-exclusive source proteins found 550 (25.6%) of them shared among at least two stages, with a core group of 137 proteins (6.1%) represented in patients of all three stages of disease (FIG. 2d). Of note, 45/49 (91.8%) of LiTAAs belong to the core group of shared source proteins represented in all three subsets. Heatmap analysis of the representation frequencies of all 49 LiTAAs across Binet stages A, B and C is shown in FIG. 2e.

Another focus was placed on determining the representation of LiTAAs in the subsets of high-risk patients carrying the 17p13 deletion (del17p, n=5) as compared to patients without this genetic aberration (no del17p, n=25). The inventors found 77.7% of the identified LiTAAs to be represented in both subsets (FIG. 2f). Together, these data support the devised strategy of cohort-comprising analysis of HLA ligandomes for selection of broadly applicable targets.

Functional Characterization of HLA Class I LiTAPs Reveals CLL-Associated Immunoreactivity In order to evaluate the immunogenicity and specificity of our HLA class I LiTAPs, the inventors next performed 12-day recall IFNγ ELISPOT assays. A panel of 15 LiTAPs (6 A*02, 4 A*03 and 5 B*07 LiTAPs) was implemented for stimulation of HLA-matched PBMC obtained from CLL patients and healthy volunteers (FIG. 3a). The inventors observed IFNγ secretion for 14/15 (93.3%) of tested LiTAPs in CLL patients (3/4 A*03 (FIG. 3c), 6/6 A*02 and 5/5 B*07 LiTAPs (FIGS. 8c, 8f)), but not in healthy controls (0/10, FIG. 3b, FIGS. 8b, 8e). These findings were confirmed exemplarily for $P_{A*03}^3$ (DMXL1$_{1271-1279}$ SSSGLHPPK (SEQ ID NO:77)) by tetramer staining of CD8$^+$ T cells and intracellular cytokine staining for IFNγ and TNFα (FIGS. 9a, 9b). ELISPOT assays using HLA-matched benign tissue-derived LiBAPs were performed to control for the CLL-specificity of the observed LiTAP-directed immune recognition in CLL patients. The inventors tested a panel of 9 LiBAPs (3 A*02, 3 A*03, 3*B*07) and observed no significant IFNγ secretion in any of the tested CLL patients (0/7 A*03 (FIG. 3d), 0/10 A*02+ and 0/5 B*07 (FIGS. 8a, 8d)).

For the 14/15 LiTAPs showing immune recognition in 1 or more patients, the inventors calculated the allele-adjusted frequencies of HLA restricted presentation (as detected by LC-MS/MS) and the frequencies of immunoreactivity (as detected by ELISPOT) in CLL patients. Strikingly, a linear correlation of these two parameters was observed (Pearson's r=0.77, $R^2$=0.59, FIG. 3e). These findings suggest two main points: First, tumor-exclusive representation is prerequisite for immune recognition. Secondly, frequency of immune recognition can be directly deduced from the frequency of HLA restricted presentation for immunoreactive LiTAPs. Together, these data demonstrate the efficacy of our approach identifying immunologically relevant targets for CLL-specific peptide vaccines.

HLA Class II Ligandome Analysis Identifies Additional CD4$^+$ T Cell Epitopes for Synergistic Vaccine Design Because of the important indirect and direct roles CD4$^+$ T cells play in anti-cancer immune responses, optimal vaccine design calls for the inclusion of additional HLA class II epitopes. The inventors performed overlap analysis of CLL and HV PBMC ligandomes and identified 937 proteins (63.0% of the identified CLL source proteins) to be exclusively represented in the ligandomes of CLL patients (FIG. 4a). Applying the same antigen-ranking strategy as described for HLA class I, the inventors identified 73 HLA class II LiTAAs represented by 460 corresponding LiTAPs (FIG. 4b). Functional characterization of a panel of 7 HLA class II LiTAPs (FIG. 4c) in IFNγ ELISPOT assays revealed significant IFNγ secretion for 6/7 (85.7%) LiTAPs in CLL patients (FIG. 4e), but not in healthy controls (0/10, FIG. 4d). Next, the inventors performed combined analysis of HLA class I and II ligandomes in order to identify shared, synergistic targets. Overlap analysis of CLL-exclusive source proteins revealed 132 proteins to be represented both in HLA class I and II ligandomes (FIG. 4f). Heatmap analysis identified 2 proteins displaying representation frequencies ≥20% in both ligandomes (B4GALT1 (26.7% class I/30.0% class II), HLA-DMA (20.0% class I/20% class II), FIG. 4g). Strikingly, one of the class I LiTAPs (HLA-DMA$_{206-214}$, HEIDRYTAI, B*18 (SEQ ID NO: 178)) was revealed to be completely embedded in the corresponding HLA class II LiTAP (VTHEIDRYTAIAY (SEQ ID No. 924)). Together, the inventors identified a panel of class II LiTAPs, which could be verified as T cell epitopes, as well as an array of potentially synergistic HLA class II ligands covering class I LiTAAs.

Longitudinal Analysis of CLL Patient Ligandomes Under Different Therapeutic Regimens The scope of peptide based immunotherapy is maintenance therapy and eradication of MRD. As a consequence, peptide vaccination in CLL would take place after standard chemo-/immunotherapy. Therefore, the inventors analyzed HLA expression and performed ligandome profiling across different time points of CLL patients undergoing different therapeutic regimens.

The inventors quantified HLA class I and II surface expression in 4 patients undergoing rituximab treatment (Rt$_{0h}$, Rt$_{24h}$) and 1 patient receiving alemtuzumab (At$_{0h}$, At$_{72h}$, At$_{7d}$, FIG. 10a-10d). HLA surface expression showed patient-individual heterogeneity with no significant changes in mean HLA class I (Rt$_{0h}$=50,500, Rt$_{24h}$=48,000; At$_{0h}$=42,500, At$_{7d}$=61,500) and HLA class II (Rt$_{0h}$=36,500, Rt$_{24h}$=27,500; At$_{0h}$=47,000, At$_{7d}$=55,500) expression over the course of either therapeutic regimen.

Longitudinal HLA class I ligandome profiling was performed in single patients undergoing rituximab-bendamustin, alemtuzumab or ofatumumab treatment, respectively (FIGS. 5a-5c). Differential presentation (≥2-fold change, p≤0.05) was observed for 11.1% of HLA class I ligands under rituximab-bendamustin treatment, for 21.6% of ligands under ofatumumab treatment and for 33.6% of ligands under alemtuzumab treatment. Overall, LiTAPs representing 8/49 (16.3%) LiTAAs were revealed to be differentially presented over the course of therapy. Taken together, these data demonstrate stable expression of surface HLA and robust presentation of LiTAPs over the course of different therapies.

Immune Responses Against LiTAPs Might be Associated with Improved Overall Survival of CLL Patients As a last step, the inventors performed retrospective survival analysis of 33 CLL patients (FIG. 6a) analyzed by ELISPOT assays comparing cases with 0-1 LiTAP-specific (n=23) versus >1 LiTAP-specific (n=10) T cell responses (FIG. 6b). In the low-responding cohort 6/23 (26.1%) of patients, in the high-responding cohort 0/11 of patients died. Overall survival seems to be prolonged in the cohort showing >1 immune reactions.

Example 2

Synthesis of Peptides

All peptides were synthesized using standard and well-established solid phase peptide synthesis using the Fmoc-strategy. After purification by preparative RP-HPLC, ion-exchange procedure was performed to incorporate physiological compatible counter ions (for example trifluoro-acetate, acetate, ammonium or chloride).

Identity and purity of each individual peptide have been determined by mass spectrometry and analytical RP-HPLC. After ion-exchange procedure the peptides were obtained as white to off-white lyophilizates in purities of 90% to 99.7%.

All TUMAPs are preferably administered as trifluoro-acetate salts or acetate salts, other salt-forms are also possible. For the measurements of example 4, trifluoro-acetate salts of the peptides were used.

Example 3

MHC Binding Assays

Candidate peptides for T cell based therapies according to the present invention were further tested for their MHC binding capacity (affinity). The individual peptide-MHC complexes were produced by peptide-ligand exchange, where a cleavage-sensitive peptide is cleaved, and exchanged with the peptide of interest as analyzed. Only peptide candidates that can effectively bind and stabilize the peptide-receptive MHC molecules prevent dissociation of the MHC complexes. To determine the yield of the exchange reaction, an ELISA was performed based on the detection of the light chain (β2m) of stabilized MHC complexes. The assay was performed as generally described in Rodenko et al. (Rodenko et al., Nat Protoc. 1 (2006): 1120-1132).

96 well MAXISorp plates (NUNC) were coated over night with 2 ug/ml streptavidin in PBS at room temperature, washed 4× and blocked for 1 h at 37° C. in 2% BSA containing blocking buffer. Refolded HLA-A*0201/MLA-001 monomers served as standards, covering the range of 15-500 ng/ml. Peptide-MHC monomers of the UV-exchange reaction were diluted 100 fold in blocking buffer. Samples were incubated for 1 h at 37° C., washed four times, incubated with 2 ug/ml HRP conjugated anti-β2m for 1 h at 37° C., washed again and detected with TMB solution that is stopped with $NH_2SO_4$. Absorption was measured at 450 nm. Candidate peptides that show a high exchange yield (preferably higher than 50%, most preferred higher than 75%) are generally preferred for a generation and production of antibodies or fragments thereof, and/or T cell receptors or fragments thereof, as they show sufficient avidity to the MHC molecules and prevent dissociation of the MHC complexes.

| Seq ID NO. | sequence | Peptide exchange |
|---|---|---|
| 229 | FRVGNVQEL | ++++ |
| 239 | SENAFYLSP | ++++ |

MHC class I binding scores for the peptides as tested were; <20% = +; 20%-49% = ++; 50%-75%. = +++; >=75% = ++++

Example 4

In Vitro Immunogenicity for MHC Class I Presented Peptides

In order to obtain information regarding the immunogenicity of the TUMAPs of the present invention, the inventors performed investigations using an in vitro T-cell priming assay based on repeated stimulations of CD8+ T cells with artificial antigen presenting cells (aAPCs) loaded with peptide/MHC complexes and anti-CD28 antibody. This way the inventors could show immunogenicity for HLA-A*0201 restricted TUMAPs of the invention, demonstrating that these peptides are T-cell epitopes against which CD8+ precursor T cells exist in humans.

In Vitro Priming of CD8+ T Cells

In order to perform in vitro stimulations by artificial antigen presenting cells loaded with peptide-MHC complex (pMHC) and anti-CD28 antibody, the inventors first isolated CD8+ T cells from fresh HLA-A*02 leukapheresis products via positive selection using CD8 microbeads (Miltenyi Biotec, Bergisch-Gladbach, Germany) of healthy donors obtained from the University clinics Mannheim, Germany, after informed consent.

PBMCs and isolated CD8+ lymphocytes were incubated in T-cell medium (TCM) until use consisting of RPMI-Glutamax (Invitrogen, Karlsruhe, Germany) supplemented with 10% heat inactivated human AB serum (PAN-Biotech, Aidenbach, Germany), 100 U/ml Penicillin/100 µg/ml Streptomycin (Cambrex, Cologne, Germany), 1 mM sodium pyruvate (CC Pro, Oberdorla, Germany), 20 µg/ml Gentamycin (Cambrex). 2.5 ng/ml IL-7 (PromoCell, Heidelberg, Germany) and 10 U/ml IL-2 (Novartis Pharma, Nürnberg, Germany) were also added to the TCM at this step.

Generation of pMHC/anti-CD28 coated beads, T-cell stimulations and readout was performed in a highly defined in vitro system using four different pMHC molecules per stimulation condition and 8 different pMHC molecules per readout condition.

The purified co-stimulatory mouse IgG2a anti human CD28 Ab 9.3 (Jung et al., Proc Natl Acad Sci USA 84 (1987): 4611-4615) was chemically biotinylated using Sulfo-N-hydroxysuccinimidobiotin as recommended by the manufacturer (Perbio, Bonn, Germany). Beads used were 5.6 µm diameter streptavidin coated polystyrene particles (Bangs Laboratories, Illinois, USA).

pMHC used for positive and negative control stimulations were A*0201/MLA-001 (peptide ELAGIGILTV (SEQ ID NO. 1017) from modified Melan-A/MART-1) and A*0201/DDX5-001 (YLLPAIVHI from DDX5, SEQ ID NO. 1018), respectively.

800.000 beads/200 µl were coated in 96-well plates in the presence of 4×12.5 ng different biotin-pMHC, washed and 600 ng biotin anti-CD28 were added subsequently in a volume of 200 µl. Stimulations were initiated in 96-well plates by co-incubating $1\times10^6$ CD8+ T cells with $2\times10^5$ washed coated beads in 200 µl TCM supplemented with 5 ng/ml IL-12 (PromoCell) for 3 days at 37° C. Half of the medium was then exchanged by fresh TCM supplemented with 80 U/ml IL-2 and incubating was continued for 4 days at 37° C. This stimulation cycle was performed for a total of three times. For the pMHC multimer readout using 8 different pMHC molecules per condition, a two-dimensional combinatorial coding approach was used as previously described (Andersen et al., Nat. Protoc. 7 (2012): 891-902) with minor modifications encompassing coupling to 5 different fluorochromes. Finally, multimeric analyses were performed by staining the cells with Live/dead near IR dye (Invitrogen, Karlsruhe, Germany), CD8-FITC antibody clone SK1 (BD, Heidelberg, Germany) and fluorescent pMHC multimers. For analysis, a BD LSRII SORP cytometer equipped with appropriate lasers and filters was used. Peptide specific cells were calculated as percentage of total CD8+cells. Evaluation of multimeric analysis was done using the FlowJo software (Tree Star, Oreg., USA). In vitro priming of specific multimer+ CD8+ lymphocytes was detected by by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific multimer+ among CD8+ T-cells and the percentage of specific multimer+cells was at least 10× the median of the negative control stimulations).

In Vitro Immunogenicity for CLL Peptides

For tested HLA class I peptides, in vitro immunogenicity could be demonstrated by generation of peptide specific T-cell lines. As an exemplary result, peptide KFAEEFYSF (SEQ ID NO. 20) led to in vitro T-cell responses in 2 of 5 tested donors.

Example 5

Identification and Quantitation of Tumor Associated Peptides Presented on the Cell Surface Tissue Samples:

In addition to the samples used for identification of peptides, an independent sample set comprising both normal and tumor (CLL) tissues was used for analysis/confirmation of HLA-A*02-associated peptides of the invention. Written informed consents of all patients had been given before surgery or autopsy. Tissues were shock-frozen immediately after excision and stored until isolation of TUMAPs at −70° C. or below.

Isolation of HLA Peptides from Tissue Samples

HLA peptide pools from shock-frozen tissue samples were obtained by immune precipitation from solid tissues according to a slightly modified protocol (Falk et al., Nature 351 (1991): 290-296; Seeger et al., Immunogenetics 49 (1999): 571-576) using the HLA-A*02-specific antibody BB7.2, the HLA-A, —B, C-specific antibody W6/32, CNBr-activated sepharose, acid treatment, and ultrafiltration.

Mass Spectrometry Analyses

The HLA peptide pools as obtained were separated according to their hydrophobicity by reversed-phase chromatography (nanoAcquity UPLC system, Waters) and the eluting peptides were analyzed in LTQ-velos and fusion hybrid mass spectrometers (ThermoElectron) equipped with an ESI source. Peptide pools were loaded directly onto the analytical fused-silica micro-capillary column (75 μm i.d.× 250 mm) packed with 1.7 μm C18 reversed-phase material (Waters) applying a flow rate of 400 nL per minute. Subsequently, the peptides were separated using a two-step 180 minute-binary gradient from 10% to 33% B at a flow rate of 300 nL per minute. The gradient was composed of Solvent A (0.1% formic acid in water) and solvent B (0.1% formic acid in acetonitrile). A gold coated glass capillary (PicoTip, New Objective) was used for introduction into the nanoESI source. The LTQ-Orbitrap mass spectrometers were operated in the data-dependent mode using a TOP5 strategy. In brief, a scan cycle was initiated with a full scan of high mass accuracy in the orbitrap (R=30 000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified peptide sequence was assured by comparison of the generated natural peptide fragmentation pattern with the fragmentation pattern of a synthetic sequence-identical reference peptide.

Label-free relative LC-MS quantitation was performed by ion counting i.e. by extraction and analysis of LC-MS features (Mueller et al., Proteomics. 7 (2007): 3470-3480). The method assumes that the peptide's LC-MS signal area correlates with its abundance in the sample. Extracted features were further processed by charge state deconvolution and retention time alignment (Mueller et al., J Proteome. Res 7 (2008): 51-61; Sturm et al., BMC. Bioinformatics. 9 (2008): 163). Finally, all LC-MS features were cross-referenced with the sequence identification results to combine quantitative data of different samples and tissues to peptide presentation profiles. The quantitative data were normalized in a two-tier fashion according to central tendency to account for variation within technical and biological replicates. Thus each identified peptide can be associated with quantitative data allowing relative quantification between samples and tissues. In addition, all quantitative data acquired for peptide candidates was inspected manually to assure data consistency and to verify the accuracy of the automated analysis. For each peptide a presentation profile was calculated showing the mean sample presentation as well as replicate variations. The profiles juxtapose CLL samples to a baseline of normal tissue samples. The presentation profile of an exemplary over-presented peptide is shown in FIG. 11.

CITED REFERENCES

Ding, M. X. et al., Asian Pac. J Cancer Prev. 13 (2012): 5653-5657
Gallardo-Perez, J. C. et al., Biochim. Biophys. Acta 1843 (2014): 1043-1053
Jardim, B. V. et al., Oncol Rep. 30 (2013): 1119-1128
Jevnikar, Z. et al., J Biol. Chem 288 (2013): 2201-2209
Liu, Y. Y. et al., Mol. Cancer 9 (2010): 145
Mayr, C. et al., Blood 105 (2005): 1566-1573
Men, T. et al., Tumour. Biol. 35 (2014): 269-275
Nagai, K. et al., Cancer Med. 3 (2014): 1085-1099
Pallasch, C. P. et al., Blood 112 (2008): 4213-4219
Poeta, M. L. et al., Genes Chromosomes. Cancer 51 (2012): 1133-1143
Teh, M. T. et al., PLoS. One. 7 (2012): e34329
Yi, S. et al., Leuk. Lymphoma 52 (2011): 72-78
Yoon, D. Y. et al., Biochem. Biophys. Res. Commun. 288 (2001): 882-886
Yu, Z. et al., Zhonghua Yi. Xue. Za Zhi. 91 (2011): 1371-1374
Zhang, K. et al., Chin Med. J (Engl.) 126 (2013): 4660-4664
Zhou, H. et al., IUBMB. Life 64 (2012): 889-900

The invention claimed is:

1. A method of eliciting an immune response in a patient who has cancer, comprising administering to said patient a population of activated T cells that selectively recognize cells, which present a peptide consisting of the amino acid sequence SEQ ID NO: 239, wherein said cancer is selected from the group consisting of chronic lymphoid leukemia (CLL), acute myelogenous leukemia (AML).

2. The method of claim 1, wherein the T cells are autologous to the patient.

3. The method of claim 1, wherein the T cells are obtained from a healthy donor.

4. The method of claim 1, wherein the T cells are obtained from tumor infiltrating lymphocytes or peripheral blood mononuclear cells.

5. The method of claim 1, wherein the activated T cells are expanded in vitro.

6. The method of claim 1, wherein the peptide is in a complex with an MHC molecule.

7. The method of claim 6, wherein the MHC molecule is a class I MHC molecule.

8. The method of claim 1, wherein the activated T cells are cytotoxic T cells produced by contacting T cells with an antigen presenting cell that expresses the peptide in a complex with an MEW class I molecule on the surface of the antigen presenting cell, for a period of time sufficient to activate said T cell.

9. The method of claim 8, wherein the antigen presenting cell is infected with recombinant virus expressing the peptide.

10. The method of claim 9, wherein the antigen presenting cell is a dendritic cell or a macrophage.

11. The method of claim 8, wherein the contacting is in vitro.

12. The method of claim 1, wherein the population of activated T cells are administered in the form of a composition.

13. The method of claim 12, wherein the composition further comprises an adjuvant.

14. The method of claim 13, wherein the adjuvant is selected from anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

15. The method of claim 1, wherein the immune response is capable of killing cancer cells that present a peptide consisting of the amino acid sequence.

16. The method of claim 15, wherein the immune response comprises a cytotoxic T cell response.

17. The method of claim 1, wherein the cancer is chronic lymphoid leukemia (CLL).

18. The method of claim 1, wherein the cancer is acute myelogenous leukemia (AML).

19. The method of claim 1, wherein the cancer is pancreas adenocarcinoma.

20. The method of claim 13, wherein the adjuvant comprises IL-2.

* * * * *